(12) United States Patent
Zhou et al.

(10) Patent No.: US 6,825,208 B2
(45) Date of Patent: Nov. 30, 2004

(54) TETRAHYDROQUINOLINE DERIVATIVES AS ANTITHROMBOTIC AGENTS

(75) Inventors: Jinglan Zhou, San Diego, CA (US); Leslie Robinson, Del Mar, CA (US); Nikolaus M. Gubernator, Del Mar, CA (US); Eddine Saiah, LaJolla, CA (US); Xu Bai, Carlsbad, CA (US); Xin Gu, Scotch Plains, NJ (US)

(73) Assignee: Bristol-Myers Squibb Pharma Company, Princeton, NJ (US)

( * ) Notice: Subject to any disclaimer, the term of this patent is extended or adjusted under 35 U.S.C. 154(b) by 0 days.

(21) Appl. No.: 10/223,860

(22) Filed: Aug. 20, 2002

(65) Prior Publication Data

US 2003/0225110 A1 Dec. 4, 2003

(Under 37 CFR 1.47)

Related U.S. Application Data

(60) Provisional application No. 60/313,549, filed on Aug. 20, 2001.

(51) Int. Cl.$^7$ ..................... A61K 31/473; C07D 221/18
(52) U.S. Cl. ..................... 514/284; 546/61; 544/125; 544/298; 514/232.8; 514/269
(58) Field of Search ..................... 514/284, 232.8, 514/269; 546/61; 544/125, 298

(56) References Cited

U.S. PATENT DOCUMENTS 5,023,236 A 6/1991 Edgington et al.
5,843,442 A 12/1998 Soule et al.
5,859,010 A 1/1999 Petersen et al.

FOREIGN PATENT DOCUMENTS

WO    WO 00/35886    12/1999

OTHER PUBLICATIONS

RN 358372–38–0.*
Babu, G. et al., "Convenient Synthesis of Pyranol[3,2–c] quinolines and Indeno[2,1–c]quinolines by Imino Diels–Alder Reactions", Tetrahedron Letters, vol. 39, pp. 3225–3228 (1998).
Babu, G. et al., "Indium Trichloride–Catalyzed Imino Diels–Alder Reactions: Synthesis of New Indolylquinoline Derivates", Synthesis, vol. 5, pp. 661–666 (2000).
Kobayashi, S. et al., "A New Methodology for Combinatorial Synthesis. Preparation of Diverse Quinoline Derivates Using a Novel Polymer–Supported Scandium Catalyst", J. Am. Chem. Soc., vol. 118, pp. 8977–8978 (1996).

* cited by examiner

Primary Examiner—Charanjit S. Aulakh
(74) Attorney, Agent, or Firm—Scott K. Larsen; Jing S. Belfield

(57) ABSTRACT

This invention relates generally to tetracyclic tetrahydroquinoline compounds, and analogues thereof, and pharmaceutically acceptable salt forms thereof, which are selective inhibitors of serine protease enzymes, especially factor VIIa; pharmaceutical compositions containing the same; and methods of using the same as anticoagulant agents for modulation of the coagulation cascade.

37 Claims, No Drawings

TETRAHYDROQUINOLINE DERIVATIVES AS ANTITHROMBOTIC AGENTS

CROSS-REFERENCE TO RELATED APPLICATIONS

This application claims the priority benefit of U.S. Provisional Application No. 60/313,549, filed Aug. 20, 2001, which is expressly incorporated fully herein by reference.

FIELD OF THE INVENTION

This invention relates generally to tetracyclic tetrahydroquinoline compounds, and analogues thereof, and pharmaceutically acceptable salt forms thereof, which are selective inhibitors of serine protease enzymes, especially factor VIIa; pharmaceutical compositions containing the same; and methods of using the same as anticoagulant agents for modulation of the coagulation cascade.

BACKGROUND OF THE INVENTION

The present invention generally relates to compounds that inhibit thrombosis. In particular it is directed to compounds that are selective inhibitors of serine protease enzymes, for example thrombin, factor Xa, factor IXa, factor XIa and factor VIIa. In particular, it relates to compounds that are factor VIIa inhibitors.

Factor VIIa is a plasma serine protease involved in the initiation of blood coagulation. Alone, it processes its substrates factor IX and factor X slowly. In the presence of its cofactor, a membrane protein called tissue factor, proteolytic activity towards its substrates is greatly enhanced. Sufficient quantities of factor IXa and factor Xa are generated by the factor VIIa/tissue factor complex to initiate coagulation. Tissue factor is not normally exposed to factor VIIa in circulating blood, but is widely expressed extravascularly. Vascular rupture results in exposure of factor VIIa to tissue factor, formation of the factor VIIa/tissue factor complex, and initiation of coagulation. See Carson, S. D. and Brozna, J. P. (1993) Blood Coag. Fibrinol. 4:281–292.

The factor VIIa/tissue factor complex initiates blood coagulation by activating factor X to factor Xa, factor IX to factor IXa and additional factor VII to factor VIIa. Ultimately, the activity of factor VIIa induces the conversion of prothrombin to thrombin. Thrombin is a proteolytic enzyzme which occupies a central role in the coagulation process. It converts fibrinogen to fibrin, an essential structural component of the blood clot, and plays a key role in activating other coagulation proteins.

While blood coagulation is a necessary and important part of an organism's normal functioning (hemostasis), it can sometimes have deleterious effects. For instance, tissue factor exposed by rupture of an atherosclerotic plaque can initiate coagulation in a coronary artery, blocking circulation and inducing a heart attack.

Because of its role in initiate of blood coagulation, it is believed that inhibition of factor VIIa could be useful for treatment or prevention of disease states involving abnormal coagulation, including thrombosis, coronary artery disease, ischemic vascular disease, intravascular clotting, stroke, embolism, etc. Work has accordingly be performed to identify and optimize factor VIIa inhibitors. For example, U.S. Pat. No. 5,859,010 discusses factor VIIa/tissue factor inhibitors that are dihydroxamates having a spacing from 0.37 nm to about 0.77 nm; U.S. Pat. No. 5,843,442 reports monoclonal-type antibodies or antibody fragments possessing inhibitory activity; and, U.S. Pat. No. 5,023,236 presents peptides and peptide derivatives that specifically inhibit the proteolytic active site of serine protease coagulation factor VII/VIIa. WO 2000/35886 discloses bicyclic heterocyclic inhibitors of serine proteases including factor Xa, urokinase-type plasminogen activator, and factor VIIa.

While a number of factor VIIa inhibitors have been discussed in the art, improved inhibitors are always desirable, especially non-peptide inhibitors.

SUMMARY OF THE INVENTION

Accordingly, the present invention provides novel tetracyclic tetrahydroquinoline compounds, which are useful as selective inhibitors of serine protease enzymes, especially factor VIIa, or pharmaceutically acceptable salts or prodrugs thereof.

The present invention also provides pharmaceutical compositions comprising a pharmaceutically acceptable carrier and a therapeutically effective amount of at least one of the compounds of the present invention or a pharmaceutically acceptable salt or prodrug form thereof.

The present invention also provides a method for modulation of the coagulation cascade comprising administering to a host in need of such treatment a therapeutically effective amount of at least one of the compounds of the present invention or a pharmaceutically acceptable salt or prodrug form thereof.

The present invention also provides a method for treating thromboembolic disorders comprising administering to a host in need of such treatment a therapeutically effective amount of at least one of the compounds of the present invention or a pharmaceutically acceptable salt or prodrug form thereof.

The present invention also provides novel tetracyclic tetrahydroquinoline compounds for use in therapy.

The present invention also provides the use of novel tetracyclic tetrahydroquinoline compounds for the manufacture of a medicament for the treatment of a thromboembolic disorder.

These and other embodiments, which will become apparent during the following detailed description, have been achieved by the inventors' discovery that the presently claimed tetracyclic compounds, or pharmaceutically acceptable salt or prodrug forms thereof, are effective factor VIIa inhibitors.

DETAILED DESCRIPTION OF PREFERRED EMBODIMENTS

Thus, in a first embodiment, the present invention provides a novel compound of Formula (I):

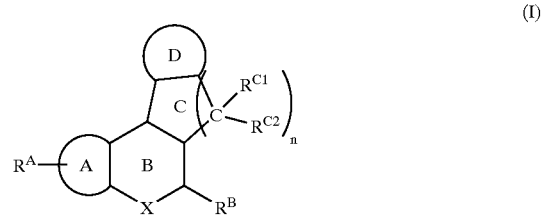

or a stereoisomer or pharmaceutically acceptable salt form thereof, wherein;

X is —NR$^x$—, —O—, —S—, —S(O)—, or —S(O)$_2$—;

R$^x$ is H, C$_{1-6}$ alkyl, C$_{2-6}$ alkenyl, C$_{2-6}$ alkynyl, C$_{3-6}$ cycloalkyl-, (C$_{3-6}$ cycloalkyl)C$_{1-3}$ alkyl-, (C$_{1-6}$ alkyl)C (=O)—, ($C_{3-6}$ cycloalkyl)C(=O)—, ($C_{3-6}$ cycloalkyl)$C_{1-3}$ alkyl-C(=O)—, phenyl-C(=O)—, benzyl-C(=O)—, ($C_{1-6}$ alkyl)—S(O)$_2$—, phenyl-S(O)$_2$—, benzyl-S(O)$_2$—, ($C_{1-6}$ alkyl)NHC(=O)—, ($C_{1-6}$ alkyl)$_2$NC(=O)—, phenyl-NHC(=O)—, benzyl-NHC(=O)—, (phenyl)($C_{1-6}$ alkyl)NC(=O)—, or (benzyl)($C_{1-6}$ alkyl)NC(=O)—;

ring A, including the two atoms of Ring B to which it is attached, is a phenyl ring; wherein, in addition to $R^A$, ring A is substituted with 0–3 $R^{AA}$;

alternatively, ring A, including the two atoms of Ring B to which it is attached, is a 5–6 membered aromatic system consisting of carbon atoms and 1 or 2 nitrogen atoms, and ring A, in addition to $R^A$, is substituted with 0–3 $R^{AA}$;

alternatively ring A and substituent $R^A$, including the two atoms of Ring B to which ring A is attached, is a 5–6 membered heterocyclic ring selected from:

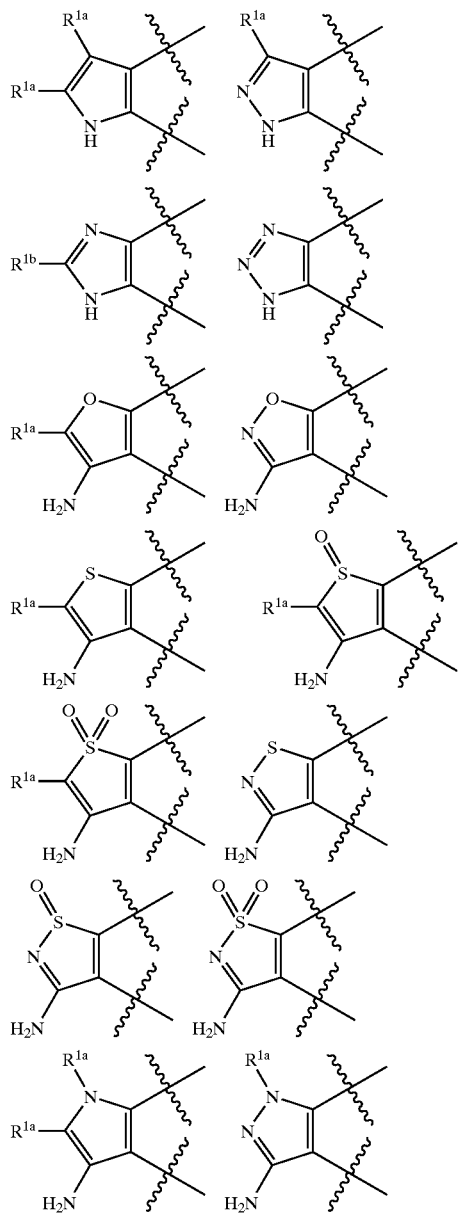

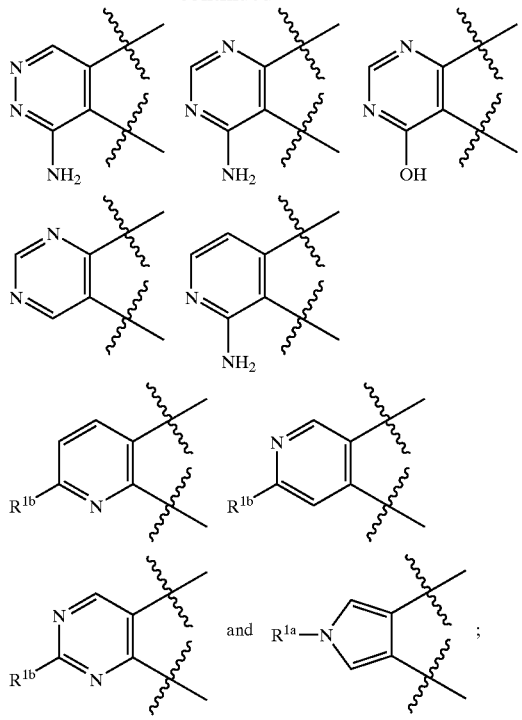

alternatively ring A and substituent $R^A$, including the two atoms of Ring B to which Ring A is attached, is a phenyl ring of formula:

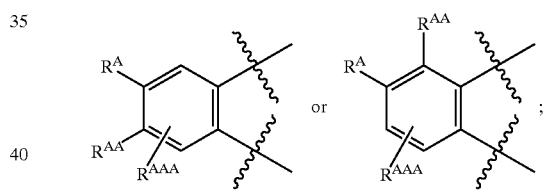

wherein $R^A$ is combined with $R^{AA}$ and two carbon atoms of Ring A to form a cyclic group selected from:

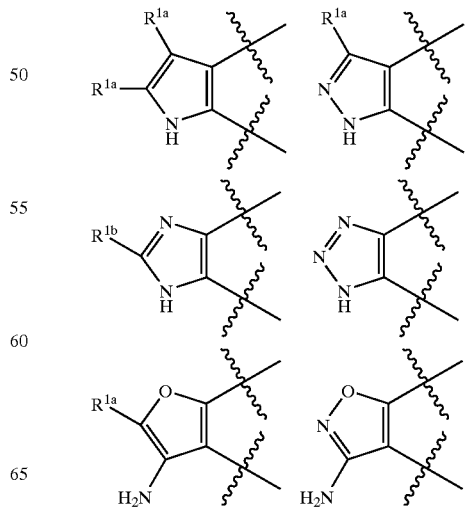

-continued

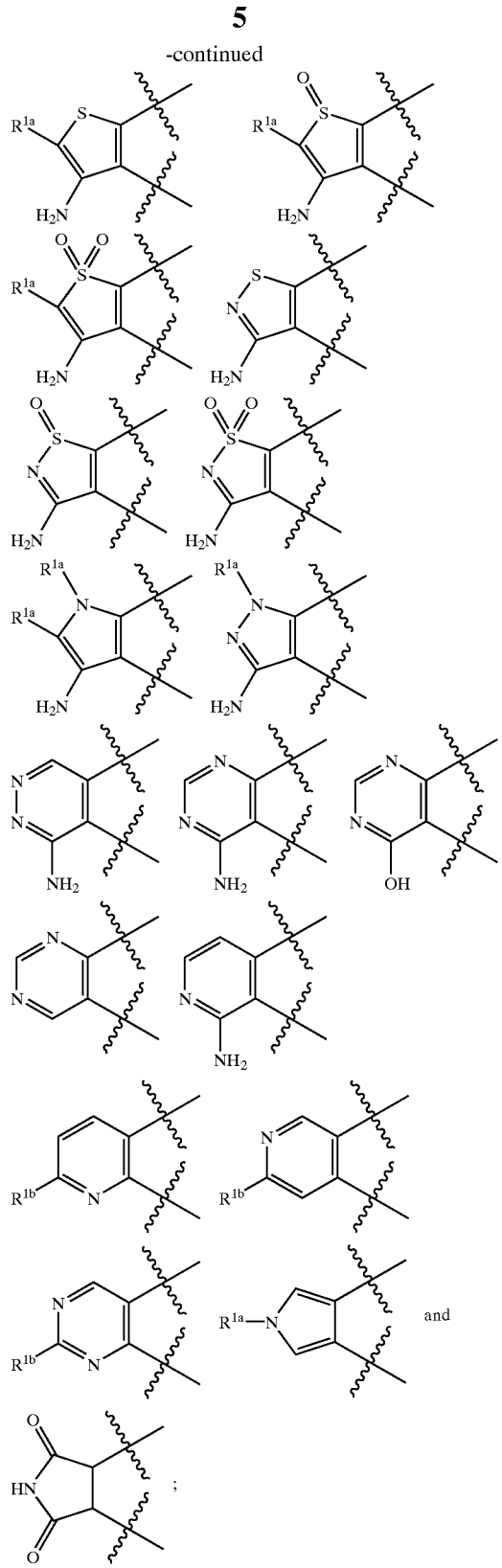

$R^A$ is selected from F, Cl, Br, OH, $OCH_3$, $OCH_2CH_3$, $OCH(CH_3)_2$, $-OCH_2CH_2CH_3$, $-OCF_3$, $-CN$, $-NH_2$, $-NH_2NH_3$, $C(=NR^1)NR^2R^3$, $-NHC(=NR^1)NR^2R^3$, $-NR^2CH(=NR^1)$, $-C(O)NR^2R^3$, $-S(O)_2NR^{2a}R^3$, $-NR^2R^3$, $-CH_2NR^2R^3$, $-CH_2CH_2NR^2R^3$, $-CH(CH_3)NR^2R^3$, $-CH_2CH_2CH_2NR^2R^3$, $-CH_2CH(CH_3)$ $NR^2R^3$, $-CH(CH_2CH_3)NR^2R^3$, $-CH(CH_3)CH_2NR^2R^3$, $-C(CH_3)_2NR^2R^3$, $-(C_{1-3}$ alkyl)$CO_2H$, $-O-(C_{1-3}$ alkyl)$CO_2H$, $-S-(C_{1-3}$ alkyl)$CO_2H$, and $-(C_{1-3}$ alkyl) $CH(NH_2)CO_2H$, $-C(O)NHCH_2CH_2NH(C_{1-3}$ alkyl), $-C(O)NHCH_2CH_2N(C_{1-3}$ alkyl)$_2$, $-CH_2NCOO(C_{1-4}$ alkyl),

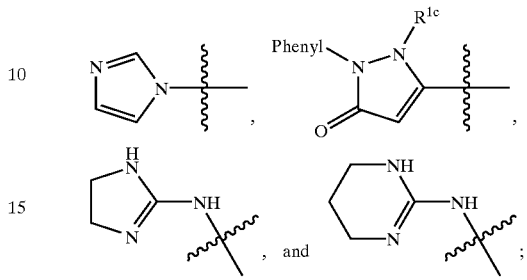

, and

;

$R^1$ is selected from H, OH, $-NH_2$, $C_{1-6}$ alkyl, $C_{1-6}$ alkoxy, phenyl$CH_2-$, and phenyl$CH_2CH_2-$;
$R^{1a}$, at each occurrence, is selected from H and $C_{1-4}$ alkyl;
$R^{1b}$ is selected from H, Cl, $C_{1-4}$ alkyl, $NH_2$, and $NHNH_2$;
$R^{1c}$ is selected from H and $C_{1-4}$ alkyl;
$R^2$, at each occurrence, is selected from:
H, OH, $C_{1-6}$ alkyl, $C_{1-6}$ alkylcarbonyl, $C_{1-4}$ alkoxycarbonyl, phenyl, phenyl($C_{1-3}$ alkyl)—, $C_{6-10}$ aryloxy, $C_{6-10}$ aryloxycarbonyl, $C_{6-10}$ arylmethylcarbonyl, ($C_{1-4}$ alkylcarbonyloxy)$C_{1-4}$ alkoxycarbonyl, ($C_{6-10}$ arylcarbonyloxy)$C_{1-4}$ alkoxycarbonyl, $C_{1-6}$ alkylaminocarbonyl, phenylaminocarbonyl, and (phenyl)$C_{1-4}$ alkoxycarbonyl;
$R^{2a}$, at each occurrence, is selected from H, $C_{1-6}$ alkyl, $-C(=NH)NH_2$, pyridinyl, pyrimidinyl, ($CH_3O$) pyrimidinyl, ($CH_3O)_2$pyrimidinyl, oxazolyl, ($CH_3$) oxazolyl, and ($CH_3)_2$oxazolyl;
$R^3$, at each occurrence, is selected from H, $C_{1-6}$ alkyl, phenyl$CH_2-$, and phenyl$CH_2CH_2-$;
$R^{AA}$ is, at each occurrence, selected from:
H, halo, $C_{1-4}$ alkyl, $C_{3-6}$ cycloalkyl-, $-OH$, $C_{1-4}$ alkoxy, ($C_{1-4}$ alkyl)$S-$, ($C_{1-4}$ alkyl)$S(O)-$, ($C_{1-4}$ alkyl)$SO_2-$, $-NH_2$, ($C_{1-4}$ alkyl)$_2N-$, ($C_{1-4}$ alkyl)$NH-$, $-CN$, $-NO_2$, ($C_{1-4}$ alkyl)$C(=O)-$, $HO_2C-$, ($C_{1-4}$ alkyl)$OC(=O)-$, $H_2NC(=O)-$, ($C_{1-4}$ alkyl)$NHC(=O)-$, ($C_{1-4}$ alkyl)$C(=O)NH-$, $C_{1-4}$ haloalkyl, and $C_{1-4}$ haloalkyloxy;
$R^{AAA}$ is H, halo, or methyl;
$R^B$ is a 5–10 membered ring system consisting of carbon atoms and 0, 1 or 2 heteroatoms selected from the group consisting of N, O, and S; wherein said ring system may be unsaturated, partially unsaturated or saturated; and $R^B$ is substituted with 0, 1, 2, 3, 4, or 5 substituents selected from $R^{b1}$, $R^{b2}$, $R^{b3}$, $R^{b4}$, and $R^{b5}$;
alternatively $R^B$ is $C_{1-4}$ alkyl substituted with 5–10 membered ring system consisting of carbon atoms and 0, 1 or 2 heteroatoms selected from the group consisting of N, O, and S; wherein said ring system may be unsaturated, partially unsaturated or saturated; and $R^B$ is substituted with 0, 1, 2, 3, 4, or 5 substituents selected from $R^{b1}$, $R^{b2}$, $R^{b3}$, $R^{b4}$, and $R^{b5}$;
$R^{b1}$, $R^{b2}$, $R^{b3}$, $R^{b4}$, and $R^{b5}$, at each occurrence, are independently selected from
H, F, Cl, Br, I, $=O$, $-CN$, $-NO_2$, $-OH$, $OR^{12}$, $SR^{12}$, $NR^{12}R^{13}$, $C(O)H$, $C(O)R^{12}$, $C(O)OR^{12}$, $C(O)NR^{12}R^{13}$, $OC(O)NR^{12}R^{13}$, $NR^{14}C(O)R^{12}$, $OC(O)R^{12}$, $CH(=NR^{14})NR^{12}R^{13}$, $NHC(=NR^{14})NR^{12}R^{13}$, $S(O)$ R$^{12}$, S(O)$_2$R$^{12}$, S(O)H, S(O)$_2$H, S(O)NR$^{12}$R$^{13}$, S(O)$_2$NR$^{12}$R$^{13}$, NR$^{14}$S(O)R$^{12}$, NR$^{14}$S(O)$_2$R$^{12}$, NR$^{12}$C(O)R$^{15}$, NR$^{12}$C(O)OR$^{15}$, NR$^{12}$S(O)$_2$R$^{15}$, NR$^{12}$C(O)NHR$^{15}$, (HO)$_2$B—, C$_{1-4}$ haloalkyl, C$_{1-4}$ alkoxy, C$_{2-4}$ alkenyloxy, C$_{2-4}$ alkynyloxy, (C$_{1-4}$ haloalkyl)oxy, C$_{1-4}$ alkyl substituted with 0–3 R$^{11}$, C$_{2-4}$ alkenyl substituted with 0–3 R$^{11}$, C$_{2-4}$ alkynyl substituted with 0–3 R$^{11}$, C$_{1-4}$ alkoxy substituted with 0–3 R$^{11}$, C$_{3-10}$ carbocyclic residue substituted with 0–3 R$^{31}$, aryl substituted with 0–5 R$^{31}$, and 5–10 membered heterocyclic ring system containing from 1–4 heteroatoms selected from the group consisting of N, O, and S substituted with 0–3 R$^{31}$;

alternatively, R$^{b1}$ and R$^{b2}$, when substituents on adjacent carbons, or R$^{b2}$ and R$^{b3}$, when substituents on adjacent carbons, may be combined to form a methylenedioxy group;

n is 1, 2, or 3;

R$^{C1}$, at each occurrence, is independently selected from

H, halo, —CN, —NO$_2$, OR$^{12}$, SR$^{12}$, NR$^{12}$R$^{13}$, C(O)H, C(O)R$^{12}$, C(O)NR$^{12}$R$^{13}$, OC(O)NR$^{12}$R$^{13}$, NR$^{14}$C(O)R$^{12}$, NR$^{14}$C(S)R$^{12}$, C(O)OR$^{12}$, OC(O)R$^{12}$, OC(O)OR$^{12}$, CH(=NR$^{14}$)NR$^{12}$R$^{13}$, NHC(=NR$^{14}$)NR$^{12}$R$^{13}$, S(O)R$^{12}$, S(O)$_2$R$^{12}$, S(O)NR$^{12}$R$^{13}$, S(O)$_2$NR$^{12}$R$^{13}$, NR$^{14}$S(O)R$^{12}$, NR$^{14}$S(O)$_2$R$^{12}$, NR$^{12}$C(O)R$^{15}$, NR$^{12}$C(S)R$^{15}$, NR$^{12}$C(O)OR$^{15}$, NR$^{12}$S(O)$_2$R$^{15}$, NR$^{12}$C(O)NHR$^{15}$, C$_{1-4}$ haloalkyl, (C$_{1-4}$ haloalkyl)oxy, C$_{1-10}$ alkyl substituted with 0–3 R$^{CC}$, C$_{2-10}$ alkenyl substituted with 0–3 R$^{CC}$, C$_{2-10}$ alkynyl substituted with 0–3 R$^{CC}$, C$_{1-10}$ alkoxy substituted with 0–3 R$^{CC}$, C$_{3-6}$ carbocyclic residue substituted with 0–3 R$^{CC}$, aryl substituted with 0–5 R$^{CC}$, and 5–6 membered heterocyclic ring system containing from 1–4 heteroatoms selected from the group consisting of N, O, and S substituted with 0–3 R$^{CC}$;

R$^{C2}$ is selected from H, C$_{1-4}$ alkyl, OH, CN, and C$_{1-4}$ alkoxy;

R$^{CC}$, at each occurrence, is independently selected from

H, halo, —CN, —NO$_2$, OR$^{12}$, SR$^{12}$, NR$^{12}$R$^{13}$, C(O)H, C(O)R$^{12}$, C(O)NR$^{12}$R$^{13}$, OC(O)NR$^{12}$R$^{13}$, NR$^{14}$C(O)R$^{12}$, NR$^{14}$C(S)R$^{12}$, C(S)NR$^{12}$R$^{13}$, C(O)OR$^{12}$, OC(O)R$^{12}$, OC(O)OR$^{12}$, CH(=NR$^{14}$)NR$^{12}$R$^{13}$, NHC(=NR$^{14}$)NR$^{12}$R$^{13}$, S(O)R$^{12}$, S(O)$_2$R$^{12}$, S(O)NR$^{12}$R$^{13}$, S(O)$_2$NR$^{12}$R$^{13}$, NR$^{14}$S(O)R$^{12}$, NR$^{14}$S(O)$_2$R$^{12}$NR$^{12}$C(O)R$^{15}$, NR$^{12}$C(S)R$^{15}$, NR$^{12}$C(O)OR$^{15}$, NR$^{12}$S(O)$_2$R$^{15}$, NR$^{12}$C(O)NHR$^{15}$, C$_{1-4}$ haloalkyl, (C$_{1-4}$ haloalkyl)oxy, C$_{1-4}$ alkyl substituted with 0–3 R$^{11}$, C$_{2-4}$ alkenyl substituted with 0–3 R$^{11}$, C$_{2-4}$ alkynyl substituted with 0–3 R$^{11}$, C$_{1-4}$ alkoxy substituted with 0–3 R$^{11}$, C$_{3-6}$ carbocyclic residue substituted with 0–3 R$^{31}$, aryl substituted with 0–5 R$^{31}$, and 5–6 membered heterocyclic ring system containing from 1–4 heteroatoms selected from the group consisting of N, O, and S substituted with 0–3 R$^{31}$;

ring D, including the two atoms of Ring C to which it is attached, is a 5–6 membered aromatic system consisting of carbon atoms and 0, 1 or 2 heteroatoms selected from the group consisting of N, O, and S; and ring D is substituted with 0–4 R$^D$;

R$^D$, at each occurrence, is independently selected from

H, halo, —CN, —NO$_2$, OR$^{16}$, SR$^{16}$, NR$^{16}$R$^{16}$, C(O)H, C(O)R$^{16}$, C(O)NR$^{16}$R$^{16}$, OC(O)NR$^{16}$R$^{16}$, NR$^{14}$C(O)R$^{16}$, C(O)OR$^{16}$, OC(O)R$^{16}$, OC(O)OR$^{16}$, CH(=NR$^{14}$)NR$^{16}$R$^{16}$, NHC(=NR$^{14}$)NR$^{16}$R$^{16}$, S(O)R$^{16}$, S(O)$_2$R$^{16}$, S(O)NR$^{16}$R$^{16}$, S(O)$_2$NR$^{16}$R$^{16}$, NR$^{14}$S(O)R$^{16}$, NR$^{14}$S(O)$_2$R$^{16}$, NR$^{16}$C(O)R$^{17}$, NR$^{16}$C(O)OR$^{17}$, NR$^{16}$S(O)$_2$R$^{17}$, NR$^{16}$C(O)NHR$^{17}$, C$_{1-4}$ haloalkyl, C$_{1-4}$ alkoxy, (C$_{1-4}$ haloalkyl)oxy, C$_{1-4}$ alkyl substituted with 0–3 R$^{31}$, C$_{2-4}$ alkenyl substituted with 0–3 R$^{31}$, and C$_{2-4}$ alkynyl substituted with 0–3 R$^{31}$;

R$^{11}$, at each occurrence, is independently selected from

H, halo, —CN, —NO$_2$, OR$^{12}$, SR$^{12}$, NR$^{12}$R$^{13}$, C(O)H, C(O)R$^{12}$, C(O)NR$^{12}$R$^{13}$, OC(O)NR$^{12}$R$^{13}$, NR$^{14}$C(O)R$^{12}$, C(O)OR$^{12}$, OC(O)R$^{12}$, OC(O)OR$^{12}$, CH((=NR$^{14}$)NR$^{12}$R$^{13}$, NHC((=NR$^{14}$)NR$^{12}$R$^{13}$, S(O)R$^{12}$, S(O)$_2$R$^{12}$, S(O)NR$^{12}$R$^{13}$, S(O)$_2$NR$^{12}$R$^{13}$, NR$^{14}$S(O)R$^{12}$, NR$^{14}$S(O)$_2$R$^{12}$, NR$^{12}$C(O)R$^{15}$, NR$^{12}$C(O)OR$^{15}$, NR$^{12}$S(O)$_2$R$^{15}$, NR$^{12}$C(O)NHR$^{15}$, C$_{1-4}$ haloalkyl, C$_{1-4}$ alkoxy, C$_{2-4}$ alkenyloxy, C$_{2-4}$ alkynyloxy, (C$_{1-4}$ haloalkyl)oxy, C$_{1-4}$ alkyl substituted with 0–3 R$^{12a}$, C$_{2-4}$ alkenyl substituted with 0–3 R$^{12a}$, C$_{3-6}$ carbocyclic residue substituted with 0–3 R$^{31}$, aryl substituted with 0–5 R$^{31}$, and 5–6 membered heterocyclic ring system containing from 1–4 heteroatoms selected from the group consisting of N, O, and S substituted with 0–3 R$^{31}$;

R$^{12}$, at each occurrence, is independently selected from H,

C$_{1-4}$ alkyl substituted with 0–1 R$^{12a}$, C$_{2-4}$ alkenyl substituted with 0–1 R$^{12a}$, C$_{2-4}$ alkynyl substituted with 0–1 R$^{12a}$, C$_{3-6}$ cycloalkyl substituted with 0–3 R$^{31}$, aryl substituted with 0–5 R$^{31}$;

C$_{3-10}$ carbocyclic residue substituted with 0–3 R$^{31}$, and

5–10 membered heterocyclic ring system containing from 1–4 heteroatoms selected from the group consisting of N, O, and S substituted with 0–3 R$^{31}$;

R$^{12a}$, at each occurrence, is independently selected from phenyl substituted with 0–5 R$^{31}$;

C$_{3-6}$ carbocyclic residue substituted with 0–3 R$^{31}$, and

5–6 membered heterocyclic ring system containing from 1–4 heteroatoms selected from the group consisting of N, O, and S substituted with 0–3 R$^{31}$;

R$^{13}$, at each occurrence, is independently selected from

H, C$_{1-4}$ alkyl, C$_{2-4}$ alkenyl, and C$_{2-4}$ alkynyl;

alternatively, R$^{12}$ and R$^{13}$ may be combined, along with the nitrogen to which they are attached, to form a 5- or 6-membered ring optionally substituted with —O— or —N(R$^{14}$)—;

R$^{14}$, at each occurrence, is independently selected from H and C$_{1-4}$ alkyl;

R$^{15}$, at each occurrence, is independently selected from

H, C$_{1-4}$ alkyl, C$_{2-4}$ alkenyl, and C$_{2-4}$ alkynyl;

R$^{16}$, at each occurrence, is independently selected from

H, C$_{1-4}$ alkyl, C$_{2-4}$ alkenyl, C$_{2-4}$ alkynyl, and phenyl;

R$^{17}$, at each occurrence, is independently selected from

H, C$_{1-4}$ alkyl, C$_{2-4}$ alkenyl, and C$_{2-4}$ alkynyl;

R$^{31}$, at each occurrence, is independently selected from

H, F, Cl, Br, I, =O, —CN, —NO$_2$, OR$^{32}$, SR$^{32}$, NR$^{32}$R$^{33}$, C(O)H, C(O)R$^{32}$, C(O)OH, C(O)OR$^{32}$, C(O)NR$^{32}$R$^{33}$, OC(O)NR$^{32}$R$^{33}$, NR$^{34}$C(O)R$^{32}$, OC(O)R$^{32}$, CH(=NR$^{34}$)NR$^{32}$R$^{33}$, NHC(=NR$^{34}$)NR$^{32}$R$^{33}$, S(O)R$^{32}$, S(O)$_2$R$^{32}$, S(O)H, S(O)$_2$H, S(O)$_3$H, S(O)NR$^{32}$R$^{33}$, S(O)$_2$NR$^{32}$R$^{33}$, NR$^{34}$S(O)R$^{32}$, NR$^{34}$S(O)$_2$R$^{32}$, NR$^{32}$C(O)R$^{35}$, NR$^{32}$C(O)OR$^{35}$, NR$^{32}$S(O)$_2$R$^{35}$, NR$^{32}$C(O)NHR$^{35}$, tetrazole, C$_{1-4}$ haloalkyl, C$_{1-4}$ alkoxy, C$_{2-4}$ alkenyloxy, C$_{2-4}$ alkynyloxy, (C$_{1-4}$ haloalkyl)oxy, C$_{1-4}$ alkyl, C$_{2-4}$ alkenyl, and C$_{2-4}$ alkynyl; and R$^{32}$, R$^{33}$, R$^{34}$, R$^{35}$, at each occurrence, are independently selected from H, C$_{1-4}$ alkyl, C$_{2-4}$ alkenyl, C$_{2-4}$ alkynyl, and benzyl;

provided when X is —O— and $R^B$ is phenyl, then $R^A$ is not methoxy; and provided when X is —NH— and $R^B$ is phenyl, then $R^A$ is not chloro or methoxy.

In a preferred embodiment, the present invention provides a novel compound of Formula (I) wherein X is —NH—, —O—, —S—, —S(O)—, or —S(O)$_2$—.

In a preferred embodiment, the present invention provides a novel compound of Formula (I) wherein X is —NH—.

In a preferred embodiment, the present invention provides a novel compound of Formula (I) wherein
X is —NH—;
n is 1, 2, or 3;
$R^{C1}$ is H, methyl, ethyl, propyl, or butyl; and
$R^{C2}$ is H or methyl.

In a preferred embodiment, the present invention provides a novel compound of Formula (I) wherein
X is —NH—; and
$R^B$ is:

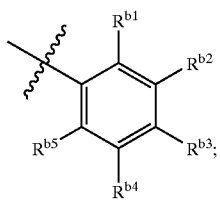

or a stereoisomer or pharmaceutically acceptable salt form thereof.

In a preferred embodiment, the present invention provides a novel compound of Formula (Ia):

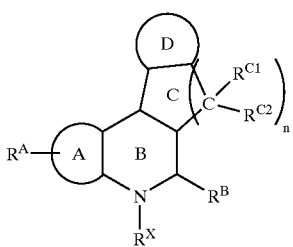

(Ia)

or a stereoisomer or pharmaceutically acceptable salt form thereof, wherein;

$R^X$ is H, $C_{1-6}$ alkyl, $C_{2-6}$ alkenyl, $C_{2-6}$ alkynyl,
  $C_{3-6}$ cycloalkyl-, ($C_{3-6}$ cycloalkyl)$C_{1-3}$ alkyl-, ($C_{1-6}$ alkyl)C(=O)—, ($C_{3-6}$ cycloalkyl)C(=O)—, ($C_{3-6}$ cycloalkyl)$C_{1-3}$ alkyl-C(=O)—, phenyl-C(=O)—, benzyl-C(=O)—, ($C_{1-6}$ alkyl)-S(O)$_2$—, phenyl-S(O)$_2$—, benzyl-S(O)$_2$—, ($C_{1-6}$ alkyl)NHC(=O)—, ($C_{1-6}$ alkyl)$_2$NC(=O)—, phenyl—NHC(=O)—, benzyl—NHC(=O)—, (phenyl)($C_{1-6}$ alkyl)NC(=O)—, or (benzyl)($C_{1-6}$ alkyl)NC(=O)—;

ring A, including the two atoms of Ring B to which it is attached, is a phenyl ring; wherein, in addition to $R^A$, ring A is substituted with 0–3 $R^{AA}$;

alternatively, ring A, including the two atoms of Ring B to which it is attached, is a 5–6 membered aromatic system consisting of carbon atoms and 1 or 2 nitrogen atoms, and ring A, in addition to $R^A$, is substituted with 0–3 $R^{AA}$;

alternatively ring A and substituent $R^A$, including the two atoms of Ring B to which Ring A is attached, is a 5–6 membered heterocyclic ring selected from:

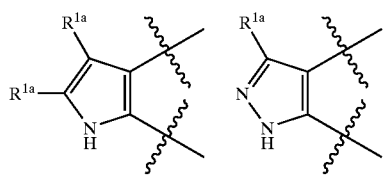

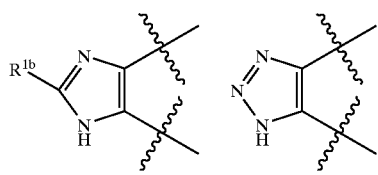

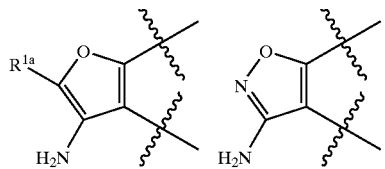

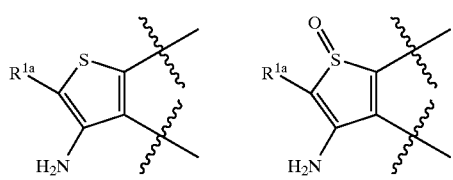

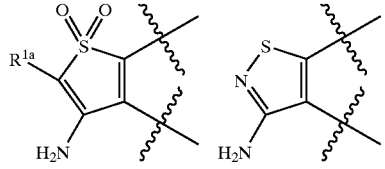

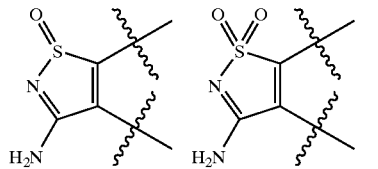

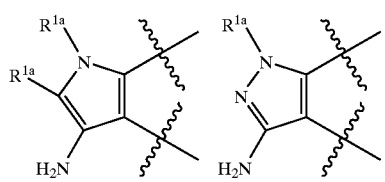

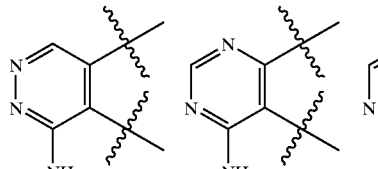

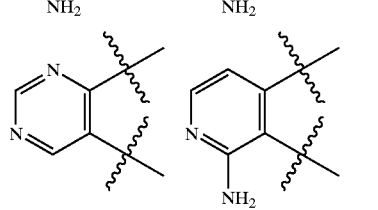

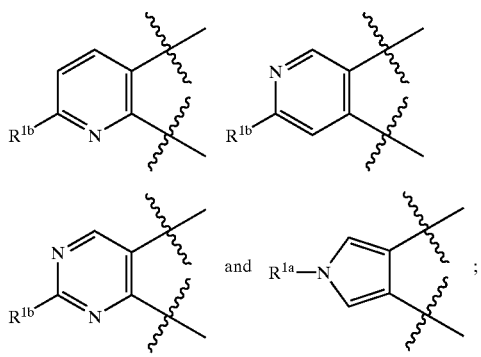

alternatively ring A and substituent $R^A$, including the two atoms of Ring B to which Ring A is attached, is a phenyl ring of formula:

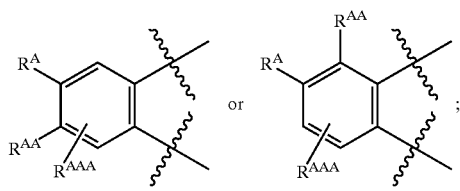

wherein $R^A$ is combined with $R^{AA}$ and two carbon atoms of Ring A to form a cyclic group selected from:

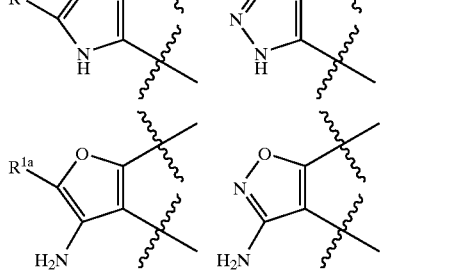

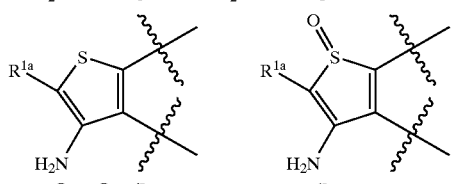

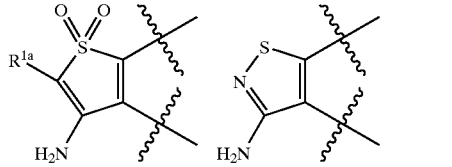

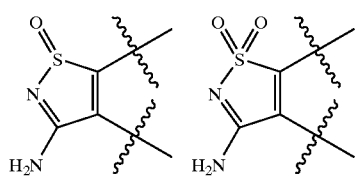

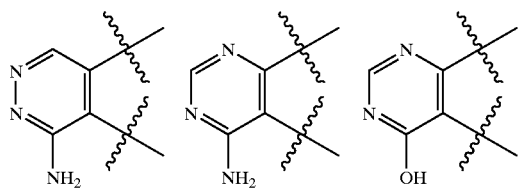

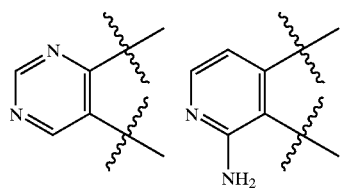

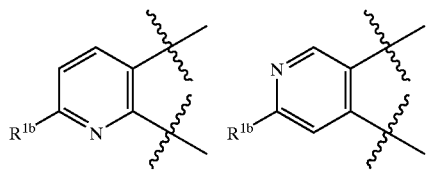

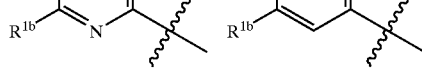

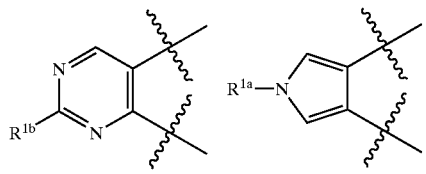

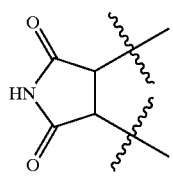

$R^A$ is selected from F, Cl, Br, OH, $OCH_3$, $OCH_2CH_3$, $OCH(CH_3)_2$,

—$OCH_2CH_2CH_3$, —$OCF_3$, —CN, —$NH_2$, —$NH_2NH_3$, $C(=NR^1)NR^2R^3$, —$NHC(=NR^1)NR^2R^3$, —$NR^2CH(=NR^1)$, —$C(O)NR^2R^3$, —$S(O)_2NR^{2a}R^3$, —$NR^2R^3$, —$CH_2NR^2R^3$, —$CH_2CH_2NR^2R^3$, —$CH(CH_3)NR^2R^3$, —$CH_2CH_2CH_2NR^2R^3$, —$CH_2CH(CH_3)NR^2R^3$, —$CH(CH_2CH_3)NR^2R^3$, —$CH(CH_3)CH_2NR^2R^3$, —$C(CH_3)_2NR^2R^3$, —($C_{1-3}$ alkyl)$CO_2H$, —O—($C_{1-3}$ alkyl)$CO_2H$, —S—($C_{1-3}$ alkyl)$CO_2H$, and —($C_{1-3}$ alkyl)$CH(NH_2)CO_2H$, —$C(O)NHCH_2CH_2NH(C_{1-3}$ alkyl), —$C(O)NHCH_2CH_2N(C_{1-3}$ alkyl)$_2$, —$CH_2NCOO(C_{1-4}$ alkyl),

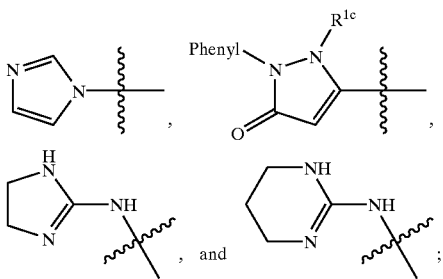

R¹ is selected from H, OH, —NH₂, C₁₋₆ alkyl, C₁₋₆ alkoxy, phenylCH₂—, and phenylCH₂CH₂—;

R$^{1a}$, at each occurrence, is selected from H and C₁₋₄ alkyl;

R$^{1b}$ is selected from H, Cl, C₁₋₄ alkyl, NH₂, and NHNH₂;

R$^{1c}$ is selected from H and C₁₋₄ alkyl;

R², at each occurrence, is selected from:
H, OH, C₁₋₆ alkyl, C₁₋₆ alkylcarbonyl, C₁₋₄ alkoxycarbonyl, phenyl, phenyl(C₁₋₃ alkyl)—, C₆₋₁₀ aryloxy, C₆₋₁₀ aryloxycarbonyl, C₆₋₁₀ arylmethylcarbonyl, (C₁₋₄ alkylcarbonyloxy)C₁₋₄ alkoxycarbonyl, (C₆₋₁₀ arylcarbonyloxy)C₁₋₄ alkoxycarbonyl, C₁₋₆ alkylaminocarbonyl, phenylaminocarbonyl, and (phenyl)C₁₋₄ alkoxycarbonyl;

R$^{2a}$, at each occurrence, is selected from H, C₁₋₆ alkyl, —C(═NH)NH₂, pyridinyl, pyrimidinyl, (CH₃O)pyrimidinyl, (CH₃O)₂pyrimidinyl, oxazolyl, (CH₃)oxazolyl, and (CH₃)₂oxazolyl;

R³, at each occurrence, is selected from H, C₁₋₆ alkyl, phenylCH₂—, and phenylCH₂CH₂—;

R$^{AA}$ is, at each occurrence, selected from:
H, halo, C₁₋₄ alkyl, C₃₋₆ cycloalkyl-, —OH, C₁₋₄ alkoxy, (C₁₋₄ alkyl)S—, (C₁₋₄ alkyl)S(O)—, (C₁₋₄ alkyl)SO₂—, —NH₂, (C₁₋₄ alkyl)₂N—, (C₁₋₄ alkyl)NH—, —CN, —NO₂, (C₁₋₄ alkyl)C(═O)—, HO₂C—, (C₁₋₄ alkyl)OC(═O)—, H₂NC(═O)—, (C₁₋₄ alkyl)NHC(═O)—, (C₁₋₄ alkyl)C(═O)NH—, C₁₋₄ haloalkyl, and C₁₋₄ haloalkyloxy;

R$^{AAA}$ is H, halo, or methyl;

R$^B$ is a 5–10 membered ring system consisting of carbon atoms and 0, 1 or 2 heteroatoms selected from the group consisting of N, O, and S; wherein said ring system may be unsaturated, partially unsaturated or saturated; and R$^B$ is substituted with 0, 1, 2, 3, 4, or 5 substituents selected from R$^{b1}$, R$^{b2}$, R$^{b3}$, R$^{b4}$, and R$^{b5}$;

alternatively R$^B$ is C₁₋₄ alkyl substituted with 5–10 membered ring system consisting of carbon atoms and 0, 1 or 2 heteroatoms selected from the group consisting of N, O, and S; wherein said ring system may be unsaturated, partially unsaturated or saturated; and R$^B$ is substituted with 0, 1, 2, 3, 4, or 5 substituents selected from R$^{b1}$, R$^{b2}$, R$^{b3}$, R$^{b4}$, and R$^{b5}$;

R$^{b1}$, R$^{b2}$, R$^{b3}$, R$^{b4}$, and R$^{b5}$, at each occurrence, are independently selected from
H, F, Cl, Br, I, ═O, —CN, —NO₂, —OH, OR¹², SR¹², NR¹²R¹³, C(O)H, C(O)R¹², C(O)OR¹², C(O)NR¹²R¹³, OC(O)NR¹²R¹³, NR¹⁴C(O)R¹², OC(O)R¹², CH(═NR¹⁴)NR¹²R¹³, NHC(═NR¹⁴)NR¹²R¹³, S(O)R¹², S(O)₂R¹², S(O)H, S(O)₂H, S(O)NR¹²R¹³, S(O)₂NR¹²R¹³, NR¹⁴S(O)R¹², NR¹⁴S(O)₂R¹², NR¹²C(O)R¹⁵, NR¹²C(O)OR¹⁵, NR¹²S(O)₂R¹⁵, NR¹²C(O)NHR¹⁵, (HO)₂B—, C₁₋₄ haloalkyl, C₁₋₄ alkoxy, C₂₋₄ alkenyloxy, C₂₋₄ alkynyloxy, (C₁₋₄ haloalkyl)oxy,
C₁₋₄ alkyl substituted with 0–3 R¹¹, C₂₋₄ alkenyl substituted with 0–3 R¹¹, C₂₋₄ alkynyl substituted with 0–3 R¹¹, C₁₋₄ alkoxy substituted with 0–3 R¹¹, C₃₋₁₀ carbocyclic residue substituted with 0–3 R³¹, aryl substituted with 0–5 R³¹, and
5–10 membered heterocyclic ring system containing from 1–4 heteroatoms selected from the group consisting of N, O, and S substituted with 0–3 R³¹;

alternatively, R$^{b1}$ and R$^{b2}$, when substituents on adjacent carbons, or R$^{b2}$ and R$^{b3}$, when substituents on adjacent carbons, may be combined to form a methylenedioxy group;

n is 1, 2, or 3;

R$^{C1}$ is H, methyl, ethyl, propyl, or butyl;

R$^{C2}$ is H or methyl;

ring D, including the two atoms of Ring C to which it is attached, is a 5–6 membered aromatic system consisting of carbon atoms and 0, 1 or 2 heteroatoms selected from the group consisting of N, O, and S; and ring D is substituted with 0–4 R$^D$;

R$^D$, at each occurrence, is independently selected from
H, halo, —CN, —NO₂, OR¹⁶, SR¹⁶, NR¹⁶R¹⁶, C(O)H, C(O)R¹⁶, C(O)NR¹⁶R¹⁶, OC(O)NR¹⁶R¹⁶, NR¹⁴C(O)R¹⁶, C(O)OR¹⁶, OC(O)R¹⁶, OC(O)OR¹⁶, CH(═NR¹⁴)NR¹⁶R¹⁶, NHC(═NR¹⁴)NR¹⁶R¹⁶, S(O)R¹⁶, S(O)₂R¹⁶, S(O)NR¹⁶R¹⁶, S(O)₂NR¹⁶R¹⁶, NR¹⁴S(O)R¹⁶, NR¹⁴S(O)₂R¹⁶, NR¹⁶C(O)R¹⁷, NR¹⁶C(O)OR¹⁷, NR¹⁶S(O)₂R¹⁷, NR¹⁶C(O)NHR¹⁷, C₁₋₄ haloalkyl, C₁₋₄ alkoxy, (C₁₋₄ haloalkyl)oxy,
C₁₋₄ alkyl substituted with 0–3 R³¹, C₂₋₄ alkenyl substituted with 0–3 R³¹, and C₂₋₄ alkynyl substituted with 0–3 R³¹;

R¹¹, at each occurrence, is independently selected from
H, halo, —CN, —NO₂, OR¹², SR¹², NR¹²R¹³, C(O)H, C(O)R¹², C(O)NR¹²R¹³, OC(O)NR¹²R¹³, NR¹⁴C(O)R¹², C(O)OR¹², OC(O)R¹², OC(O)OR¹², CH(═NR¹⁴)NR¹²R¹³, NHC(═NR¹⁴)NR¹²R¹³, S(O)R¹², S(O)₂R¹², S(O)NR¹²R¹³, S(O)₂NR¹²R¹³, NR¹⁴S(O)R¹², NR¹⁴S(O)₂R¹², NR¹²C(O)R¹⁵, NR¹²C(O)OR¹⁵, NR¹²S(O)₂R¹⁵, NR¹²C(O)NHR¹⁵, C₁₋₄ haloalkyl, C₁₋₄ alkoxy, C₂₋₄ alkenyloxy, C₂₋₄ alkynyloxy, (C₁₋₄ haloalkyl)oxy,
C₁₋₄ alkyl substituted with 0–3 R$^{12a}$, C₂₋₄ alkenyl substituted with 0–3 R$^{12a}$, C₃₋₆ carbocyclic residue substituted with 0–3 R³¹, aryl substituted with 0–5 R³¹, and
5–6 membered heterocyclic ring system containing from 1–4 heteroatoms selected from the group consisting of N, O, and S substituted with 0–3 R³¹;

R¹², at each occurrence, is independently selected from H, C₁₋₄ alkyl substituted with 0–1 R$^{12a}$, C₂₋₄ alkenyl substituted with 0–1 R$^{12a}$, C₂₋₄ alkynyl substituted with 0–1 R$^{12a}$, C₃₋₆ cycloalkyl substituted with 0–3 R³¹, aryl substituted with 0–5 R³¹, C₃₋₁₀ carbocyclic residue substituted with 0–3 R³¹, and
5–10 membered heterocyclic ring system containing from 1–4 heteroatoms selected from the group consisting of N, O, and S substituted with 0–3 R³¹;

R$^{12a}$, at each occurrence, is independently selected from phenyl substituted with 0–5 R³¹;
C₃₋₆ carbocyclic residue substituted with 0–3 R³¹, and
5–6 membered heterocyclic ring system containing from 1–4 heteroatoms selected from the group consisting of N, O, and S substituted with 0–3 R³¹;

R¹³, at each occurrence, is independently selected from
H, C₁₋₄ alkyl, C₂₋₄ alkenyl, and C₂₋₄ alkynyl;

alternatively, R¹² and R¹³ may be combined, along with the nitrogen to which they are attached, to form a 5- or 6-membered ring optionally substituted with —O— or —N(R¹⁴)—;

$R^{14}$, at each occurrence, is independently selected from H and $C_{1-4}$ alkyl;

$R^{15}$, at each occurrence, is independently selected from H, $C_{1-4}$ alkyl, $C_{2-4}$ alkenyl, and $C_{2-4}$ alkynyl;

$R^{16}$, at each occurrence, is independently selected from H, $C_{1-4}$ alkyl, $C_{2-4}$ alkenyl, $C_{2-4}$ alkynyl, and phenyl;

$R^{17}$, at each occurrence, is independently selected from H, $C_{1-4}$ alkyl, $C_{2-4}$ alkenyl, and $C_{2-4}$ alkynyl;

$R^{31}$, at each occurrence, is independently selected from H, F, Cl, Br, I, =O, —CN, —NO$_2$, OR$^{32}$, SR$^{32}$, NR$^{32}$R$^{33}$, C(O)H, C(O)R$^{32}$, C(O)OH, C(O)OR$^{32}$, C(O)NR$^{32}$R$^{33}$, OC(O)NR$^{32}$R$^{33}$, NR$^{34}$C(O)R$^{32}$, OC(O)R$^{32}$, CH(=NR$^{34}$)NR$^{32}$R$^{33}$, NHC(=NR$^{34}$)NR$^{32}$R$^{33}$, S(O)R$^{32}$, S(O)$_2$R$^{32}$, S(O)H, S(O)$_2$H, S(O)$_3$H, S(O)NR$^{32}$R$^{33}$, S(O)$_2$NR$^{32}$R$^{33}$, NR$^{34}$S(O)R$^{32}$, NR$^{34}$S(O)$_2$R$^{32}$, NR$^{32}$C(O)R$^{35}$, NR$^{32}$C(O)OR$^{35}$, NR$^{32}$S(O)$_2$R$^{35}$, NR$^{32}$C(O)NHR$^{35}$, tetrazole, $C_{1-4}$ haloalkyl, $C_{1-4}$ alkoxy, $C_{2-4}$ alkenyloxy, $C_{2-4}$ alkynyloxy, ($C_{1-4}$ haloalkyl)oxy, $C_{1-4}$ alkyl, $C_{2-4}$ alkenyl, and $C_{2-4}$ alkynyl;

$R^{32}$, $R^{33}$, $R^{34}$, $R^{35}$, at each occurrence, are independently selected from H, $C_{1-4}$ alkyl, $C_{2-4}$ alkenyl, $C_{2-4}$ alkynyl, and benzyl.

In a more preferred embodiment, the present invention provides a novel compound of Formula (Ib):

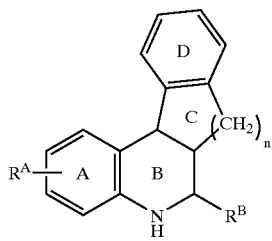

(Ib)

or a stereoisomer or pharmaceutically acceptable salt form thereof, wherein;

ring A, including the two atoms of Ring B to which it is attached, is a phenyl ring; wherein, in addition to $R^A$, ring A is substituted with 0–1 $R^{AA}$;

alternatively ring A and substituent $R^A$, including the two atoms of Ring B to which Ring A is attached, is a phenyl ring of formula:

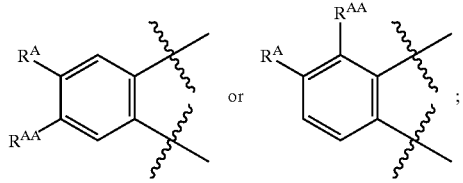

wherein $R^A$ is combined with $R^{AA}$ and two carbon atoms of Ring A to form a cyclic group selected from:

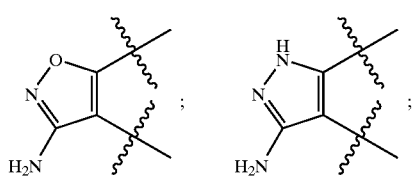

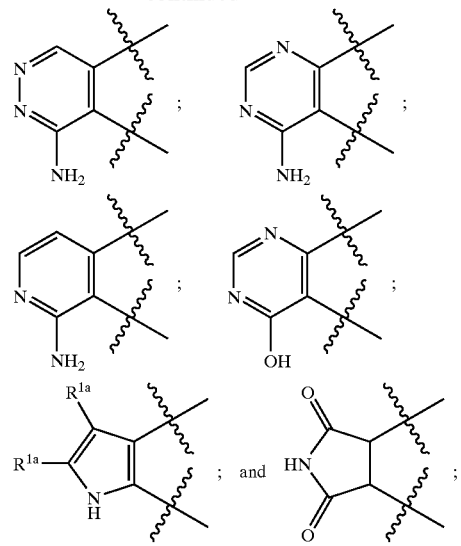

$R^A$ is selected from Cl, OCH$_3$, C(=NH)NH$_2$, C(O)NH$_2$, S(O)$_2$NH$_2$, —NH$_2$, —NH$_2$NH$_3$, —CH$_2$NH$_2$, —NR$^2$R$^3$, —CH$_2$NR$^2$R$^3$, and —CH(CH$_3$)NR$^2$R$^3$;

$R^{1a}$, at each occurrence, is selected from H and $C_{1-4}$ alkyl;

$R^2$ is selected from H and $C_{1-4}$ alkyl;

$R^3$ is selected from H and $C_{1-4}$ alkyl;

$R^{AA}$ is H, F, Cl, methoxy, —NH$_2$, and —CH$_2$NH$_2$;

$R^B$ is a 5–10 membered ring system consisting of carbon atoms and 0, 1 or 2 heteroatoms selected from the group consisting of N, O, and S; wherein said ring system may be unsaturated, partially unsaturated or saturated; and $R^B$ is substituted with 0, 1, 2, 3, 4, or 5 substituents selected from $R^{b1}$, $R^{b2}$, $R^{b3}$, $R^{b4}$, and $R^{b5}$;

alternatively $R^B$ is $C_{1-4}$ alkyl substituted with 5–10 membered ring system consisting of carbon atoms and 0, 1 or 2 heteroatoms selected from the group consisting of N, O, and S; wherein said ring system may be unsaturated, partially unsaturated or saturated; and $R^B$ is substituted with 0, 1, 2, 3, 4, or 5 substituents selected from $R^{b1}$, $R^{b2}$, $R^{b3}$, $R^{b4}$, and $R^{b5}$;

$R^{b1}$, $R^{b2}$, $R^{b3}$, $R^{b4}$, and $R^{b5}$, at each occurrence, are independently selected from H, F, Cl, Br, I, =O, —CN, —NO$_2$, —OH, OR$^{12}$, SR$^{12}$, NR$^{12}$R$^{13}$, C(O)H, C(O)R$^{12}$, C(O)OR$^{12}$, C(O)NR$^{12}$R$^{13}$, OC(O)NR$^{12}$R$^{13}$, NR$^{14}$C(O)R$^{12}$, OC(O)R$^{12}$, CH(=NR$^{14}$)NR$^{12}$R$^{13}$, NHC(=NR$^{14}$)NR$^{12}$R$^{13}$, S(O)R$^{12}$, S(O)$_2$R$^{12}$, S(O)H, S(O)$_2$H, S(O)NR$^{12}$R$^{13}$, S(O)$_2$NR$^{12}$R$^{13}$, NR$^{14}$S(O)R$^{12}$, NR$^{14}$S(O)$_2$R$^{12}$, NR$^{12}$C(O)R$^{15}$, NR$^{12}$C(O)OR$^{15}$, NR$^{12}$S(O)$_2$R$^{15}$, NR$^{12}$C(O)NHR$^{15}$, (HO)$_2$B—, $C_{1-4}$ haloalkyl, $C_{1-4}$ alkoxy, $C_{2-4}$ alkenyloxy, $C_{2-4}$ alkynyloxy, ($C_{1-4}$ haloalkyl)oxy, $C_{1-4}$ alkyl substituted with 0–3 $R^{11}$, $C_{2-4}$ alkenyl substituted with 0–3 $R^{11}$, $C_{2-4}$ alkynyl substituted with 0–3 $R^{11}$, $C_{1-4}$ alkoxy substituted with 0–3 $R^{11}$, $C_{3-10}$ carbocyclic residue substituted with 0–3 $R^{31}$, aryl substituted with 0–5 $R^{31}$, and 5–10 membered heterocyclic ring system containing from 1–4 heteroatoms selected from the group consisting of N, O, and S substituted with 0–3 $R^{31}$;

alternatively, $R^{b1}$ and $R^{b2}$, when substituents on adjacent carbons, or $R^{b2}$ and $R^{b3}$, when substituents on adjacent carbons, may be combined to form a methylenedioxy group;

n is 1, 2, or 3;

$R^{C1}$ is H, methyl ethyl, propyl, or butyl;

$R^{C2}$ is H or methyl;

ring D, including the two atoms of Ring C to which it is attached, is a phenyl ring; and ring D is substituted with 0–2 $R^D$;

$R^D$, at each occurrence, is independently selected from

H, halo, —CN, —NO$_2$, OR$^{16}$, SR$^{16}$, NR$^{16}$R$^{16}$, C(O)H, C(O)R$^{16}$, C(O)NR$^{16}$R$^{16}$, OC(O)NR$^{16}$R$^{16}$, NR$^{14}$C(O)R$^{16}$, C(O)OR$^{16}$, OC(O)R$^{16}$, OC(O)OR$^{16}$, CH(=NR$^{14}$)NR$^{16}$R$^{16}$, NHC(=NR$^{14}$)NR$^{16}$R$^{16}$, S(O)R$^{16}$, S(O)$_2$R$^{16}$, S(O)NR$^{16}$R$^{16}$, S(O)$_2$NR$^{16}$R$^{16}$, NR$^{14}$S(O)R$^{16}$, NR$^{14}$S(O)$_2$R$^{16}$, NR$^{16}$C(O)R$^{17}$, NR$^{16}$C(O)OR$^{17}$, NR$^{16}$S(O)$_2$R$^{17}$, NR$^{16}$C(O)NHR$^{17}$, C$_{1-3}$ haloalkyl, (C$_{1-2}$ haloalkyl)oxy, C$_{1-4}$ alkoxy, and C$_{1-4}$ alkyl;

$R^{11}$, at each occurrence, is independently selected from

H, halo, —CN, —NO$_2$, OR$^{12}$, SR$^{12}$, NR$^{12}$R$^{13}$, C(O)H, C(O)R$^{12}$, C(O)NR$^{12}$R$^{13}$, OC(O)NR$^{12}$R$^{13}$, NR$^{14}$C(O)R$^{12}$, C(O)OR$^{12}$, OC(O)R$^{12}$, OC(O)OR$^{12}$, CH(=NR$^{14}$)NR$^{12}$R$^{13}$, NHC(=NR$^{14}$)NR$^{12}$R$^{13}$, S(O)R$^{12}$, S(O)$_2$R$^{12}$, S(O)NR$^{12}$R$^{13}$, S(O)$_2$NR$^{12}$R$^{13}$, NR$^{14}$S(O)R$^{12}$, NR$^{14}$S(O)$_2$R$^{12}$, NR$^{12}$C(O)R$^{15}$, NR$^{12}$C(O)OR$^{15}$NR$^{12}$S(O)$_2$R$^{15}$, NR$^{12}$C(O)NHR$^{15}$, C$_{1-4}$ haloalkyl, C$_{1-4}$ alkoxy, C$_{2-4}$ alkenyloxy, C$_{2-4}$ alkynyloxy, (C$_{1-4}$ haloalkyl)oxy, C$_{1-4}$ alkyl substituted with 0–3 R$^{12a}$, C$_{2-4}$ alkenyl substituted with 0–3 R$^{12a}$, C$_{3-6}$ carbocyclic residue substituted with 0–3 R$^{31}$, aryl substituted with 0–5 R$^{31}$, and 5–6 membered heterocyclic ring system containing from 1–4 heteroatoms selected from the group consisting of N, O, and S substituted with 0–3 R$^{31}$;

$R^{12}$, at each occurrence, is independently selected from H, C$_{1-4}$ alkyl substituted with 0–1 R$^{12a}$, C$_{2-4}$ alkenyl substituted with 0–1 R$^{12a}$, C$_{2-4}$ alkynyl substituted with 0–1 R$^{12a}$, C$_{3-6}$ cycloalkyl substituted with 0–3 R$^{31}$, aryl substituted with 0–5 R$^{31}$; C$_{3-10}$ carbocyclic residue substituted with 0–3 R$^{31}$, and 5–10 membered heterocyclic ring system containing from 1–4 heteroatoms selected from the group , consisting of N, O, and S substituted with 0–3 R$^{31}$;

$R^{12a}$, at each occurrence, is independently selected from phenyl substituted with 0–5 R$^{31}$;

C$_{3-6}$ carbocyclic residue substituted with 0–3 R$^{31}$, and

5–6 membered heterocyclic ring system containing from 1–4 heteroatoms selected from the group consisting of N, O, and S substituted with 0–3 R$^{31}$;

$R^{13}$, at each occurrence, is independently selected from

H, C$_{1-4}$ alkyl, C$_{2-4}$ alkenyl, and C$_{2-4}$ alkynyl;

alternatively, R$^{12}$ and R$^{13}$ may be combined, along with the nitrogen to which they are attached, to form a 5- or 6-membered ring optionally substituted with —O— or —N(R$^{14}$)—;

$R^{14}$, at each occurrence, is independently selected from H and C$_{1-4}$ alkyl;

$R^{15}$, at each occurrence, is independently selected from

H, C$_{1-4}$ alkyl, C$_{2-4}$ alkenyl, and C$_{2-4}$ alkynyl;

$R^{16}$, at each occurrence, is independently selected from

H, methyl, and ethyl;

$R^{17}$, at each occurrence, is independently selected from

H, methyl, and ethyl;

$R^{31}$, at each occurrence, is independently selected from

H, F, Cl, Br, I, =O, —CN, —NO$_2$, OR$^{32}$, SR$^{32}$, NR$^{32}$R$^{33}$, C(O)H, C(O)R$^{32}$, C(O)OH, C(O)OR$^{32}$, C(O)NR$^{32}$R$^{33}$, OC(O)NR$^{32}$R$^{33}$, NR$^{34}$C(O)R$^{32}$, OC(O)R$^{32}$, CH(=NR$^{34}$)NR$^{32}$R$^{33}$, NHC(=NR$^{34}$)NR$^{32}$R$^{33}$, S(O)R$^{32}$, S(O)$_2$R$^{32}$, S(O)H, S(O)$_2$H, S(O)$_3$H, S(O)NR$^{32}$R$^{33}$, S(O)$_2$NR$^{32}$R$^{33}$, NR$^{34}$S(O)R$^{32}$, NR$^{34}$S(O)$_2$R$^{32}$, NR$^{32}$C(O)R$^{35}$, NR$^{32}$C(O)OR$^{35}$, NR$^{32}$S(O)$_2$R$^{35}$, NR$^{32}$C(O)NHR$^{35}$, tetrazole, C$_{1-4}$ haloalkyl, C$_{1-4}$ alkoxy, C$_{2-4}$ alkenyloxy, C$_{2-4}$ alkynyloxy, (C$_{1-4}$ haloalkyl)oxy, C$_{1-4}$ alkyl, C$_{2-4}$ alkenyl, and C$_{2-4}$ alkynyl;

$R^{32}$, $R^{33}$, $R^{34}$, $R^{35}$, at each occurrence, are independently selected from H, C$_{1-4}$ alkyl, C$_{2-4}$ alkenyl, C$_{2-4}$ alkynyl, and benzyl.

In a more preferred embodiment, the present invention provides a novel compound of Formula (Ib) wherein $R^B$ is a 5–10 membered ring system consisting of carbon atoms and 0, 1 or 2 heteroatoms selected from the group consisting of N, O, and S; wherein said ring system may be unsaturated, partially unsaturated or saturated; and $R^B$ is substituted with 0, 1, 2, 3, 4, or 5 substituents selected from R$^{b1}$, R$^{b2}$, R$^{b3}$, R$^{b4}$, and R$^{b5}$.

In a more preferred embodiment, the present invention provides a novel compound of Formula (Ib) or a stereoisomer or pharmaceutically acceptable salt form thereof, wherein;

ring A, including the two atoms of Ring B to which it is attached, is a phenyl ring; wherein, in addition to R$^A$, ring A is substituted with 0–1 R$^{AA}$;

$R^A$ is selected from —C(=NH)NH$_2$, —C(O)NH$_2$, —S(O)$_2$NH$_2$, —NH$_2$, and —CH$_2$NH$_2$; and $R^{AA}$ is H, F, Cl, methoxy, —NH$_2$, and —CH$_2$NH$_2$.

In a more preferred embodiment, the present invention provides a novel compound of Formula (Ic):

(Ic)

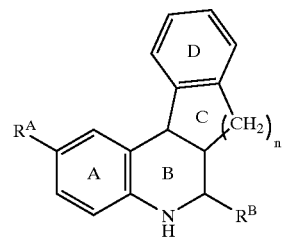

or a stereoisomer or pharmaceutically acceptable salt form thereof, wherein;

$R^A$ is C(=NH)NH$_2$ and —CH$_2$NH$_2$; and $R^B$ is a 5–10 membered ring system consisting of carbon atoms and 0, 1 or 2 heteroatoms selected from the group consisting of N, O, and S; wherein said ring system is selected from phenyl, naphthyl, furanyl, thienyl, pyrrolyl, imidazolyl, triazinyl, thiazolyl, oxazolyl, isoxazolyl, tetrazolyl, pyrazolyl, pyridinyl, pyrimidinyl, pyridazinyl, quinolinyl, isoquinolinyl, benzofuranyl, 1H-indazolyl, benzothienyl, benzotriazolyl, benzoxazolyl, benzisoxazolyl, indolyl, chromanyl, benzimidazolyl; and $R^B$ is substituted with 0, 1, 2, 3, 4, or 5 substituents selected from R$^{b1}$, R$^{b2}$, R$^{b3}$, R$^{b4}$, and R$^{b5}$.

In another more preferred embodiment, the present invention provides a novel compound of Formula (Ib):

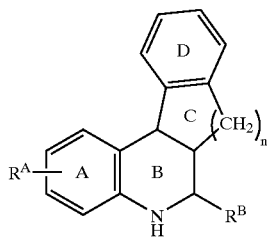

(Ib)

or a stereoisomer or pharmaceutically acceptable salt form thereof, wherein;

ring A, including the two atoms of Ring B to which it is attached, is a phenyl ring; wherein, in addition to $R^A$, ring A is substituted with 0–1 $R^{AA}$;

$R^A$ is selected from —C(=NH)NH$_2$, —C(O)NH$_2$, —S(O)$_2$NH$_2$, —NH$_2$, and —CH$_2$NH$_2$;

$R^{AA}$ is H, F, Cl, methoxy, —NH$_2$, and —CH$_2$NH$_2$;

$R^B$ is a 5–10 membered ring system consisting of carbon atoms and 0, 1 or 2 heteroatoms selected from the group consisting of N, O, and S; wherein said ring system is selected from phenyl, naphthyl, furanyl, thienyl, pyrrolyl, imidazolyl, triazinyl, thiazolyl, oxazolyl, isoxazolyl, tetrazolyl, pyrazolyl, pyridinyl, pyrimidinyl, quinolinyl, isoquinolinyl, benzofuranyl, benzothiofuranyl, 1H-indazolyl, oxazolidinyl, isoxazolidinyl, benzotriazolyl, benzisoxazolyl, oxindolyl, benzoxazolinyl, indolyl, chromanyl, benzimidazolyl; and $R^B$ is substituted with 0, 1, 2, 3, 4, or 5 substituents selected from $R^{b1}$, $R^{b2}$, $R^{b3}$, $R^{b4}$, and $R^{b5}$;

alternatively $R^B$ is $C_{1-4}$ alkyl substituted with 5–10 membered ring system consisting of carbon atoms and 0, 1 or 2 heteroatoms selected from the group consisting of N, O, and S; wherein said ring system is selected from phenyl, furanyl, thiophenyl, pyrrolyl, imidazolyl, benzimidazolyl; and $R^B$ is substituted with 0, 1, 2, 3, 4, or 5 substituents selected from $R^{b1}$, $R^{b2}$, $R^{b3}$, $R^{b4}$, and $R^{b5}$;

$R^{b1}$, $R^{b2}$, $R^{b3}$, $R^{b4}$, and $R^{b5}$, at each occurrence, are independently selected from H, F, Cl, Br, I, =O, —CN, —NO$_2$, —OH, OR$^{12}$, SR$^{12}$, NR$^{12}$R$^{13}$, C(O)H, C(O)R$^{12}$, C(O)OR$^{12}$, C(O)NR$^{12}$R$^{13}$, OC(O)NR$^{12}$R$^{13}$, NR$^{14}$C(O)R$^{12}$, OC(O)R$^{12}$, CH(=NR$^{14}$)NR$^{12}$R$^{13}$, NHC(=NR$^{14}$)NR$^{12}$R$^{13}$, S(O)R$^{12}$, S(O)$_2$R$^{12}$, S(O)H, S(O)$_2$H, S(O)NR$^{12}$R$^{13}$, S(O)$_2$NR$^{12}$R$^{13}$, NR$^{14}$S(O)R$^{12}$, NR$^{14}$S(O)$_2$R$^{12}$, NR$^{12}$C(O)R$^{15}$, NR$^{12}$C(O)OR$^{15}$, NR$^{12}$S(O)$_2$R$^{15}$, NR$^{12}$C(O)NHR$^{15}$, (HO)$_2$B—, $C_{1-4}$ haloalkyl, $C_{1-4}$ alkoxy, $C_{2-4}$ alkenyloxy, $C_{2-4}$ alkynyloxy, ($C_{1-4}$ haloalkyl)oxy, $C_{1-4}$ alkyl substituted with 0–3 $R^{11}$, $C_{2-4}$ alkenyl substituted with 0–3 $R^{11}$, $C_{2-4}$ alkynyl substituted with 0–3 $R^{11}$, $C_{1-4}$ alkoxy substituted with 0–3 $R^{11}$, $C_{3-10}$ carbocyclic residue substituted with 0–3 $R^{31}$, aryl substituted with 0–5 $R^{31}$, and 5–10 membered heterocyclic ring system containing from 1–4 heteroatoms selected from the group consisting of N, O, and S substituted with 0–3 $R^{31}$;

alternatively, $R^{b1}$ and $R^{b2}$, when substituents on adjacent carbons, or $R^{b2}$ and $R^{b3}$, when substituents on adjacent carbons, may be combined to form a methylenedioxy group;

n is 1, 2, or 3;

ring D, including the two atoms of Ring C to which it is attached, is a phenyl ring; and ring D is substituted with 0–2 $R^D$;

$R^D$, at each occurrence, is independently selected from

H, halo, —CN, OH, $C_{1-4}$ alkoxy, and $C_{1-4}$ alkyl;

$R^{11}$, at each occurrence, is independently selected from

H, halo, —CN, —NO$_2$, OR$^{12}$, SR$^{12}$, NR$^{12}$R$^{13}$, C(O)H, C(O)R$^{12}$, C(O)NR$^{12}$R$^{13}$, OC(O)NR$^{12}$R$^{13}$, NR$^{14}$C(O)R$^{12}$, C(O)OR$^{12}$, OC(O)R$^{12}$, OC(O)OR$^{12}$, CH(=NR$^{14}$)NR$^{12}$R$^{13}$, NHC(=NR$^{14}$)NR$^{12}$R$^{13}$, S(O)R$^{12}$, S(O)$_2$R$^{12}$, S(O)NR$^{12}$R$^{13}$, S(O)$_2$NR$^{12}$R$^{13}$, NR$^{14}$S(O)R$^{12}$, NR$^{14}$S(O)$_2$R$^{12}$, NR$^{12}$C(O)R$^{15}$, NR$^{12}$C(O)OR$^{15}$, NR$^{12}$S(O)$_2$R$^{15}$, NR$^{12}$C(O)NHR$^{15}$, $C_{1-4}$ haloalkyl, $C_{1-4}$ alkoxy, $C_{2-4}$ alkenyloxy, $C_{2-4}$ alkynyloxy, ($C_{1-4}$ haloalkyl)oxy, $C_{1-4}$ alkyl substituted with 0–3 $R^{12a}$, $C_{2-4}$ alkenyl substituted with 0–3 $R^{12a}$, $C_{3-6}$ carbocyclic residue substituted with 0–3 $R^{31}$, aryl substituted with 0–5 $R^{31}$, and 5–6 membered heterocyclic ring system containing from 1–4 heteroatoms selected from the group consisting of N, O, and S substituted with 0–3 $R^{31}$;

$R^{12}$, at each occurrence, is independently selected from H, $C_{1-4}$ alkyl substituted with 0–1 $R^{12a}$, $C_{2-4}$ alkenyl substituted with 0–1 $R^{12a}$, $C_{2-4}$ alkynyl substituted with 0–1 $R^{12a}$, $C_{3-6}$ cycloalkyl substituted with 0–3 $R^{31}$, aryl substituted with 0–5 $R^{31}$; $C_{3-10}$ carbocyclic residue substituted with 0–3 $R^{31}$, and 5–10 membered heterocyclic ring system containing from 1–4 heteroatoms selected from the group consisting of N, O, and S substituted with 0–3 $R^{31}$;

$R^{12a}$, at each occurrence, is independently selected from phenyl substituted with 0–5 $R^{31}$;

$C_{3-6}$ carbocyclic residue substituted with 0–3 $R^{31}$, and

5–6 membered heterocyclic ring system containing from 1–4 heteroatoms selected from the group consisting of N, O, and S substituted with 0–3 $R^{31}$;

$R^{13}$, at each occurrence, is independently selected from

H, $C_{1-4}$ alkyl, $C_{2-4}$ alkenyl, and $C_{2-4}$ alkynyl;

alternatively, $R^{12}$ and $R^{13}$ may be combined, along with the nitrogen to which they are attached, to form a 5- or 6-membered ring optionally substituted with —O— or —N(R$^{14}$)—;

$R^{14}$, at each occurrence, is independently selected from H and $C_{1-4}$ alkyl;

$R^{15}$, at each occurrence, is independently selected from

H, $C_{1-4}$ alkyl, $C_{2-4}$ alkenyl, and $C_{2-4}$ alkynyl;

$R^{31}$, at each occurrence, is independently selected from

H, F, Cl, Br, I, =O, —CN, —NO$_2$, OR$^{32}$, SR$^{32}$, NR$^{32}$R$^{33}$, C(O)H, C(O)R$^{32}$, C(O)OH, C(O)OR$^{32}$, C(O)NR$^{32}$R$^{33}$, OC(O)NR$^{32}$R$^{33}$, NR$^{34}$C(O)R$^{32}$, OC(O)R$^{32}$, CH(=NR$^{34}$)NR$^{32}$R$^{33}$, NHC(=NR$^{34}$)NR$^{32}$R$^{33}$, S(O)R$^{32}$, S(O)$_2$R$^{32}$, S(O)H, S(O)$_2$H, S(O)$_3$H, S(O)NR$^{32}$R$^{33}$, S(O)$_2$NR$^{32}$R$^{33}$, NR$^{34}$S(O)R$^{32}$, NR$^{34}$S(O)$_2$R$^{32}$, NR$^{32}$C(O)R$^{35}$, NR$^{32}$C(O)OR$^{35}$, NR$^{32}$S(O)$_2$R$^{35}$, NR$^{32}$C(O)NHR$^{35}$, tetrazole, $C_{1-4}$ haloalkyl, $C_{1-4}$ alkoxy, $C_{2-4}$ alkenyloxy, $C_{2-4}$ alkynyloxy, ($C_{1-4}$ haloalkyl)oxy, $C_{1-4}$ alkyl, $C_{2-4}$ alkenyl, and $C_{2-4}$ alkynyl;

$R^{32}$, $R^{33}$, $R^{34}$, $R^{35}$, at each occurrence, are independently selected from H, $C_{1-4}$ alkyl, $C_{2-4}$ alkenyl, $C_{2-4}$ alkynyl, and benzyl.

In another more preferred embodiment, the present invention provides a novel compound of Formula (Ib):

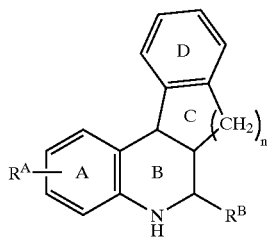

(Ib)

or a stereoisomer or pharmaceutically acceptable salt form thereof, wherein;

ring A, including the two atoms of Ring B to which it is attached, is a phenyl ring; wherein, in addition to $R^A$, ring A is substituted with 0–1 $R^{AA}$;

$R^A$ is selected from —C(=NH)NH$_2$, —C(O)NH$_2$, —S(O)$_2$NH$_2$, —NH$_2$, and —CH$_2$NH$_2$;

$R^{AA}$ is H, F, Cl, methoxy, —NH$_2$, and —CH$_2$NH$_2$;

$R^B$ is a 5–10 membered ring system consisting of carbon atoms and 0, 1 or 2 heteroatoms selected from the group consisting of N, O, and S; wherein said ring system is selected from phenyl, naphthyl, furanyl, thienyl, pyrrolyl, imidazolyl, triazinyl, thiazolyl, oxazolyl, isoxazolyl, tetrazolyl, pyrazolyl, pyridinyl, pyrimidinyl, pyridazinyl, quinolinyl, isoquinolinyl, benzofuranyl, benzothienyl, 1H-indazolyl, oxazolidinyl, isoxazolidinyl, benzotriazolyl, benzoxazolyl, benzisoxazolyl, oxindolyl, benzoxazolinyl, indolyl, chromanyl, benzimidazolyl; and $R^B$ is substituted with 0, 1, 2, 3, 4, or 5 substituents selected from $R^{b1}$, $R^{b2}$, $R^{b3}$, $R^{b4}$, and $R^{b5}$;

$R^{b1}$, $R^{b2}$, $R^{b3}$, $R^{b4}$, and $R^{b5}$, at each occurrence, are independently selected from H, F, Cl, Br, I, =O, —CN, —NO$_2$, —OH, OR$^{12}$, SR$^{12}$, NR$^{12}$R$^{13}$, C(O)H, C(O)R$^{12}$, C(O)OR$^{12}$, C(O)NR$^{12}$R$^{13}$, OC(O)NR$^{12}$R$^{13}$, NR$^{14}$C(O)R$^{12}$, OC(O)R$^{12}$, CH(=NR$^{14}$)NR$^{12}$R$^{13}$, NHC(=NR$^{14}$)NR$^{12}$R$^{13}$, S(O)R$^{12}$ S(O)$_2$R$^{12}$, S(O)H, S(O)$_2$H, S(O)NR$^{12}$R$^{13}$, S(O)$_2$NR$^{12}$R$^{13}$, NR$^{14}$S(O)R$^{12}$, NR$^{14}$S(O)$_2$R$^{12}$, NR$^{12}$C(O)R$^{15}$, NR$^{12}$C(O)OR$^{15}$, NR$^{12}$S(O)$_2$R$^{15}$, NR$^{12}$C(O)NHR$^{15}$, (HO)$_2$B—, C$_{1-4}$ haloalkyl, C$_{1-4}$ alkoxy, C$_{2-4}$ alkenyloxy, C$_{2-4}$ alkynyloxy, (C$_{1-4}$ haloalkyl)oxy, C$_{1-4}$ alkyl substituted with 0–3 R$^{11}$, C$_{2-4}$ alkenyl substituted with 0–3 R$^{11}$, C$_{2-4}$ alkynyl substituted with 0–3 R$^{11}$, C$_{1-4}$ alkoxy substituted with 0–3 R$^{11}$, C$_{3-10}$ carbocyclic residue substituted with 0–3 R$^{31}$, aryl substituted with 0–5 R$^{31}$, and 5–10 membered heterocyclic ring system containing from 1–4 heteroatoms selected from the group consisting of N, O, and S substituted with 0–3 R$^{31}$;

alternatively, $R^{b1}$ and $R^{b2}$, when substituents on adjacent carbons, or $R^{b2}$ and $R^{b3}$, when substituents on adjacent carbons, may be combined to form a methylenedioxy group;

n is 1, 2, or 3;

ring D, including the two atoms of Ring C to which it is attached, is a phenyl ring; and ring D is substituted with 0–2 $R^D$;

$R^D$, at each occurrence, is independently selected from

H, halo, —CN, OH, —COOH, —CONH$_2$, —CF$_3$, —SO$_2$CH$_3$, C$_{1-4}$ alkoxy, and C$_{1-4}$ alkyl;

$R^{11}$, at each occurrence, is independently selected from

H, halo, —CN, —NO$_2$, OR$^{12}$, SR$^{12}$, NR$^{12}$R$^{13}$, C(O)H, C(O)R$^{12}$, C(O)NR$^{12}$R$^{13}$, OC(O)NR$^{12}$R$^{13}$, NR$^{14}$C(O) R$^{12}$, C(O)OR$^{12}$, OC(O)R$^{12}$, OC(O)OR$^{12}$, CH(=NR$^{14}$) NR$^{12}$R$^{13}$, NHC(=NR$^{14}$)NR$^{12}$R$^{13}$, S(O)R$^{12}$, S(O)$_2$R$^{12}$, S(O)NR$^{12}$R$^{13}$, S(O)$_2$NR$^{12}$R$^{13}$, NR$^{14}$S(O)R$^{12}$, NR$^{14}$S (O)$_2$R$^{12}$, NR$^{12}$C(O)R$^{15}$, NR$^{12}$C(O)OR$^{15}$, NR$^{12}$S(O)$_2$ R$^{15}$, NR$^{12}$C(O)NHR$^{15}$, C$_{1-4}$ haloalkyl, C$_{1-4}$ alkoxy, C$_{2-4}$ alkenyloxy, C$_{2-4}$ alkynyloxy, (C$_{1-4}$ haloalkyl)oxy, C$_{1-4}$ alkyl substituted with 0–3 R$^{12a}$, C$_{2-4}$ alkenyl substituted with 0–3 R$^{12a}$, C$_{3-6}$ carbocyclic residue substituted with 0–3 R$^{31}$, aryl substituted with 0–5 R$^{31}$, and 5–6 membered heterocyclic ring system containing from 1–4 heteroatoms selected from the group consisting of N, O, and S substituted with 0–3 R$^{31}$;

$R^{12}$, at each occurrence, is independently selected from H,

C$_{1-4}$ alkyl substituted with 0–1 R$^{12a}$, C$_{2-4}$ alkenyl substituted with 0–1 R$^{12a}$, C$_{2-4}$ alkynyl substituted with 0–1 R$^{12a}$, C$_{3-6}$ cycloalkyl substituted with 0–3 R$^{31}$, aryl substituted with 0–5 R$^{31}$; C$_{3-10}$ carbocyclic residue substituted with 0–3 R$^{31}$, and 5–10 membered heterocyclic ring system containing from 1–4 heteroatoms selected from the group consisting of N, O, and S substituted with 0–3 R$^{31}$;

$R^{12a}$, at each occurrence, is independently selected from phenyl substituted with 0–5 R$^{31}$;

C$_{3-6}$ carbocyclic residue substituted with 0–3 R$^{31}$, and

5–6 membered heterocyclic ring system containing from 1–4 heteroatoms selected from the group consisting of N, O, and S substituted with 0–3 R$^{31}$;

$R^{13}$, at each occurrence, is independently selected from

H, C$_{1-4}$ alkyl, C$_{2-4}$ alkenyl, and C$_{2-4}$ alkynyl;

alternatively, $R^{12}$ and $R^{13}$ may be combined, along with the nitrogen to which they are attached, to form a 5- or 6-membered ring optionally substituted with —O— or —N(R$^{14}$)—;

$R^{14}$, at each occurrence, is independently selected from H and C$_{1-4}$ alkyl;

$R^{15}$, at each occurrence, is independently selected from

H, C$_{1-4}$ alkyl, C$_{2-4}$ alkenyl, and C$_{2-4}$ alkynyl;

$R^{31}$, at each occurrence, is independently selected from

H, F, Cl, Br, I, =O, —CN, —NO$_2$, OR$^{32}$, SR$^{32}$, NR$^{32}$R$^{33}$, C(O)H, C(O)R$^{32}$, C(O)OH, C(O)OR$^{32}$, C(O)NR$^{32}$R$^{33}$, OC(O)NR$^{32}$R$^{33}$, NR$^{34}$C(O)R$^{32}$, OC(O)R$^{32}$, CH(=NR$^{34}$)NR$^{32}$R$^{33}$, NHC(=NR$^{34}$)NR$^{32}$R$^{33}$, S(O) R$^{32}$, S(O)$_2$R$^{32}$, S(O)H, S(O)$_2$H, S(O)$_3$H, S(O) NR$^{32}$R$^{33}$, S(O)$_2$NR$^{32}$R$^{33}$, NR$^{34}$S(O)R$^{32}$, NR$^{34}$S(O)$_2$ R$^{32}$, NR$^{32}$C(O)R$^{35}$, NR$^{32}$C(O)OR$^{35}$, NR$^{32}$S(O)$_2$R$^{35}$, NR$^{32}$C(O)NHR$^{35}$, tetrazole, C$_{1-4}$ haloalkyl, C$_{1-4}$ alkoxy, C$_{2-4}$ alkenyloxy, C$_{2-4}$ alkynyloxy, (C$_{1-4}$ haloalkyl)oxy, C$_{1-4}$ alkyl, C$_{2-4}$ alkenyl, and C$_{2-4}$ alkynyl;

$R^{32}$, $R^{33}$, $R^{34}$, $R^{35}$, at each occurrence, are independently selected from H, C$_{1-4}$ alkyl, C$_{2-4}$ alkenyl, C$_{2-4}$ alkynyl, and benzyl.

In another more preferred embodiment, the present invention provides a novel compound of Formula (Ic):

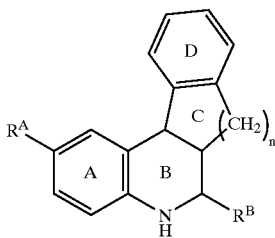

(Ic)

or a stereoisomer or pharmaceutically acceptable salt form thereof, wherein;

$R^A$ is C(=NH)NH$_2$ and —CH$_2$NH$_2$;

$R^B$ is a 5–10 membered ring system selected from phenyl, naphthyl, furanyl, thienyl, pyrrolyl, imidazolyl, pyrazolyl, pyridinyl, indolyl, and benzimidazolyl; and $R^B$ is substituted with 0, 1, 2, 3, 4, or 5 substituents selected from $R^{b1}$, $R^{b2}$, $R^{b3}$, $R^{b4}$, and $R^{b5}$;

$R^{b1}$, $R^{b2}$, $R^{b3}$, $R^{b4}$, and $R^{b5}$, at each occurrence; are independently selected from:

H, F, Cl, Br, I, =O, —CN, —NO$_2$, —OH, OR$^{12}$, SR$^{12}$, NR$^{12}$R$^{13}$, C(O)H, C(O)R$^{12}$, C(O)OR$^{12}$, C(O)NR$^{12}$R$^{13}$, OC(O)NR$^{12}$R$^{13}$, NR$^{14}$C(O)R$^{12}$, OC(O)R$^{12}$, CH(=NR$^{14}$)NR$^{12}$R$^{13}$, NHC(=NR$^{14}$)NR$^{12}$R$^{13}$, S(O)R$^{12}$, S(O)$_2$R$^{12}$, S(O)H, S(O)$_2$H, S(O)NR$^{12}$R$^{13}$, S(O)$_2$NR$^{12}$R$^{13}$, NR$^{14}$S(O)R$^{12}$, NR$^{14}$S(O)$_2$R$^{12}$, NR$^{12}$C(O)R$^{15}$, NR$^{12}$C(O)OR$^{15}$, NR$^{12}$S(O)$_2$R$^{15}$, NR$^{12}$C(O)NHR$^{15}$, (HO)$_2$B—, —CF$_3$, —OCF$_3$, methoxy, ethoxy, propoxy, butoxy, methyl, ethyl, propyl, butyl, C$_{1-4}$ alkyl substituted with 0–3 R$^{11}$, C$_{2-4}$ alkenyl substituted with 0–3 R$^{11}$, C$_{2-4}$ alkynyl substituted with 0–3 R$^{11}$, C$_{1-4}$ alkoxy substituted with 0–3 R$^{11}$, C$_{3-6}$ carbocyclic residue substituted with 0–3 R$^{31}$, phenyl substituted with 0–5 R$^{31}$, and 5–10 membered heterocyclic ring system selected from furanyl, thienyl, pyrrolyl, pyrrolidinyl, imidazolyl, pyrazolyl, pyridinyl, pyrimidinyl, indolyl, and N-morpholinyl, said heterocyclic ring system substituted with 0–3 R$^{31}$;

alternatively, $R^{b1}$ and $R^{b2}$, when substituents on adjacent carbons, or $R^{b2}$ and $R^{b3}$, when substituents on adjacent carbons, may be combined to form a methylenedioxy group;

n is 1, 2, or 3;

ring D, including the two atoms of Ring C to which it is attached, is a phenyl ring; and ring D is substituted with 0–2 R$^D$;

$R^D$, at each occurrence, is independently selected from

H, F, Cl, Br, OH, methoxy, and methyl;

$R^{11}$, at each occurrence, is independently selected from

H, halo, —CN, —NO$_2$, OH, OR$^{12}$, SR$^{12}$, NR$^{12}$R$^{13}$, C(O)H, C(O)R$^{12}$, C(O)NR$^{12}$R$^{13}$, OC(O)NR$^{12}$R$^{13}$, NR$^{14}$C(O)R$^{12}$, C(O)OR$^{12}$, OC(O)R$^{12}$, OC(O)OR$^{12}$, CH(=NR$^{14}$)NR$^{12}$R$^{13}$, NHC(=NR$^{14}$)NR$^{12}$R$^{13}$, S(O)R$^{12}$, S(O)$_2$R$^{12}$, S(O)NR$^{12}$R$^{13}$, S(O)$_2$NR$^{12}$R$^{13}$, NR$^{14}$S(O)$_2$R$^{12}$, NR$^{14}$S(O)$_2$R$^{12}$, NR$^{12}$C(O)R$^{15}$, NR$^{12}$C(O)OR$^{15}$, NR$^{12}$S(O)$_2$R$^{15}$, NR$^{12}$C(O)NHR$^{15}$, —CF$_3$, —OCF$_3$, methoxy, ethoxy, propoxy, butoxy, C$_{1-4}$ alkyl substituted with 0–3 R$^{12a}$, C$_{2-4}$ alkenyl substituted with 0–3 R$^{12a}$, C$_{3-6}$ carbocyclic residue substituted with 0–3 R$^{31}$, phenyl substituted with 0–5 R$^{31}$, and 5–6 membered heterocyclic ring system selected from furanyl, thienyl, pyrrolyl, pyrrolidinyl, imidazolyl, pyrazolyl, pyridinyl, pyrimidinyl, and N-morpholinyl, said heterocyclic ring system substituted with 0–3 R$^{31}$;

$R^{12}$, at each occurrence, is independently selected from H, C$_{1-4}$ alkyl substituted with 0–1 R$^{12a}$, C$_{2-4}$ alkenyl substituted with 0–1 R$^{12a}$, C$_{2-4}$ alkynyl substituted with 0–1 R$^{12a}$, C$_{3-6}$ cycloalkyl substituted with 0–3 R$^{31}$, phenyl substituted with 0–5 R$^{31}$; and 5–6 membered heterocyclic ring system selected from furanyl, thienyl, pyrrolyl, pyrrolidinyl, imidazolyl, pyrazolyl, pyridinyl, and pyrimidinyl, said heterocyclic ring system substituted with 0–3 R$^{31}$;

$R^{12a}$, at each occurrence, is independently selected from phenyl substituted with 0–5 R$^{31}$;

C$_{3-6}$ carbocyclic residue substituted with 0–3 R$^{31}$, and

5–6 membered heterocyclic ring system selected from furanyl, thienyl, pyrrolyl, pyrrolidinyl, imidazolyl, pyrazolyl, pyridinyl, and pyrimidinyl, said heterocyclic ring system substituted with 0–3 R$^{31}$;

$R^{13}$, at each occurrence, is independently selected from

H, methyl, ethyl, propyl, butyl, ethenyl, propenyl, butenyl, ethynyl, propynyl, and butynyl;

alternatively, $R^{12}$ and $R^{13}$ may be combined, along with the nitrogen to which they are attached, to form a 5- or 6-membered ring optionally substituted with —O— or —N(R$^{14}$)—;

$R^{14}$, at each occurrence, is independently selected from H, methyl, ethyl, propyl, and butyl;

$R^{15}$, at each occurrence, is independently selected from

H, methyl, ethyl, propyl, butyl, ethenyl, propenyl, butenyl, ethynyl, propynyl, and butynyl;

$R^{31}$, at each occurrence, is independently selected from

H, F, Cl, Br, I, =O, —CN, —NO$_2$, —OH, —OR$^{32}$, —SR$^{32}$, —NR$^{32}$R$^{33}$, —C(O)H, —C(O)R$^{32}$, —C(O)OH, —C(O)OR$^{32}$, —C(O)NR$^{32}$R$^{33}$, —OC(O)NR$^{32}$R$^{33}$, —NR$^{34}$C(O)R$^{32}$, —OC(O)R$^{32}$, —CH(=NR$^{34}$)NR$^{32}$R$^{33}$, —NHC(=NR$^{34}$)NR$^{32}$R$^{33}$, —S(O)R$^{32}$, —S(O)$_2$R$^{32}$, —S(O)H, —S(O)$_2$H, —S(O)$_3$H, —S(O)NR$^{32}$R$^{33}$, —S(O)$_2$NR$^{32}$R$^{33}$, —S(O)$_2$NH$_2$, —NR$^{34}$S(O)R$^{32}$, —NR$^{34}$S(O)$_2$R$^{32}$, —NR$^{32}$C(O)R$^{35}$, —NR$^{32}$C(O)OR$^{35}$, —NR$^{32}$S(O)$_2$R$^{35}$, —NR$^{32}$C(O)NHR$^{35}$, tetrazolyl, —CF$_3$, —OCF$_3$, methoxy, ethoxy, n-propoxy, i-propoxy, methyl, ethyl, n-propyl, i-propyl, n-butyl, i-butyl, s-butyl, t-butyl, hydroxymethyl-, hydroxyethyl-, vinyl, and allyl;

$R^{32}$, $R^{33}$, $R^{34}$, $R^{35}$, at each occurrence, are independently selected from H, methyl, ethyl, n-propyl, i-propyl, n-butyl, i-butyl, s-butyl, t-butyl, and benzyl.

In another more preferred embodiment, the present invention provides a novel compound of Formula (I), (Ia), (Ib), (Ic), (Id), (Ie), or (If) wherein $R^{b1}$, $R^{b2}$, $R^{b3}$, $R^{b4}$, and $R^{b5}$, at each occurrence, are independently selected from:

H, F, Cl, Br, cyano, nitro, methyl, ethyl, n-propyl, i-propyl, vinyl, allyl, hydroxy, hydroxymethyl, hydroxyethyl, hydroxy-n-propyl, hydroxy-i-propyl, methoxy, ethoxy, n-propoxy, i-propoxy, allyloxy-, methyl-S—, ethyl-S—, n-propyl-S—, i-propyl-S—, allyl-S—, —CF$_3$, —CHF$_2$, —OCF$_3$, —SCF$_3$, —CO$_2$H, —C(=O)OCH$_3$, —C(=O)CH$_3$, —SO$_2$CH$_3$, and —SO$_2$CH$_2$CH$_3$.

In another more preferred embodiment, the present invention provides a novel compound of Formula (I), (Ia), (Ib), (Ic), (Id), (Ie), or (If) wherein $R^D$, at each occurrence, is independently selected from H, halo, —CN, OH, —COOH, —CONH$_2$, —CF$_3$, —SO$_2$CH$_3$, C$_{1-4}$ alkoxy, and C$_{1-4}$ alkyl;

In another more preferred embodiment, the present invention provides a novel compound of Formula (I), (Ia), (Ib), (Ic), (Id), (Ie), or (If) wherein $R^D$, at each occurrence, is independently selected from
H, F, Cl, Br, —CN, OH, —COOH, —CONH$_2$, —CF$_3$, —SO$_2$CH$_3$, methoxy, ethoxy, methyl and ethyl;

In another more preferred embodiment, the present invention provides a novel compound of Formula (I), (Ia), (Ib), (Ic), (Id), (Ie), or (If) wherein $R^D$, at each occurrence, is independently selected from
H, F, Cl, OH, —CF$_3$, methoxy, and methyl.

In another more preferred embodiment, the present invention provides a novel compound of Formula (Id):

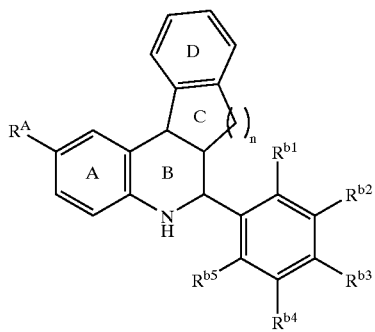

(Id)

or a stereoisomer or pharmaceutically acceptable salt form thereof, wherein;

ring A, including the two atoms of Ring B to which it is attached, is a phenyl ring; wherein, in addition to $R^A$, ring A is substituted with 0–1 $R^{AA}$;

alternatively ring A and substituent $R^A$, including the two atoms of Ring B to which Ring A is attached, is a phenyl ring of formula:

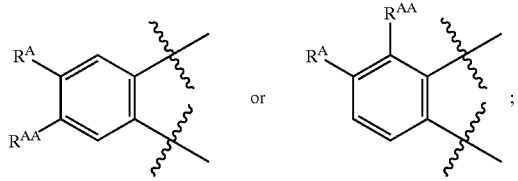

wherein $R^A$ is combined with $R^{AA}$ and two carbon atoms of Ring A to form a cyclic group selected from:

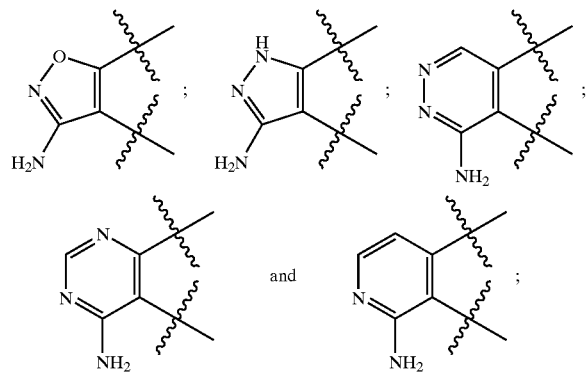

$R^A$ is selected from Cl, OCH$_3$, C(=NH)NH$_2$, C(O)NH$_2$, S(O)$_2$NH$_2$, —NH$_2$, and —CH$_2$NH$_2$;

$R^{AA}$ is H, F, Cl, methoxy, —NH$_2$, and —CH$_2$NH$_2$;

$R^{b1}$, $R^{b2}$, $R^{b3}$, and $R^{b4}$, at each occurrence, are independently selected from
H, F, Cl, Br, I, —CN, —NO$_2$, —OH, OR$^{12}$, SR$^{12}$, NR$^{12}$R$^{13}$, C(O)H, C(O)R$^{12}$, C(O)OR$^{12}$, C(O)NR$^{12}$R$^{13}$, OC(O)NR$^{12}$R$^{13}$, NR$^{14}$C(O)R$^{12}$, OC(O)R$^{12}$, CH(=NR$^{14}$)NR$^{12}$R$^{13}$, NHC(=NR$^{14}$)NR$^{12}$R$^{13}$, S(O)R$^{12}$, S(O)$_2$R$^{12}$, S(O)H, S(O)$_2$H, S(O)NR$^{12}$R$^{13}$, S(O)$_2$NR$^{12}$R$^{13}$, NR$^{14}$S(O)R$^{12}$, NR$^{14}$S(O)$_2$R$^{12}$, NR$^{12}$C(O)R$^{15}$, NR$^{12}$C(O)OR$^{15}$, NR$^{12}$S(O)$_2$R$^{15}$, NR$^{12}$C(O)NHR$^{15}$, (HO)$_2$B—, C$_{1-4}$ haloalkyl, C$_{1-4}$ alkoxy, C$_{2-4}$ alkenyloxy, C$_{2-4}$ alkynyloxy, (C$_{1-4}$ haloalkyl)oxy, C$_{1-4}$ alkyl substituted with 0–3 R$^{11}$, C$_{2-4}$ alkenyl substituted with 0–3 R$^{11}$, C$_{2-4}$ alkynyl substituted with 0–3 R$^{11}$, C$_{1-4}$ alkoxy substituted with 0–3 R$^{11}$, C$_{3-10}$ carbocyclic residue substituted with 0–3 R$^{31}$, aryl substituted with 0–5 R$^{31}$, and 5–10 membered heterocyclic ring system containing from 1–4 heteroatoms selected from the group consisting of N, O, and S substituted with 0–3 R$^{31}$;

$R^{b5}$ is phenyl substituted with 0–5 R$^{31}$;

n is 1, 2, or 3;

$R^{C1}$ is H, methyl ethyl, propyl, or butyl;

$R^{C2}$ is H or methyl;

ring D, including the two atoms of Ring C to which it is attached, is a phenyl ring; and ring D is substituted with 0–2 R$^D$;

$R^D$, at each occurrence, is independently selected from
H, halo, —CN, —NO$_2$, OR$^{16}$, SR$^{16}$, NR$^{16}$R$^{16}$, C(O)H, C(O)R$^{16}$, C(O)NR$^{16}$R$^{16}$, OC(O)NR$^{16}$R$^{16}$, NR$^{14}$C(O)R$^{16}$, C(O)OR$^{16}$, OC(O)R$^{16}$, OC(O)OR$^{16}$, CH(=NR$^{14}$)NR$^{16}$R$^{16}$, NHC(=NR$^{14}$)NR$^{16}$R$^{16}$, S(O)R$^{16}$, S(O)$_2$R$^{16}$, S(O)NR$^{16}$R$^{16}$, S(O)$_2$NR$^{16}$R$^{16}$, NR$^{14}$S(O)R$^{16}$, NR$^{14}$S(O)$_2$R$^{16}$, NR$^{16}$C(O)R$^{17}$, NR$^{16}$C(O)OR$^{17}$, NR$^{16}$S(O)$_2$R$^{17}$, NR$^{16}$C(O)NHR$^{17}$, C$_{1-3}$ haloalkyl, (C$_{1-2}$ haloalkyl)oxy, C$_{1-4}$ alkoxy, and C$_{1-4}$ alkyl;

$R^{11}$, at each occurrence, is independently selected from
H, halo, —CN, —NO$_2$, OR$^{12}$, SR$^{12}$, NR$^{12}$R$^{13}$, C(O)H, C(O)R$^{12}$, C(O)NR$^{12}$R$^{13}$, OC(O)NR$^{12}$R$^{13}$, NR$^{14}$C(O)R$^{12}$, C(O)OR$^{12}$, OC(O)R$^{12}$, OC(O)OR$^{12}$, CH(=NR$^{14}$)NR$^{12}$R$^{13}$, NHC(=NR$^{14}$)NR$^{12}$R$^{13}$, S(O)R$^{12}$, S(O)$_2$R$^{12}$, S(O)NR$^{12}$R$^{13}$, S(O)$_2$NR$^{12}$R$^{13}$, NR$^{14}$S(O)R$^{12}$, NR$^{14}$S(O)$_2$R$^{12}$, NR$^{12}$C(O)R$^{15}$, NR$^{12}$C(O)OR$^{5}$, NR$^{12}$S(O)$_2$R$^{15}$, NR$^{12}$C(O)NHR$^{15}$, C$_{1-4}$ haloalkyl, C$_{1-4}$ alkoxy, C$_{2-4}$ alkenyloxy, C$_{2-4}$ alkynyloxy, (C$_{1-4}$ haloalkyl)oxy, C$_{1-4}$ alkyl substituted with 0–3 R$^{12a}$, C$_{2-4}$ alkenyl substituted with 0–3 R$^{12a}$, C$_{3-6}$ carbocyclic residue substituted with 0–3 R$^{31}$, aryl substituted with 0–5 R$^{31}$, and 5–6 membered heterocyclic ring system containing from 1–4 heteroatoms selected from the group consisting of N, O, and S substituted with 0–3 R$^{31}$;

$R^{12}$, at each occurrence, is independently selected from H, C$_{1-4}$ alkyl substituted with 0–1 R$^{12a}$, C$_{2-4}$ alkenyl substituted with 0–1 R$^{12a}$, C$_{2-4}$ alkynyl substituted with 0–1 R$^{12a}$, C$_{3-6}$ cycloalkyl substituted with 0–3 R$^{31}$, aryl substituted with 0–5 R$^{31}$; C$_{3-10}$ carbocyclic residue substituted with 0–3 R$^{31}$, and 5–10 membered heterocyclic ring system containing from 1–4 heteroatoms selected from the group consisting of N, O, and S substituted with 0–3 R$^{31}$;

$R^{12a}$, at each occurrence, is independently selected from phenyl substituted with 0–5 R$^{31}$;

C$_{3-6}$ carbocyclic residue substituted with 0–3 R$^{31}$, and

5–6 membered heterocyclic ring system containing from 1–4 heteroatoms selected from the group consisting of N, O, and S substituted with 0–3 R$^{31}$;

$R^{13}$, at each occurrence, is independently selected from
H, $C_{1-4}$ alkyl, $C_{2-4}$ alkenyl, and $C_{2-4}$ alkynyl;
alternatively, $R^{12}$ and $R^{13}$ may be combined, along with the nitrogen to which they are attached, to form a 5- or 6-membered ring optionally substituted with —O— or —N($R^{14}$)—;

$R^{14}$, at each occurrence, is independently selected from H and $C_{1-4}$ alkyl;

$R^{15}$, at each occurrence, is independently selected from
H, $C_{1-4}$ alkyl, $C_{2-4}$ alkenyl, and $C_{2-4}$ alkynyl;

$R^{16}$, at each occurrence, is independently selected from
H, methyl, and ethyl;

$R^{17}$, at each occurrence, is independently selected from
H, methyl, and ethyl;

$R^{31}$, at each occurrence, is independently selected from
H, F, Cl, Br, I, —CN, —NO$_2$, OR$^{32}$, SR$^{32}$, NR$^{32}$R$^{33}$, C(O)H, C(O)R$^{32}$, C(O)OH, C(O)OR$^{32}$, C(O)NR$^{32}$R$^{33}$, OC(O)NR$^{32}$R$^{33}$, NR$^{34}$C(O)R$^{32}$, OC(O)R$^{32}$, CH(=NR$^{34}$)NR$^{32}$R$^{33}$, NHC(=NR$^{34}$)NR$^{32}$R$^{33}$, S(O)R$^{32}$, S(O)$_2$R$^{32}$, S(O)H, S(O)$_2$H, S(O)$_3$H, S(O)NR$^{32}$R$^{33}$, S(O)$_2$NR$^{32}$R$^{33}$, NR$^{34}$S(O)R$^{32}$, NR$^{34}$S(O)$_2$R$^{32}$, NR$^{32}$C(O)R$^{35}$, NR$^{32}$C(O)OR$^{35}$, NR$^{32}$S(O)$_2$R$^{35}$, NR$^{32}$C(O)NHR$^{35}$, tetrazole, $C_{1-4}$ haloalkyl, $C_{1-4}$ alkoxy, $C_{2-4}$ alkenyloxy, $C_{2-4}$ alkynyloxy, ($C_{1-4}$ haloalkyl)oxy, $C_{1-4}$ alkyl, $C_{2-4}$ alkenyl, and $C_{2-4}$ alkynyl;

$R^{32}$, $R^{33}$, $R^{34}$, $R^{35}$, at each occurrence, are independently selected from H, $C_{1-4}$ alkyl, $C_{2-4}$ alkenyl, $C_{2-4}$ alkynyl, and benzyl.

In a still more preferred embodiment, the present invention provides a novel compound of Formula (Id):

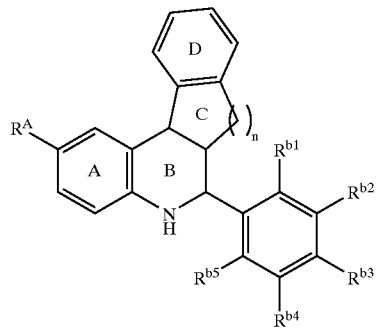

(Id)

or a stereoisomer or pharmaceutically acceptable salt form thereof, wherein;

ring A, including the two atoms of Ring B to which it is attached, is a phenyl ring; wherein, in addition to $R^A$, ring A is substituted with 0–1 $R^{AA}$;

$R^A$ is selected from Cl, OCH$_3$, C(=NH)NH$_2$, C(O)NH$_2$, S(O)$_2$NH$_2$, —NH$_2$, and —CH$_2$NH$_2$;

$R^{AA}$ is H, F, Cl, methoxy, —NH$_2$, and —CH$_2$NH$_2$;

$R^{b1}$, $R^{b2}$, $R^{b3}$, and $R^{b4}$, at each occurrence, are independently selected from
H, F, Cl, Br, I, —CN, —NO$_2$, —OH, OR$^{12}$, SR$^{12}$, NR$^{12}$R$^{13}$, C(O)H, C(O)R$^{12}$, C(O)OR$^{12}$, C(O)NR$^{12}$R$^{13}$, OC(O)NR$^{12}$R$^{13}$, NR$^{14}$C(O)R$^{12}$, OC(O)R$^{12}$, CH(=NR$^{14}$)NR$^{12}$R$^{13}$, NHC(=NR$^{14}$)NR$^{12}$R$^{13}$, S(O)R$^{12}$, S(O)$_2$R$^{12}$, S(O)H, S(O)$_2$H, S(O)NR$^{12}$R$^{13}$, S(O)$_2$NR$^{12}$R$^{13}$, NR$^{14}$S(O)R$^{12}$, NR$^{14}$S(O)$_2$R$^{12}$, NR$^{12}$C(O)R$^{15}$, NR$^{12}$C(O)OR$^{15}$, NR$^{12}$S(O)$_2$R$^{15}$, NR$^{12}$C(O)NHR$^{15}$, (HO)$_2$B—, $C_{1-4}$ haloalkyl, $C_{1-4}$ alkoxy, $C_{2-4}$ alkenyloxy, $C_{2-4}$ alkynyloxy, ($C_{1-4}$ haloalkyl)oxy,
$C_{1-4}$ alkyl substituted with 0–3 $R^{11}$, $C_{2-4}$ alkenyl substituted with 0–3 $R^{11}$, $C_{2-4}$ alkynyl substituted with 0–3 $R^{11}$, and $C_{1-4}$ alkoxy substituted with 0–3 $R^{11}$;

$R^{b5}$ is phenyl substituted with 0–5 $R^{31}$;

n is 1, 2, or 3;

ring D, including the two atoms of Ring C to which it is attached, is a phenyl ring; and ring D is substituted with 0–2 $R^D$;

$R^D$, at each occurrence, is independently selected from
H, halo, —CN, OH, $C_{1-4}$ alkoxy, and $C_{1-4}$ alkyl;

$R^{11}$, at each occurrence, is independently selected from
H, halo, —CN, —NO$_2$, OR$^{12}$, SR$^{12}$, NR$^{12}$R$^{13}$, C(O)H, C(O)R$^{12}$, C(O)NR$^{12}$R$^{13}$, OC(O)NR$^{12}$R$^{13}$, NR$^{14}$C(O)R$^{12}$ C(O)OR$^{12}$, OC(O)R$^{12}$, OC(O)OR$^{12}$, CH(=NR$^{14}$)NR$^{12}$R$^{13}$, NHC(=NR$^{14}$)NR$^{12}$R$^{13}$, S(O)R$^{12}$, S(O)$_2$R$^{12}$, S(O)NR$^{12}$R$^{13}$, S(O)$_2$NR$^{12}$R$^{13}$, NR$^{14}$S(O)R$^{12}$, NR$^{14}$S(O)$_2$R$^{12}$, NR$^{12}$C(O)R$^{15}$, NR$^{12}$C(O)OR$^{15}$, NR$^{12}$S(O)$_2$R$^{15}$, NR$^{12}$C(O)NHR$^{15}$, $C_{1-4}$ haloalkyl, $C_{1-4}$ alkoxy, $C_{2-4}$ alkenyloxy, $C_{2-4}$ alkynyloxy, ($C_{1-4}$ haloalkyl)oxy,
$C_{1-4}$ alkyl substituted with 0–3 $R^{12a}$, $C_{2-4}$ alkenyl substituted with 0–3 $R^{12a}$, $C_{3-6}$ carbocyclic residue substituted with 0–3 $R^{31}$, aryl substituted with 0–5 $R^{31}$, and
5–6 membered heterocyclic ring system containing from 1–4 heteroatoms selected from the group consisting of N, O, and S substituted with 0–3 $R^{31}$;

$R^{12}$, at each occurrence, is independently selected from H, $C_{1-4}$ alkyl substituted with 0–1 $R^{12a}$, $C_{2-4}$ alkenyl substituted with 0–1 $R^{12a}$, $C_{2-4}$ alkynyl substituted with 0–1 $R^{12a}$, $C_{3-6}$ cycloalkyl substituted with 0–3 $R^{31}$, aryl substituted with 0–5 $R^{31}$; $C_{3-10}$ carbocyclic residue substituted with 0–3 $R^{31}$, and
5–10 membered heterocyclic ring system containing from 1–4 heteroatoms selected from the group consisting of N, O, and S substituted with 0–3 $R^{31}$;

$R^{12a}$, at each occurrence, is independently selected from phenyl substituted with 0–5 $R^{31}$;
$C_{3-6}$ carbocyclic residue substituted with 0–3 $R^{31}$, and
5–6 membered heterocyclic ring system containing from 1–4 heteroatoms selected from the group consisting of N, O, and S substituted with 0–3 $R^{31}$;

$R^{13}$, at each occurrence, is independently selected from
H, $C_{1-4}$ alkyl, $C_{2-4}$ alkenyl, and $C_{2-4}$ alkynyl;
alternatively, $R^{12}$ and $R^{13}$ may be combined, along with the nitrogen to which they are attached, to form a 5- or 6-membered ring optionally substituted with —O— or —N($R^{14}$)—;

$R^{14}$, at each occurrence, is independently selected from H and $C_{1-4}$ alkyl;

$R^{15}$, at each occurrence, is independently selected from
H, $C_{1-4}$ alkyl, $C_{2-4}$ alkenyl, and $C_{2-4}$ alkynyl;

$R^{31}$, at each occurrence, is independently selected from
H, F, Cl, Br, I, —CN, —NO$_2$, OR$^{32}$, SR$^{32}$, NR$^{32}$R$^{33}$, C(O)H, C(O)R$^{32}$, C(O)OH, C(O)OR$^{32}$, C(O)NR$^{32}$R$^{33}$, OC(O)NR$^{32}$R$^{33}$, NR$^{34}$C(O)R$^{32}$, OC(O)R$^{32}$, CH(=NR$^{34}$)NR$^{32}$R$^{33}$, NHC(=NR$^{34}$)NR$^{32}$R$^{33}$, S(O)R$^{32}$, S(O)$_2$R$^{32}$, S(O)H, S(O)$_2$H, S(O)$_3$H, S(O)NR$^{32}$R$^{33}$, S(O)$_2$NR$^{32}$R$^{33}$, NR$^{34}$S(O)R$^{32}$, NR$^{34}$S(O)$_2$R$^{32}$, NR$^{32}$C(O)R$^{35}$, NR$^{32}$C(O)OR$^{35}$, NR$^{32}$S(O)$_2$R$^{35}$, NR$^{32}$C(O)NHR$^{35}$, tetrazole, $C_{1-4}$ haloalkyl, $C_{1-4}$ alkoxy, $C_{2-4}$ alkenyloxy, $C_{2-4}$ alkynyloxy, ($C_{1-4}$ haloalkyl)oxy, $C_{1-4}$ alkyl, $C_{2-4}$ alkenyl, and $C_{2-4}$ alkynyl;

$R^{32}$, $R^{33}$, $R^{34}$, $R^{35}$, at each occurrence, are independently selected from H, $C_{1-4}$ alkyl, $C_{2-4}$ alkenyl, $C_{2-4}$ alkynyl, and benzyl.

In a still more preferred embodiment, the present invention provides a novel compound of Formula (Id):

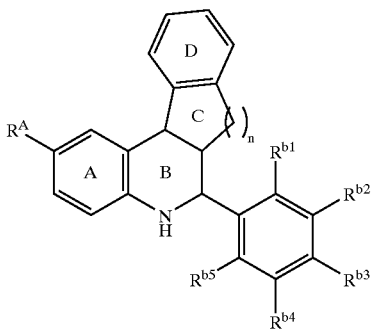

(Id)

or a stereoisomer or pharmaceutically acceptable salt form thereof, wherein;

$R^A$ is $C(=NH)NH_2$ and $-CH_2NH_2$;

$R^{b1}$, $R^{b2}$, $R^{b3}$, and $R^{b4}$, at each occurrence, are independently selected from:

H, F, Cl, Br, I, —CN, —NO$_2$, —OH, $OR^{12}$, $SR^{12}$, $NR^{12}R^{13}$, C(O)H, C(O)$R^{12}$, C(O)O$R^{12}$, C(O)N$R^{12}R^{13}$, OC(O)N$R^{12}R^{13}$, $NR^{14}$C(O)$R^{12}$, OC(O)$R^{12}$, CH(=N$R^{14}$)N$R^{12}R^{13}$, NHC(=N$R^{14}$)N$R^{12}R^{13}$, S(O)$R^{12}$, S(O)$_2R^{12}$, S(O)H, S(O)$_2$H, S(O)N$R^{12}R^{13}$, S(O)$_2$N$R^{12}R^{13}$, $NR^{14}$S(O)$R^{12}$, $NR^{14}$S(O)$_2R^{12}$, $NR^{12}$C(O)$R^{15}$, $NR^{12}$C(O)O$R^{15}$, $NR^{12}$S(O)$_2R^{15}$, $NR^{12}$C(O)NH$R^{15}$, (HO)$_2$B—, —CF$_3$, —OCF$_3$, methoxy, ethoxy, propoxy, butoxy, methyl, ethyl, propyl, butyl, C$_{1-4}$ alkyl substituted with 0–3 $R^{11}$, C$_{2-4}$ alkenyl substituted with 0–3 $R^{11}$, C$_{2-4}$ alkynyl substituted with 0–3 $R^{11}$, and C$_{1-4}$ alkoxy substituted with 0–3 $R^{11}$;

$R^{b5}$ is phenyl substituted with 0–5 $R^{31}$;

n is 1, 2, or 3;

ring D, including the two atoms of Ring C to which it is attached, is a phenyl ring; and ring D is substituted with 0–2 $R^D$;

$R^D$, at each occurrence, is independently selected from

H, F, Cl, Br, OH, methoxy, and methyl;

$R^{11}$, at each occurrence, is independently selected from

H, halo, —CN, —NO$_2$, OH, $OR^{12}$, $SR^{12}$, $NR^{12}R^{13}$, C(O)H, C(O)$R^{12}$, C(O)N$R^{12}R^{13}$, OC(O)N$R^{12}R^{13}$, $NR^{14}$C(O)$R^{12}$, C(O)O$R^{12}$, OC(O)$R^{12}$, OC(O)O$R^{12}$, CH(=N$R^{14}$)N$R^{12}R^{13}$, NHC(=N$R^{14}$)N$R^{12}R^{13}$, S(O)$R^{12}$, S(O)$_2R^{12}$, S(O)N$R^{12}R^{13}$, S(O)$_2$N$R^{12}R^{13}$, $NR^{14}$S(O)$R^{12}$, $NR^{14}$S(O)$_2R^{12}$, $NR^{12}$C(O)$R^{15}$, $NR^{12}$C(O)O$R^{15}$, $NR^{12}$S(O)$_2R^{15}$, $NR^{12}$C(O)NH$R^{15}$, —CF$_3$, —OCF$_3$, methoxy, ethoxy, propoxy, butoxy, C$_{1-4}$ alkyl substituted with 0–3 $R^{12a}$, C$_{2-4}$ alkenyl substituted with 0–3 $R^{12a}$, C$_{3-6}$ carbocyclic residue substituted with 0–3 $R^{31}$, phenyl substituted with 0–5 $R^{31}$, and 5–6 membered heterocyclic ring system selected from furanyl, thienyl, pyrrolyl, pyrrolidinyl, imidazolyl, pyrazolyl, pyridinyl, pyrimidinyl, and N-morpholinyl, said heterocyclic ring system substituted with 0–3 $R^{31}$;

$R^{12}$, at each occurrence, is independently selected from H,

C$_{1-4}$ alkyl substituted with 0–1 $R^{12a}$, C$_{2-4}$ alkenyl substituted with 0–1 $R^{12a}$, C$_{2-4}$ alkynyl substituted with 0–1 $R^{12a}$, C$_{3-6}$ cycloalkyl substituted with 0–3 $R^{31}$, phenyl substituted with 0–5 $R^{31}$; and 5–6 membered heterocyclic ring system selected from furanyl, thienyl, pyrrolyl, pyrrolidinyl, imidazolyl, pyrazolyl, pyridinyl, and pyrimidinyl, said heterocyclic ring system substituted with 0–3 $R^{31}$;

$R^{12a}$, at each occurrence, is independently selected from phenyl substituted with 0–5 $R^{31}$;

C$_{3-6}$ carbocyclic residue substituted with 0–3 $R^{31}$, and

5–6 membered heterocyclic ring system selected from furanyl, thienyl, pyrrolyl, pyrrolidinyl, imidazolyl, pyrazolyl, pyridinyl, and pyrimidinyl, said heterocyclic ring system substituted with 0–3 $R^{31}$;

$R^{13}$, at each occurrence, is independently selected from

H, methyl, ethyl, propyl, butyl, ethenyl, propenyl, butenyl, ethynyl, propynyl, and butynyl;

alternatively, $R^{12}$ and $R^{13}$ may be combined, along with the nitrogen to which they are attached, to form a 5- or 6-membered ring optionally substituted with —O— or —N($R^{14}$)—;

$R^{14}$, at each occurrence, is independently selected from H, methyl, ethyl, propyl, and butyl;

$R^{15}$, at each occurrence, is independently selected from

H, methyl, ethyl, propyl, butyl, ethenyl, propenyl, butenyl, ethynyl, propynyl, and butynyl;

$R^{31}$, at each occurrence, is independently selected from

H, F, Cl, Br, I, —CN, —NO$_2$, —OH, —O$R^{32}$, —S$R^{32}$, —N$R^{32}R^{33}$, —C(O)H, —C(O)$R^{32}$, —C(O)OH, —C(O)O$R^{32}$, —C(O)N$R^{32}R^{33}$, —OC(O)N$R^{32}R^{33}$, —N$R^{34}$C(O)$R^{32}$, —OC(O)$R^{32}$, —CH(=N$R^{34}$) N$R^{32}R^{33}$, —NHC(=N$R^{34}$)N$R^{32}R^{33}$, —S(O)$R^{32}$, —S(O)$_2R^{32}$, —S(O)H, —S(O)$_2$H, —S(O)$_3$H, —S(O) N$R^{32}R^{33}$, —S(O)$_2$N$R^{32}R^{33}$, —S(O)$_2$NH$_2$, —N$R^{34}$S (O)$R^{32}$, —N$R^{34}$S(O)$_2R^{32}$, —N$R^{32}$C(O)$R^{35}$, —N$R^{32}$C (O)O$R^{35}$, —N$R^{32}$S(O)$_2R^{35}$, —N$R^{32}$C(O)NH$R^{35}$, tetrazolyl, —CF$_3$, —OCF$_3$, methoxy, ethoxy, n-propoxy, i-propoxy, methyl, ethyl, n-propyl, i-propyl, n-butyl, i-butyl, s-butyl, t-butyl, hydroxymethyl-, hydroxyethyl-, vinyl, and allyl;

$R^{32}$, $R^{33}$, $R^{34}$, $R^{35}$, at each occurrence, are independently selected from H, methyl, ethyl, n-propyl, i-propyl, n-butyl, i-butyl, s-butyl, t-butyl, and benzyl.

In a still more preferred embodiment, the present invention provides a novel compound of Formula (Id):

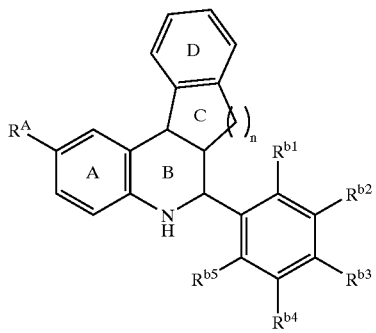

(Id)

or a stereoisomer or pharmaceutically acceptable salt form thereof, wherein;

$R^A$ is $C(=NH)NH_2$ and $-CH_2NH_2$;

n is 1 or 2;

$R^{b1}$, $R^{b2}$, $R^{b3}$, and $R^{b4}$, at each occurrence, are independently selected from:

H, F, Cl, Br, cyano, nitro, methyl, ethyl, n-propyl, i-propyl, vinyl, allyl, hydroxy, hydroxymethyl, hydroxyethyl, methoxy, ethoxy, n-propoxy, i-propoxy, allyloxy-, methyl-S—, ethyl-S—, n-propyl-S—, i-propyl-S—, allyl-S—, —CF$_3$, —CHF$_2$, —OCF$_3$, —SCF$_3$, —CO$_2$H, —C(=O)OCH$_3$, —C(=O)CH$_3$, —SO$_2$CH$_3$, and —SO$_2$CH$_2$CH$_3$;

$R^{b5}$ is phenyl substituted with 0–5 $R^{31}$;

$R^{31}$, at each occurrence, is independently selected from
H, F, Cl, Br, I, —CN, —NO$_2$, —OH, —OR$^{32}$, —SR$^{32}$, —NR$^{32}$R$^{33}$, —C(O)H, —C(O)R$^{32}$, —C(O)OH, —C(O)OR$^{32}$, —C(O)NR$^{32}$R$^{33}$, —OC(O)NR$^{32}$R$^{33}$, —NR$^{34}$C(O)R$^{32}$, —OC(O)R$^{32}$, —CH(=NR$^{34}$)NR$^{32}$R$^{33}$, —NHC(=NR$^{34}$)NR$^{32}$R$^{33}$, —S(O)R$^{32}$, —S(O)$_2$R$^{32}$, —S(O)H, —S(O)$_2$H, —S(O)$_3$H, —S(O)NR$^{32}$R$^{33}$, —S(O)$_2$NR$^{32}$R$^{33}$, —S(O)$_2$NH$_2$, —NR$^{34}$S(O)R$^{32}$, —NR$^{34}$S(O)$_2$R$^{32}$, —NR$^{32}$C(O)R$^{35}$, —NR$^{32}$C(O)OR$^{35}$, —NR$^{32}$S(O)$_2$R$^{35}$, —NR$^{32}$C(O)NHR$^{35}$, tetrazolyl, —CF$_3$, —OCF$_3$, methoxy, ethoxy, n-propoxy, i-propoxy, methyl, ethyl, n-propyl, i-propyl, n-butyl, i-butyl, s-butyl, t-butyl, hydroxymethyl-, hydroxyethyl-, vinyl, and allyl; and $R^{32}$, $R^{33}$, $R^{34}$, $R^{35}$, at each occurrence, are independently selected from H, methyl, ethyl, n-propyl, i-propyl, n-butyl, i-butyl, s-butyl, t-butyl, and benzyl.

In a still more preferred embodiment, the present invention provides a novel compound of Formula (Id):

(Id)

or a stereoisomer or pharmaceutically acceptable salt form thereof, wherein;

$R^A$ is C(=NH)NH$_2$ and —CH$_2$NH$_2$;

n is 1 or 2;

$R^{b1}$ is selected from:
H, F, Cl, Br, cyano, nitro, methyl, ethyl, hydroxy, methoxy, ethoxy, n-propoxy, i-propoxy, allyloxy-, methyl-S—, ethyl-S—, n-propyl-S—, i-propyl-S—, allyl-S—, —CF$_3$, —CHF$_2$, —OCF$_3$, —SCF$_3$, —SO$_2$CH$_3$, and —SO$_2$CH$_2$CH$_3$;

$R^{b2}$ is H, methoxy or ethoxy;

$R^{b3}$ is hydroxy;

$R^{b4}$ is selected from:
H, F, Cl, Br, cyano, nitro, methyl, ethyl, hydroxy, methoxy, ethoxy, n-propoxy, i-propoxy, allyloxy-, methyl-S—, ethyl-S—, n-propyl-S—, i-propyl-S—, allyl-S—, —CF$_3$, —CHF$_2$, —OCF$_3$, —SCF$_3$, —SO$_2$CH$_3$, and —SO$_2$CH$_2$CH$_3$;

$R^{b5}$ is phenyl substituted with 0–2 $R^{31}$;

$R^{31}$, at each occurrence, is independently selected from
H, F, Cl, Br, I, —CN, —NO$_2$, —OH, —OR$^{32}$, —SR$^{32}$, —NR$^{32}$R$^{33}$, —C(O)H, —C(O)R$^{32}$, —C(O)OH, —C(O)OR$^{32}$, —C(O)NR$^{32}$R$^{33}$, —OC(O)NR$^{32}$R$^{33}$, —NR$^{34}$C(O)R$^{32}$, —OC(O)R$^{32}$, —CH(=NR$^{34}$)NR$^{32}$R$^{33}$, —NHC(=NR$^{34}$)NR$^{32}$R$^{33}$, —S(O)R$^{32}$, —S(O)$_2$R$^{32}$, —S(O)H, —S(O)$_2$H, —S(O)$_3$H, —S(O)NR$^{32}$R$^{33}$, —S(O)$_2$NR$^{32}$R$^{33}$, —S(O)$_2$NH$_2$, —NR$^{34}$S(O)R$^{32}$, —NR$^{34}$S(O)$_2$R$^{32}$, —NR$^{32}$C(O)R$^{35}$, —NR$^{32}$C(O)OR$^{35}$, —NR$^{32}$S(O)$_2$R$^{35}$, —NR$^{32}$C(O)NHR$^{35}$, tetrazolyl, —CF$_3$, —OCF$_3$, methoxy, ethoxy, n-propoxy, i-propoxy, methyl, ethyl, n-propyl, i-propyl, n-butyl, i-butyl, s-butyl, t-butyl, hydroxymethyl-, hydroxyethyl-, vinyl, and allyl; and $R^{32}$, $R^{33}$, $R^{34}$, $R^{35}$, at each occurrence, are independently selected from H, methyl, ethyl, n-propyl, i-propyl, n-butyl, i-butyl, s-butyl, t-butyl, and benzyl.

In a still more preferred embodiment, the present invention provides a novel compound of Formula (Id):

(Id)

or a stereoisomer or pharmaceutically acceptable salt form thereof, wherein;

$R^A$ is C(=NH)NH$_2$ and —CH$_2$NH$_2$;

n is 1 or 2;

$R^{b1}$ is selected from:
H, F, Cl, Br, cyano, nitro, methyl, ethyl, hydroxy, methoxy, ethoxy, n-propoxy, i-propoxy, allyloxy-, methyl-S—, ethyl-S—, n-propyl-S—, i-propyl-S—, allyl-S—, —CF$_3$, —CHF$_2$, —OCF$_3$, —SCF$_3$, —SO$_2$CH$_3$, and —SO$_2$CH$_2$CH$_3$;

$R^{b2}$ is H, methoxy or ethoxy;

$R^{b3}$ is hydroxy;

$R^{b4}$ is selected from:
H, F, Cl, Br, cyano, nitro, methyl, ethyl, hydroxy, methoxy, ethoxy, n-propoxy, i-propoxy, allyloxy-, methyl-S—, ethyl-S—, n-propyl-S—, i-propyl-S—, allyl-S—, —CF$_3$, —CHF$_2$, —OCF$_3$, —SCF$_3$, —SO$_2$CH$_3$, and —SO$_2$CH$_2$CH$_3$; and $R^{b5}$ is phenyl-; 2-chloro-phenyl-; 2-fluoro-phenyl-; 2-cyano-phenyl-; 2-HO$_2$C-phenyl-; 2-methyl-phenyl-; 2-ethyl-phenyl-; 2-methoxy-phenyl-; 2-ethoxy-phenyl-; 2-H$_3$CS-phenyl-; 2-trifluoromethoxy-phenyl-; 3-fluoro-phenyl-; 3-chloro-phenyl-; 3-HO$_2$C-phenyl-; 3-H$_2$NCO-phenyl-; 3-cyano-phenyl-; 3-HOCH$_2$-phenyl-; 3-H$_2$NSO$_2$-phenyl-; 3-F$_3$C-phenyl-; 3-F$_3$CO-phenyl-; 4-methyl-phenyl-; 4-ethyl-phenyl-; 4-i-Pr-phenyl-; 4-i-butyl-phenyl-; 4-t-butyl-phenyl-; 4-MeSO$_2$NH-phenyl-; 4-HO$_2$C-phenyl-; 4-H$_2$NCO-phenyl-; 4-(methyl-NHCO)-phenyl-; 4-(ethyl-NHCO)-phenyl-; 4-(n-propyl-NHCO)-phenyl-; 4-(i-propyl-NHCO)-phenyl-; 4-(i-butyl—NHCO)-phenyl-; 4-methoxy-phenyl-; 4-ethoxy-phenyl-; 4-H$_3$CS-phenyl-; 4-trifluoromethoxy-phenyl-; 4-cyano-phenyl-; 4-HOCH$_2$-phenyl-; 4-MeSO$_2$-phenyl-; 4-H$_2$NSO$_2$-phenyl-; 4-trifluoromethyl-phenyl-; 4-Me2N-phenyl-; 4-tetrazol-5-yl-phenyl-; 2,4-bis-trifluoromethyl-phenyl-; 3,5-difluoro-phenyl-; 2,6-difluoro-phenyl-; 2,4-dichloro-phenyl-; 2,5-dimethoxy-phenyl-; 2,4-dimethoxy-phenyl-; 2,6-dimethoxy-phenyl-; 2-methoxy-4-cyclohexylNHCO-phenyl-; 2-methoxy-4-cyclopentylNHCO-phenyl-; 2-methoxy-4-cyclobutylNHCO-phenyl-; 2-methoxy-4-cyclopropylNHCO-phenyl-; 2-methoxy-4-HO$_2$C-phenyl-; 2-methoxy-4-iBuNHCO-phenyl-; 2-methoxy-5-fluoro-phenyl-; 2-methoxy-5-chloro-phenyl-; 2-methoxy-5-methyl-phenyl-; 2-methoxy-5-ethyl-phenyl-;

2-methoxy-5-i-propyl-phenyl-; or 4-(iBu-NHCO)-2-HO₂C-phenyl-.

In a still more preferred embodiment, the present invention provides a novel compound of Formula (I), (Ia), (Ib), (Ic), (Id), (Ie), or (If) wherein:
X is —NH—; and
R^B is

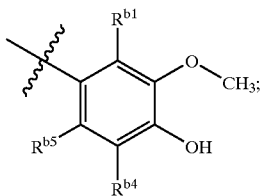

or a stereoisomer or pharmaceutically acceptable salt form thereof.

In a still more preferred embodiment, the present invention provides a novel compound of Formula (Ie):

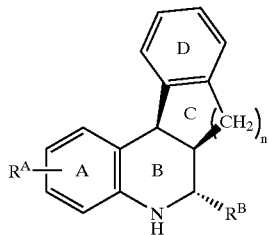

(Ie)

or pharmaceutically acceptable salt form thereof.

In a still more preferred embodiment, the present invention provides a novel compound of Formula (If):

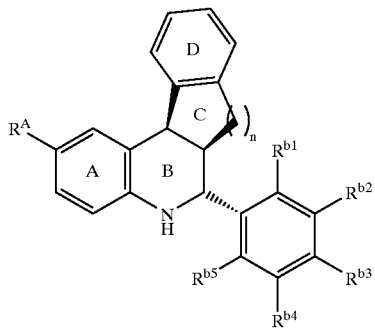

(If)

or pharmaceutically acceptable salt form thereof.

In a still more preferred embodiment, the present invention provides a novel compound selected from:
6-(3-Chloro-phenyl)-5,6a,7,11b-tetrahydro-6H-indeno[2,1-c]quinoline-3-carboxamidine;
6-(4-Hydroxy-3-methoxy-phenyl)-5,6a,7,11b-tetrahydro-6H-indeno[2,1-c]quinoline-2-carboxamidine;
6-(4-Hydroxy-3-ethoxy-phenyl)-5,6a,7,11b-tetrahydro-6H-indeno[2,1-c]quinoline-2-carboxamidine;
6-(2,3-Dimethoxy-phenyl)-5,6a,7,11b-tetrahydro-6H-indeno[2,1-c]quinoline-2-carboxamidine;
6-(2,5-Dimethoxy-phenyl)-5,6a,7,11b-tetrahydro-6H-indeno[2,1-c]quinoline-2-carboxamidine;
6-(2-Hydroxy-3-methoxy-phenyl)-5,6a,7,11b-tetrahydro-6H-indeno[2,1-c]quinoline-2-carboxamidine;
6-(2-Hydroxy-5-methoxy-phenyl)-5,6a,7,11b-tetrahydro-6H-indeno[2,1-c]quinoline-2-carboxamidine,
6-(2,3,4-Trimethoxy-phenyl)-5,6a,7,11b-tetrahydro-6H-indeno[2,1-c]quinoline-2-carboxamidine;
6-(4-Methoxy-2,3-dimethyl-phenyl)-5,6a,7,11b-tetrahydro-6H-indeno[2,1-c]quinoline-2-carboxamidine;
6-(4-Methoxy-2,5-dimethyl-phenyl)-5,6a,7,11b-tetrahydro-6H-indeno[2,1-c]quinoline-2-carboxamidine;
6-(3-Hydroxy-4-methoxy-phenyl)-5,6a,7,11b-tetrahydro-6H-indeno[2,1-c]quinoline-2-carboxamidine;
6-(4-Methoxy-phenyl)-5,6a,7,11b-tetrahydro-6H-indeno[2,1-c]quinoline-2-carboxamidine;
6-(4-Hydroxy-3,5-dimethoxy-phenyl)-5,6a,7,11b-tetrahydro-6H-indeno[2,1-c]quinoline-2-carboxamidine;
4-(2-Carbamimidoyl-5,6a,7,11b-tetrahydro-6H-indeno[2,1-c]quinolin-6-yl)-benzoic acid methyl ester;
6-(4-Hydroxy-3-methoxy-5-nitro-phenyl)-5,6a,7,11b-tetrahydro-6H-indeno[2,1-c]quinoline-2-carboxamidine;
6-(3-Hydroxy-4,5-dimethoxy-phenyl)-5,6a,7,11b-tetrahydro-6H-indeno[2,1-c]quinoline-2-carboxamidine;
6-(2-Hydroxy-3-methoxy-5-nitro-phenyl)-5,6a,7,11b-tetrahydro-6H-indeno[2,1-c]quinoline-2-carboxamidine;
(5-Chloro-2-methoxy-phenyl)-carbamic acid 4-(2-carbamimidoyl-5,6a,7,11b-tetrahydro-6H-indeno[2,1-c]quinolin-6-yl)-2-methoxy-phenyl ester;
6-(6-Bromo-2-hydroxy-3-methoxy-phenyl)-5,6a,7,11b-tetrahydro-6H-indeno[2,1-c]quinoline-2-carboxamidine;
6-(2-Fluoro-5-methoxy-phenyl)-5,6a,7,11b-tetrahydro-6H-indeno[2,1-c]quinoline-2-carboxamidine;
6-(2-Benzyloxy-3-methoxy-phenyl)-5,6a,7,11b-tetrahydro-6H-indeno[2,1-c]quinoline-2-carboxamidine;
6-(2-Fluoro-4-methoxy-phenyl)-5,6a,7,11b-tetrahydro-6H-indeno[2,1-c]quinoline-2-carboxamidine;
6-(3-Iodo-4,5-dimethoxy-phenyl)-5,6a,7,11b-tetrahydro-6H-indeno[2,1-c]quinoline-2-carboxamidine;
6-[2-(2,6-Dichloro-benzyloxy)-phenyl]-5,6a,7,11b-tetrahydro-6H-indeno[2,1-c]quinoline-2-carboxamidine;
6-[2-(4-Chloro-phenylthio)-phenyl]-5,6a,7,11b-tetrahydro-6H-indeno[2,1-c]quinoline-2-carboxamidine;
6-Benzo[1,3]dioxol-4-yl-5,6a,7,11b-tetrahydro-6H-indeno[2,1-c]quinoline-2-carboxamidine;
6-(2-Benzyloxy-phenyl)-5,6a,7,11b-tetrahydro-6H-indeno[2,1-c]quinoline-2-carboxamidine;
6-(2-Allyloxy-phenyl)-5,6a,7,11b-tetrahydro-6H-indeno[2,1-c]quinoline-2-carboxamidine;
6-(5-Bromo-2-methoxy-phenyl)-5,6a,7,11b-tetrahydro-6H-indeno[2,1-c]quinoline-2-carboxamidine;
6-[3-(4-Methoxy-phenoxy)-phenyl]-5,6a,7,11b-tetrahydro-6H-indeno[2,1-c]quinoline-2-carboxamidine;
6-(3,4-Dimethoxy-phenyl)-5,6a,7,11b-tetrahydro-6H-indeno[2,1-c]quinoline-2-carboxamidine;
6-(4-Methanesulfonyl-phenyl)-5,6a,7,11b-tetrahydro-6H-indeno[2,1-c]quinoline-2-carboxamidine;
6-[4-(2-Hydroxy-ethoxy)-phenyl]-5,6a,7,11b-tetrahydro-6H-indeno[2,1-c]quinoline-2-carboxamidine;
6-(2-Chloro-3,4-dimethoxy-phenyl)-5,6a,7,11b-tetrahydro-6H-indeno[2,1-c]quinoline-2-carboxamidine;
6-(2-Hydroxy-6-methoxy-phenyl)-5,6a,7,11b-tetrahydro-6H-indeno[2,1-c]quinoline-2-carboxamidine;
3-(2-Carbamimidoyl-5,6a,7,11b-tetrahydro-6H-indeno[2,1-c]quinolin-6-yl)-benzoic acid methyl ester;
5-(2-Carbamimidoyl-5,6a,7,11b-tetrahydro-6H-indeno[2,1-c]quinolin-6-yl)-2-methoxybenzeneboronic acid;
6-(3-Bromo-4-hydroxy-5-methoxy-phenyl)-5,6a,7,11b-tetrahydro-6H-indeno[2,1-c]quinoline-2-carboxamidine;
6-Pentafluorophenyl-5,6a,7,11b-tetrahydro-6H-indeno[2,1-c]quinoline-2-carboxamidine;
6-(2,4-Dichloro-phenyl)-5,6a,7,11b-tetrahydro-6H-indeno[2,1-c]quinoline-2-carboxamidine;

6-(2-Chloro-6-fluoro-phenyl)-5,6a,7,11b-tetrahydro-6H-indeno[2,1-c]quinoline-2-carboxamidine;
6-(3,4-Dichloro-phenyl)-5,6a,7,11b-tetrahydro-6H-indeno[2,1-c]quinoline-2-carboxamidine;
6-(3,5-Dichloro-phenyl)-5,6a,7,11b-tetrahydro-6H-indeno[2,1-c]quinoline-2-carboxamidine;
6-[3-(3,5-Dichloro-phenoxy)-phenyl]-5,6a,7,11b-tetrahydro-6H-indeno[2,1-c]quinoline-2-carboxamidine;
6-(3-Benzyloxy-phenyl)-5,6a,7,11b-tetrahydro-6H-indeno[2,1-c]quinoline-2-carboxamidine;
6-(3-Trifluoromethyl-phenyl)-5,6a,7,11b-tetrahydro-6H-indeno[2,1-c]quinoline-2-carboxamidine;
6-(4-Bromo-phenyl)-5,6a,7,11b-tetrahydro-6H-indeno[2,1-c]quinoline-2-carboxamidine;
6-(4-Fluoro-phenyl)-5,6a,7,11b-tetrahydro-6H-indeno[2,1-c]quinoline-2-carboxamidine;
6-(4-Chloro-phenyl)-5,6a,7,11b-tetrahydro-6H-indeno[2,1-c]quinoline-2-carboxamidine;
6-(4-Ethoxy-phenyl)-5,6a,7,11b-tetrahydro-6H-indeno[2,1-c]quinoline-2-carboxamidine;
6-(4-Methoxy-naphthalen-1-yl)-5,6a,7,11b-tetrahydro-6H-indeno[2,1-c]quinoline-2-carboxamidine;
6-(4-Trifluoromethyl-phenyl)-5,6a,7,11b-tetrahydro-6H-indeno[2,1-c]quinoline-2-carboxamidine;
6-(2,3-Difluoro-phenyl)-5,6a,7,11b-tetrahydro-6H-indeno[2,1-c]quinoline-2-carboxamidine;
6-(2,4-Difluoro-phenyl)-5,6a,7,11b-tetrahydro-6H-indeno[2,1-c]quinoline-2-carboxamidine;
6-(2,5-Difluoro-phenyl)-5,6a,7,11b-tetrahydro-6H-indeno[2,1-c]quinoline-2-carboxamidine;
6-(3,4-Difluoro-phenyl)-5,6a,7,11b-tetrahydro-6H-indeno[2,1-c]quinoline-2-carboxamidine;
6-(3-Chloro-4-fluoro-phenyl)-5,6a,7,11b-tetrahydro-6H-indeno[2,1-c]quinoline-2-carboxamidine;
6-(4-Pyrrolidin-1-yl-phenyl)-5,6a,7,11b-tetrahydro-6H-indeno[2,1-c]quinoline-2-carboxamidine;
6-(5-Bromo-2-ethoxy-phenyl)-5,6a,7,11b-tetrahydro-6H-indeno[2,1-c]quinoline-2-carboxamidine;
6-(4-Trifluoromethoxy-phenyl)-5,6a,7,11b-tetrahydro-6H-indeno[2,1-c]quinoline-2-carboxamidine;
6-(4-Propyl-phenyl)-5,6a,7,11b-tetrahydro-6H-indeno[2,1-c]quinoline-2-carboxamidine;
6-(3-Bromo-4-fluoro-phenyl)-5,6a,7,11b-tetrahydro-6H-indeno[2,1-c]quinoline-2-carboxamidine;
6-(2,2-Dimethyl-chroman-6-yl)-5,6a,7,11b-tetrahydro-6H-indeno[2,1-c]quinoline-2-carboxamidine;
6-(2,3,6-Trifluoro-phenyl)-5,6a,7,11b-tetrahydro-6H-indeno[2,1-c]quinoline-2-carboxamidine;
6-(2,4,5-Trifluoro-phenyl)-5,6a,7,11b-tetrahydro-6H-indeno[2,1-c]quinoline-2-carboxamidine;
6-(2,4,6-Trifluoro-phenyl)-5,6a,7,11b-tetrahydro-6H-indeno[2,1-c]quinoline-2-carboxamidine;
6-(2,3,4-Trifluoro-phenyl)-5,6a,7,11b-tetrahydro-6H-indeno[2,1-c]quinoline-2-carboxamidine;
6-(2-Fluoro-3-trifluoromethyl-phenyl)-5,6a,7,11b-tetrahydro-6H-indeno[2,1-c]quinoline-2-carboxamidine;
6-(2-Fluoro-6-trifluoromethyl-phenyl)-5,6a,7,11b-tetrahydro-6H-indeno[2,1-c]quinoline-2-carboxamidine;
6-(3-Fluoro-5-trifluoromethyl-phenyl)-5,6a,7,11b-tetrahydro-6H-indeno[2,1-c]quinoline-2-carboxamidine;
6-(4-Fluoro-2-trifluoromethyl-phenyl)-5,6a,7,11b-tetrahydro-6H-indeno[2,1-c]quinoline-2-carboxamidine;
6-(2,3,5-Trifluoro-phenyl)-5,6a,7,11b-tetrahydro-6H-indeno[2,1-c]quinoline-2-carboxamidine;
6-[2-(4-tert-Butyl-phenoxy)-5-nitro-phenyl]-5,6a,7,11b-tetrahydro-6H-indeno[2,1-c]quinoline-2-carboxamidine;
6-(2-Chloro-5-trifluoromethyl-phenyl)-5,6a,7,11b-tetrahydro-6H-indeno[2,1-c]quinoline-2-carboxamidine;
6-(4-Chloro-2-fluoro-phenyl)-5,6a,7,11b-tetrahydro-6H-indeno[2,1-c]quinoline-2-carboxamidine;
6-(4-Chloro-3-fluoro-phenyl)-5,6a,7,11b-tetrahydro-6H-indeno[2,1-c]quinoline-2-carboxamidine;
6-(2-Benzylmercapto-5-nitro-phenyl)-5,6a,7,11b-tetrahydro-6H-indeno[2,1-c]quinoline-2-carboxamidine;
6-(2-Morpholin-4-yl-5-nitro-phenyl)-5,6a,7,11b-tetrahydro-6H-indeno[2,1-c]quinoline-2-carboxamidine;
6-(3-Phenyl-1H-pyrazol-4-yl)-5,6a,7,11b-tetrahydro-6H-indeno[2,1-c]quinoline-2-carboxamidine;
6-(2,4-Dioxo-1,2,3,4-tetrahydro-pyrimidin-5-yl)-5,6a,7,11b-tetrahydro-6H-indeno[2,1-c]quinoline-2-carboxamidine;
6-(2-Phenyl-1H-imidazol-4-yl)-5,6a,7,11b-tetrahydro-6H-indeno[2,1-c]quinoline-2-carboxamidine;
6-(1H-Imidazol-4-yl)-5,6a,7,11b-tetrahydro-6H-indeno[2,1-c]quinoline-2-carboxamidine;
6-(5-Methyl-1H-pyrazol-4-yl)-5,6a,7,11b-tetrahydro-6H-indeno[2,1-c]quinoline-2-carboxamidine;
6-Thiophen-2-yl-5,6a,7,11b-tetrahydro-6H-indeno[2,1-c]quinoline-2-carboxamidine;
6-[5-(3-Trifluoromethyl-phenyl)-furan-2-yl]-5,6a,7,11b-tetrahydro-6H-indeno[2,1-c]quinoline-2-carboxamidine;
6-[5-(2-Chloro-phenyl)-furan-2-yl]-5,6a,7,11b-tetrahydro-6H-indeno[2,1-c]quinoline-2-carboxamidine;
6-[5-(2,5-Dichloro-phenyl)-furan-2-yl]-5,6a,7,11b-tetrahydro-6H-indeno[2,1-c]quinoline-2-carboxamidine;
6-[5-(2-Trifluoromethoxy-phenyl)-furan-2-yl]-5,6a,7,11b-tetrahydro-6H-indeno[2,1-c]quinoline-2-carboxamidine;
6-(4,5-Dibromo-thiophen-2-yl)-5,6a,7,11b-tetrahydro-6H-indeno[2,1-c]quinoline-2-carboxamidine;
6-[5-(1-Methyl-5-trifluoromethyl-1H-pyrazol-3-yl)-thiophen-2-yl]-5,6a,7,11b-tetrahydro-6H-indeno[2,1-c]quinoline-2-carboxamidine;
6-(3-Phenoxy-phenyl)-5,6,6a,7,8,12b-hexahydro-benzo[k]phenanthridine-3-carboxamidine;
6-(2-Chloro-4-fluoro-phenyl)-5,6,6a,7,8,12b-hexahydro-benzo[k]phenanthridine-2-carboxamidine;
6-(4-Hydroxy-3-methoxy-phenyl)-5,6,6a,7,8,12b-hexahydro-benzo[k]phenanthridine-2-carboxamidine;
6-(3,5-Dibromo-4-hydroxy-phenyl)-5,6,6a,7,8,12b-hexahydro-benzo[k]phenanthridine-2-carboxamidine;
6-(3,5-Dimethoxy-phenyl)-5,6,6a,7,8,12b-hexahydro-benzo[k]phenanthridine-2-carboxamidine;
6-(2-Hydroxy-3-methoxy-5-nitro-phenyl)-5,6,6a,7,8,12b-hexahydro-benzo[k]phenanthridine-2-carboxamidine;
Acetic acid 4-(2-carbamimidoyl-5,6,6a,7,8,12b-hexahydro-benzo[k]phenanthridin-6-yl)-2-methoxy-phenyl ester
6-(5-Bromo-2-methoxy-phenyl)-5,6,6a,7,8,12b-hexahydro-benzo[k]phenanthridine-2-carboxamidine;
6-(2-Fluoro-5-methoxy-phenyl)-5,6,6a,7,8,12b-hexahydro-benzo[k]phenanthridine-2-carboxamidine;
3-(2-Carbamimidoyl-5,6,6a,7,8,12b-hexahydro-benzo[k]phenanthridin-6-yl)-benzoic acid methyl ester;
6-(2-Benzyloxy-3-methoxy-phenyl)-5,6,6a,7,8,12b-hexahydro-benzo[k]phenanthridine-2-carboxamidine;
6-(2-Fluoro-4-methoxy-phenyl)-5,6,6a,7,8,12b-hexahydro-benzo[k]phenanthridine-2-carboxamidine;
6-(4-Methanesulfonyl-phenyl)-5,6,6a,7,8,12b-hexahydro-benzo[k]phenanthridine-2-carboxamidine;
6-(2-Benzyloxy-phenyl)-5,6,6a,7,8,12b-hexahydro-benzo[k]phenanthridine-2-carboxamidine;
6-Benzo[1,3]dioxol-4-yl-5,6,6a,7,8,12b-hexahydro-benzo[k]phenanthridine-2-carboxamidine;
6-(3-Trifluoromethyl-phenyl)-5,6,6a,7,8,12b-hexahydro-benzo[k]phenanthridine-2-carboxamidine;
6-(2-Morpholin-4-yl-5-nitro-phenyl)-5,6,6a,7,8,12b-hexahydro-benzo[k]phenanthridine-2-carboxamidine;

6-(4-Hydroxy-naphthalen-1-yl)-5,6,6a,7,8,12b-hexahydro-benzo[k]phenanthridine-2-carboxamidine;
N-[4-(2-Carbamimidoyl-5,6,6a,7,8,12b-hexahydro-benzo[k]phenanthridin-6-yl)-phenyl]-acetamide;
6-(4-Hydroxy-3-iodo-5-methoxy-phenyl)-5,6,6a,7,8,12b-hexahydro-benzo[k]phenanthridine-2-carboxamidine;
6-(3-Bromo-4-hydroxy-5-methoxy-phenyl)-5,6,6a,7,8,12b-hexahydro-benzo[k]phenanthridine-2-carboxamidine;
6-(3-Ethoxy-4-hydroxy-phenyl)-5,6,6a,7,8,12b-hexahydro-benzo[k]phenanthridine-2-carboxamidine;
6-(4-Hydroxy-3,5-dimethyl-phenyl)-5,6,6a,7,8,12b-hexahydro-benzo[k]phenanthridine-2-carboxamidine;
6-(4-Hydroxy-3,5-dimethoxy-phenyl)-5,6,6a,7,8,12b-hexahydro-benzo[k]phenanthridine-2-carboxamidine;
6-(3-Fluoro-4-hydroxy-phenyl)-5,6,6a,7,8,12b-hexahydro-benzo[k]phenanthridine-2-carboxamidine;
6-(4-Hydroxy-3-methyl-phenyl)-5,6,6a,7,8,12b-hexahydro-benzo[k]phenanthridine-2-carboxamidine;
6-(2-Chloro-4-hydroxy-phenyl)-5,6,6a,7,8,12b-hexahydro-benzo[k]phenanthridine-2-carboxamidine;
4-(2-Carbamimidoyl-5,6,6a,7,8,12b-hexahydro-benzo[k]phenanthridin-6-yl)-benzoic acid;
6-Phenethyl-5,6,6a,7,8,12b-hexahydro-benzo[k]-phenanthridine-2-carboxamidine;
6-(3,4-Dimethyl-thieno[2,3-b]thiophen-2-yl)-5,6,6a,7,8,12b-hexahydro-benzo[k]phenanthridine-2-carboxamidine;
6-(4-Phenylethynyl-thiophen-2-yl)-5,6,6a,7,8,12b-hexahydro-benzo[k]phenanthridine-2-carboxamidine;
6-(3-Phenoxy-thiophen-2-yl)-5,6,6a,7,8,12b-hexahydro-benzo[k]phenanthridine-2-carboxamidine;
6–3-(2-Carbamimidoyl-5,6,6a,7,8,12b-hexahydro-benzo[k]phenanthridin-6-yl)-1H-indole-6-carboxylic acid methyl ester;
6-[5-(2-Trifluoromethoxy-phenyl)-furan-2-yl]-5,6,6a,7,8,12b-hexahydro-benzo[k]phenanthridine-2-carboxamidine;
6-(4-Bromo-thiophen-2-yl)-5,6,6a,7,8,12b-hexahydro-benzo[k]phenanthridine-2-carboxamidine;
6-(5-Methyl-thiophen-2-yl)-5,6,6a,7,8,12b-hexahydro-benzo[k]phenanthridine-2-carboxamidine;
6-(3,4-Dibromo-5-methyl-1H-pyrrol-2-yl)-5,6,6a,7,8,12b-hexahydro-benzo[k]phenanthridine-2-carboxamidine;
6-[5-(1-Methyl-5-trifluoromethyl-1H-pyrazol-3-yl)-thiophen-2-yl]-5,6,6a,7,8,12b-hexahydro-benzo[k]phenanthridine-2-carboxamidine;
6-(5-Phenylethynyl-thiophen-2-yl)-5,6,6a,7,8,12b-hexahydro-benzo[k]phenanthridine-2-carboxamidine;
6-(1-Methyl-1H-benzoimidazol-2-yl)-5,6,6a,7,8,12b-hexahydro-benzo[k]phenanthridine-2-carboxamidine;
6-[5-(4-Sulfamoyl-phenyl)-furan-2-yl]-5,6,6a,7,8,12b-hexahydro-benzo[k]phenanthridine-2-carboxamidine;
6-[5-(2-Chloro-phenyl)-furan-2-yl]-5,6,6a,7,8,12b-hexahydro-benzo[k]phenanthridine-2-carboxamidine;
6-(1-Methyl-3-phenyl-5-p-tolylsulfanyl-1H-pyrazol-4-yl)-5,6,6a,7,8,12b-hexahydro-benzo[k]phenanthridine-2-carboxamidine;
6-[5-(2-Trifluoromethyl-phenyl)-furan-2-yl]-5,6,6a,7,8,12b-hexahydro-benzo[k]phenanthridine-2-carboxamidine;
6-(4-Bromo-furan-2-yl)-5,6,6a,7,8,12b-hexahydro-benzo[k]phenanthridine-2-carboxamidine;
6-[2,2']Bithiophenyl-5-yl-5,6,6a,7,8,12b-hexahydro-benzo[k]phenanthridine-2-carboxamidine;
6-[4-(2-Cyano-thiophen-3-ylmethoxy)-phenyl]-5,6,6a,7,8,12b-hexahydro-benzo[k]phenanthridine-2-carboxamidine;
6-[1-(4-Chloro-phenyl)-1H-pyrrol-2-yl]-5,6,6a,7,8,12b-hexahydro-benzo[k]phenanthridine-2-carboxamidine;
6-(2,3-Dibromo-4-hydroxy-5-methoxy-phenyl)-5,6,6a,7,8,12b-hexahydro-benzo[k]phenanthridine-2-carboxamidine;
[4-(2-Carbamimidoyl-5,6,6a,7,8,12b-hexahydro-benzo[k]phenanthridin-6-yl)-2-methoxy-phenoxy]-acetic acid;
6-(1,3-Dioxo-1,3-dihydro-isoindol-2-ylmethyl)-5,6,6a,7,8,12b-hexahydro-benzo[k]phenanthridine-2-carboxamidine;
6-(4-Hydroxy-3-methoxy-phenyl)-5,6a,7,8,9,13b-hexahydro-6H-5-aza-benzo[6,7]cyclohepta[1,2-a]naphthalene-2-carboxamidine;
6-(5-Hydroxy-4'-isopropyl-4-methoxy-biphenyl-2-yl)-5,6a,7,11b-tetrahydro-6H-indeno[2,1-c]quinoline-2-carboxamidine;
2'-(2-Carbamimidoyl-5,6a,7,11b-tetrahydro-6H-indeno[2,1-c]quinolin-6-yl)-5'-hydroxy-4'-methoxy-biphenyl-4-carboxylic acid;
2'-(2-Carbamimidoyl-5,6a,7,11b-tetrahydro-6H-indeno[2,1-c]quinolin-6-yl)-5'-hydroxy-4'-methoxy-biphenyl-4-carboxylic acid isobutyl-amide;
2'-(2-Carbamimidoyl-5,6a,7,11b-tetrahydro-6H-indeno[2,1-c]quinolin-6-yl)-5'-hydroxy-4'-methoxy-biphenyl-2-carboxylic acid;
2'-(2-Carbamimidoyl-5,6a,7,11b-tetrahydro-6H-indeno[2,1-c]quinolin-6-yl)-5'-hydroxy-4'-methoxy-biphenyl-3-carboxylic acid;
6-(5-Hydroxy-4-methoxy-biphenyl-2-yl)-5,6a,7,11b-tetrahydro-6H-indeno[2,1-c]quinoline-2-carboxamidine;
6-(5-Hydroxy-4,2'-dimethoxy-biphenyl-2-yl)-5,6a,7,11b-tetrahydro-6H-indeno[2,1-c]quinoline-2-carboxamidine;
6-(4'-Ethoxy-5-hydroxy-4-methoxy-biphenyl-2-yl)-5,6a,7,11b-tetrahydro-6H-indeno[2,1-c]quinoline-2-carboxamidine;
6-(3'-Cyano-5-hydroxy-4-methoxy-biphenyl-2-yl)-5,6a,7,11b-tetrahydro-6H-indeno[2,1-c]quinoline-2-carboxamidine;
6-(4'-Cyano-5-hydroxy-4-methoxy-biphenyl-2-yl)-5,6a,7,11b-tetrahydro-6H-indeno[2,1-c]quinoline-2-carboxamidine;
6-(5-Hydroxy-3'-hydroxymethyl-4-methoxy-biphenyl-2-yl)-5,6a,7,11b-tetrahydro-6H-indeno[2,1-c]quinoline-2-carboxamidine;
6-(5-Hydroxy-4'-methanesulfonylamino-4-methoxy-biphenyl-2-yl)-5,6a,7,11b-tetrahydro-6H-indeno[2,1-c]quinoline-2-carboxamidine;
6-(5-Hydroxy-4'-methanesulfonyl-4-methoxy-biphenyl-2-yl)-5,6a,7,11b-tetrahydro-6H-indeno[2,1-c]quinoline-2-carboxamidine;
6-(5-Hydroxy-4'-hydroxymethyl-4-methoxy-biphenyl-2-yl)-5,6a,7,11b-tetrahydro-6H-indeno[2,1-c]quinoline-2-carboxamidine;
6-(4-Hydroxy-5-methoxy-2-pyridin-3-yl-phenyl)-5,6a,7,11b-tetrahydro-6H-indeno[2,1-c]quinoline-2-carboxamidine;
6-[2-(2,4-Dimethoxy-pyrimidin-5-yl)-4-hydroxy-5-methoxy-phenyl]-5,6a,7,11b-tetrahydro-6H-indeno[2,1-c]quinoline-2-carboxamidine;
2'-(2-Carbamimidoyl-5,6a,7,11b-tetrahydro-6H-indeno[2,1-c]quinolin-6-yl)-5'-hydroxy-4-isobutylcarbamoyl-4'-methoxy-biphenyl-2-carboxylic acid benzyl ester;
2'-(2-Carbamimidoyl-5,6a,7,11b-tetrahydro-6H-indeno[2,1-c]quinolin-6-yl)-5'-hydroxy-4-isobutylcarbamoyl-4'-methoxy-biphenyl-2-carboxylic acid;
6'-(2-Carbamimidoyl-5,6a,7,11b-tetrahydro-6H-indeno[2,1-c]quinolin-6-yl)-3'-hydroxy-2',4'-dimethoxy-biphenyl-2-carboxylic acid;

2'-(2-Carbamimidoyl-5,6,6a,7,8,12b-hexahydro-benzo[k]
    phenanthridin-6-yl)-5'-hydroxy-4'-methoxy-biphenyl-3-
    carboxylic acid;
2'-(2-Carbamimidoyl-5,6,6a,7,8,12b-hexahydro-benzo[k]
    phenanthridin-6-yl)-5'-hydroxy-4'-methoxy-biphenyl-4-
    carboxylic acid;
2'-(2-Carbamimidoyl-5,6a,7,11b-tetrahydro-6H-indeno[2,1-
    c]quinolin-6-yl)-5'-hydroxy-4'-methoxy-biphenyl-3-
    carboxylic acid amide;
6-(5-Hydroxy-4-methoxy-4'-sulfamoyl-biphenyl-2-yl)-5,6a,
    7,11b-tetrahydro-6H-indeno[2,1-c]quinoline-2-
    carboxamidine;
6-(5-Hydroxy-4-methoxy-3'-sulfamoyl-biphenyl-2-yl)-5,6a,
    7,11b-tetrahydro-6H-indeno[2,1-c]quinoline-2-
    carboxamidine;
2'-(2-Carbamimidoyl-5,6,6a,7,8,12b-hexahydro-benzo[k]
    phenanthridin-6-yl)-5'-hydroxy-4'-methoxy-biphenyl-2-
    carboxylic acid;
6'-(2-Carbamimidoyl-5,6a,7,11b-tetrahydro-6H-indeno[2,1-
    c]quinolin-6-yl)-3'-hydroxy-2',4'-dimethoxy-biphenyl-3-
    carboxylic acid;
6'-(2-Carbamimidoyl-5,6a,7,11b-tetrahydro-6H-indeno[2,1-
    c]quinolin-6-yl)-3'-hydroxy-2',4'-dimethoxy-biphenyl-4-
    carboxylic acid;
6-(4-Hydroxy-5-methoxy-2-thiophen-3-yl-phenyl)-5,6a,7,
    11b-tetrahydro-6H-indeno[2,1-c]quinoline-2-
    carboxamidine;
6-(5-Hydroxy-4,2',5'-trimethoxy-biphenyl-2-yl)-5,6a,7,11b-
    tetrahydro-6H-indeno[2,1-c]quinoline-2-carboxamidine;
6-(2'-Chloro-5-hydroxy-4-methoxy-biphenyl-2-yl)-5,6a,7,
    11b-tetrahydro-6H-indeno[2,1-c]quinoline-2-
    carboxamidine;
6-(5-Hydroxy-4,2',6'-trimethoxy-biphenyl-2-yl)-5,6a,7,11b-
    tetrahydro-6H-indeno[2,1-c]quinoline-2-carboxamidine;
6-(5-Hydroxy-4-methoxy-2'-methylsulfanyl-biphenyl-2-
    yl)-5,6a,7,11b-tetrahydro-6H-indeno[2,1-c]quinoline-2-
    carboxamidine;
6-(5-Hydroxy-4-methoxy-[1,1';2',1"]terphenyl-2-yl)-5,6a,7,
    11b-tetrahydro-6H-indeno[2,1-c]quinoline-2-
    carboxamidine;
6-(5'-Fluoro-5-hydroxy-4,2'-dimethoxy-biphenyl-2-yl)-5,
    6a,7,11b-tetrahydro-6H-indeno[2,1-c]quinoline-2-
    carboxamidine;
6-(2',4'-Dichloro-5-hydroxy-4-methoxy-biphenyl-2-yl)-5,
    6a,7,11b-tetrahydro-6H-indeno[2,1-c]quinoline-2-
    carboxamidine;
6-(2',6'-Difluoro-5-hydroxy-4-methoxy-biphenyl-2-yl)-5,
    6a,7,11b-tetrahydro-6H-indeno[2,1-c]quinoline-2-
    carboxamidine;
6-(5-Hydroxy-4-methoxy-3'-trifluoromethoxy-biphenyl-2-
    yl)-5,6a,7,11b-tetrahydro-6H-indeno[2,1-c]quinoline-2-
    carboxamidine;
6-(3'-Chloro-5-hydroxy-4-methoxy-biphenyl-2-yl)-5,6a,7,
    11b-tetrahydro-6H-indeno[2,1-c]quinoline-2-
    carboxamidine;
6-(5-Hydroxy-4-methoxy-4'-methylsulfanyl-biphenyl-2-
    yl)-5,6a,7,11b-tetrahydro-6H-indeno[2,1-c]quinoline-2-
    carboxamidine;
6-(5-Hydroxy-4-methoxy-2'-methyl-biphenyl-2-yl)-5,6a,7,
    11b-tetrahydro-6H-indeno[2,1-c]quinoline-2-
    carboxamidine;
6-[2-(5-Chloro-thiophen-2-yl)-4-hydroxy-5-methoxy-
    phenyl]-5,6a,7,11b-tetrahydro-6H-indeno[2,1-c]
    quinoline-2-carboxamidine;
6-(5-Hydroxy-5'-isopropyl-4,2'-dimethoxy-biphenyl-2-yl)-
    5,6a,7,11b-tetrahydro-6H-indeno[2,1-c]quinoline-2-
    carboxamidine;

6-(5-Hydroxy-4-methoxy-4'-trifluoromethyl-biphenyl-2-
    yl)-5,6a,7,11b-tetrahydro-6H-indeno[2,1-c]quinoline-2-
    carboxamidine;
6-(5-Hydroxy-4-methoxy-3'-trifluoromethyl-biphenyl-2-
    yl)-5,6a,7,11b-tetrahydro-6H-indeno[2,1-c]quinoline-2-
    carboxamidine;
6-(5-Hydroxy-4,4'-dimethoxy-biphenyl-2-yl)-5,6a,7,11b-
    tetrahydro-6H-indeno[2,1-c]quinoline-2-carboxamidine;
6-(2'-Fluoro-5-hydroxy-4-methoxy-biphenyl-2-yl)-5,6a,7,
    11b-tetrahydro-6H-indeno[2,1-c]quinoline-2-
    carboxamidine;
6-(5-Hydroxy-4,2',4'-trimethoxy-biphenyl-2-yl)-5,6a,7,11b-
    tetrahydro-6H-indeno[2,1-c]quinoline-2-carboxamidine;
6-(5-Hydroxy-4-methoxy-[1,1';3,1"]terphenyl-2-yl)-5,6a,7,
    11b-tetrahydro-6H-indeno[2,1-c]quinoline-2-
    carboxamidine;
6-(5'-Chloro-5-hydroxy-4,2'-dimethoxy-biphenyl-2-yl)-5,
    6a,7,11b-tetrahydro-6H-indeno[2,1-c]quinoline-2-
    carboxamidine;
6-(4'-Dimethylamino-5-hydroxy-4-methoxy-biphenyl-2-
    yl)-5,6a,7,11b-tetrahydro-6H-indeno[2,1-c]quinoline-2-
    carboxamidine;
6-[4-Hydroxy-5-methoxy-2-(6-methoxy-pyridin-3-yl)-
    phenyl]-5,6a,7,11b-tetrahydro-6H-indeno[2,1-c]
    quinoline-2-carboxamidine;
6-(4'-Benzyloxy-5-hydroxy-4-methoxy-biphenyl-2-yl)-5,
    6a,7,11b-tetrahydro-6H-indeno[2,1-c]quinoline-2-
    carboxamidine;
6-(4'-tert-Butyl-5-hydroxy-4-methoxy-biphenyl-2-yl)-5,6a,
    7,11b-tetrahydro-6H-indeno[2,1-c]quinoline-2-
    carboxamidine;
6-(5-Hydroxy-4,2'-dimethoxy-5'-methyl-biphenyl-2-yl)-5,
    6a,7,11b-tetrahydro-6H-indeno[2,1-c]quinoline-2-
    carboxamidine;
6-(5-Hydroxy-4'-isobutyl-4-methoxy-biphenyl-2-yl)-5,6a,7,
    11b-tetrahydro-6H-indeno[2,1-c]quinoline-2-
    carboxamidine;
6-(2'-Ethoxy-5-hydroxy-4-methoxy-biphenyl-2-yl)-5,6a,7,
    11b-tetrahydro-6H-indeno[2,1-c]quinoline-2-
    carboxamidine;
6-(5-Hydroxy-4-methoxy-2'-trifluoromethoxy-biphenyl-2-
    yl)-5,6a,7,11b-tetrahydro-6H-indeno[2,1-c]quinoline-2-
    carboxamidine;
6-(2'-Benzyloxy-5-hydroxy-4-methoxy-biphenyl-2-yl)-5,
    6a,7,11b-tetrahydro-6H-indeno[2,1-c]quinoline-2-
    carboxamidine;
6-(2'-Ethyl-5-hydroxy-4-methoxy-biphenyl-2-yl)-5,6a,7,
    11b-tetrahydro-6H-indeno[2,1-c]quinoline-2-
    carboxamidine;
6-(5-Hydroxy-4-methoxy-4'-phenoxy-biphenyl-2-yl)-5,6a,
    7,11b-tetrahydro-6H-indeno[2,1-c]quinoline-2-
    carboxamidine;
6-(5-Hydroxy-4-methoxy-2',4'-bis-trifluoromethyl-
    biphenyl-2-yl)-5,6a,7,11b-tetrahydro-6H-indeno[2,1-c]
    quinoline-2-carboxamidine;
[2'-(2-Carbamimidoyl-5,6a,7,11b-tetrahydro-6H-indeno[2,
    1-c]quinolin-6-yl)-5'-hydroxy-4'-methoxy-biphenyl-4-
    yl]-carbamic acid benzyl ester;
6-(5-Hydroxy-4-methoxy-4'-trifluoromethoxy-biphenyl-2-
    yl)-5,6a,7,11b-tetrahydro-6H-indeno[2,1-c]quinoline-2-
    carboxamidine;
6-(3',5'-Difluoro-5-hydroxy-4-methoxy-biphenyl-2-yl)-5,
    6a,7,11b-tetrahydro-6H-indeno[2,1-c]quinoline-2-
    carboxamidine;
4-[2-(2-Carbamimidoyl-5,6a,7,11b-tetrahydro-6H-indeno
    [2,1-c]quinolin-6-yl)-5-hydroxy-4-methoxy-phenoxy]-
    benzoic acid;

3-[2-(2-Carbamimidoyl-5,6a,7,11b-tetrahydro-6H-indeno [2,1-c]quinolin-6-yl)-5-hydroxy-4-methoxy-phenoxy]-benzoic acid;
4-[5-Benzyloxy-2-(2-carbamimidoyl-5,6a,7,11b-tetrahydro-6H-indeno[2,1-c]quinolin-6-yl)-4-methoxy-phenoxy]-benzoic acid;
3-[5-Benzyloxy-2-(2-carbamimidoyl-5,6a,7,11b-tetrahydro-6H-indeno[2,1-c]quinolin-6-yl)-4-methoxy-phenoxy]-benzoic acid;
4-(2-Aminomethyl-5,6,6a,7,8,12b-hexahydro-benzo[k]phenanthridin-6-yl)-2-methoxy-phenol;
2'-(2-Aminomethyl-5,6a,7,11b-tetrahydro-6H-indeno[2,1-c]quinolin-6-yl)-5'-hydroxy-4'-methoxy-biphenyl-2-carboxylic acid;
2'-(2-Carbamimidoyl-5,6a,7,11b-tetrahydro-6H-indeno[2,1-c]quinolin-6-yl)-5'-hydroxy-4'-methoxy-biphenyl-4-carboxylic acid amide; and
9-Hydroxy-6-(4-hydroxy-3-methoxy-phenyl)-5,6,6a,7,8,12b-hexahydro-benzo[k]phenanthridine-2-carboxamidine.

In a still more preferred embodiment, the present invention provides a novel compound selected from:

6-(2-Aminomethyl-5,6a,7,11b-tetrahydro-6H-indeno[2,1-c]quinolin-6-yl)-4,2'-dimethoxy-biphenyl-3-ol;
6-(2-Aminomethyl-5,6a,7,11b-tetrahydro-6H-indeno[2,1-c]quinolin-6-yl)-4,2'-dimethoxy-5'-methyl-biphenyl-3-ol;
6-(2-Aminomethyl-5,6a,7,11b-tetrahydro-6H-indeno[2,1-c]quinolin-6-yl)-4-methoxy-2'-methylsulfanyl-biphenyl-3-ol;
6-(2-Aminomethyl-5,6a,7,11b-tetrahydro-6H-indeno[2,1-c]quinolin-6-yl)-2'-fluoro-4-methoxy-biphenyl-3-ol;
6-(2-Aminomethyl-5,6a,7,11b-tetrahydro-6H-indeno[2,1-c]quinolin-6-yl)-5'-fluoro-4,2'-dimethoxy-biphenyl-3-ol;
6-(2-Aminomethyl-5,6a,7,11b-tetrahydro-6H-indeno[2,1-c]quinolin-6-yl)-5'-chloro-4,2'-dimethoxy-biphenyl-3-ol;
6-(2-Aminomethyl-5,6a,7,11b-tetrahydro-6H-indeno[2,1-c]quinolin-6-yl)-2'-ethoxy-4-methoxy-biphenyl-3-ol;
6-(2-Aminomethyl-5,6a,7,11b-tetrahydro-6H-indeno[2,1-c]quinolin-6-yl)-2'-ethyl-4-methoxy-biphenyl-3-ol;
6-(2-Aminomethyl-5,6a,7,11b-tetrahydro-6H-indeno[2,1-c]quinolin-6-yl)-4-methoxy-2'-trifluoromethoxy-biphenyl-3-ol;
6-(2-Aminomethyl-5,6a,7,11b-tetrahydro-6H-indeno[2,1-c]quinolin-6-yl)-2'-benzyloxy-4-methoxy-biphenyl-3-ol;
N-[2'-(2-Aminomethyl-5,6a,7,11b-tetrahydro-6H-indeno[2,1-c]quinolin-6-yl)-5'-hydroxy-4'-methoxy-biphenyl-4-yl]-methanesulfonamide;
6-(2-Aminomethyl-5,6a,7,11b-tetrahydro-6H-indeno[2,1-c]quinolin-6-yl)-4,2',4'-trimethoxy-biphenyl-3-ol;
6-(2-Aminomethyl-5,6a,7,11b-tetrahydro-6H-indeno[2,1-c]quinolin-6-yl)-2',6'-difluoro-4-methoxy-biphenyl-3-ol;
2'-(2-Aminomethyl-5,6a,7,11b-tetrahydro-6H-indeno[2,1-c]quinolin-6-yl)-5'-hydroxy-4'-methoxy-biphenyl-3-carboxylic acid;
2'-(2-Aminomethyl-5,6a,7,11b-tetrahydro-6H-indeno[2,1-c]quinolin-6-yl)-5'-hydroxy-2,4'-dimethoxy-biphenyl-4-carboxylic acid;
4-(2-Aminomethyl-5,6a,7,11b-tetrahydro-6H-indeno[2,1-c]quinolin-6-yl)-2-methoxy-5-(2-methoxy-phenoxy)-phenol;
6-(2-Aminomethyl-5,6a,7,11b-tetrahydro-6H-indeno[2,1-c]quinolin-6-yl)-4,2',6'-trimethoxy-biphenyl-3-ol;
6-[5-Hydroxy-4-methoxy-4'-(1H-tetrazol-5-yl)-biphenyl-2-yl]-5,6a,7,11b-tetrahydro-6H-indeno[2,1-c]quinoline-2-carboxamidine;
2'-(2-Carbamimidoyl-5,6a,7,11b-tetrahydro-6H-indeno[2,1-c]quinolin-6-yl)-5'-hydroxy-2,4'-dimethoxy-biphenyl-4-carboxylic acid;
2'-(2-Carbamimidoyl-5,6a,7,11b-tetrahydro-6H-indeno[2,1-c]quinolin-6-yl)-5'-hydroxy-2,4'-dimethoxy-biphenyl-4-carboxylic acid isobutyl-amide;
2'-(2-Carbamimidoyl-5,6a,7,11b-tetrahydro-6H-indeno[2,1-c]quinolin-6-yl)-5'-hydroxy-2,4'-dimethoxy-biphenyl-4-carboxylic acid benzylamide;
2'-(2-Carbamimidoyl-5,6a,7,11b-tetrahydro-6H-indeno[2,1-c]quinolin-6-yl)-5'-hydroxy-2,4'-dimethoxy-biphenyl-4-carboxylic acid(2-morpholin-4-yl-ethyl)-amide;
2'-(2-Carbamimidoyl-5,6a,7,11b-tetrahydro-6H-indeno[2,1-c]quinolin-6-yl)-5'-hydroxy-2,4'-dimethoxy-biphenyl-4-carboxylic acid cyclohexylamide;
2'-(2-Carbamimidoyl-5,6a,7,11b-tetrahydro-6H-indeno[2,1-c]quinolin-6-yl)-5'-hydroxy-2,4'-dimethoxy-biphenyl-4-carboxylic acid cyclopropylamide; and
2'-(2-Carbamimidoyl-5,6a,7,11b-tetrahydro-6H-indeno[2,1-c]quinolin-6-yl)-5'-hydroxy-2,4'-dimethoxy-biphenyl-4-carboxylic acid(2-pyrrolidin-1-yl-ethyl)-amide;

or a stereoisomer or pharmaceutically acceptable salt form thereof.

In another embodiment, the present invention provides novel pharmaceutical compositions, comprising: a pharmaceutically acceptable carrier and a therapeutically effective amount of a compound of the present invention or a pharmaceutically acceptable salt form thereof.

In another embodiment, the present invention provides a novel method for treating or preventing a thromboembolic disorder, comprising: administering to a patient in need thereof a therapeutically effective amount of a compound of the present invention or a pharmaceutically acceptable salt form thereof.

In another preferred embodiment, the present invention provides a novel method, wherein the thromboembolic disorder is selected from the group consisting of arterial cardiovascular thromboembolic disorders, venous cardiovascular thromboembolic disorders, and thromboembolic disorders in the chambers of the heart.

In another preferred embodiment, the present invention provides a novel method, wherein the thromboembolic disorder is selected from unstable angina, an acute coronary syndrome, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis.

In another embodiment, the present invention provides a novel method of treating a patient in need of thromboembolic disorder treatment, comprising: administering a compound of the present invention or a pharmaceutically acceptable salt form thereof in an amount effective to treat a thromboembolic disorder In another embodiment, the present invention provides a novel method, comprising: administering a compound of the present invention or a pharmaceutically acceptable salt form thereof in an amount effective to treat a thromboembolic disorder.

In another embodiment, the present invention provides a novel method for treating a thromboembolic disorder, comprising: administering to a patient in need thereof a therapeutically effective amount of a first and second therapeutic agent, wherein the first therapeutic agent is compound of the present invention or a pharmaceutically acceptable salt thereof and the second therapeutic agent is at least one agent selected from a second factor Xa inhibitor, an anti-coagulant agent, an anti-platelet agent, a thrombin inhibiting agent, a thrombolytic agent, and a fibrinolytic agent.

In another preferred embodiment, the present invention provides a novel method, wherein the second therapeutic agent is at least one agent selected from warfarin, unfractionated heparin, low molecular weight heparin, synthetic pentasaccharide, hirudin, argatrobanas, aspirin, ibuprofen, naproxen, sulindac, indomethacin, mefenamate, droxicam, diclofenac, sulfinpyrazone, piroxicam, ticlopidine, clopidogrel, tirofiban, eptifibatide, abciximab, melagatran, disulfatohirudin, tissue plasminogen activator, modified tissue plasminogen activator, anistreplase, urokinase, and streptokinase.

In another preferred embodiment, the present invention provides a novel method, wherein the second therapeutic agent is at least one anti-platelet agent.

In another preferred embodiment, the present invention provides a novel method, wherein the anti-platelet agent is aspirin and clopidogrel.

In another preferred embodiment, the present invention provides a novel method, wherein the anti-platelet agent is clopidogrel.

In another embodiment, the present invention provides a novel article of manufacture, comprising:

(a) a first container;

(b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment of a thromboembolic disorder.

In another preferred embodiment, the present invention provides a novel article of manufacture, further comprising:

(d) a second container;

wherein components (a) and (b) are located within the second container and component (c) is located within or outside of the second container.

In another embodiment, the present invention provides a novel article of manufacture, comprising:

(a) a first container;

(b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used in combination with a second therapeutic agent to treat a thromboembolic disorder.

In another preferred embodiment, the present invention provides a novel article of manufacture, further comprising:

(d) a second container;

wherein components (a) and (b) are located within the second container and component (c) is located within or outside of the second container.

In another embodiment, the present invention provides novel compounds as described above for use in therapy.

In another embodiment, the present invention provides the use of novel compounds as described above for the manufacture of a medicament for the treatment of a thromboembolic disorder.

DEFINITIONS

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated. All processes used to prepare compounds of the present invention and intermediates made therein are considered to be part of the present invention. Tautomers of compounds shown or described herein are considered to be part of the present invention.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. For example, 1,3-dioxo-1,3-dihydro-isoindolyl may be a 1,3-dihydro-isoindole ring system substituted by two keto substituents; or 2,4-dioxo-1,2,3,4-tetrahydro-pyrimidinyl may be a tetrahydro-pyrimidine ring system substituted by two keto substituents. Keto substituents are not present on aromatic moieties.

The present invention is intended to include all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

When any variable (e.g. $R^{11}$) occurs more than one time in any constituent or formula for a compound, its definition at each occurrence is independent of its definition at every other occurrence. Thus, for example, if a group is shown to be substituted with 0–3 $R^{11}$, then said group may optionally be substituted with up to three $R^{11}$ groups and $R^{11}$ at each occurrence is selected independently from the definition of $R^{11}$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "alkyl" is intended to include both branched and straight-chain saturated aliphatic hydrocarbon groups having the specified number of carbon atoms. $C_{1-10}$ alkyl, is intended to include $C_1$, $C_2$, $C_3$, $C_4$, $C_5$, $C_6$, $C_7$, $C_8$, $C_9$, and $C_{10}$ alkyl groups. Examples of alkyl include, but are not limited to, methyl, ethyl, n-propyl, i-propyl, n-butyl, s-butyl, t-butyl, n-pentyl, and s-pentyl.

"Haloalkyl", as used herein, is intended to include both branched and straight-chain saturated aliphatic hydrocarbon groups having the specified number of carbon atoms, substituted with 1 or more halogen (for example —$C_vF_w$ where v=1 to 3 and w=1 to (2v+1)). Examples of haloalkyl include, but are not limited to, trifluoromethyl, trichloromethyl, pentafluoroethyl, and pentachloroethyl.

"Alkoxy", as used herein, represents an alkyl group as defined above with the indicated number of carbon atoms attached through an oxygen bridge. $C_{1-10}$ alkoxy, is intended to include $C_1$, $C_2$, $C_3$, $C_4$, $C_5$, $C_6$, $C_7$, $C_8$, $C_9$, and $C_{10}$ alkoxy groups. Examples of alkoxy include, but are not limited to, methoxy, ethoxy, n-propoxy, i-propoxy, n-butoxy, s-butoxy, t-butoxy, n-pentoxy, and s-pentoxy.

"Cycloalkyl", as used herein, is intended to include saturated ring groups, such as cyclopropyl, cyclobutyl, or cyclopentyl. $C_{3-7}$ cycloalkyl is intended to include $C_3$, $C_4$, $C_5$, $C_6$, and $C_7$ cycloalkyl groups.

"Alkenyl", as used herein, is intended to include hydrocarbon chains of either straight or branched configuration and one or more unsaturated carbon-carbon bonds that may occur in any stable point along the chain, such as ethenyl and propenyl. $C_{2-10}$ alkenyl is intended to include $C_2$, $C_3$, $C_4$, $C_5$, $C_6$, $C_7$, $C_8$, $C_9$, and $C_{10}$ alkenyl groups.

"Alkynyl", as used herein, is intended to include hydrocarbon chains of either straight or branched configuration and one or more triple carbon-carbon bonds that may occur in any stable point along the chain, such as ethynyl and propynyl. $C_{2-10}$ Alkynyl is intended to include $C_2$, $C_3$, $C_4$, $C_5$, $C_6$, $C_7$, $C_8$, $C_9$, and $C_{10}$ alkynyl groups.

"Halo" or "halogen" as used herein refers to fluoro, chloro, bromo, and iodo; and "counterion" is used to represent a small, negatively charged species such as chloride, bromide, hydroxide, acetate, and sulfate.

As used herein, "aryl" is intended to mean an aromatic moiety containing the specified number of carbon atoms, such as phenyl or naphthyl.

As used herein, "aromatic system" is intended to mean a five or six membered aromatic moiety, fused to Ring B or Ring C, containing carbon atoms and zero, one or two heteroatoms selected from N, S, or O. Examples of an aromatic system are phenyl, pyridyl, pyridazinyl, pyrimidinyl, pyrazinyl, imidazolyl, furanyl, and thienyl.

As used herein, "ring system" is intended to mean any stable 5 to 10 membered cyclic group selected from a carbocycle, as defined herein, an aryl, as defined herein, and a heterocyclic ring system, as defined herein. Examples of a ring system include, but are not limited to, phenyl, naphthyl, furanyl, thienyl, pyrrolyl, imidazolyl, triazinyl, thiazolyl, oxazolyl, isoxazolyl, tetrazolyl, pyrazolyl, pyridinyl, pyrimidinyl, quinolinyl, isoquinolinyl, benzofuranyl, benzothiofuranyl, 1H-indazolyl, oxazolidinyl, isoxazolidinyl, benzotriazolyl, benzisoxazolyl, oxindolyl, benzoxazolinyl, indolyl, chromanyl, and benzimidazolyl.

As used herein, "carbocycle" or "carbocyclic residue" is intended to mean any stable 3, 4, 5, 6, or 7-membered monocyclic or bicyclic or 7, 8, 9, 10, 11, 12, or 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane, [2.2.2] bicyclooctane, fluorenyl, phenyl, naphthyl, indanyl, adamantyl, and tetrahydronaphthyl.

As used herein, the term "heterocycle" or "heterocyclic ring system" is intended to mean a stable 5, 6, or 7-membered monocyclic or bicyclic or 7, 8, 9, or 10-membered bicyclic heterocyclic ring which is saturated, partially unsaturated or unsaturated(aromatic), and which consists of carbon atoms and 1, 2, 3, or 4 heteroatoms independently selected from the group consisting of N, O, and S and including any bicyclic group in which any of the above-defined heterocyclic rings is fused to a benzene ring. The nitrogen and sulfur heteroatoms may optionally be oxidized. The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. As used herein, the term "aromatic heterocyclic ring system" or "heteroaryl" is intended to mean a stable 5, 6, or 7-membered monocyclic or bicyclic or 7, 8, 9, or 10-membered bicyclic heterocyclic aromatic ring which consists of carbon atoms and 1, 2, 3, or 4 heteroatoms independently selected from the group consisting of N, O, and S. It is to be noted that total number of S and O atoms in the aromatic heterocycle is not more than 1.

Examples of heterocycles include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2, 3-triazolyl, 1,2,4-triazolyl, 1,2,5-triazolyl, 1,3,4-triazolyl, and xanthenyl. Preferred 5 to 10 membered heterocycles include, but are not limited to, pyridinyl, pyrimidinyl, triazinyl, furanyl, thienyl, thiazolyl, pyrrolyl, pyrazolyl, imidazolyl, oxazolyl, isoxazolyl, tetrazolyl, benzofuranyl, benzothiofuranyl, indolyl, benzimidazolyl, 1H-indazolyl, oxazolidinyl, isoxazolidinyl, benzotriazolyl, benzisoxazolyl, oxindolyl, benzoxazolinyl, quinolinyl, and isoquinolinyl.

Preferred 5 to 6 membered heterocycles include, but are not limited to, pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, tetrazolyl. Also included are fused ring and spiro compounds containing, for example, the above heterocycles.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

Since prodrugs are known to enhance numerous desirable qualities of pharmaceuticals (e.g., solubility, bioavailability, manufacturing, etc.) the compounds of the present invention may be delivered in prodrug form. Thus, the present invention is intended to cover prodrugs of the presently claimed compounds, methods of delivering the same and compositions containing the same. "Prodrugs" are intended to include any covalently bonded carriers that release an active parent drug of the present invention in vivo when such prodrug is administered to a mammalian subject. Prodrugs the present invention are prepared by modifying functional groups present in the compound in such a way that the modifications are cleaved, either in routine manipulation or in vivo, to the parent compound. Prodrugs include compounds of the present invention wherein a hydroxy, amino, sulfhydryl or amidino group is bonded to any group that, when the prodrug of the present invention is administered to a mammalian subject, it cleaves to form a free hydroxyl, free amino, free sulfhydryl or free amidino group, respectively.

Examples of prodrugs include, but are not limited to, acetate, formate and benzoate derivatives of alcohol and amine functional groups in the compounds of the present invention. Preferred prodrugs are amidine prodrugs wherein $R^A$ is $C(=NR^1)NH_2$ or its tautomer $C(=NH)NHR^2$ and $R^1$ or $R^2$ is selected from OH, $C_{1-4}$ alkoxy, $C_{6-10}$ aryloxy, $C_{1-4}$ alkoxycarbonyl, $C_{6-10}$ aryloxycarbonyl, $C_{6-10}$ arylmethylcarbonyl, $C_{1-4}$ alkylcarbonyloxy $C_{1-4}$ alkoxycarbonyl, and $C_{6-10}$ arylcarbonyloxy $C_{1-4}$ alkoxycarbonyl. More preferred prodrugs are where $R^1$ or $R^2$ is OH, methoxy, ethoxy, benzyloxycarbonyl, methoxycarbonyl, or methylcarbonyloxymethoxycarbonyl.

"Stable compound" and "stable structure" are meant to indicate a compound that is sufficiently robust to survive isolation to a useful degree of purity from a reaction mixture, and formulation into an efficacious therapeutic agent.

"Therapeutically effective amount" is intended to include an amount of a compound of the present invention or an amount of the combination of compounds claimed effective to inhibit factor VIIa. The combination of compounds is preferably a synergistic combination. Synergy, as described, for example, by Chou and Talalay, *Adv. Enzyme Regul.* 1984, 22:27–55, occurs when the effect(in this case, inhibition of factor VIIa) of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased antiviral effect, or some other beneficial effect of the combination compared with the individual components.

SYNTHESIS

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art.(See for example 1) March, Jerry; Advanced Organic Chemistry: Reactions, Mechanisms, and Structure, Fourth Edition. USA.(1992), 1495 pp. Publisher: (Wiley, New York, N.Y.) and 2) Larock, R. C.; Synthetic Organic Methodology: Comprehensive Organic Transformations. A Guide to Functional Group Preparations. Fed. Rep. Ger. (1989), 1060 pp. Publisher: (VCH, Weinheim, Fed. Rep. Ger.)) Preferred methods include, but are not limited to, those described below. The reactions are performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Wiley and Sons, 1999). All references cited herein are hereby incorporated in their entirety herein by reference.

The tetrahydroquinoline moieties, TQ, of the present inventionare generally constructed according to the method outlined in Scheme-1. An aniline, A, or salt thereof, is suspended in a suitable solvent, such as acetonitrile. The suspension is treated with a suitably substituted aldehyde, B, and a suitably substituted olefin, C, in stochiometric proportions. A catalyst, such as indium triflate or scandium triflate, is added and the reaction is allowed to react at temperatures ranging from room temperature to 70° C. Reaction times vary from a few hours to 48 hours. The reaction temperature and time is readily recognized by one skilled in the art. The desired products were purified using reverse phase chromatography; a standard method being disclosed herein.

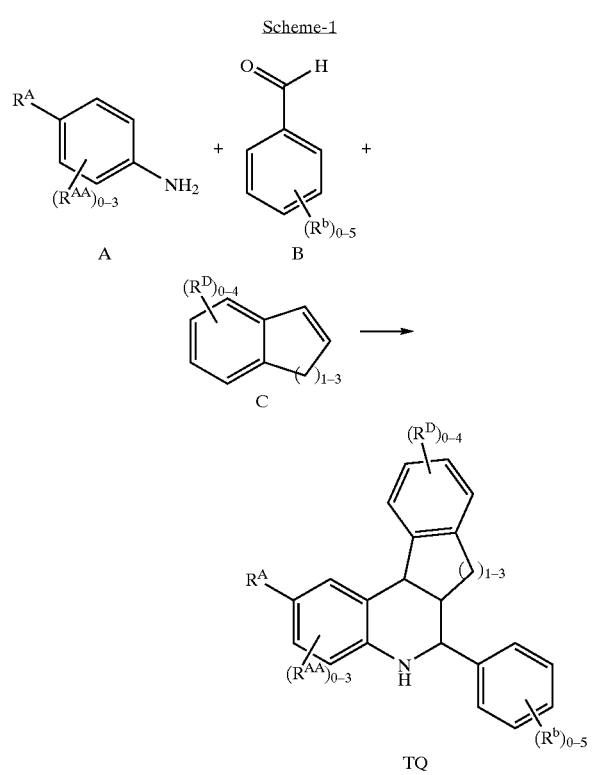

Other features of the invention will become apparent in the course of the following descriptions of exemplary embodiments that are given for illustration of the invention and are not intended to be limiting thereof. The basic reaction for the synthesis of the compounds of formula TQ require 3 components: an aryl amine, A, an aldehyde input, B, and an olefin, C. When the desired inputs for the reaction are not commercially available, they were synthesized according to the methods described below and/or methods readily known to one skilled in the art.

Standard Procedure for Tetrahydroquinoline Synthesis:

As outlined in Scheme-2, an aniline, like 4-amino-benzamidine mono HCl salt, is suspended in a solvent such as acetonitrile. The suspension is treated with a suitably substituted aldehyde, such as 4-acetoxy-3-methoxybenzaldehyde and a suitably substituted olefin, such as dihydronaphthylene, in stochiometric proportions. A catalyst such as indium triflate or scandium triflate is added and the reaction is allowed to react at temperatures ranging from room temperature to 70° C. Reaction times vary from few hours to 48 hours. The desired products were purified using reverse phase chromatography.

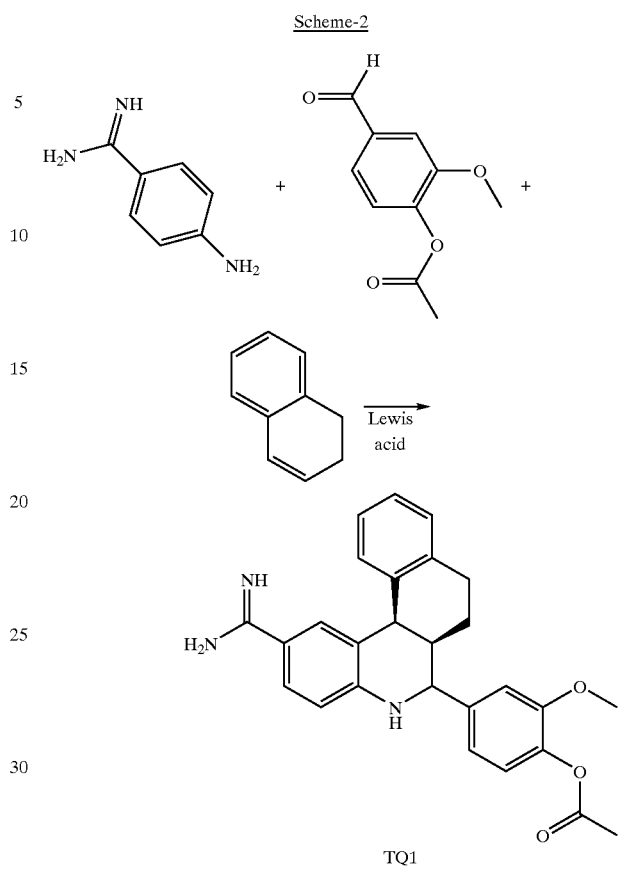

Use of the 3-component reaction for the synthesis of tetrahydroquinolines(TQ): It is realized that a large number of reagents for the construction of the TQ moieties may be obtained from commercial sources. Use of these reagents in the method outlined in Scheme 2 enables the construction of TQ moieties of the present invention. The products from this reaction may be further modified as required. Scheme 2 outlines the synthesis of TQ moieties derived from the aniline, 4-amino-benzamidine mono HCl salt. Alternatively, aryl amines, either commercially available or readily synthesized by one skilled in the art, may also be used. For example, commercial aryl amines like 4-aminobenzonitrile (Scheme 2a) may also be used in this reaction in which case the product, TQ2, is obtained.

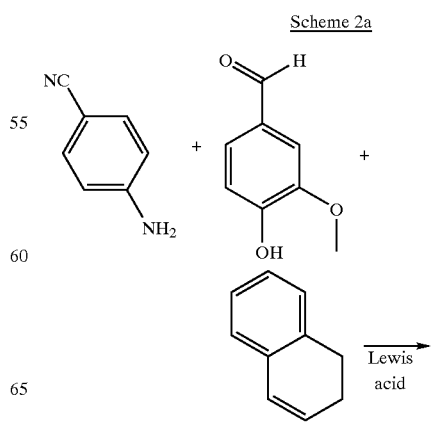

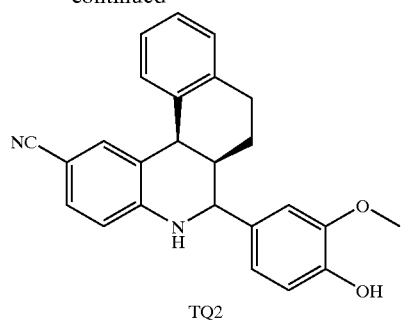

TQ2

Using similar methodology as is outlined in Scheme 2b, protected aryl amines, for example 4-N-Boc-aminomethyl-phenyl amine, may be used to construct the TQ moiety TQ3 that incorporates a protected aminomethyl function into the tetrahydroquinoline.

Scheme 2b

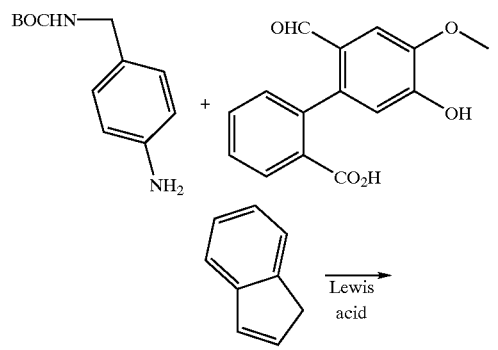

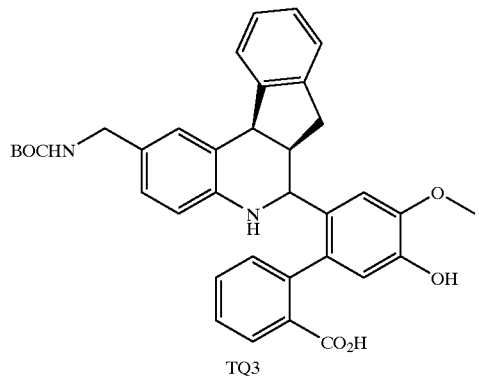

TQ3

Standard procedure for hydrolysis of ester protected phenol compounds: The final compounds containing a free phenol such as compounds of formula (TQ4) are sometimes prepared starting from an ester-containing precursor of formula (TQ1). The following general procedure, as shown in Scheme 3, was used to cleave the ester group in those type of compounds: the tetrahydroquinoline acetate compound was suspended in a suitable solvent like methanol or acetonitrile. A suitable base, like ammonium hydroxide is added and the reaction mixture was stirred for reaction times varying from 30 minutes to 48 hours. Aqueous work up and/or reverse phase purification lead to the desired products containing the free phenol.

Scheme-3

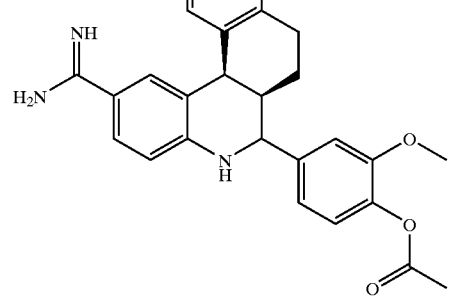

TQ1

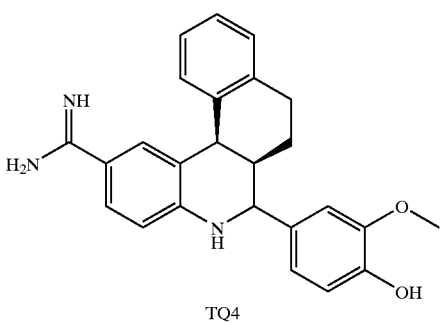

TQ4

When desirable aminomethyl functionality may be incorporated into the final TQ product. This may be accomplished by reduction of the carbonitrile (TQ2, Scheme 2a) with a reagent such as sodium borohydride as outlined in Scheme 3a. In this way reaction with the hydride following aqueous work up yields the benzylamine TQ5.

Scheme 3a

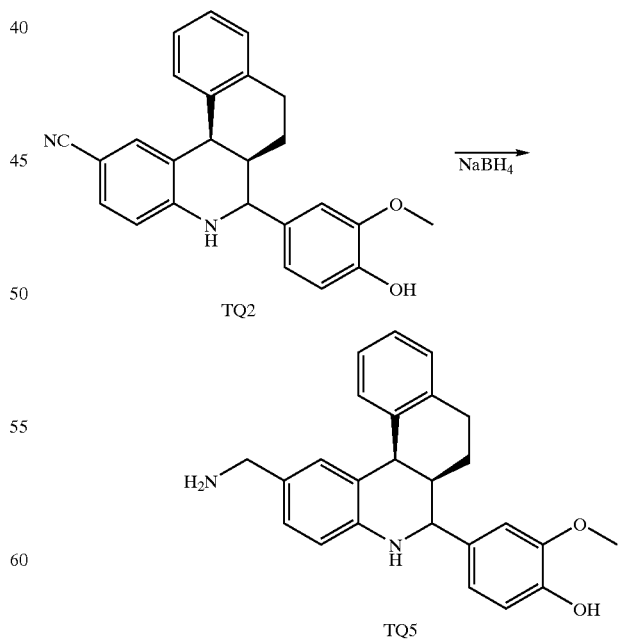

Aminomethyl compounds of this type may also be sometimes prepared through conversion of the protected tetrahydroquinolines such as TQ3 (Scheme 2b) to their deprotected form. Scheme 3b outlines the deprotection of TQ3 in the presence of an acid such as trifluoroacetic acid which results in the generation of the desired benzylamine TQ6.

Scheme 3b

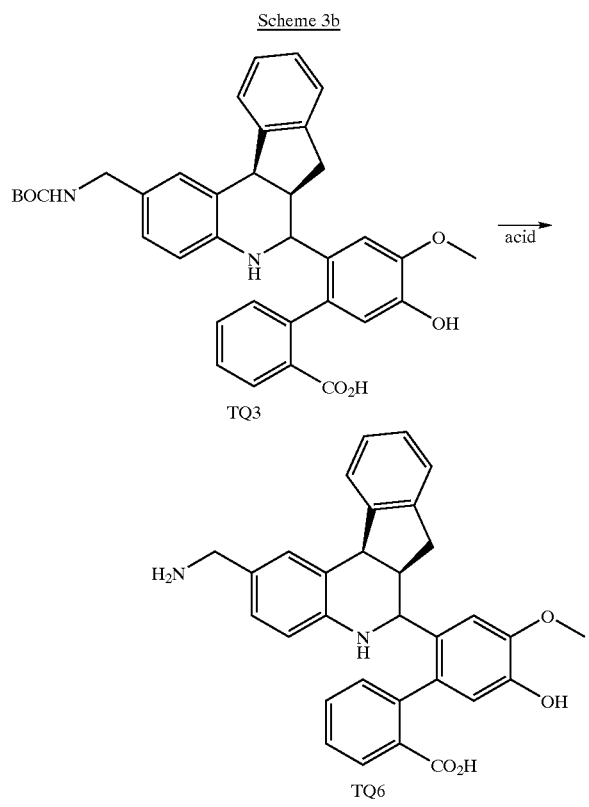

TQ3

TQ6

Amidine compounds TQ4 may be obtained from nitrile compounds TQ2 as shown in Scheme 3c. Treatment of TQ2 with an alcoholic solution of hydrogen chloride, for instance, hydrogen chloride saturated methanol, affords an imidate. The imidate is treated with, for instance, ammonium carbonate in methanol, to generate the amidine compound TQ4. There are alternative methods to convert compounds TQ2 to compounds TQ4. Reaction of TQ2 with excess hydroxylamine in a solvent such as dimethyl sulfoxide gives the amidoxime. Acetylation of the amidoxime with acetic anhydride in methylene chloride and triethylamine, followed by catalytic hydrogenation over 10% palladium on carbon in methanol/acetic acid affords the amidine compound TQ4.

Scheme 3c

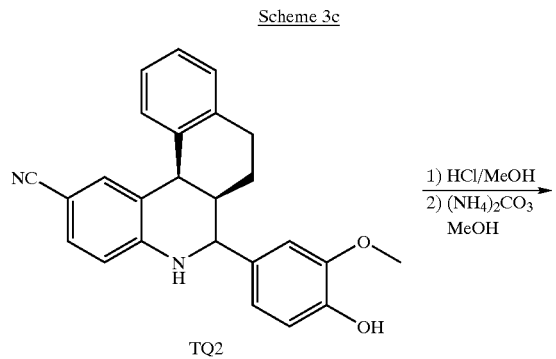

TQ2

1) HCl/MeOH
2) (NH$_4$)$_2$CO$_3$
MeOH

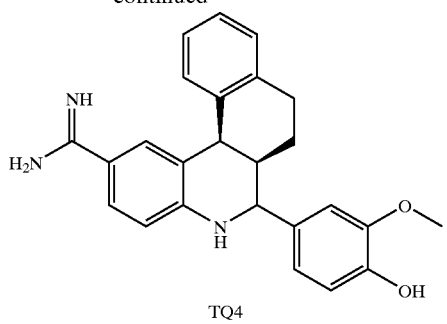

TQ4

Synthesis of substituted inputs for the preparation of tetrahydroquinolines: In cases where tetrahydroquinolines are not accessible from commercial sources a number of straightforward approaches known to those skilled in the art can be employed to prepare samples of the three types of chemical inputs required for the synthesis of the tetrahydroquinoline TQ.

Synthesis of aryl amines: Non-commercial aryl amines of general formula A may be readily accessed from reduction of the corresponding nitro aromatic as taught in "Advanced Organic Chemistry" (Jerry March, Wiley Interscience pg 1103 and references therein) and is outlined in Scheme 4.

Scheme 4

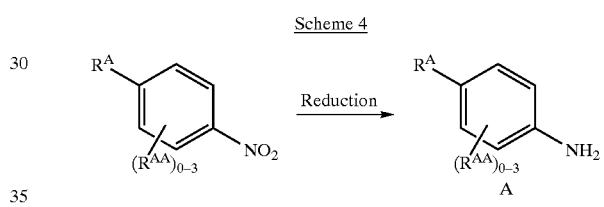

Synthesis of substituted aldehyde inputs: Aldehyde inputs of the general formula B are accessible from a variety of straightforward chemical transformations as is outlined in Scheme 5. In Scheme 5 aldehydes may be obtained through oxidation of the corresponding alcohol or halide as taught in "Advanced Organic Chemistry" (Jerry March, Wiley Interscience pg 1057–60 and pg 1081 and references therein). Alternatively aldehydes may be prepared following reduction of the corresponding carboxylic acid (Scheme 5, R=H) or ester as taught for example in Tetrahedron Letters (1998, 39 (8), 909–910) by Chandrasekhar et al. And Chemistry Letters (1998, (11),1143–1144) by Nagayama et al.

Scheme 5

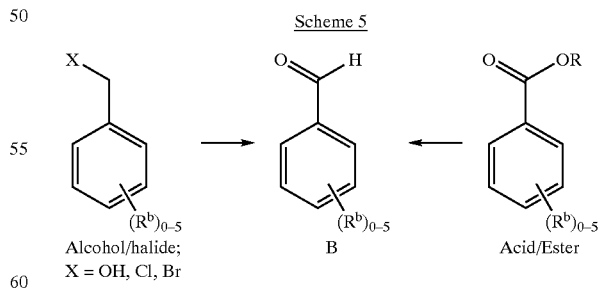

Alcohol/halide;
X = OH, Cl, Br

B

Acid/Ester

Additional features to the present invention include substituted aldehydes of general Formulae (III), (IV) and (V) that are shown below. More specific features of the present invention are the aldehyde inputs of general Formulae (IIIa), (IVa) and (Va) in which the aldehyde is synthesized containing an ortho substitution as either aryl, aryloxy or aryl amino groups. Substituted aldehydes described according to the general Formulae (III), (IV) and (V) may be prepared according to one or more of the methods described for the examples shown below for the aldehydes of Formulae (IIIa), (IVa) and (Va).

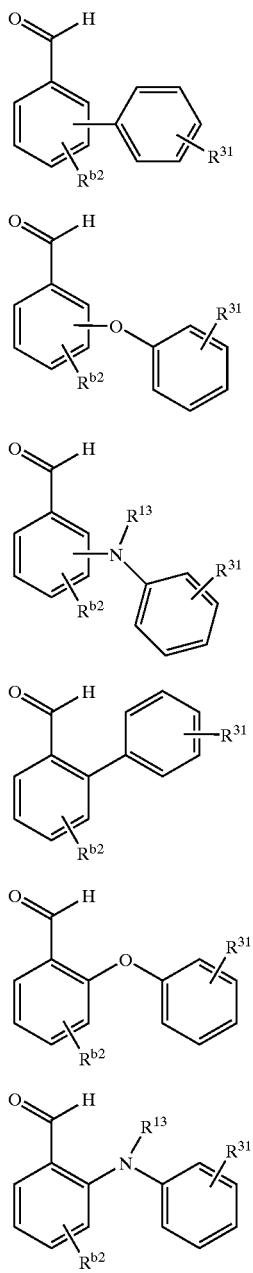

Synthesis of an aldehyde input Formulae (IIIa). Scheme-6 discloses the synthesis of Aryl substituted aldehyde intermediates of general Formulae (IIIa). It is appreciated that one skilled in the art could readily apply the methods described below to make additional substituted biphenyl aldehydes of Formula (III). In this approach, an intermediate aryl bromide such as 4-acetoxy-2-bromo-3-methoxybenzaldehyde (compound 2, Scheme 6) is prepared through electrophilic bromination of the corresponding 4-acetoxy-3-methoxybenzaldehyde (compound 1). The resulting bromide can then be used as a common intermediate for the preparation of bi-aryl intermediates (compound 3) through metal mediated cross coupling reactions of the type described by Fu et al. In Journal of the American Chemical Society (2000, 122, p4020–4028).

In the example shown in Scheme 6, a Suzuki coupling of the bromide 2 with the commercially available acid substituted boronic acids (R=H) yields the acid substituted biphenyls (3,R=H) that may be used directly to synthesize tetrahydroquinolines, TQ. In cases where the acid is protected as an ester functionality, an intermediate deprotection step using alkali base may be utilized to generate the desired acid substituted biphenyl.

Scheme-6

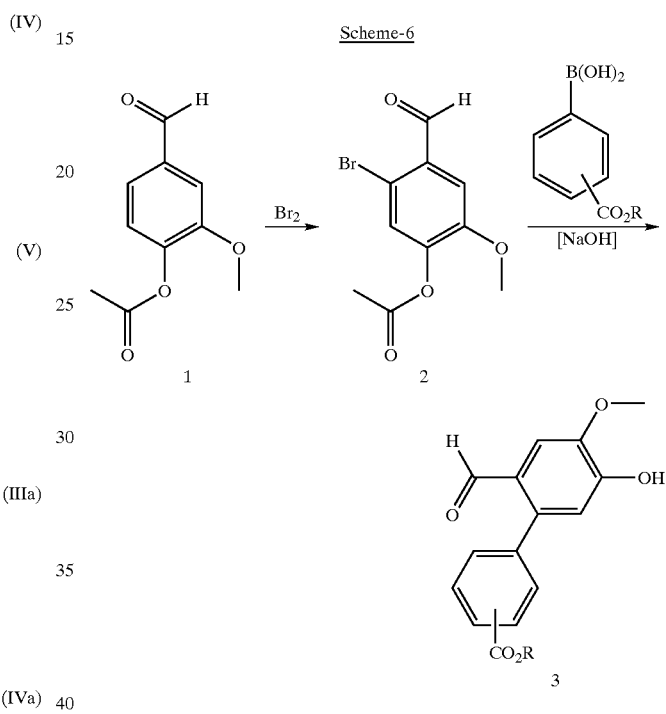

In cases where suitable boronic acids are not commercially available, a modification to this approach may be adopted as is outlined in Scheme 6b. In this case the aryl bromide intermediate, 4-acetoxy-2-bromo-3-methoxybenzaldehyde (compound 4, Scheme 6a) is subjected to a palladium mediated coupling with a diboron species such as bis(pinacolato) diboron. This reaction results in the synthesis of the intermediate 4-Hydroxy-5-methoxy-2-(4,4,5,5-tetramethyl-[1,3,2]dioxaborolan-2-yl)-benzaldehyde (compound 5, Scheme 6a).

Scheme 6a

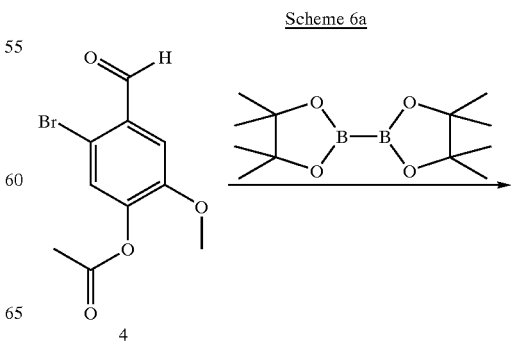

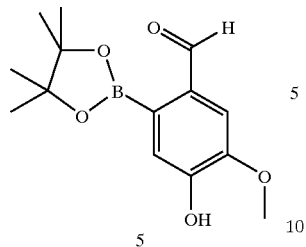

The intermediate pinacolate (5) can be used as a precursor for the synthesis of additional substituted aldehydes of Formula (IIIa) as outlined in Scheme 6b through reaction with an aryl bromide. In this example coupling with 4-bromobenzene sulfonamide (6) facilitates the synthesis of the biphenyl sulfonamide (7).

Scheme 6b

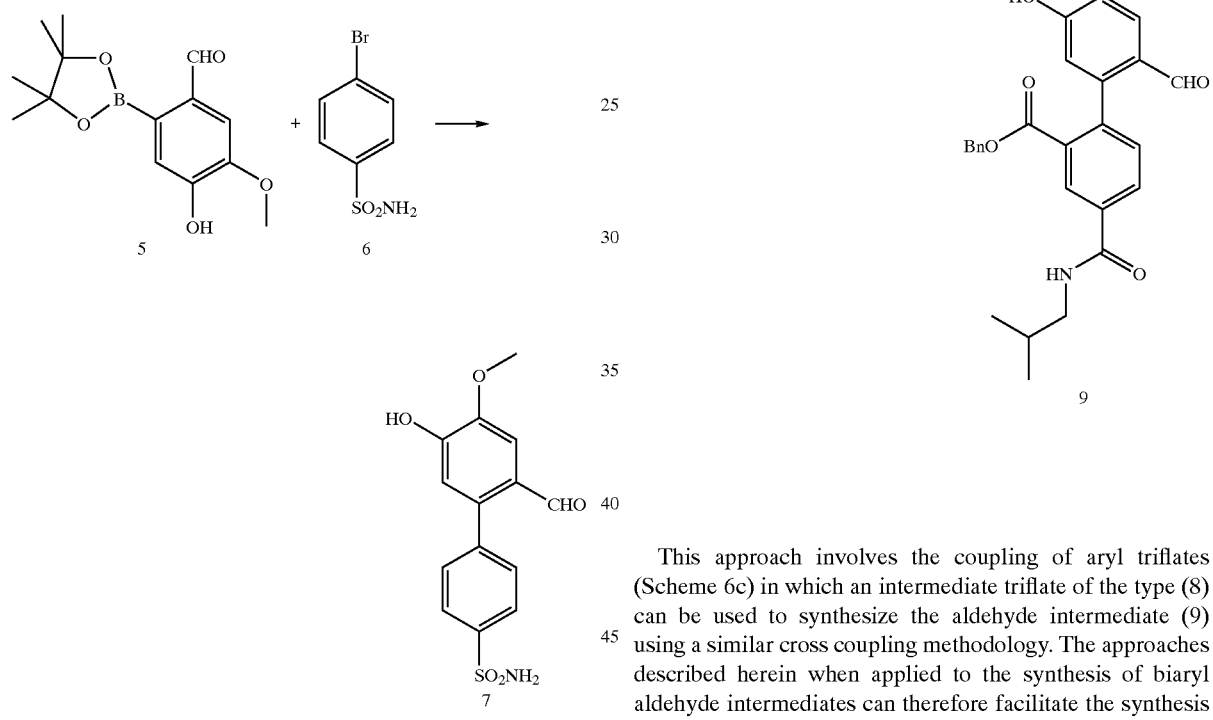

It is also realized that this procedure is not restricted to the coupling of aryl bromides and is also useful for the expansion of the biaryl aldehyde class as is outlined in an additional feature of the present invention described below.

Scheme 6c

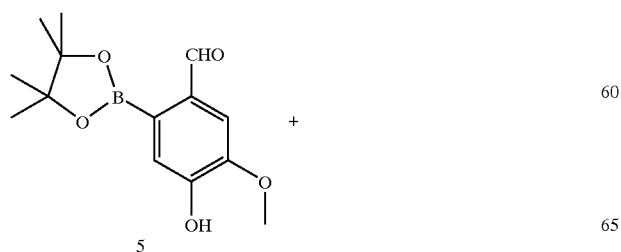

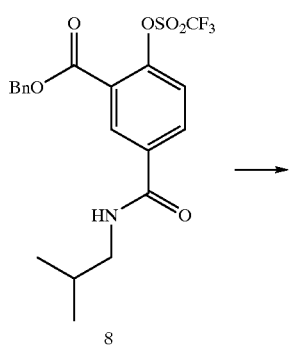

This approach involves the coupling of aryl triflates (Scheme 6c) in which an intermediate triflate of the type (8) can be used to synthesize the aldehyde intermediate (9) using a similar cross coupling methodology. The approaches described herein when applied to the synthesis of biaryl aldehyde intermediates can therefore facilitate the synthesis of a wide range of intermediates derived from either aryl halides or phenols, the precursors to aryl triflates.

It is also realized that the scope of intermediate synthesis can be further extended outside the use of Suzuki methodology since the precursor aryl halides or triflates are also precursors for Stille-type cross coupling methodologies. This methodology can be applied to the synthesis of substituted aldehydes of this type as taught in Tetrahedron letters (2000, 41, 6041–44) by Kohrt et al.

Synthesis of an aldehyde input Formulae (IVa).

Intermediate aldehydes of the general Formula (IVa) may be synthesized according to the chemistry outlined in Scheme 7.

Scheme 7

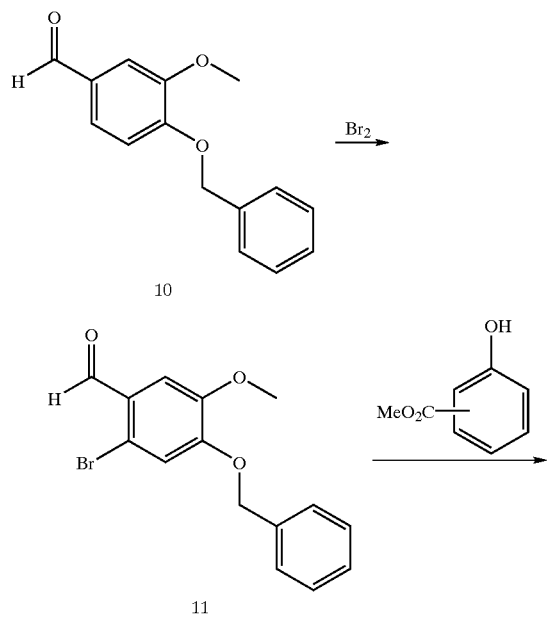

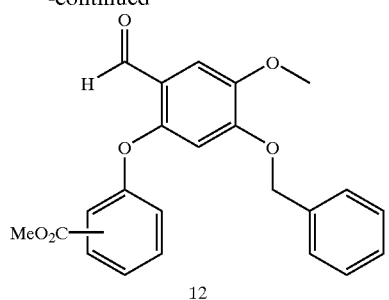

Compounds of Formula (IVa) are synthesized beginning with the preparation of 4-benzyloxy-2-bromo-3-methoxybenzaldehyde (compound 11) from 4-benzyloxy-3-methoxybenzaldehyde (10) via electrophilic bromination. The aryl bromide is a suitable substrate for a copper-mediated displacement of bromide by phenols. In the example shown the ester-substituted phenols can be used to synthesize the intermediate aldehyde (12). This intermediate once isolated can be used directly in the synthesis of the tetrahydroquinolines (TQs) in an analogous manner to the procedure described in Scheme 2.

Scheme 8

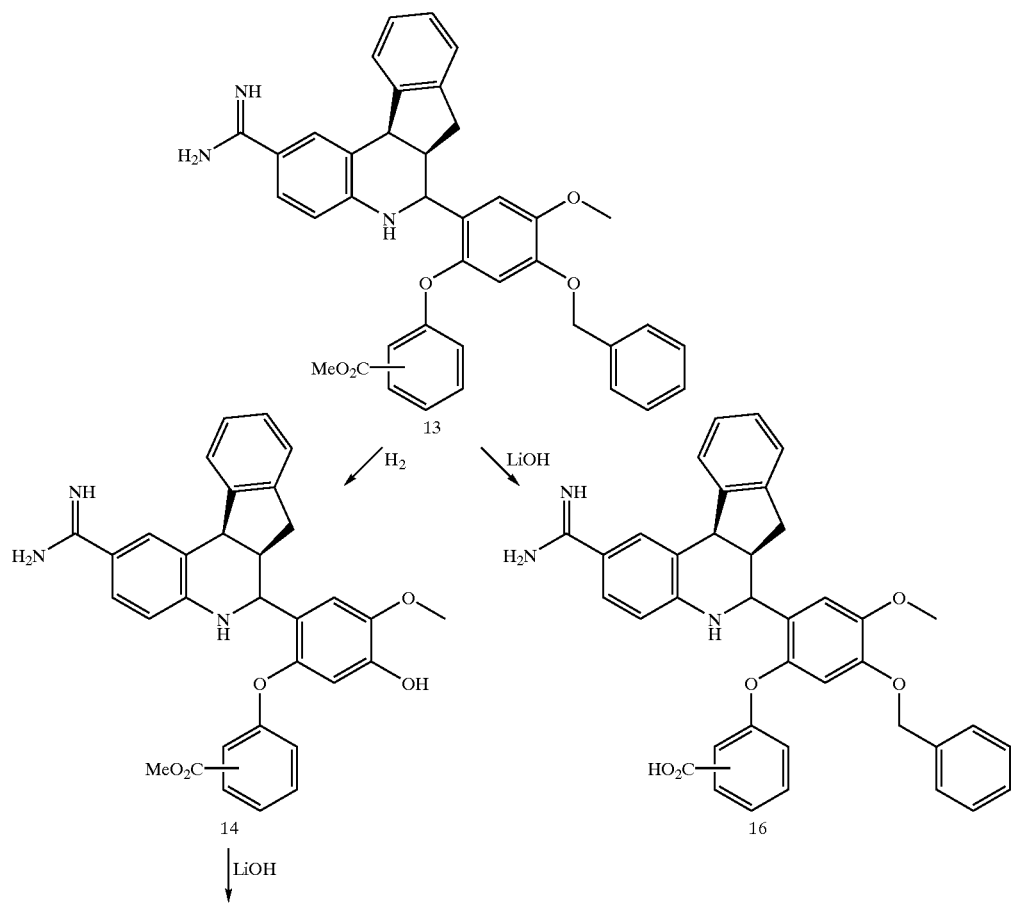

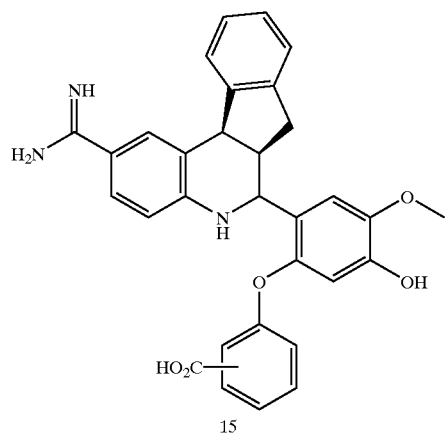

15

Products derived from the tetrahydroquinoline chemistry such as the examples outlined in Scheme 8 (13) may sometimes be further deprotected according to the following procedure. In some cases the tetrahydroquinolines (13) may be treated with hydrogen to generate the intermediates (14). This intermediate is treated with a base such as lithium hydroxide to produce the acids (15). Alternatively (13) may be treated directly with base to generate the products (16).

Synthesis of an aldehyde input Formulae (Va).

Aldehyde intermediates of the general Formula (Va) may be derived using the picolinate derivative (5) described earlier in Scheme 6a. Protection of this intermediate first with acetic anhydride followed by ethylene glycol provides the dioxalanyl compound (5a). This derivative may be effectively coupled with anilines as outlined in Scheme 9 to generate the arylamino protected benzaldehyde intermediate (17) using a coupling methodology similar to that described in Tetrahedron letters (1998, 39, 2933–36) by Chan et al.

Scheme 9

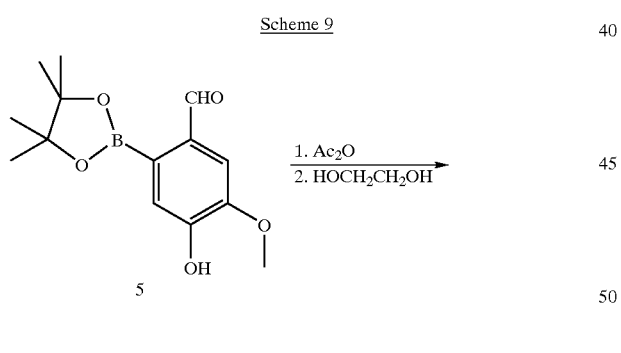

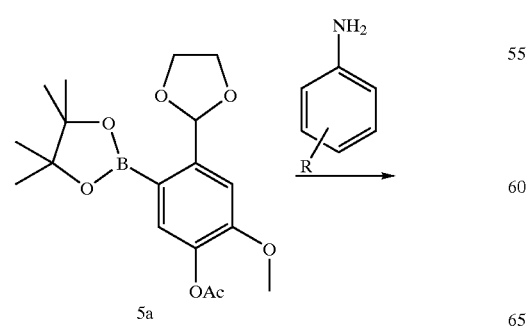

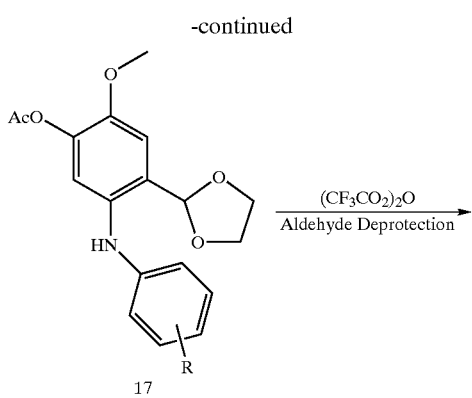

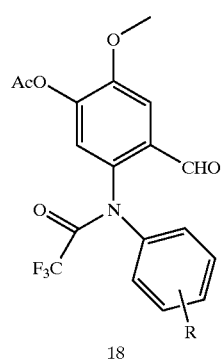

18

Protection of the aniline as the trifluoroacetate followed by deprotection of the dioxolane function provides the intermediate (18). This intermediate may be used directly in the synthesis of the tetrahydroquinolines (TQs) in an analogous manner to the procedure described in Scheme 2. Example compounds (19) synthesized as tetrahydroquinolines in this way may sometimes be deprotected as outlined in Scheme 10 through treatment with a base such as potassium carbonate to yield the desired products (20).

Scheme 10

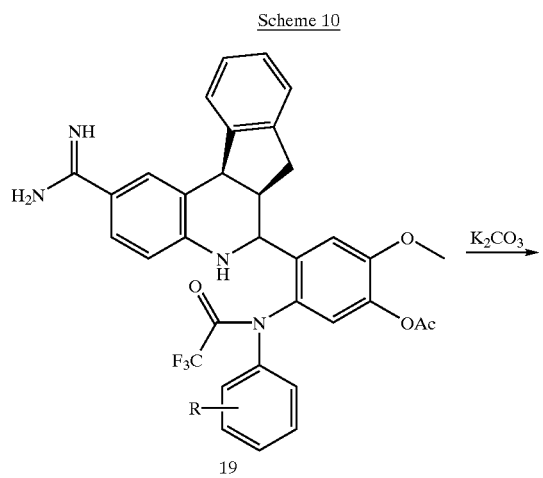

Synthesis of the olefins: Olefins of general Formula (VI) when not commercially available may be prepared according to one or more of the methods described below from either alcohols of general Formula (VIIa) or the ketones of general Formula (VIIb).

VI (VIIa)

(VIIb)

n = 1, 2, 3

A specific example is outlined in Scheme 11. The approach involves initial reduction of the corresponding ketone (21) followed by elimination of the alcohol(22) to produce the olefin (23). The method is general enough for the synthesis of rings where n=1,2,3 . . . providing fused olefins with ring sizes of 5, 6 and 7.

Scheme 11

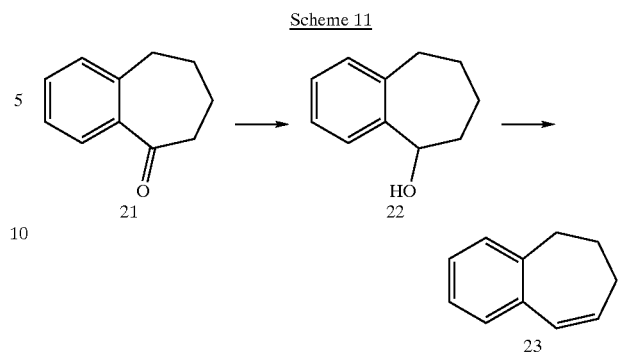

Olefins of this type may be directly prepared through the elimination of the alcohol to the corresponding olefin where the alcohols are available. Scheme 12 outlines a specific example for the substituted napthol (24) that can be converted to the corresponding dihydronapthalene (25, n=2). As previously described the method is general enough to provide bicyclic olefins with variable ring sizes in the olefin-containing moiety up to 5, 6 and 7 member rings

Scheme 12

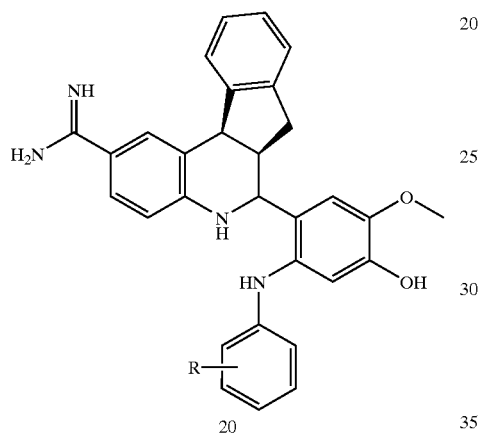

Other specific examples describing the synthesis of olefins of the general Formula(VI) where n=1 from ketones of general Formula(VIIb, n=1) are available in the literature using sodium borohydride to reduce the ketone followed by treatment with para-toluene sulfonic acid to effect the elimination step are described in the Journal of the Chemical Society, Chemical Communications, 1996, (24), 2711–2712).

Similarly, compounds of general Formula (VI) where n=1 and 2 can be obtained from compounds of general Formula (VIIa) according to procedures described by Zhu et al. in J. Org. Chem. (1996, 61, 324–328). In this procedure, methylrhenium trioxide or MTO (0.2 mmol) was dissolved in 15 mL of the desired alcohol with or without a solvent like benzene and allowed to stand for 3 days. The desired olefins were purified by distillation.

Expansion of the chemistry in the synthesis of olefin inputs can be further realized through methodologies taught in the literature. In this way, for example, indenes of general Formulae VIIc, VIId, VIIe and VIIf may be prepared that can be used as the olefin input in the various methods described for the synthesis of tetrahydroquinolines in the present invention.

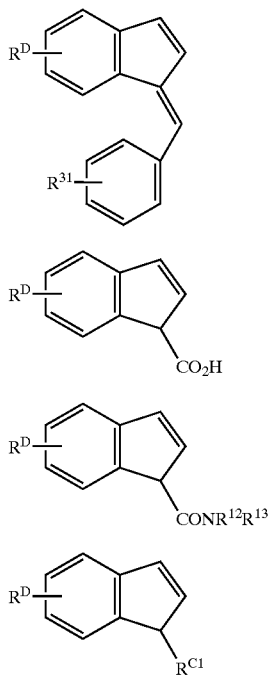

VIIc

VIId

VIIe

VIIf

Indenes may be further functionalized to olefins of general Formula (VIIc) by treating an indene derivative(26, compound of general Formula (VI)) with an aldehyde and potassium fluoride/alumina under refluxing methanol to give the intermediate (27, the compound of general Formula (VIIc),scheme 13). Methods to effect this transformation are described in Synthetic Communications, (1997, 27, (22), 3985–3990). The resulting indene products (27) may sometimes be used to modify the exocyclic olefin through reduction to the corresponding functionalized indene (28, a compound belonging to the class of general Formula VIIf where $R^{C1}$ are benzyl derivatives). Both intermediates (27) and (28) may be used as the olefin input in the various methods described for the synthesis of tetrahydroquinolines in the present invention.

Scheme 13

26 → 27 → 28

Substituted indenes may also be further functionalized to olefins of general Formula (VIId) as outlined in scheme 14 by treating an indene derivative (VI) with carbon dioxide in presence of a base such as potassium carbonate as described in Chemistry Letters (1992, (6), 923–926).

Scheme 14

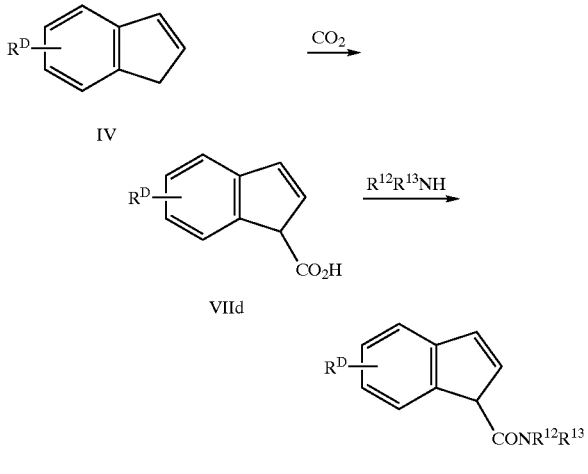

Substituted indenes of general Formula (VIId)may in turn be coupled with primary and secondary amines to yield amides of general Formula (VIIe). Both classes of substituted indene of general Formulae (VIId) and (VIIe) may be used as the olefin input in the various methods described for the synthesis of tetrahydroquinolines in the present invention.

Scheme 15 outlines the synthesis of substituted indenes of general Formula (VIIf). Substituted indenes of general Formula (VIIf) may sometimes be prepared by alkylation of an indene derivative according to scheme 15. In this case the alkylation of indene of general Formula (VI) is effected using an alkyl halide and a base such as butyl lithium to yield the branched indenes of general Formula (VIId). Indenes of this type may be prepared according to protocols described in the Journal of Organic Chemistry (1973, 38, 1439) and Acta Chemica Scandinavia (1974, 28, 295).

Scheme 15

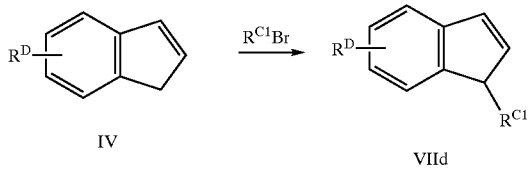

Indenes of general Formula (VIId) could be used as the olefin input in the various methods described for the synthesis of tetrahydroquinolines in the present invention.

General synthesis of tetrahydroquinoline tetracycles TQ wherein the —NH— atom is replaced by —O—, —S—, —SO—, —SO$_2$—, or —CH$_2$—.

The —O—, —S—, —S(O)— and —S(O)$_2$— analogues of Formula (I) may be generally synthesized according to the following methods. Scheme-16 discloses the general synthesis of forming substituted chromanyl cores. Compounds of general Formula (IX) can be obtained by treating alcohols of general Formula (VIII) with an aqueous acid such as hydrochloric acid (see Bull. Chem. Soc. Jpn. 1999, 72 (1), 73–83).

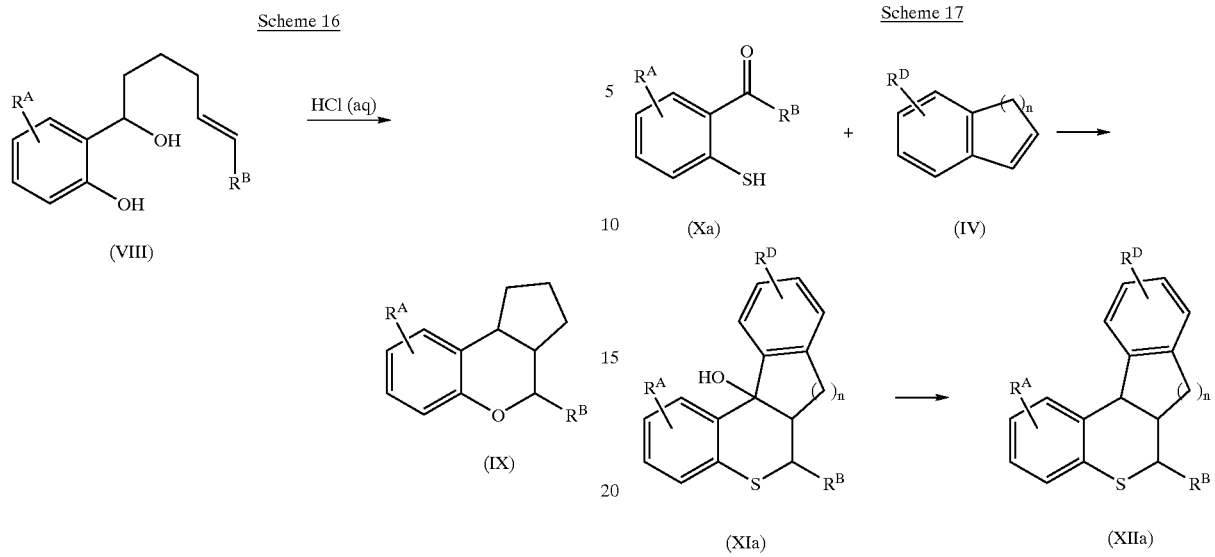

Similarly, compounds of general Formula (IXa), Scheme 16a, can be obtained by treating alcohols of general Formula (VIIIa) under acidic conditions according to the methods described in Bull. Chem. Soc. Jpn. (1999, 72 (1), 73–83).

n = 1, 2, or 3

Compounds of general Formula (XIa) can be obtained as disclosed in Scheme 17 by treating keto-thiols of general Formula (X) with olefins of Formula (IV) according to the procedure described in J. Chem. Soc. Perkin Tans 1 ( 1999, (11), 1447–1551). The tertiary alcohol (XIa) can be eliminated by treatment with a reducing agent such as Raney-Nickel or any other reducing agent to give the compounds of general Formula (XIIa). (see Synlett, 1997, (5), 561–562).

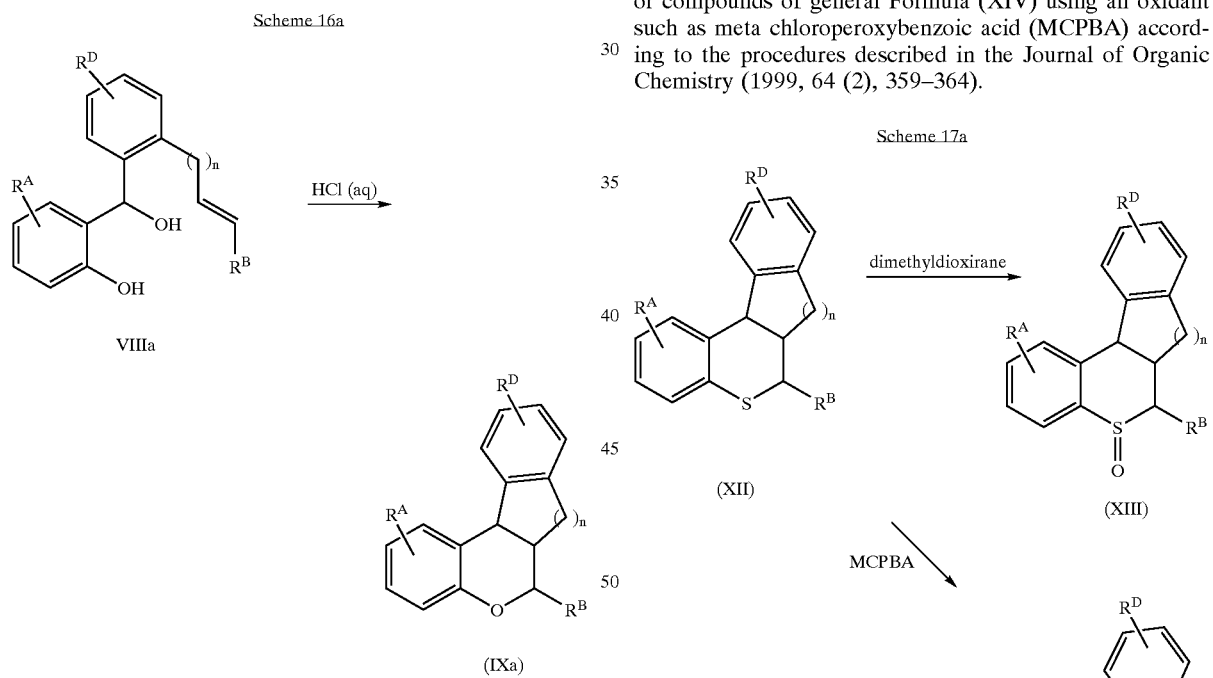

Compounds of the general Formula (XIIa) can be further transformed to compounds of general Formula (XIII), as disclosed in Scheme 17a using an oxidizing agent such as dimethyldioxirane (Tetrahedron, 1994, 50 (46), 1313–1320) or compounds of general Formula (XIV) using an oxidant such as meta chloroperoxybenzoic acid (MCPBA) according to the procedures described in the Journal of Organic Chemistry (1999, 64 (2), 359–364).

Tetrahydronaphthalene compounds of general Formula (XVI) can be obtained from the cyclo-addition of a non-cyclic olefin (XV) with a cyclic olefin (IV), see Scheme 18 in the presence of a suitable solvent, like DCM or HFP, and an aminium salt, such as tris(2,4-dibromophenyl)aminium hexachloroantimonate or as tris-(4-bromophenyl)aminium hexachloroantimonate (Tetrahedron Letters, 1999, 40, 7267–7270).

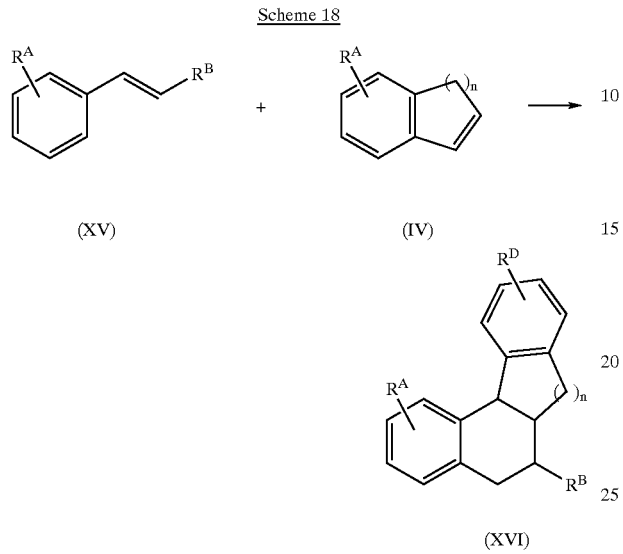

Scheme 18

(XV)  (IV)  (XVI)

Purification of Compounds:

Compounds were purified by preparative HPLC/MS. In the preparative HPLC/MS experiment (so-called PrepLCMS), the compounds are eluted from a reversed phase C18 chromatographic column and detected on-line by electrospray ionization mass spectrometry. It is understood that one skilled in the art will be able to determine the specificity, selectivity and sensitivity of the mass spectrometer required to guide fraction collection. Fraction collection is initiated at the precise time when the target compound elutes from the chromatographic column and a small portion of its effluent flow stream is detected in the mass spectrometer.

The reagents for the HPLC mobile phase are:

$H_2O$: Deionized tap water

Acetonitrile: Fisher HPLC grade

TFA: 99+% purity (Sequencing grade)

Mobile Phase A was 0.05% TFA in $H_2O$

Mobile Phase B was 0.035% TFA in Acetonitrile.

The following gradient profile was used:

| Time (min) | Mobile phase A | Mobile phase B |
|---|---|---|
| 0.00 | 90.00 | 10.00 |
| 0.50 | 90.00 | 10.00 |
| 7.20 | 10.00 | 90.00 |
| 7.60 | 90.00 | 10.00 |
| 8.00 | 90.00 | 10.00 |

A more detailed description of the preparative HPLC/MS is available in a number of scientific papers such as: 1) Zeng, L., Burton, L., Yung, K., Shushan. B. and Kassel, D. B.: "Automated Analytical/Preparative High Performance Liquid Chromatography-Mass Spectrometry System for the Rapid Characterization and Purification of Combinatorial Libraries," (1998) *J. Chromatogr. A*. 794, 3–13; and 2) Zeng, L., Wang, X., Wang, T. and Kassel, D. B.: "New Developments in Automated PrepLCMS Extends The Robustness and Utility of the Method For Compound Library Analysis and Purification," (1998) *J. Comb. Chem. High Thr. Screening* 1(2), 101–111.

The compounds of the invention herein described may have asymmetric centers. For example the chiral carbon atoms within the tetracyclic core of the tetrahydroquinoline moieties, TQ, exist in either an S or R configuration. Thus, the stereoisomeric configurations of each tetrahydroquinoline moiety of Formula (I) are considered part of the invention. For example, but not limited to therein, in the 6-phenyl-5,6a,7,11b-tetrahydro-6H-indeno[2,1-c]quinoline core the following four stereoisomeric configurations are possible:

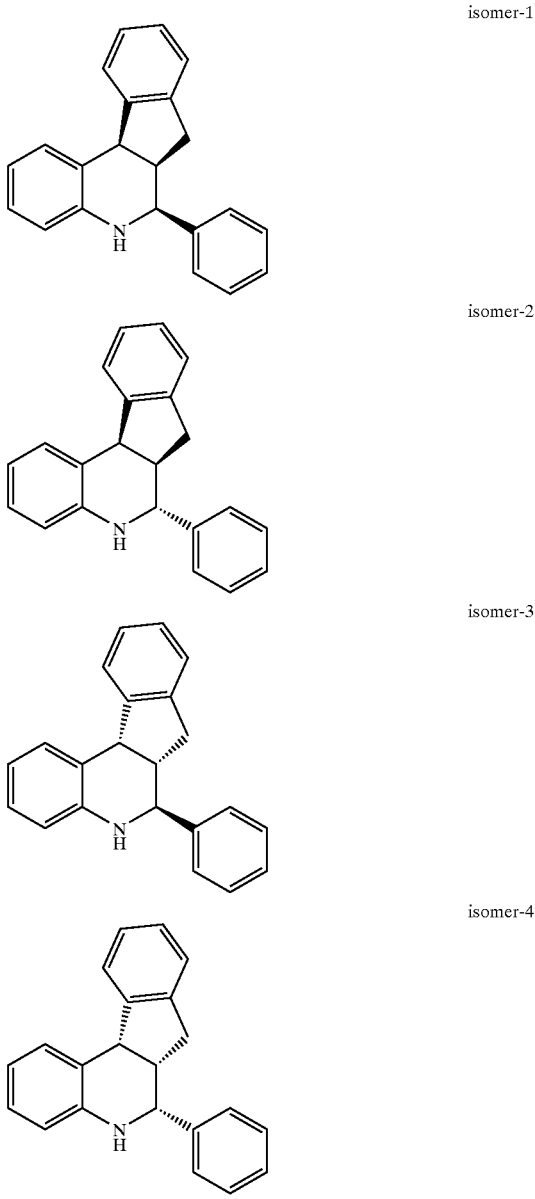

isomer-1 isomer-2 isomer-3 isomer-4 and are collectively, as well as individually, considered part of the invention. In a preferred stereoisomeric embodiment the present invention provides for a stereoisomeric configuration of isomer-2 for all embodiments of Formula (I) and pharmaceutically acceptable salts thereof.

When required, separation of the racemic material can be achieved by methods known in the art and/or as described herein. All isomeric configurations are considered part of the invention.

The synthetic schemes described above may produce products as mixtures of stereoisomers (for instance, TQ in Scheme-1, TQ1 in Scheme-2, TQ2 in Scheme-2a, and TQ3 in Scheme-2b). Separation of product diastereomers may be achieved by chromatography, for instance short column chromatography on silica gel or high performance liquid chromatography (HPLC) on silica gel or on C18 reverse phase silica gel. A preferred method for obtaining the compounds of the invention as pure diastereomers is separation of a nitrile containing compound as exemplified in structure TQ2. Preferred methods for achieving this separation include short column chromatography on silica gel using a stepwise gradient from, for instance, 20% ethyl acetate/80% hexanes (v/v) to 30% ethyl acetate/70% hexanes. A more preferred method for separating diastereomeric nitrites TQ2 involves HPLC on silica gel (Rainin DYNAMAX 60 Å column, 2.5×25 cm) eluting with a mixture of, for instance, 14:6 (v/v) hexanes/ethyl acetate. After separation, the individual diastereomeric nitrites TQ2 may be converted to amidines as described in Scheme 3c or to benzyl amines as described in Scheme 3a.

In order to obtain the compounds of the invention as pure enantiomers, chiral HPLC may be used. A preferred method is the chiral HPLC separation of a nitrile containing intermediate as exemplified in structure TQ2 using a CHIRALCEL OG column (0.46×25 cm) eluting with 1/500/500 diethylamine/isopropyl alcohol/hexane (v/v/v) at a flow rate of 1 ml/min with ultraviolet absorbance detection at 254 nm. Preferred methods also include other chiral stationary phases, for instance, CHIRALCEL OD, other mobile phase solvents, including ethanol and ethyl acetate, and other modifiers, including trifluoroacetic acid. In a more preferred method to obtain compounds of the invention as single enantiomers, separation of diastereomers of nitrile compounds exemplified by TQ2 may be achieved by short column chromatography or HPLC as described above. Subsequent chiral HPLC separation, as described above, of each of the diastereomeric nitrile compounds may afford the compounds as single enantiomers. After chiral separation, the individual nitrile enantiomers may, for instance, be converted to amidines as described in Scheme 3c or to benzyl amines as described in Scheme 3a.

Abbreviations used in the description of the chemistry and in the examples that follow are:
$Cs_2CO_3$ is cesium carbonate;
CuO is copper(II)oxide;
DCM is dichloromethane;
DMF is dimethyl formamide;
DMSO is dimethyl sulfoxide;
HOAc is acetic acid;
EtOAc is ethyl acetate;
HCl is hydrochloride acid;
Hex is hexane;
HFP is 1,1,1,3,3,3-Hexafluoroproan-2-ol;
HPLC is high performance liquid chromatography;
$In(OTf)_3$ is indium triflate;
LC/MS is liquid chromatography/mass spectroscopy;
$LiAlH_4$ is lithium aluminium hydride;
LR is Lawesson reagent;
MgSO4 is magnesium sulfate;
MTO is methyl rhenium trioxide;
NaOAc is sodium actetate;
NaOH is sodium hydroxide;
$NEt_3$ is triethylamine;
$Pd(dppf)Cl_2$ is [1,1-Bis(diphenylphosphino)ferocene] dichloropalladium(II);
Pd(OAc) is palladium acetate;
Pol is polymer;
$PPh_3$ is triphenyl phosphine;
$PPh_3O$ is triphenyl phosphine oxide;
RT is room temperature; and
THF is tetrahydrofuran.

EXAMPLES

The following Examples have been prepared, isolated and characterized using the methods disclosed herein. The following Examples demonstrate a partial scope of the invention and are not meant to be limiting of the scope of the invention.

Example 1

6-(3-Chloro-phenyl)-5,6a,7,11b-tetrahydro-6H-indeno[2,1-c]quinoline-3-carboxamidine.

4-amino-benzamidine mono HCl salt (17.2 mg, 0.1 mmole) was suspended in acetonitrile (1 mL). The suspension was treated with 3-chlorobenzaldehyde (14.0 mg, 0.1 mmole) and indene(11.6 mg, 0.1 mmole). Indium triflate (11.2 mg, 0.02 mmole) was added and the reaction was heated at 70° C. for 24 hours. The desired product was purified using reverse phase HPLC. Mass spectrum: 374 (M+1).

Example 2

6-(4-Hydroxy-3-methoxy-phenyl)-5,6a,7,11b-tetrahydro-6H-indeno[2,1-c]quinoline-2-carboxamidine.

Step a: 4-amino-benzamidine mono HCl salt (17.2 mg, 0.1 mmole) was suspended in acetonitrile (1 mL). The suspension was treated with 4-acetoxy-3-methoxybenzaldehyde (19.0 mg, 0.1 mmole) and indene (11.6 mg, 0.1 mmole). Indium triflate (11.2 mg, 0.02 mmole) was added and the reaction was heated at 70° C. for 48 hours. To the above mixture was added 100 uL of ammonium hydroxide. After stirring at rt overnight, the desired product 6-(4-Hydroxy-3-methoxy-phenyl)-5,6a,7,11b-tetrahydro-6H-indeno[2,1-c]quinoline-2-carboxamidine was purified using reverse phase HPLC. Mass spectrum: 385(M+1).

Example 2A 6-(4-Hydroxy-3-ethoxy-phenyl)-5,6a,7,11b-tetrahydro-6H-indeno[2,1-c]quinoline-2-carboxamidine.

Example 2A, was prepared using the procedure described for Example 2 from indene and 4-acetoxy-3-ethoxybenzaldehyde. Mass spectrum: 399(M+1).

Example 3

6-(2,3-Dimethoxy-phenyl)-5,6a,7,11b-tetrahydro-6H-indeno[2,1-c]quinoline-2-carboxamidine.

Example 3, was prepared using the procedure described for Example 1 from indene and 2,3-dimethoxybenzaldehyde. Mass spectrum: 400(M+1).

Example 4

6-(2,5-Dimethoxy-phenyl)-5,6a,7,11b-tetrahydro-6H-indeno[2,1-c]quinoline-2-carboxamidine.

Example 4, was prepared using the procedure described for Example 1 from indene and 2,5-dimethoxybenzaldehyde. Mass spectrum: 400(M+1).

Example 5
6-(2-Hydroxy-3-methoxy-phenyl)-5,6a,7,11b-tetrahydro-6H-indeno[2,1-c]quinoline-2-carboxamidine.

Example 5, was prepared using the procedure described for Example 1 from indene and 2-hydroxy-3-methoxybenzaldehyde. Mass spectrum: 386(M+1).

Example 6
6-(2-Hydroxy-5-methoxy-phenyl)-5,6a,7,11b-tetrahydro-6H-indeno[2,1-c]quinoline-2-carboxamidine.

Example 6, was prepared using the procedure described for Example 1 from indene and 2-hydroxy-5-methoxybenzaldehyde. Mass spectrum: 386(M+1).

Example 7
6-(2,3,4-Trimethoxy-phenyl)-5,6a,7,11b-tetrahydro-6H-indeno[2,1-c]quinoline-2-carboxamidine.

Example 7, was prepared using the procedure described for Example 1 from indene and 2,3,4-trimethoxybenzaldehyde. Mass spectrum: 430(M+1).

Example 8
6-(4-Methoxy-2,3-dimethyl-phenyl)-5,6a,7,11b-tetrahydro-6H-indeno[2,1-c]quinoline-2-carboxamidine.

Example 8, was prepared using the procedure described for Example 1 from indene and 4-methoxy-2,3-dimethylbenzaldehyde. Mass spectrum: 398(M+1).

Example 9
6-(4-Methoxy-2,5-dimethyl-phenyl)-5,6a,7,11b-tetrahydro-6H-indeno[2,1-c]quinoline-2-carboxamidine.

Example 9, was prepared using the procedure described for Example 1 from indene and 4-methoxy-2,5-dimethylbenzaldehyde. Mass spectrum: 398(M+1).

Example 10
6-(3-Hydroxy-4-methoxy-phenyl)-5,6a,7,11b-tetrahydro-6H-indeno[2,1-c]quinoline-2-carboxamidine.

Example 10, was prepared using the procedure described for Example 1 from indene and 3-hydroxy-4-methoxybenzaldehyde. Mass spectrum: 386(M+1).

Example 11
6-(4-Methoxy-phenyl)-5,6a,7,11b-tetrahydro-6H-indeno[2,1-c]quinoline-2-carboxamidine.

Example 11, was prepared using the procedure described for Example 1 from indene and 4-methoxybenzaldehyde. Mass spectrum: 370(M+1).

Example 12
6-(4-Hydroxy-3,5-dimethoxy-phenyl)-5,6a,7,11b-tetrahydro-6H-indeno[2,1-c]quinoline-2-carboxamidine.

Example 12, was prepared using the procedure described for Example 2 from indene and 4-acetoxy-3,5-dimethoxybenzaldehyde. Mass spectrum: 416(M+1).

Example 13
4-(2-Carbamimidoyl-5,6a,7,11b-tetrahydro-6H-indeno[2,1-c]quinolin-6-yl)-benzoic acid methyl ester.

Example 13, was prepared using the procedure described for Example 1 from indene and 4-Formylbenzoic acid methyl ester. Mass spectrum: 398(M+1).

Example 14
6-(4-Hydroxy-3-methoxy-5-nitro-phenyl)-5,6a,7,11b-tetrahydro-6H-indeno[2,1-c]quinoline-2-carboxamidine.

Example 14, was prepared using the procedure described for Example 1 from indene and 4-hydroxy-3-methoxy-5-nitrobenzaldehyde. Mass spectrum: 431(M+1).

Example 15
6-(3-Hydroxy-4,5-dimethoxy-phenyl)-5,6a,7,11b-tetrahydro-6H-indeno[2,1-c]quinoline-2-carboxamidine.

Example 15, was prepared using the procedure described for Example 1 from indene and 3-hydroxy-4,5-dimethoxybenzaldehyde. Mass spectrum: 416(M+1).

Example 16
6-(2-Hydroxy-3-methoxy-5-nitro-phenyl)-5,6a,7,11b-tetrahydro-6H-indeno[2,1-c]quinoline-2-carboxamidine.

Example 16, was prepared using the procedure described for Example 1 from indene and 2-hydroxy-3-methoxy-5-nitrobenzaldehyde. Mass spectrum: 431(M+1).

Example 17
(5-Chloro-2-methoxy-phenyl)-carbamic acid 4-(2-carbamimidoyl-5,6a,7,11b-tetrahydro-6H-indeno[2,1-c]quinolin-6-yl)-2-methoxy-phenyl ester, Example 17, was prepared using the procedure described for Example 1 from indene and (5-Chloro-2-methoxy-phenyl)-carbamic acid 4-formyl-2-methoxy-phenyl ester. Mass spectrum: 569(M+1).

Example 18
6-(6-Bromo-2-hydroxy-3-methoxy-phenyl)-5,6a,7,11b-tetrahydro-6H-indeno[2,1-c]quinoline-2-carboxamidine.

Example 18, was prepared using the procedure described for Example 1 from indene and 6-bromo-2-hydroxy-3-methoxybenzaldehyde. Mass spectrum: 464(M+1).

Example 19
6-(2-Fluoro-5-methoxy-phenyl)-5,6a,7,11b-tetrahydro-6H-indeno[2,1-c]quinoline-2-carboxamidine.

Example 19, was prepared using the procedure described for Example 1 from indene and 2-fluoro-5-methoxybenzaldehyde. Mass spectrum: 388(M+1).

Example 20
6-(2-Benzyloxy-3-methoxy-phenyl)-5,6a,7,11b-tetrahydro-6H-indeno[2,1-c]quinoline-2-carboxamidine.

Example 20, was prepared using the procedure described for Example 1 from indene and 2-benzyloxy-3-methoxybenzaldehyde. Mass spectrum: 476(M+1).

Example 21
6-(2-Fluoro-4-methoxy-phenyl)-5,6a,7,11b-tetrahydro-6H-indeno[2,1-c]quinoline-2-carboxamidine.

Example 21, was prepared using the procedure described for Example 1 from indene and 2-fluoro-4-methoxybenzaldehyde. Mass spectrum: 388(M+1).

Example 22
6-(3-Iodo-4,5-dimethoxy-phenyl)-5,6a,7,11b-tetrahydro-6H-indeno[2,1-c]quinoline-2-carboxamidine.

Example 22, was prepared using the procedure described for Example 1 from indene and 3-iodo-4,5-dimethoxybenzaldehyde. Mass spectrum: 525(M+1).

Example 23
6-[2-(2,6-Dichloro-benzyloxy)-phenyl]-5,6a,7,11b-tetrahydro-6H-indeno[2,1-c]quinoline-2-carboxamidine.

Example 23, was prepared using the procedure described for Example 1 from indene and 2-(2,6-dichlorobenzyloxy)benzaldehyde. Mass spectrum: 515(M+1).

Example 24
6-[2-(4-Chloro-phenylthio)-phenyl]-5,6a,7,11b-tetrahydro-6H-indeno[2,1-c]quinoline-2-carboxamidine.

Example 24, was prepared using the procedure described for Example 1 from indene and 2-(4-chlorophenylthio) benzaldehyde. Mass spectrum: 482(M+1).

Example 25
6-Benzo[1,3]dioxol-4-yl-5,6a,7,11b-tetrahydro-6H-indeno[2,1-c]quinoline-2-carboxamidine.

Example 25, was prepared using the procedure described for Example 1 from indene and Benzo[1,3]dioxole-4-carbaldehyde. Mass spectrum: 383(M+1).

Example 26
6-(2-Benzyloxy-phenyl)-5,6a,7,11b-tetrahydro-6H-indeno[2,1-c]quinoline-2-carboxamidine.

Example 26, was prepared using the procedure described for Example 1 from indene and 2-benzyloxybenzaldehyde. Mass spectrum: 446(M+1).

Example 27
6-(2-Allyloxy-phenyl)-5,6a,7,11b-tetrahydro-6H-indeno[2,1-c]quinoline-2-carboxamidine.

Example 27, was prepared using the procedure described for Example 1 from indene and 2-allyloxybenzaldehyde. Mass spectrum: 396(M+1).

Example 28
6-(5-Bromo-2-methoxy-phenyl)-5,6a,7,11b-tetrahydro-6H-indeno[2,1-c]quinoline-2-carboxamidine.

Example 28, was prepared using the procedure described for Example 1 from indene and 5-bromo-2-methoxybenzaldehyde. Mass spectrum: 448(M+1).

Example 29
6-[3-(4-Methoxy-phenoxy)-phenyl]-5,6a,7,11b-tetrahydro-6H-indeno[2,1-c]quinoline-2-carboxamidine.

Example 29, was prepared using the procedure described for Example 1 from indene and 3-(4-methoxyphenoxy) benzaldehyde. Mass spectrum: 462(M+1).

Example 30
6-(3,4-Dimethoxy-phenyl)-5,6a,7,11b-tetrahydro-6H-indeno[2,1-c]quinoline-2-carboxamidine.

Example 30, was prepared using the procedure described for Example 1 from indene and 3,4-dimethoxybenzaldehyde. Mass spectrum: 400(M+1).

Example 31
6-(4-Methanesulfonyl-phenyl)-5,6a,7,11b-tetrahydro-6H-indeno[2,1-c]quinoline-2-carboxamidine.

Example 31, was prepared using the procedure described for Example 1 from indene and 4-methanesulfonylbenzaldehyde. Mass spectrum: 418(M+1).

Example 32
6-[4-(2-Hydroxy-ethoxy)-phenyl]-5,6a,7,11b-tetrahydro-6H-indeno[2,1-c]quinoline-2-carboxamidine.

Example 32, was prepared using the procedure described for Example 1 from indene and 4-(2-hydroxyethoxy) benzaldehyde. Mass spectrum: 400(M+1).

Example 33
6-(2-Chloro-3,4-dimethoxy-phenyl)-5,6a,7,11b-tetrahydro-6H-indeno[2,1-c]quinoline-2-carboxamidine.

Example 33, was prepared using the procedure described for Example 1 from indene and 2-chloro-3,4-dimethoxybenzaldehyde. Mass spectrum: 434(M+1).

Example 34
6-(2-Hydroxy-6-methoxy-phenyl)-5,6a,7,11b-tetrahydro-6H-indeno[2,1-c]quinoline-2-carboxamidine.

Example 34, was prepared using the procedure described for Example 1 from indene and 2-hydroxy-6-methoxybenzaldehyde. Mass spectrum: 386(M+1).

Example 35
3-(2-Carbamimidoyl-5,6a,7,11b-tetrahydro-6H-indeno[2,1-c]quinolin-6-yl)-benzoic acid methyl ester, Example 35, was prepared using the procedure described for Example 1 from indene and 3-formyl-benzoic acid methyl ester. Mass spectrum: 398(M+1).

Example 36
5-(2-Carbamimidoyl-5,6a,7,11b-tetrahydro-6H-indeno[2,1-c]quinolin-6-yl)-2-methoxybenzeneboronic acid, Example 36, was prepared using the procedure described for Example 1 from indene and 5-formyl-2-methoxybenzeneboronic acid. Mass spectrum: 413(M+1).

Example 37
6-(3-Bromo-4-hydroxy-5-methoxy-phenyl)-5,6a,7,11b-tetrahydro-6H-indeno[2,1-c]quinoline-2-carboxamidine.

Example 37, was prepared using the procedure described for Example 1 from indene and 3-bromo-4-hydroxy-5-methoxybenzaldehyde. Mass spectrum: 464(M+1).

Example 38
6-Pentafluorophenyl-5,6a,7,11b-tetrahydro-6H-indeno[2,1-c]quinoline-2-carboxamidine.

Example 38, was prepared using the procedure described for Example 1 from indene and pentafluorobenzaldehyde. Mass spectrum: 429(M+1).

Example 39
6-(2,4-Dichloro-phenyl)-5,6a,7,11b-tetrahydro-6H-indeno[2,1-c]quinoline-2-carboxamidine.

Example 39, was prepared using the procedure described for Example 1 from indene and 2,4-dichlorobenzaldehyde. Mass spectrum: 408(M+1).

Example 40
6-(2-Chloro-6-fluoro-phenyl)-5,6a,7,11b-tetrahydro-6H-indeno[2,1-c]quinoline-2-carboxamidine.

Example 40, was prepared using the procedure described for Example 1 from indene and 2-chloro-6-fluorobenzaldehyde. Mass spectrum: 392(M+1).

Example 41
6-(3,4-Dichloro-phenyl)-5,6a,7,11b-tetrahydro-6H-indeno[2,1-c]quinoline-2-carboxamidine.

Example 41, was prepared using the procedure described for Example 1 from indene and 3,4-dichlorobenzaldehyde. Mass spectrum: 408(M+1).

Example 42
6-(3,5-Dichloro-phenyl)-5,6a,7,11b-tetrahydro-6H-indeno[2,1-c]quinoline-2-carboxamidine.

Example 42, was prepared using the procedure described for Example 1 from indene and 3,5-dichlorobenzaldehyde. Mass spectrum: 408(M+1).

Example 43
6-[3-(3,5-Dichloro-phenoxy)-phenyl]-5,6a,7,11b-tetrahydro-6H-indeno[2,1-c]quinoline-2-carboxamidine.

Example 43, was prepared using the procedure described for Example 1 from indene and 3-(3,5-dichloro-phenoxy)-benzaldehyde. Mass spectrum: 500(M+1).

Example 44
6-(3-Benzyloxy-phenyl)-5,6a,7,11b-tetrahydro-6H-indeno[2,1-c]quinoline-2-carboxamidine.

Example 44, was prepared using the procedure described for Example 1 from indene and 3-benzyloxybenzaldehyde. Mass spectrum: 446(M+1).

Example 45
6-(3-Trifluoromethyl-phenyl)-5,6a,7,11b-tetrahydro-6H-indeno[2,1-c]quinoline-2-carboxamidine.

Example 45, was prepared using the procedure described for Example 1 from indene and 3-trifluoromethylbenzaldehyde. Mass spectrum: 407(M+1).

Example 46
6-(4-Bromo-phenyl)-5,6a,7,11b-tetrahydro-6H-indeno[2,1-c]quinoline-2-carboxamidine.

Example 46, was prepared using the procedure described for Example 1 from indene and 4-bromobenzaldehyde. Mass spectrum: 418(M+1).

Example 47
6-(4-Fluoro-phenyl)-5,6a,7,11b-tetrahydro-6H-indeno[2,1-c]quinoline-2-carboxamidine.

Example 47, was prepared using the procedure described for Example 1 from indene and 4-fluorobenzaldehyde. Mass spectrum: 357(M+1).

Example 48
6-(4-Chloro-phenyl)-5,6a,7,11b-tetrahydro-6H-indeno[2,1-c]quinoline-2-carboxamidine.

Example 48, was prepared using the procedure described for Example 1 from indene and 4-chlorobenzaldehyde. Mass spectrum: 374(M+1).

Example 49
6-(4-Ethoxy-phenyl)-5,6a,7,11b-tetrahydro-6H-indeno[2,1-c]quinoline-2-carboxamidine.

Example 49, was prepared using the procedure described for Example 1 from indene and 4-ethoxybenzaldehyde. Mass spectrum: 384(M+1).

Example 50
6-(4-Methoxy-naphthalen-1-yl)-5,6a,7,11b-tetrahydro-6H-indeno[2,1-c]quinoline-2-carboxamidine.

Example 50, was prepared using the procedure described for Example 1 from indene and 4-Methoxy-naphthalene-1-carbaldehyde. Mass spectrum: 420(M+1).

Example 51
6-(4-Trifluoromethyl-phenyl)-5,6a,7,11b-tetrahydro-6H-indeno[2,1-c]quinoline-2-carboxamidine.

Example 50, was prepared using the procedure described for Example 1 from indene and 4-trifluoromethylbenzaldehyde. Mass spectrum: 407(M+1).

Example 52
6-(2,3-Difluoro-phenyl)-5,6a,7,11b-tetrahydro-6H-indeno[2,1-c]quinoline-2-carboxamidine.

Example 52, was prepared using the procedure described for Example 1 from indene and 2,3-difluorobenzaldehyde. Mass spectrum: 375(M+1).

Example 53
6-(2,4-Difluoro-phenyl)-5,6a,7,11b-tetrahydro-6H-indeno[2,1-c]quinoline-2-carboxamidine.

Example 53, was prepared using the procedure described for Example 1 from indene and 2,4-difluorobenzaldehyde. Mass spectrum: 375(M+1).

Example 54
6-(2,5-Difluoro-phenyl)-5,6a,7,11b-tetrahydro-6H-indeno[2,1-c]quinoline-2-carboxamidine.

Example 54, was prepared using the procedure described for Example 1 from indene and 2,5-difluorobenzaldehyde. Mass spectrum: 375(M+1).

Example 55
6-(3,4-Difluoro-phenyl)-5,6a,7,11b-tetrahydro-6H-indeno[2,1-c]quinoline-2-carboxamidine.

Example 55, was prepared using the procedure described for Example 1 from indene and 3,4-difluorobenzaldehyde. Mass spectrum: 375(M+1).

Example 56
6-(3-Chloro-4-fluoro-phenyl)-5,6a,7,11b-tetrahydro-6H-indeno[2,1-c]quinoline-2-carboxamidine.

Example 56, was prepared using the procedure described for Example 1 from indene and 3-chloro-4-fluorobenzaldehyde. Mass spectrum: 392(M+1).

Example 57
6-(4-Pyrrolidin-1-yl-phenyl)-5,6a,7,11b-tetrahydro-6H-indeno[2,1-c]quinoline-2-carboxamidine.

Example 57, was prepared using the procedure described for Example 1 from indene and 4-pyrrolidin-1-ylbenzaldehyde. Mass spectrum: 409(M+1).

Example 58
6-(5-Bromo-2-ethoxy-phenyl)-5,6a,7,11b-tetrahydro-6H-indeno[2,1-c]quinoline-2-carboxamidine.

Example 58, was prepared using the procedure described for Example 1 from indene and 5-bromo-2-ethoxybenzaldehyde. Mass spectrum: 462(M+1).

Example 59
6-(4-Trifluoromethoxy-phenyl)-5,6a,7,11b-tetrahydro-6H-indeno[2,1-c]quinoline-2-carboxamidine.

Example 59, was prepared using the procedure described for Example 1 from indene and 4-trifluoromethoxybenzaldehyde. Mass spectrum: 423(M+1).

Example 60
6-(4-Propyl-phenyl)-5,6a,7,11b-tetrahydro-6H-indeno[2,1-c]quinoline-2-carboxamidine.

Example 60, was prepared using the procedure described for Example 1 from indene and 4-propylbenzaldehyde. Mass spectrum: 382(M+1).

Example 61
6-(3-Bromo-4-fluoro-phenyl)-5,6a,7,11b-tetrahydro-6H-indeno[2,1-c]quinoline-2-carboxamidine.

Example 61, was prepared using the procedure described for Example 1 from indene and 3-bromo-4-fluorobenzaldehyde. Mass spectrum: 436(M+1).

Example 62
6-(2,2-Dimethyl-chroman-6-yl)-5,6a,7,11b-tetrahydro-6H-indeno[2,1-c]quinoline-2-carboxamidine.

Example 62, was prepared using the procedure described for Example 1 from indene and 2,2-Dimethyl-chroman-6-carbaldehyde. Mass spectrum: 424(M+1).

Example 63
6-(2,3,6-Trifluoro-phenyl)-5,6a,7,11b-tetrahydro-6H-indeno[2,1-c]quinoline-2-carboxamidine.

Example 63, was prepared using the procedure described for Example 1 from indene and 2,3,6-trifluorobenzaldehyde. Mass spectrum: 393(M+1).

Example 64
6-(2,4,5-Trifluoro-phenyl)-5,6a,7,11b-tetrahydro-6H-indeno[2,1-c]quinoline-2-carboxamidine.

Example 64, was prepared using the procedure described for Example 1 from indene and 2,4,5-trifluorobenzaldehyde. Mass spectrum: 393(M+1).

Example 65
6-(2,4,6-Trifluoro-phenyl)-5,6a,7,11b-tetrahydro-6H-indeno[2,1-c]quinoline-2-carboxamidine.

Example 65, was prepared using the procedure described for Example 1 from indene and 2,4,6-trifluorobenzaldehyde. Mass spectrum: 393(M+1).

Example 66
6-(2,3,4-Trifluoro-phenyl)-5,6a,7,11b-tetrahydro-6H-indeno[2,1-c]quinoline-2-carboxamidine.

Example 66, was prepared using the procedure described for Example 1 from indene and 2,3,4-trifluorobenzaldehyde. Mass spectrum: 393(M+1).

Example 67
6-(2-Fluoro-3-trifluoromethyl-phenyl)-5,6a,7,11b-tetrahydro-6H-indeno[2,1-c]quinoline-2-carboxamidine.

Example 67, was prepared using the procedure described for Example 1 from indene and 2-fluoro-3-trifluoromethylbenzaldehyde. Mass spectrum: 425(M+1).

Example 68
6-(2-Fluoro-6-trifluoromethyl-phenyl)-5,6a,7,11b-tetrahydro-6H-indeno[2,1-c]quinoline-2-carboxamidine.

Example 68, was prepared using the procedure described for Example 1 from indene and 2-fluoro-6-trifluoromethylbenzaldehyde. Mass spectrum: 425(M+1).

Example 69
6-(3-Fluoro-5-trifluoromethyl-phenyl)-5,6a,7,11b-tetrahydro-6H-indeno[2,1-c]quinoline-2-carboxamidine.

Example 69, was prepared using the procedure described for Example 1 from indene and 3-fluoro-5-trifluoromethylbenzaldehyde. Mass spectrum: 425(M+1).

Example 70
6-(4-Fluoro-2-trifluoromethyl-phenyl)-5,6a,7,11b-tetrahydro-6H-indeno[2,1-c]quinoline-2-carboxamidine.

Example 70, was prepared using the procedure described for Example 1 from indene and 4-fluoro-2-trifluoromethylbenzaldehyde. Mass spectrum: 425(M+1).

Example 71
6-(2,3,5-Trifluoro-phenyl)-5,6a,7,11b-tetrahydro-6H-indeno[2,1-c]quinoline-2-carboxamidine.

Example 71, was prepared using the procedure described for Example 1 from indene and 2,3,5-trifluorobenzaldehyde. Mass spectrum: 393(M+1).

Example 72
6-[2-(4-tert-Butyl-phenoxy)-5-nitro-phenyl]-5,6a,7,11b-tetrahydro-6H-indeno[2,1-c]quinoline-2-carboxamidine.

Example 72, was prepared using the procedure described for Example 1 from indene and 2-(4-tert-Butyl-phenoxy)-5-nitro benzaldehyde. Mass spectrum: 533(M+1).

Example 73
6-(2-Chloro-5-trifluoromethyl-phenyl)-5,6a,7,11b-tetrahydro-6H-indeno[2,1-c]quinoline-2-carboxamidine.

Example 73, was prepared using the procedure described for Example 1 from indene and 2-chloro-5-trifluoromethylbenzaldehyde. Mass spectrum: 442(M+1).

Example 74
6-(4-Chloro-2-fluoro-phenyl)-5,6a,7,11b-tetrahydro-6H-indeno[2,1-c]quinoline-2-carboxamidine.

Example 74, was prepared using the procedure described for Example 1 from indene and 4-chloro-2-fluorobenzaldehyde. Mass spectrum: 392(M+1).

Example 75
6-(4-Chloro-3-fluoro-phenyl)-5,6a,7,11b-tetrahydro-6H-indeno[2,1-c]quinoline-2-carboxamidine.

Example 75, was prepared using the procedure described for Example 1 from indene and 4-chloro-3-fluorobenzaldehyde. Mass spectrum: 392(M+1).

Example 76
6-(2-Benzylmercapto-5-nitro-phenyl)-5,6a,7,11b-tetrahydro-6H-indeno[2,1-c]quinoline-2-carboxamidine.

Example 76, was prepared using the procedure described for Example 1 from indene and 2-benzylmercapto-5-nitrobenzaldehyde. Mass spectrum: 507(M+1).

Example 77
6-(2-Morpholin-4-yl-5-nitro-phenyl)-5,6a,7,11b-tetrahydro-6H-indeno[2,1-c]quinoline-2-carboxamidine.

Example 77, was prepared using the procedure described for Example 1 from indene and 2-morpholin-4-yl-5-nitrobenzaldehyde. Mass spectrum: 470(M+1).

Example 78
6-(3-Phenyl-1H-pyrazol-4-yl)-5,6a,7,11b-tetrahydro-6H-indeno[2,1-c]quinoline-2-carboxamidine.

Example 78, was prepared using the procedure described for Example 1 from indene and 4-phenyl-1H-pyrazole-3-carbaldehyde. Mass spectrum: 406(M+1).

Example 79
6-(2,4-Dioxo-1,2,3,4-tetrahydro-pyrimidin-5-yl)-5,6a,7,11b-tetrahydro-6H-indeno[2,1-c]quinoline-2-carboxamidine.

Example 79, was prepared using the procedure described for Example 1 from indene and 2,4-dioxo-1,2,3,4-tetrahydro-pyrimidine-5-carbaldehyde. Mass spectrum: 373(M+1).

Example 80
6-(2-Phenyl-1H-imidazol-4-yl)-5,6a,7,11b-tetrahydro-6H-indeno[2,1-c]quinoline-2-carboxamidine.

Example 80, was prepared using the procedure described for Example 1 from indene and 2-phenyl-3H-imidazole-4-carbaldehyde. Mass spectrum: 406(M+1).

Example 81
6-(1H-Imidazol-4-yl)-5,6a,7,11b-tetrahydro-6H-indeno[2,1-c]quinoline-2-carboxamidine.

Example 81, was prepared using the procedure described for Example 1 from indene and 3H-imidazole-4-carbaldehyde. Mass spectrum: 329(M+1).

Example 82
6-(5-Methyl-1H-pyrazol-4-yl)-5,6a,7,11b-tetrahydro-6H-indeno[2,1-c]quinoline-2-carboxamidine.

Example 82, was prepared using the procedure described for Example 1 from indene and 5-methyl-1H-pyrazole-4-carbaldehyde. Mass spectrum: 343(M+1).

Example 83

6-Thiophen-2-yl-5,6a,7,11b-tetrahydro-6H-indeno[2,1-c]quinoline-2-carboxamidine.

Example 83, was prepared using the procedure described for Example 1 from indene and thiophene-2-carbaldehyde. Mass spectrum: 346(M+1).

Example 84

6-[5-(3-Trifluoromethyl-phenyl)-furan-2-yl]-5,6a,7,11b-tetrahydro-6H-indeno[2,1-c]quinoline-2-carboxamidine.

Example 84, was prepared using the procedure described for Example 1 from indene and 5-(3-trifluoromethyl-phenyl)-furan-2-carbaldehyde. Mass spectrum: 474(M+1).

Example 85

6-[5-(2-Chloro-phenyl)-furan-2-yl]-5,6a,7,11b-tetrahydro-6H-indeno[2,1-c]quinoline-2-carboxamidine.

Example 85, was prepared using the procedure described for Example 1 from indene and 5-(2-chloro-phenyl)-furan-2-carbaldehyde. Mass spectrum: 440(M+1).

Example 86

6-[5-(2,5-Dichloro-phenyl)-furan-2-yl]-5,6a,7,11b-tetrahydro-6H-indeno[2,1-c]quinoline-2-carboxamidine.

Example 86, was prepared using the procedure described for Example 1 from indene and 5-(2,5-dichloro-phenyl)-furan-2-carbaldehyde. Mass spectrum: 474(M+1).

Example 87

6-[5-(2-Trifluoromethoxy-phenyl)-furan-2-yl]-5,6a,7,11b-tetrahydro-6H-indeno[2,1-c]quinoline-2-carboxamidine.

Example 87, was prepared using the procedure described for Example 1 from indene and 5-(2-trifluoromethoxy-phenyl)-furan-2-carbaldehyde. Mass spectrum: 490(M+1).

Example 88

6-(4,5-Dibromo-thiophen-2-yl)-5,6a,7,11b-tetrahydro-6H-indeno[2,1-c]quinoline-2-carboxamidine.

Example 88, was prepared using the procedure described for Example 1 from indene and 4,5-dibromo-thiophene-2-carbaldehyde. Mass spectrum: 503(M+1).

Example 89

6-[5-(1-Methyl-5-trifluoromethyl-1H-pyrazol-3-yl)-thiophen-2-yl]-5,6a,7,11b-tetrahydro-6H-indeno[2,1-c]quinoline-2-carboxamidine.

Example 89, was prepared using the procedure described for Example 1 from indene and 5-(1-methyl-5-trifluoromethyl-1H-pyrazol-3-yl)-thiophene-2-carbaldehyde. Mass spectrum: 494(M+1).

Example 90

6-(3-Phenoxy-phenyl)-5,6,6a,7,8,12b-hexahydro-benzo[k]phenanthridine-3-carboxamidine.

4-amino-benzamidine mono HCl salt (17.2 mg, 0.1 mmole) was suspended in acetonitrile (1 mL). The suspension was treated with 3-phenoxybenzaldehyde (19.8 mg, 0.1 mmole) and 1,2-dihydronapthalene(13.0 mg, 0.1 mmole). Indium triflate (11 mg, 0.02 mmole) was added and the reaction was heated at 70° C. for 48 hours. The desired products were purified using reverse phase HPLC. Mass spectrum: 446 (M+1).

Example 91

6-(2-Chloro-4-fluoro-phenyl)-5,6,6a,7,8,12b-hexahydro-benzo[k]phenanthridine-2-carboxamidine was made according to the protocol for Example 90 using 1,2-Dihydro-naphthalene and 2-Chloro-4-fluoro-benzaldehyde. Mass spectrum: 406 (M+1).

Example 92

6-(4-Hydroxy-3-methoxy-phenyl)-5,6,6a,7,8,12b-hexahydro-benzo[k]phenanthridine-2-carboxamidine was made according to the protocol for Example 2 using 1,2-Dihydro-naphthalene and 4-acetoxy-2-methoxy-benzaldehyde. Mass spectrum: 400 (M+1).

Example 93

6-(3,5-Dibromo-4-hydroxy-phenyl)-5,6,6a,7,8,12b-hexahydro-benzo[k]phenanthridine-2-carboxamidine was made according to the protocol for Example 90 using 1,2-Dihydro-naphthalene and 2,5-Dibromo-4-hydroxy-benzaldehyde. Mass spectrum: 528 (M+1).

Example 94

6-(3,5-Dimethoxy-phenyl)-5,6,6a,7,8,12b-hexahydro-benzo[k]phenanthridine-2-carboxamidine was made according to the protocol for Example 90 using 1,2-Dihydro-naphthalene and 3,5-Dimethoxy-benzaldehyde. Mass spectrum: 414 (M+1).

Example 95

6 6-(2-Hydroxy-3-methoxy-5-nitro-phenyl)-5,6,6a,7,8,12b-hexahydro-benzo[k]phenanthridine-2-carboxamidine was made to the protocol for Example 90 using 1,2-Dihydro-naphthalene and 2-Hydroxy-3-methoxy-5-nitro-benzaldehyde. Mass spectrum: 445 (M+1).

Example 96

Acetic acid 4-(2-carbamimidoyl-5,6,6a,7,8,12b-hexahydro-benzo[k]phenanthridin-6-yl)-2-methoxy-phenyl ester was made according to the protocol for Example 90 using 1,2-Dihydro-naphthalene and Acetic acid 4-formyl-2-methoxy-phenyl ester. Mass spectrum: 442 (M+1).

Example 97

6-(5-Bromo-2-methoxy-phenyl)-5,6,6a,7,8,12b-hexahydro-benzo[k]phenanthridine-2-carboxamidine was made according to the protocol for Example 90 using 1,2-Dihydro-naphthalene and 5-Bromo-2-methoxy-benzaldehyde. Mass spectrum: 463 (M+1).

Example 98

6-(2-Fluoro-5-methoxy-phenyl)-5,6,6a,7,8,12b-hexahydro-benzo[k]phenanthridine-2-carboxamidine was made according to the protocol for Example 90 using 1,2-Dihydro-naphthalene and 2-Fluoro-5-methoxy-benzaldehyde. Mass spectrum: 402 (M+1).

Example 99

3-(2-Carbamimidoyl-5,6,6a,7,8,12b-hexahydro-benzo[k]phenanthridin-6-yl)-benzoic acid methyl ester was made according to the protocol for Example 90 using 1,2-Dihydro-naphthalene and 3-Formyl-benzoic acid methyl ester. Mass spectrum: 412 (M+1).

Example 100

6-(2-Benzyloxy-3-methoxy-phenyl)-5,6,6a,7,8,12b-hexahydro-benzo[k]phenanthridine-2-carboxamidine was made according to the protocol for Example 90 using 1,2-Dihydro-naphthalene and 2-Benzyl-3-methoxy-benzaldehyde. Mass spectrum: 490 (M+1).

Example 101

6-(2-Fluoro-4-methoxy-phenyl)-5,6,6a,7,8,12b-hexahydro-benzo[k]phenanthridine-2-carboxamidine was made according to the protocol for Example 90 using 1,2-Dihydro-naphthalene and 2-Fluoro-4-methoxy-benzaldehyde. Mass spectrum: 402 (M+1).

Example 102

6-(4-Methanesulfonyl-phenyl)-5,6,6a,7,8,12b-hexahydro-benzo[k]phenanthridine-2-carboxamidine was made according to the protocol for Example 90 using 1,2-Dihydro-naphthalene and 4-Methanesulfonyl-benzaldehyde. Mass spectrum: 432 (M+1).

Example 103

6-(2-Benzyloxy-phenyl)-5,6,6a,7,8,12b-hexahydro-benzo[k]phenanthridine-2-carboxamidine was made according to the protocol for Example 90 using 1,2-Dihydro-naphthalene and 2-Benzyloxy-benzaldehyde. Mass spectrum: 460 (M+1).

Example 104

6-Benzo[1,3]dioxol-4-yl-5,6,6a,7,8,12b-hexahydro-benzo[k]phenanthridine-2-carboxamidine was made according to the protocol for Example 90 using 1,2-Dihydro-naphthalene and Benzo[1,3]dioxole-4-carbaldehyde. Mass spectrum: 398 (M+1).

Example 105

6-(3-Trifluoromethyl-phenyl)-5,6,6a,7,8,12b-hexahydro-benzo[k]phenanthridine-2-carboxamidine was made according to the protocol for Example 90 using 1,2-Dihydro-naphthalene and 3-Trifluoromethyl-benzaldehyde. Mass spectrum: 422 (M+1).

Example 106

6-(2-Morpholin-4-yl-5-nitro-phenyl)-5,6,6a,7,8,12b-hexahydro-benzo[k]phenanthridine-2-carboxamidine was made according to the protocol for Example 90 using 1,2-Dihydro-naphthalene and 2-Morpholin-4-yl-5-nitro-benzaldehyde. Mass spectrum: 484 (M+1).

Example 107

6-(4-Hydroxy-naphthalen-1-yl)-5,6,6a,7,8,12b-hexahydro-benzo[k]phenanthridine-2-carboxamidine was made according to the protocol for Example 90 using 1,2-Dihydro-naphthalene and 4-Hydroxy-naphthalene-1-carbaldehyde. Mass spectrum: 420 (M+1).

Example 108

N-[4-(2-Carbamimidoyl-5,6,6a,7,8,12b-hexahydro-benzo[k]phenanthridin-6-yl)-phenyl]-acetamide was made according to the protocol for Example 90 using 1,2-Dihydro-naphthalene and N-(4-Formyl-phenyl)-acetamide. Mass spectrum: 411 (M+1).

Example 109

6-(4-Hydroxy-3-iodo-5-methoxy-phenyl)-5,6,6a,7,8,12b-hexahydro-benzo[k]phenanthridine-2-carboxamidine was made according to the protocol for Example 90 using 1,2-Dihydro-naphthalene and 4-Hydroxy-3-iodo-5-methoxy-benzaldehyde. Mass spectrum: 526 (M+1).

Example 110

6-(3-Bromo-4-hydroxy-5-methoxy-phenyl)-5,6,6a,7,8,12b-hexahydro-benzo[k]phenanthridine-2-carboxamidine was made according to the protocol for Example 90 using 1,2-Dihydro-naphthalene and 3-Bromo-4-hydroxy-5-methoxy-benzaldehyde. Mass spectrum: 479 (M+1).

Example 111

6-(3-Ethoxy-4-hydroxy-phenyl)-5,6,6a,7,8,12b-hexahydro-benzo[k]phenanthridine-2-carboxamidine was made according to the protocol for Example 90 using 1,2-Dihydro-naphthalene and 3-Ethoxy-4-hydroxy-benzaldehyde. Mass spectrum: 414 (M+1).

Example 112

6-(4-Hydroxy-3,5-dimethyl-phenyl)-5,6,6a,7,8,12b-hexahydro-benzo[k]phenanthridine-2-carboxamidine was made according to the protocol for Example 90 using 1,2-Dihydro-naphthalene and 4-Hydroxy-3,5-dimethyl-benzaldehyde. Mass spectrum: 398 (M+1).

Example 113

6-(4-Hydroxy-3,5-dimethoxy-phenyl)-5,6,6a,7,8,12b-hexahydro-benzo[k]phenanthridine-2-carboxamidine was made according to the protocol for Example 2 using 1,2-Dihydro-naphthalene and 4-acetoxy-3,5-dimethoxy-benzaldehyde. Mass spectrum: 430 (M+1).

Example 114

6-(3-Fluoro-4-hydroxy-phenyl)-5,6,6a,7,8,12b-hexahydro-benzo[k]phenanthridine-2-carboxamidine was made according to the protocol for Example 90 using 1,2-Dihydro-naphthalene and 3-Fluoro-4-hydroxy-benzaldehyde. Mass spectrum: 388 (M+1).

Example 115

6-(4-Hydroxy-3-methyl-phenyl)-5,6,6a,7,8,12b-hexahydro-benzo[k]phenanthridine-2-carboxamidine was made according to the protocol for Example 90 using 1,2-Dihydro-naphthalene and 4-Hydroxy-3-methyl-benzaldehyde. Mass spectrum: 384 (M+1).

Example 116

6-(2-Chloro-4-hydroxy-phenyl)-5,6,6a,7,8,12b-hexahydro-benzo[k]phenanthridine-2-carboxamidine was made according to the protocol for Example 90 using 1,2-Dihydro-naphthalene and 2-Chloro-4-hydroxy-benzaldehyde. Mass spectrum: 404 (M+1).

Example 117

4-(2-Carbamimidoyl-5,6,6a,7,8,12b-hexahydro-benzo[k]phenanthridin-6-yl)-benzoic acid was made according to the protocol for Example 90 using 1,2-Dihydro-naphthalene and 4-Formyl-benzoic acid. Mass spectrum: 398 (M+1).

Example 118
6-Phenethyl-5,6,6a,7,8,12b-hexahydro-benzo[k]-phenanthridine-2-carboxamidine.

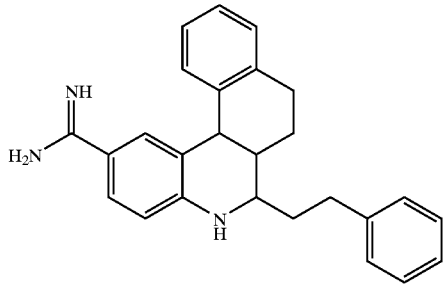

Example 118 was made according to the protocol for Example 90 using 1,2-Dihydro-naphthalene and 3-Phenyl-propionaldehyde. Mass spectrum: 382 (M+1).

Example 121

6-(3,4-Dimethyl-thieno[2,3-b]thiophen-2-yl)-5,6,6a,7,8,12b-hexahydro-benzo[k]phenanthridine-2-carboxamidine was made according to the protocol for Example 90 using 1,2-Dihydro-naphthalene and 3,4-Dimethyl-thieno[2,3-b]thiophene-2-carbaldehyde. Mass spectrum: 444 (M+1).

Example 122

6-(4-Phenylethynyl-thiophen-2-yl)-5,6,6a,7,8,12b-hexahydro-benzo[k]phenanthridine-2-carboxamidine was made according to the protocol for Example 90 using 1,2-Dihydro-naphthalene and 4-Phenylethynyl-thiophene-2-carbaldehyde. Mass spectrum: 460 (M+1).

Example 123

6-(3-Phenoxy-thiophen-2-yl)-5,6,6a,7,8,12b-hexahydro-benzo[k]phenanthridine-2-carboxamidine was made according to the protocol for Example 90 using 1,2-Dihydro-naphthalene and 3-Phenoxy-thiophene-2-carbaldehyde. Mass spectrum: 452 (M+1).

Example 124

6–3-(2-Carbamimidoyl-5,6,6a,7,8,12b-hexahydro-benzo[k]phenanthridin-6-yl)-1H-indole-6-carboxylic acid methyl ester was made according to the protocol for Example 90 using 1,2-Dihydro-naphthalene and 3-Formyl-1H-indole-6-carboxylic acid methyl ester. Mass spectrum: 451 (M+1).

Example 125

6-[5-(2-Trifluoromethoxy-phenyl)-furan-2-yl]-5,6,6a,7,8,12b-hexahydro-benzo[k]phenanthridine-2-carboxamidine was made according to the protocol for Example 90 using 1,2-Dihydro-naphthalene and 5-(2-Trifluoromethoxy-phenyl)-furan-2-carbaldehyde. Mass spectrum: 504 (M+1).

Example 126

6-(4-Bromo-thiophen-2-yl)-5,6,6a,7,8,12b-hexahydro-benzo[k]phenanthridine-2-carboxamidine was made according to the protocol for Example 90 using 1,2-Dihydro-naphthalene and 4-Bromo-thiophene-2-carbaldehyde. Mass spectrum: 439 (M+1).

Example 127

6-(5-Methyl-thiophen-2-yl)-5,6,6a,7,8,12b-hexahydro-benzo[k]phenanthridine-2-carboxamidine was made according to the protocol for Example 90 using 1,2-Dihydro-naphthalene and 5-Methyl-thiophene-2-carbaldehyde. Mass spectrum: 374 (M+1).

Example 128

6-(3,4-Dibromo-5-methyl-1H-pyrrol-2-yl)-5,6,6a,7,8,12b-hexahydro-benzo[k]phenanthridine-2-carboxamidine was made according to the protocol for Example 90 using 1,2-Dihydro-naphthalene and 3,4-Dibromo-5-methyl-1H-pyrrole-2-carbaldehyde. Mass spectrum: 515 (M+1).

Example 129

6-[5-(1-Methyl-5-trifluoromethyl-1H-pyrazol-3-yl)-thiophen-2-yl]-5,6,6a,7,8,12b-hexahydro-benzo[k]phenanthridine-2-carboxamidine was made according to the protocol for Example 90 using 1,2-Dihydro-naphthalene and 5-(1-Methyl-5-trifluoromethyl-1H-pyrazol-3-yl)-thiophene-2-carbaldehyde. Mass spectrum: 508 (M+1).

Example 130

6-(5-Phenylethynyl-thiophen-2-yl)-5,6,6a,7,8,12b-hexahydro-benzo[k]phenanthridine-2-carboxamidine was made according to the protocol for Example 90 using 1,2-Dihydro-naphthalene and 5-Phenylethynyl-thiophene-2-carbaldehyde. Mass spectrum: 460 (M+1).

Example 131

6-(1-Methyl-1H-benzoimidazol-2-yl)-5,6,6a,7,8,12b-hexahydro-benzo[k]phenanthridine-2-carboxamidine was made according to the protocol for Example 90 using 1,2-Dihydro-naphthalene and 1-Methyl-1H-benzoimidazole-2-carbaldehyde. Mass spectrum: 408 (M+1).

Example 132

6-[5-(4-Sulfamoyl-phenyl)-furan-2-yl]-5,6,6a,7,8,12b-hexahydro-benzo[k]phenanthridine-2-carboxamidine was made according to the protocol for Example 90 using 1,2-Dihydro-naphthalene and 4-(5-Formyl-furan-2-yl)-benzenesulfonamide. Mass spectrum: 499 (M+1).

Example 133

6-[5-(2-Chloro-phenyl)-furan-2-yl]-5,6,6a,7,8,12b-hexahydro-benzo[k]phenanthridine-2-carboxamidine was made according to the protocol for Example 90 using 1,2-Dihydro-naphthalene and 5-(2-Chloro-phenyl)-furan-2-carbaldehyde. Mass spectrum: 454 (M+1).

Example 134

6-(1-Methyl-3-phenyl-5-p-tolylsulfanyl-1H-pyrazol-4-yl)-5,6,6a,7,8,12b-hexahydro-benzo[k]phenanthridine-2-carboxamidine was made according to the protocol for Example 90 using 1,2-Dihydro-naphthalene and 1-Methyl-3-phenyl-5-p-tolylsulfanyl-1H-pyrazole-4-carbaldehyde. Mass spectrum: 556 (M+1).

Example 135

6-[5-(2-Trifluoromethyl-phenyl)-furan-2-yl]-5,6,6a,7,8,12b-hexahydro-benzo[k]phenanthridine-2-carboxamidine was made according to the protocol for Example 90 using 1,2-Dihydro-naphthalene and 5-(2-Trifluoromethyl-phenyl)-furan-2-carbaldehyde. Mass spectrum: 488 (M+1).

Example 136

6-(4-Bromo-furan-2-yl)-5,6,6a,7,8,12b-hexahydro-benzo[k]phenanthridine-2-carboxamidine was made according to the protocol for Example 90 using 1,2-Dihydro-naphthalene and 4-Bromo-furan-2-carbaldehyde. Mass spectrum: 423 (M+1).

Example 137

6-[2,2']Bithiophenyl-5-yl-5,6,6a,7,8,12b-hexahydro-benzo[k]phenanthridine-2-carboxamidine was made according to the protocol for Example 90 using 1,2-Dihydro-naphthalene and [2,2']Bithiophenyl-5-carbaldehyde. Mass spectrum: 442 (M+1).

Example 138

6-[4-(2-Cyano-thiophen-3-ylmethoxy)-phenyl]-5,6,6a,7,8,12b-hexahydro-benzo[k]phenanthridine-2-carboxamidine was made according to the protocol for Example 90 using 1,2-Dihydro-naphthalene and 3-(4-Formyl-phenoxymethyl)-thiophene-2-carbonitrile. Mass spectrum: 491 (M+1).

Example 139

6-[1-(4-Chloro-phenyl)-1H-pyrrol-2-yl]-5,6,6a,7,8,12b-hexahydro-benzo[k]phenanthridine-2-carboxamidine was made according to the protocol for Example 90 using 1,2-Dihydro-naphthalene and 1-(4-Chloro-phenyl)-1H-pyrrole-2-carbaldehyde. Mass spectrum: 453 (M+1).

Example 140

6-(2,3-Dibromo-4-hydroxy-5-methoxy-phenyl)-5,6,6a,7,8,12b-hexahydro-benzo[k]phenanthridine-2-carboxamidine was made according to the protocol for Example 90 using 1,2-Dihydro-naphthalene and 2,3-Dibromo-4-hydroxy-5-methoxy-benzaldehyde. Mass spectrum: 558 (M+1).

Example 141

[4-(2-Carbamimidoyl-5,6,6a,7,8,12b-hexahydro-benzo[k]phenanthridin-6-yl)-2-methoxy-phenoxy]-acetic acid was made according to the protocol for Example 90 using 1,2-Dihydro-naphthalene and (4-Formyl-2-methoxy-phenoxy)-acetic acid. Mass spectrum: 458 (M+1).

Example 142

6-(1,3-Dioxo-1,3-dihydro-isoindol-2-ylmethyl)-5,6,6a,7,8,12b-hexahydro-benzo[k]phenanthridine-2-carboxamidine was made according to the protocol for Example 90 using 1,2-Dihydro-naphthalene and (1,3-Dioxo-1,3-dihydro-isoindol-2-yl)-acetaldehyde. Mass spectrum: 437 (M+1).

Example 143

6-(4-Hydroxy-3-methoxy-phenyl)-5,6a,7,8,9,13b-hexahydro-6H-5-aza-benzo[6,7]cyclohepta[1,2-a]naphthalene-2-carboxamidine.

Step a: To a solution of 1-benzosuberone (compound 21,scheme 11) (1.6 g, 10 mmol) in 20 mL of THF was added dropwise LiAlH4 (15 mL,15 mmol; 1M in THF) at 0° C. The mixture was stirred for 3 h and quenched with ice-H₂O. After filtration to remove inorganic salts, the filtrate was extracted with ethyl acetate and washed with 5% HCl, 5% NaOH solutions, water and brine and dried over anhydrous sodium sulfate. Removal of the solvent gave 1.5 g (93%) of 6,7,8,9-Tetrahydro-5H-benzocyclohepten-5-ol(compound 22, scheme 11) as a colorless oil.

Step b: To a solution of 1.6 g (10 mmol) of 6,7,8,9-Tetrahydro-5H-benzocyclohepten-5-ol in 75 mL of benzene was added p-toluene sulfonic acid (19 mg, 0.1 mmol). The mixture was refluxed overnight using Dean-Stark equipment. After removal of the solvent, the residue was repartitioned between ethyl acetate and water. The organic layers was washed with saturated sodium bicarbonate solution, water and brine and dried over sodium sulfate. Removal of the solvent gave 1.3 g (88%) of 6,7-Dihydro-5H-benzocycloheptene(compound 23,scheme 11).

Step c: 6-(4-Hydroxy-3-methoxy-phenyl)-5,6a,7,8,9,13b-hexahydro-6H-5-aza-benzo[6,7]cyclohepta[1,2-a]naphthalene-2-carboxamidine was prepared according to the procedure described in Example 2 using 6,7-Dihydro-5H-benzocycloheptene and 4-acetoxy-3-methoxybenzaldehyde. Mass spectrum: 414 (M+1).

Synthesis of 4-Acetoxy-2-bromo-5-methoxybenzaldehyde (Compound 2, scheme 4)

To a mixture of 7.8 g (40 mmol) of 4-acetoxy-3-methoxybenzaldehyde (1, scheme 6) and 12 g (80 mmol) of NaOAc.3H₂O in 30 mL of HOAC and 6 mL of H₂O was added dropwise 3.0 mL (60 mmol) of Br₂. The mixture was stirred at RT overnight and quenched with H₂O. After stirring at RT for ca. 15 min, the precipitate was collected via filtration and chromatographed (20% EtOAc-Hex) to give 6.3 g of 4-Acetoxy-2-bromo-5methoxybenzaldehyde (2, scheme 6) (58%).

Example 144

6-(5-Hydroxy-4'-isopropyl-4-methoxy-biphenyl-2-yl)-5,6a,7,11b-tetrahydro-6H-indeno[2,1-c]quinoline-2-carboxamidine Step a: To a mixture of (273 mg, 1 mmol) of 4-Acetoxy-2-bromo-5-methoxybenzaldehyde, (164 mg, 1 mmol) of 4-isopropylphenylboronic acid and 276 mg (2 mmol) of K₂CO₃ in 5 mL of DMF and 1 mL of H₂O was added 73.1 mg (0.1 mmol) of Pd(dppf)Cl₂. The mixture was heated at 80° C. overnight. After the removal of the catalyst via filtration, the mixture was repartitioned between EtOAc and H₂O. Aqueous layer was extracted 3 times with EtOAc and organic layers were combined and dried over Na₂SO₄. After the removal of the solvent, the residue was chromatographed to give 362 mg of 5-Hydroxy-4'-isopropyl-4-methoxy-biphenyl-2-carbaldehyde (72%).

Step b: 4-amino-benzamidine mono HCl salt (34.5 mg, 0.2 mmole) was suspended in acetonitrile (1 mL). The suspension was treated with 5-Hydroxy-4'-isopropyl-4-methoxy-biphenyl-2-carbaldehyde (27.0 mg, 0.1 mmole) and indene(23.2 mg, 0.2 mmole). Indium triflate (11.2 mg, 0.02 mmole) was added and the reaction was heated at 70° C. for 24 hours. The desired product was purified using reverse phase HPLC. Mass spectrum: 504 (M+1).

Example 145

2'-(2-Carbamimidoyl-5,6a,7,11b-tetrahydro-6H-indeno[2,1-c]quinolin-6-yl)-5'-hydroxy-4'-methoxy-biphenyl-4-carboxylic acid.

Step a: 2'-Formyl-5'-hydroxy-4'-methoxy-biphenyl-4-carboxylic acid was made according to the protocol used for Example 144, step a using 4-carboxyphenyl boronic acid. Mass Spectrum: 273 (M+1).

Step b: 2'-(2-Carbamimidoyl-5,6a,7,11b-tetrahydro-6H-indeno[2,1-c]quinolin-6-yl)-5'-hydroxy-4'-methoxy-biphenyl-4-carboxylic acid was prepared according to the protocol used for Example 144, step b using indene and 2'-Formyl-5'-hydroxy-4'-methoxy-biphenyl-4-carboxylic acid. Mass spectrum: 506 (M+1).

Example 146

2'-(2-Carbamimidoyl-5,6a,7,11b-tetrahydro-6H-indeno[2,1-c]quinolin-6-yl)-5'-hydroxy-4'-methoxy-biphenyl-4-carboxylic acid isobutyl-amide.

Step a: 2'-Formyl-5'-hydroxy-4'-methoxy-biphenyl-4-carboxylic acid was made according to the protocol used for Example 144, step a using 4-carboxyphenyl boronic acid. Mass Spectrum: 273 (M+1).

Step b: 2'-(2-Carbamimidoyl-5,6a,7,11b-tetrahydro-6H-indeno[2,1-c]quinolin-6-yl)-5'-hydroxy-4'-methoxy-biphenyl-4-carboxylic acid was prepared according to the protocol used for Example 144, step b using indene and 2'-Formyl-5'-hydroxy-4'-methoxy-biphenyl-4-carboxylic acid. Mass spectrum: 506 (M+1).

Step c: (0.1 mmol; 50.5 mg) of 2'-(2-Carbamimidoyl-5,6a,7,11b-tetrahydro-6H-indeno[2,1-c]quinolin-6-yl)-5'-hydroxy-4'-methoxy-biphenyl-4-carboxylic acid was dissolved in 4 mL of DMF followed by the addition of HATU (0.3 mmol; 114 mg), N,N-diisoproplyethylamine (0.6 mmol; 0.1 mL) and isobutylamine (0.6 mmol; 0.6 ml). The reaction was stirred at room temperature for 18 hours, filtered and purified by LC/MS prep system to give 2'-(2-Carbamimidoyl-5,6a,7,11b-tetrahydro-6H-indeno[2,1-c]quinolin-6-yl)-5'-hydroxy-4'-methoxy-biphenyl-4-carboxylic acid isobutyl-amide. Mass spectrum: 561 (M+1).

Example 147

2'-(2-Carbamimidoyl-5,6a,7,11b-tetrahydro-6H-indeno[2,1-c]quinolin-6-yl)-5'-hydroxy-4'-methoxy-biphenyl-2-carboxylic acid.

Step a: To a mixture of 4-acetoxy-2-bromo-5-methoxybenzaldehyde(273 mg, 1 mmol), 194 mg (1 mmol) of 2-ethoxycarbonylphenyl boronic acid and 276 mg (2 mmol) of $K_2CO_3$ in 5 mL of DMF and 1 mL of $H_2O$ was added 73.1 mg (0.1 mmol) of Pd(dppf)$Cl_2$. The mixture was heated at 80° C. overnight. After the removal of the catalyst via filtration, the mixture was repartitioned between EtOAc and $H_2O$. Aqueous layer was extracted 3 times with EtOAc and organic layers were combined and dried over $Na_2SO_4$. After the removal of the solvent, the residue was chromatographed to give 217 mg of 2'-Formyl-5'-hydroxy-4'-methoxy-biphenyl-2-carboxylic acid ethyl ester(3 with ortho substitution, scheme 6; 72%).Mass Spectrum: 301 (M+1).

Step b: To a solution of 2'-Formyl-5'-hydroxy-4'-methoxy-biphenyl-2-carboxylic acid ethyl ester (300 mg, 1 mmol)in 5 mL of THF and 2 mL of $H_2O$ was added 200 mg (5 mmol) of NaOH. The mixture was stirred at RT for ca. 2 h and was repartitioned between EtOAc and $H_2O$. Aqueous layer was acidified with conc. HCl to pH at 3. The precipitate was collected via filtration and washed with cold $H_2O$ to give 231 mg of 2'-Formyl-5'-hydroxy-4'-methoxy-biphenyl-2-carboxylic acid (4, scheme 4; 85%).Mass Spectrum 258 (M+1).

Step c: 2'-(2-Carbamimidoyl-5,6a,7,11b-tetrahydro-6H-indeno[2,1-c]quinolin-6-yl)-5'-hydroxy-4'-methoxy-biphenyl-2-carboxylic acid was prepared according to the protocol used for Example 144, step b using indene and 2'-Formyl-5'-hydroxy-4'-methoxy-biphenyl-2-carboxylic acid. Mass spectrum: 506 (M+1).

Example 148

2'-(2-Carbamimidoyl-5,6a,7,11b-tetrahydro-6H-indeno[2,1-c]quinolin-6-yl)-5'-hydroxy-4'-methoxy-biphenyl-3-carboxylic acid Step a: 2'-Formyl-5'-hydroxy-4'-methoxy-biphenyl-3-carboxylic acid was made according to the protocol used for Example 144, step a using 3-carboxyphenyl boronic acid. Mass Spectrum: 273 (M+1).

Step b: 2'-(2-Carbamimidoyl-5,6a,7,11b-tetrahydro-6H-indeno[2,1-c]quinolin-6-yl)-5'-hydroxy-4'-methoxy-biphenyl-4-carboxylic acid was prepared according to the protocol used for Example 144, step b using indene and 2'-Formyl-5'-hydroxy-4'-methoxy-biphenyl-3-carboxylic acid. Mass spectrum: 506 (M+1).

Example 149

6-(5-Hydroxy-4-methoxy-biphenyl-2-yl)-5,6a,7,11b-tetrahydro-6H-indeno[2,1-c]quinoline-2-carboxamidine.

Step a: 5-Hydroxy-4-methoxy-biphenyl-2-carbaldehyde was made according to the protocol used for Example 144, step a using phenyl boronic acid. Mass Spectrum: 229 (M+1).

Step b: 6-(5-Hydroxy-4-methoxy-biphenyl-2-yl)-5,6a,7,11b-tetrahydro-6H-indeno[2,1-c]quinoline-2-carboxamidine was prepared according to the protocol used for Example 144, step b using indene and 5-Hydroxy-4-methoxy-biphenyl-2-carbaldehyde. Mass spectrum: 462 (M+1).

Example 150

6-(5-Hydroxy-4,2'-dimethoxy-biphenyl-2-yl)-5,6a,7,11b-tetrahydro-6H-indeno[2,1-c]quinoline-2-carboxamidine.

Step a: 5-Hydroxy-4,2'-dimethoxy-biphenyl-2-carbaldehyde was made according to the protocol used for Example 144, step a using 2-methoxyphenyl boronic acid. Mass Spectrum: 259 (M+1).

Step b: 6-(5-Hydroxy-4,2'-dimethoxy-biphenyl-2-yl)-5,6a,7,11b-tetrahydro-6H-indeno[2,1-c]quinoline-2-carboxamidine was prepared according to the protocol used for Example 144, step b using indene and 5-Hydroxy-4,2'-dimethoxy-biphenyl-2-carbaldehyde. Mass spectrum: 492 (M+1).

Example 151

6-(4'-Ethoxy-5-hydroxy-4-methoxy-biphenyl-2-yl)-5,6a,7,11b-tetrahydro-6H-indeno[2,1-c]quinoline-2-carboxamidine.

Step a: 4'-Ethoxy-5-hydroxy-4-methoxy-biphenyl-2-carbaldehyde was made according to the protocol used for Example 144, step a using 4-ethoxyphenyl boronic acid. Mass Spectrum: 273 (M+1).

Step b: 6-(4'-Ethoxy-5-hydroxy-4-methoxy-biphenyl-2-yl)-5,6a,7,11b-tetrahydro-6H-indeno[2,1-c]quinoline-2-carboxamidine was prepared according to the protocol used for Example 144, step b using indene and 4'-Ethoxy-5-hydroxy-4-methoxy-biphenyl-2-carbaldehyde. Mass spectrum: 506 (M+1).

Example 152

6-(3'-Cyano-5-hydroxy-4-methoxy-biphenyl-2-yl)-5,6a,7,11b-tetrahydro-6H-indeno[2,1-c]quinoline-2-carboxamidine.

Step a: 3'-Cyano-5-hydroxy-4-methoxy-biphenyl-2-carbaldehyde was made according to the protocol used for Example 144, step a using 3-cyanophenyl boronic acid. Mass Spectrum: 254 (M+1).

Step b: 6-(3'-Cyano-5-hydroxy-4-methoxy-biphenyl-2-yl)-5,6a,7,11b-tetrahydro-6H-indeno[2,1-c]quinoline-2-carboxamidine was prepared according to the protocol used for Example 144, step b using indene and 3'-cyano-5-hydroxy-4-methoxy-biphenyl-2-carbaldehyde. Mass spectrum: 487 (M+1).

Example 153
6-(4'-Cyano-5-hydroxy-4-methoxy-biphenyl-2-yl)-5,6a,7,11b-tetrahydro-6H-indeno[2,1-c]quinoline-2-carboxamidine.

Step a: 4'-Cyano-5-hydroxy-4-methoxy-biphenyl-2-carbaldehyde was made according to the protocol used for Example 144, step a using 4-cyanophenyl boronic acid. Mass Spectrum: 254 (M+1).

Step b: 6-(4'-Cyano-5-hydroxy-4-methoxy-biphenyl-2-yl)-5,6a,7,11b-tetrahydro-6H-indeno[2,1-c]quinoline-2-carboxamidine was prepared according to the protocol used for Example 144, step b using indene and 4'-Cyano-5-hydroxy-4-methoxy-biphenyl-2-carbaldehyde. Mass spectrum: 487 (M+1).

Example 154
6-(5-Hydroxy-3'-hydroxymethyl-4-methoxy-biphenyl-2-yl)-5,6a,7,11b-tetrahydro-6H-indeno[2,1-c]quinoline-2-carboxamidine.

Step a: 5-Hydroxy-3'-hydroxymethyl-4-methoxy-biphenyl-2-carbaldehyde was made according to the protocol used for Example 144, step a using 3-hydroxymethylphenyl boronic acid. Mass Spectrum: 259 (M+1).

Step b: 6-(5-Hydroxy-3'-hydroxymethyl-4-methoxy-biphenyl-2-yl)-5,6a,7,11b-tetrahydro-6H-indeno[2,1-c]quinoline-2-carboxamidine was prepared according to the protocol used for Example 144, step b using indene and 5-Hydroxy-3'-hydroxymethyl-4-methoxy-biphenyl-2-carbaldehyde. Mass spectrum: 492 (M+1).

Example 155
6-(5-Hydroxy-4'-methanesulfonylamino-4-methoxy-biphenyl-2-yl)-5,6a,7,11b-tetrahydro-6H-indeno[2,1-c]quinoline-2-carboxamidine.

Step a: N-(2'-Formyl-5'-hydroxy-4'-methoxy-biphenyl-4-yl)-methanesulfonamide was made according to the protocol used for Example 144, step a using 4-N-methanesulfonamidophenyl boronic acid. Mass Spectrum: 322 (M+1).

Step b: 6-(5-Hydroxy-4'-methanesulfonylamino-4-methoxy-biphenyl-2-yl)-5,6a,7,11b-tetrahydro-6H-indeno[2,1-c]quinoline-2-carboxamidine was prepared according to the protocol used for Example 144, step b using indene and N-(2'-Formyl-5'-hydroxy-4'-methoxy-biphenyl-4-yl)-methanesulfonamide. Mass spectrum: 554 (M+1).

Example 156
6-(5-Hydroxy-4'-methanesulfonyl-4-methoxy-biphenyl-2-yl)-5,6a,7,11b-tetrahydro-6H-indeno[2,1-c]quinoline-2-carboxamidine.

Step a: 5-Hydroxy-4'-methanesulfonyl-4-methoxy-biphenyl-2-carbaldehyde was made according to the protocol used for Example 144, step a using 4-methansulfonylphenyl boronic acid. Mass Spectrum: 307 (M+1).

Step b: 6-(5-Hydroxy-4'-methanesulfonyl-4-methoxy-biphenyl-2-yl)-5,6a,7,11b-tetrahydro-6H-indeno[2,1-c]quinoline-2-carboxamidine was prepared according to the protocol used for Example 144, step b using indene and 5-Hydroxy-4'-methanesulfonyl-4-methoxy-biphenyl-2-carbaldehyde. Mass spectrum: 539 (M+1).

Example 157
6-(5-Hydroxy-4'-hydroxymethyl-4-methoxy-biphenyl-2-yl)-5,6a,7,11b-tetrahydro-6H-indeno[2,1-c]quinoline-2-carboxamidine.

Step a: 5-Hydroxy-4'-hydroxymethyl-4-methoxy-biphenyl-2-carbaldehyde was made according to the protocol used for Example 144, step a using 3-hydroxymethylphenyl boronic acid. Mass Spectrum: 259 (M+1).

Step b: 6-(5-Hydroxy-3'-hydroxymethyl-4-methoxy-biphenyl-2-yl)-5,6a,7,11b-tetrahydro-6H-indeno[2,1-c]quinoline-2-carboxamidine was prepared according to the protocol used for Example 144, step b using indene and 5-Hydroxy-4'-hydroxymethyl-4-methoxy-biphenyl-2-carbaldehyde. Mass spectrum: 491 (M+1).

Example 158
6-(4-Hydroxy-5-methoxy-2-pyridin-3-yl-phenyl)-5,6a,7,11b-tetrahydro-6H-indeno[2,1-c]quinoline-2-carboxamidine.

Step a: 4-Hydroxy-5-methoxy-2-pyridin-3-yl-benzaldehyde was made according to the protocol used for Example 144, step a using 3-pyridyl boronic acid. Mass Spectrum: 230 (M+1).

Step b: 6-(4-Hydroxy-5-methoxy-2-pyridin-3-yl-phenyl)-5,6a,7,11b-tetrahydro-6H-indeno[2,1-c]quinoline-2-carboxamidine was prepared according to the protocol used for Example 144, step b using indene and 4-Hydroxy-5-methoxy-2-pyridin-3-yl-benzaldehyde. Mass spectrum: 462 (M+1).

Example 159
6-[2-(2,4-Dimethoxy-pyrimidin-5-yl)-4-hydroxy-5-methoxy-phenyl]-5,6a,7,11b-tetrahydro-6H-indeno[2,1-c]quinoline-2-carboxamidine.

Step a: 2-(2,4-Dimethoxy-pyrimidin-5-yl)-4-hydroxy-5-methoxy-benzaldehyde was made according to the protocol used for Example 144, step a using 4-carboxyphenyl boronic acid. Mass Spectrum: 291 (M+1).

Step b: 6-[2-(2,4-Dimethoxy-pyrimidin-5-yl)-4-hydroxy-5-methoxy-phenyl]-5,6a,7,11b-tetrahydro-6H-indeno[2,1-c]quinoline-2-carboxamidine was prepared according to the protocol used for Example 144, step b using indene and 2-(2,4-Dimethoxy-pyrimidin-5-yl)-4-hydroxy-5-methoxy-benzaldehyde. Mass spectrum: 523 (M+1).

Example 160
2'-(2-Carbamimidoyl-5,6a,7,11b-tetrahydro-6H-indeno[2,1-c]quinolin-6-yl)-5'-hydroxy-4-isobutylcarbamoyl-4'-methoxy-biphenyl-2-carboxylic acid benzyl ester.

This Example was prepared according to protocols published in EP1078917A1.

Step a: Potassium bicarbonate (3.3 g) and benzyl bromide (3.9 ml), successively, were added to a solution of 2-hydroxy-5-formylbenzoic acid (5 g) in dimethylformamide (80 ml) under an atmosphere of argon at room temperature. The mixture was stirred for 14 hours at room temperature. The reaction mixture was poured into water (150 ml). The solution was extracted with ethyl acetate. The extract was washed with a saturated aqueous solution of sodium chloride, dried over anhydrous magnesium sulfate and concentrated. To a solution of the residue (5.9 g) in methylene chloride (25 ml), pyridine (9.3 ml) and trifluoromethanesulfonic acid anhydrous (7.7 ml), successively, were added under an atmosphere of argon at 0° C. The mixture was stirred for 30 minutes. The reaction mixture was poured into water (6030 ml). The solution was extracted with ethyl acetate (150 ml). The extract was washed with a saturated aqueous solution of sodium chloride, dried over anhydrous magnesium sulfate and concentrated. The residue was purified by column chromatography on silica gel (hexane:ethyl acetate=5:1) to give the present compound Benzyl 2-trifluoromethylsulfonyloxy-5-formylbenzoate (6.23 g)

Step b: To the mixed solution of Benzyl 2-trifluoromethylsulfonyloxy-5-formylbenzoate (1.86 g)in t-butanol-acetonitrile-water (27 ml; 6:1:2), 2-methyl-2-butene (2.3 ml), sodium dihydrogenphosphate (690 mg) and sodium chloride (1.925 g), successively, were added. The mixture was stirred for 20 minutes at room temperature. The reaction mixture was poured into ice-water. The solution was extracted with ethyl acetate (60 ml, 2 times). The extract was washed with a saturated aqueous solution of sodium chloride, dried over anhydrous magnesium sulfate and concentrated. The residue of 3-benzyloxycarbonyl-4-trifluoromethylsulfonyloxybenzoic acid (1.94 g) was used in the next reaction without being purified.

Step c: Oxalyl chloride (0.21 ml) and dimethylformamide (1 drop) were added to a solution of 3-benzyloxycarbonyl-4-trifluoromethylsulfonyloxybenzoic acid (808 mg) in methylene chloride (8 ml) under an atmosphere of argon at 0° C. The mixture was stirred for 3 minutes at 0° C., and stirred for 1 hour at room temperature. The reaction mixture was concentrated. The residue was distilled off an azeotropic mixture with toluene (5 ml, 2 times). The residue was dissolved into methyl-ene chloride (8 ml), and cooled to 0° C. Triethylamine (0.5 ml) and 2,2-dimethylpropylamine (0.24 ml) were added to the solution. The mixture was stirred for 5 minutes at 0° C., stirred for 10 minutes at room temperature. The reaction mixture was poured into ice-water (30 ml). The solution was extracted with ethyl acetate (30 ml, 2 times). The extract was washed with a saturated aqueous solution of sodium chloride, dried over anhydrous magnesium sulfate and concentrated. The residue was purified by column chromatography on silica gel (hexane:ethyl acetate=5:1) to give the present compound Benzyl 2-trifluoromethylsulfonyloxy-5-((2,2-dimethylpropyl) carbamoyl) benzoate (857 mg).

Step d: Synthesis of 4-Hydroxy-5-methoxy-2-(4,4,5,5-tetramethyl-[1,3,2]dioxaborolan-2-yl)-benzaldehyde (Compound 5, scheme 6a). To a mixture of 2.7 g (10 mmol) of 4-Acetoxy-2-bromo-5-methoxybenzaldehyde (Compound 10, scheme 4b), 3.8 g (15 mmol) of bis(pinacolato) diboron and 2.94 g (30 mmol) of KOAc in 30 mL of DMSO was added 146 mg (0.2 mmol) of Pd(dppf)$_2$Cl$_2$. The mixture was heated at 100° C. overnight and was repartitioned between EtOAc and H$_2$O. Aqueous layer was extracted with EtOAc (3×) and organic layers were combined and dried over Na$_2$SO$_4$. After the removal of the solvent, the residue was chromatographed (30% EtOAc-Hex) to give 1.52 g of 4-Hydroxy-5-methoxy-2-(4,4,5,5-tetramethyl-[1,3,2]dioxaborolan-2-yl)-benzaldehyde (55%).

Step e: 4-Hydroxy-5-methoxy-2-(4,4,5,5-tetramethyl-[1,3,2]dioxaborolan-2-yl)-benzaldehyde (Example 160,step d, 0.5 mmol, 140 mg) was mixed with benzyl 2-trifluoromethyl-sulfonyloxy-5-((2,2-dimethylpropyl) carbamoyl) benzoate (Example 160, step c, 0.5 mmol, 230 mg); Pd(dppf)$_2$Cl$_2$ (0.1 mmol, 73 mg) and potassium carbonate (1mmol, 138 mg). DMF (25 mL) and water (0.5 mL) were added and the mixture was heated overnight at 80° C. The resulting mixture was partitioned between ethyl acetate and water. The aqueous layer was extracted with ethyl acetate (3×). The organic layer was evaporated and the residue chromatographed to yield 2'-Formyl-5'-hydroxy-4-isobutylcarbamoyl-4'-methoxy-biphenyl-2-carboxylic acid benzyl ester 192 mg (86%) Mass Spectrum: 462 (M+1).

Step f: 2'-(2-Carbamimidoyl-5,6a,7,11b-tetrahydro-6H-indeno[2,1-c]quinolin-6-yl)-5'-hydroxy-4-isobutylcarbamoyl-4'-methoxy-biphenyl-2-carboxylic acid benzyl ester was prepared according to the protocol used for Example 144, step b using indene and 2'-Formyl-5'-hydroxy-4-isobutylcarbamoyl-4'-methoxy-biphenyl-2-carboxylic acid benzyl ester. Mass spectrum: 694 (M+1).

Example 161

2'-(2-Carbamimidoyl-5,6a,7,11b-tetrahydro-6H-indeno[2,1-c]quinolin-6-yl)-5'-hydroxy-4-isobutylcarbamoyl-4'-methoxy-biphenyl-2-carboxylic acid.

A solution of 2'-(2-Carbamimidoyl-5,6a,7,11b-tetrahydro-6H-indeno[2,1-c]quinolin-6-yl)-5'-hydroxy-4-isobutylcarbamoyl-4'-methoxy-biphenyl-2-carboxylic acid benzyl ester (Example 160, step f) (35 mg, 0.05 mmol) in 1 mL of MeOH was hydrogenated using 10%Pd-C (20 mg)overnight to give 2'-(2-carbamimidoyl-5,6a,7,11b-tetrahydro-6H-indeno[2,1-c]quinolin-6-yl)-5'-hydroxy-4'-methoxy-biphenyl-4-carboxylic acid which was purified using reverse phase HPLC. Mass spectrum: 604 (M+1).

Example 162

6'-(2-Carbamimidoyl-5,6a,7,11b-tetrahydro-6H-indeno[2,1-c]quinolin-6-yl)-3'-hydroxy-2',4'-dimethoxy-biphenyl-2-carboxylic acid.

Step a: Synthesis of 4-acetoxy-2-bromo-3,5-dimethoxybenzaldehyde. To a mixture of 4-acetoxy-3,5-dimethoxy benzaldehyde (5.4 g, 20 mmol) and 5.4 g (40 mmol) of NaOAc.3H$_2$O in acetic acid (14 mL) and water (2 mL) was added dropwise bromine (1.2 mL, 24 mmol). The mixture was stirred at RT overnight and repartitioned between ethyl acetate and water. The aqueous layer was extracted with ethyl acetate (3×) and the combined organic layer was washed with saturated sodium bicarbonate solution, water and brine and dried over anhydrous sodium sulfate. Removal of the solvent gave 5.6 g of 4-acetoxy-2-bromo-3,5-dimethoxybenzaldehyde (80%).

Step b: 6'-Formyl-3'-hydroxy-2',4'-dimethoxy-biphenyl-2-carboxylic acid ethyl ester was prepared from 4-acetoxy-2-bromo-3,5-dimethoxybenzaldehyde (Example 162, step a) and 2-ethoxycarbonylphenyl boronic acid using the protocol described in Example 147, step a. Mass Spectrum: 331 (M+1).

Step c: 6'-Formyl-3'-hydroxy-2',4'-dimethoxy-biphenyl-2-carboxylic acid was prepared from 6'-Formyl-3'-hydroxy-2',4'-dimethoxy-biphenyl-2-carboxylic acid ethyl ester using the protocol described in Example 147, step b.Mass Spectrum 288 (M+1).

Step d: 6'-(2-Carbamimidoyl-5,6a,7,11b-tetrahydro-6H-indeno[2,1-c]quinolin-6-yl)-3'-hydroxy-2',4'-dimethoxy-biphenyl-2-carboxylic acid was prepared according to the protocol used for Example 144, step b using indene and 6'-Formyl-3'-hydroxy-2',4'-dimethoxy-biphenyl-2-carboxylic acid. Mass spectrum: 535 (M+1).

Example 163

2'-(2-Carbamimidoyl-5,6,6a,7,8,12b-hexahydro-benzo[k]phenanthridin-6-yl)-5'-hydroxy-4'-methoxy-biphenyl-3-carboxylic acid.

Step a: 2'-Formyl-5'-hydroxy-4'-methoxy-biphenyl-3-carboxylic acid was made according to the protocol used for Example 144, step a using 3-carboxyphenyl boronic acid. Mass Spectrum: 273 (M+1).

Step b: 2'-(2-Carbamimidoyl-5,6,6a,7,8,12b-hexahydrobenzo[k]phenanthridin-6-yl)-5'-hydroxy-4'-methoxy-biphenyl-3-carboxylic acid was prepared according to the protocol used for Example 144, step b using 1,2-dihydronapthalene and 2'-Formyl-5'-hydroxy-4'-methoxy-biphenyl-3-carboxylic acid. Mass spectrum: 519 (M+1).

Example 164
2'-(2-Carbamimidoyl-5,6,6a,7,8,12b-hexahydro-benzo[k]phenanthridin-6-yl)-5'-hydroxy-4'-methoxy-biphenyl-4-carboxylic acid.

Step a: 2'-Formyl-5'-hydroxy-4'-methoxy-biphenyl-4-carboxylic acid was made according to the protocol used for Example 144, step a using 4-carboxyphenyl boronic acid. Mass Spectrum: 273 (M+1).

Step b: 2'-(2-Carbamimidoyl-5,6a,7,11b-tetrahydro-6H-indeno[2,1-c]quinolin-6-yl)-5'-hydroxy-4'-methoxy-biphenyl-4-carboxylic acid was prepared according to the protocol used for Example 144, step b using 1,2-dihydronapthalene and 2'-Formyl-5'-hydroxy-4'-methoxy-biphenyl-4-carboxylic acid. Mass spectrum: 519 (M+1).

Example 165
2'-(2-Carbamimidoyl-5,6a,7,11b-tetrahydro-6H-indeno[2,1-c]quinolin-6-yl)-5'-hydroxy-4'-methoxy-biphenyl-3-carboxylic acid amide.

Step a: To a tube charged with 3-Bromo-benzamide (180 mg, 0.9 mmol) and Pd(dppf)Cl$_2$ (40 mg, 0.054 mmol), was added 4-Hydroxy-5-methoxy-2-(4,4,5,5-tetramethyl-[1,3,2]dioxaborolan-2-yl)-benzaldehyde (250 mg, 0.9 mmol, Example 160, step d) as a solution in 2 mL of DMF followed by the addition of K$_2$CO$_3$ (248 mg, 1.8 mmol) in 0.5 mL H$_2$O. The tube was sealed with a cap and allowed to heat for 16 hours at 85° C. Reaction mixture was then filtered and purified on reverse phase HPLC. Fractions containing the desired product were combined and the solvent was removed under reduced pressure to yield 82 mg of product 2'-Formyl-5'-hydroxy-4'-methoxy-biphenyl-3-carboxylic acid amide.

Step b: 2'-(2-Carbamimidoyl-5,6a,7,11b-tetrahydro-6H-indeno[2,1-c]quinolin-6-yl)-5'-hydroxy-4'-methoxy-biphenyl-3-carboxylic acid amide was prepared according to the protocol used for Example 144, step b using indene and 2'-Formyl-5'-hydroxy-4'-methoxy-biphenyl-3-carboxylic acid amide. Mass spectrum: 504 (M+1).

Example 166
6-(5-Hydroxy-4-methoxy-4'-sulfamoyl-biphenyl-2-yl)-5,6a,7,11b-tetrahydro-6H-indeno[2,1-c]quinoline-2-carboxamidine.

Step a: 2'-Formyl-5'-hydroxy-4'-methoxy-biphenyl-4-sulfonic acid amide was made according to the protocol used for Example 165, step a using 4-bromobenzenesulfonamide. Mass spectrum: 308 (M+1).

Step b: 6-(5-Hydroxy-4-methoxy-4'-sulfamoyl-biphenyl-2-yl)-5,6a,7,11b-tetrahydro-6H-indeno[2,1-c]quinoline-2-carboxamidine was prepared according to the protocol used for Example 144, step b using indene and 2'-Formyl-5'-hydroxy-4'-methoxy-biphenyl-4-sulfonic acid amide. Mass spectrum: 540 (M+1).

Example 167
6-(5-Hydroxy-4-methoxy-3'-sulfamoyl-biphenyl-2-yl)-5,6a,7,11b-tetrahydro-6H-indeno[2,1-c]quinoline-2-carboxamidine.

Step a: 2'-Formyl-5'-hydroxy-4'-methoxy-biphenyl-3-sulfonic acid amide was made according to the protocol used for Example 165, step a using 3-bromobenzenesulfonamide. Mass spectrum: 308 (M+1).

Step b: 6-(5-Hydroxy-4-methoxy-3'-sulfamoyl-biphenyl-2-yl)-5,6a,7,11b-tetrahydro-6H-indeno[2,1-c]quinoline-2-carboxamidine was prepared according to the protocol used for Example 144, step b using indene and 2'-Formyl-5'-hydroxy-4'-methoxy-biphenyl-3-sulfonic acid amide. Mass spectrum: 540 (M+1).

Example 168
2'-(2-Carbamimidoyl-5,6,6a,7,8,12b-hexahydro-benzo[k]phenanthridin-6-yl)-5'-hydroxy-4'-methoxy-biphenyl-2-carboxylic acid.

Step a: 2'-Formyl-5'-hydroxy-4'-methoxy-biphenyl-2-carboxylic acid was made according to the protocol used in Example 147, steps a and b. Mass spectrum: 258 (M+1).

Step b: 2'-(2-Carbamimidoyl-5,6,6a,7,8,12b-hexahydro-benzo[k]phenanthridin-6-yl)-5'-hydroxy-4'-methoxy-biphenyl-2-carboxylic acid was prepared according to the protocol used for Example 147, step c using 1,2-dihydronapthalene and 2'-Formyl-5'-hydroxy-4'-methoxy-biphenyl-2-carboxylic acid. Mass spectrum: 519 (M+1).

Example 169
6'-(2-Carbamimidoyl-5,6a,7,11b-tetrahydro-6H-indeno[2,1-c]quinolin-6-yl)-3'-hydroxy-2',4'-dimethoxy-biphenyl-3-carboxylic acid.

Step a: 6'-Formyl-3'-hydroxy-2',4'-dimethoxy-biphenyl-3-carboxylic acid was prepared from 4-acetoxy-2-bromo-3,5-dimethoxybenzaldehyde (Example 162, step a) and 3-carboxyphenyl boronic acid using the protocol described in Example 145, step a. Mass Spectrum 288 (M+1).

Step b: 6'-(2-Carbamimidoyl-5,6a,7,11b-tetrahydro-6H-indeno[2,1-c]quinolin-6-yl)-3'-hydroxy-2',4'-dimethoxy-biphenyl-3-carboxylic acid was prepared according to the protocol used for Example 144, step b using indene and 6'-Formyl-3'-hydroxy-2',4'-dimethoxy-biphenyl-3-carboxylic acid. Mass spectrum: 535 (M+1).

Example 170
6'-(2-Carbamimidoyl-5,6a,7,11b-tetrahydro-6H-indeno[2,1-c]quinolin-6-yl)-3'-hydroxy-2',4'-dimethoxy-biphenyl-4-carboxylic acid.

Step a: 6'-Formyl-3'-hydroxy-2',4'-dimethoxy-biphenyl-4-carboxylic acid was prepared from 4-acetoxy-2-bromo-3,5-dimethoxybenzaldehyde (Example 162, step a) and 4-carboxyphenyl boronic acid using the protocol described in Example 145, step a. Mass Spectrum 288 (M+1).

Step b: 6'-(2-Carbamimidoyl-5,6a,7,11b-tetrahydro-6H-indeno[2,1-c]quinolin-6-yl)-3'-hydroxy-2',4'-dimethoxy-biphenyl-4-carboxylic acid was prepared according to the protocol used for Example 144, step b using indene and 6'-Formyl-3'-hydroxy-2',4'-dimethoxy-biphenyl-3-carboxylic acid. Mass spectrum: 535 (M+1).

Example 171
6-(4-Hydroxy-5-methoxy-2-thiophen-3-yl-phenyl)-5,6a,7,11b-tetrahydro-6H-indeno[2,1-c]quinoline-2-carboxamidine.

Step a: 4-Hydroxy-5-methoxy-2-thiophen-3-yl-benzaldehyde was made according to the protocol used for Example 144, step a using thiophen-3-yl boronic acid. Mass Spectrum: 235 (M+1).

Step b: 6-(4-Hydroxy-5-methoxy-2-thiophen-3-yl-phenyl)-5,6a,7,11b-tetrahydro-6H-indeno[2,1-c]quinoline-2-carboxamidine was prepared according to the protocol used for Example 144, step b using indene and 4-Hydroxy-5-methoxy-2-thiophen-3-yl-benzaldehyde. Mass spectrum: 467 (M+1).

Example 172
6-(5-Hydroxy-4,2',5'-trimethoxy-biphenyl-2-yl)-5,6a,7,11b-tetrahydro-6H-indeno[2,1-c]quinoline-2-carboxamidine.

Step a: 5-Hydroxy-4,2',5'-trimethoxy-biphenyl-2-carbaldehyde was made according to the protocol used for Example 144, step a using 2,5-dimethoxyphenyl boronic acid. Mass Spectrum: 289 (M+1).

Step b: 6-(5-Hydroxy-4,2',5'-trimethoxy-biphenyl-2-yl)-5,6a,7,11b-tetrahydro-6H-indeno[2,1-c]quinoline-2-carboxamidine was prepared according to the protocol used for Example 144, step b using indene and 5-Hydroxy-4,2',5'-trimethoxy-biphenyl-2-carbaldehyde. Mass spectrum: 521 (M+1).

Example 173

6-(2'-Chloro-5-hydroxy-4-methoxy-biphenyl-2-yl)-5,6a,7,11b-tetrahydro-6H-indeno[2,1-c]quinoline-2-carboxamidine.

Step a: 2'-Chloro-5-hydroxy-4-methoxy-biphenyl-2-carbaldehyde was made according to the protocol used for Example 144, step a using 2-chlorophenyl boronic acid. Mass Spectrum: 263 (M+1).

Step b: 6-(2'-Chloro-5-hydroxy-4-methoxy-biphenyl-2-yl)-5,6a,7,11b-tetrahydro-6H-indeno[2,1-c]quinoline-2-carboxamidine was prepared according to the protocol used for Example 144, step b using indene and 2'-Chloro-5-hydroxy-4-methoxy-biphenyl-2-carbaldehyde. Mass spectrum: 495 (M+1).

Example 174

6-(5-Hydroxy-4,2',6'-trimethoxy-biphenyl-2-yl)-5,6a,7,11b-tetrahydro-6H-indeno[2,1-c]quinoline-2-carboxamidine.

Step a: 5-Hydroxy-4,2',6'-trimethoxy-biphenyl-2-carbaldehyde was made according to the protocol used for Example 144, step a using 2,6-dimethoxyphenyl boronic acid. Mass Spectrum: 289 (M+1).

Step b: 6-(5-Hydroxy-4,2',6'-trimethoxy-biphenyl-2-yl)-5,6a,7,11b-tetrahydro-6H-indeno[2,1-c]quinoline-2-carboxamidine was prepared according to the protocol used for Example 144, step b using indene and 5-Hydroxy-4,2',6'-trimethoxy-biphenyl-2-carbaldehyde. Mass spectrum: 521 (M+1).

Example 175

6-(5-Hydroxy-4-methoxy-2'-methylsulfanyl-biphenyl-2-yl)-5,6a,7,11b-tetrahydro-6H-indeno[2,1-c]quinoline-2-carboxamidine.

Step a: 5-Hydroxy-4-methoxy-2'-methylsulfanyl-biphenyl-2-carbaldehyde was made according to the protocol used for Example 144, step a using 2-methylsulfanylphenyl boronic acid. Mass Spectrum: 275 (M+1).

Step b: 6-(5-Hydroxy-4-methoxy-2'-methylsulfanyl-biphenyl-2-yl)-5,6a,7,11b-tetrahydro-6H-indeno[2,1-c]quinoline-2-carboxamidine was prepared according to the protocol used for Example 144, step b using indene and 5-Hydroxy-4-methoxy-2'-methylsulfanyl-biphenyl-2-carbaldehyde. Mass spectrum: 507 (M+1).

Example 176

6-(5-Hydroxy-4-methoxy-[1,1';2',1"]terphenyl-2-yl)-5,6a,7,11b-tetrahydro-6H-indeno[2,1-c]quinoline-2-carboxamidine.

Step a: 5-Hydroxy-4-methoxy-[1,1';2',1"]terphenyl-2-carbaldehyde was made according to the protocol used for Example 144, step a using 2-biphenyl boronic acid. Mass Spectrum: 305 (M+1).

Step b: 6-(5-Hydroxy-4-methoxy-[1,1';2',1"]terphenyl-2-yl)-5,6a,7,11b-tetrahydro-6H-indeno[2,1-c]quinoline-2-carboxamidine was prepared according to the protocol used for Example 144, step b using indene and 5-Hydroxy-4-methoxy-[1,1';2',1"]terphenyl-2-carbaldehyde. Mass spectrum: 537 (M+1).

Example 177

6-(5'-Fluoro-5-hydroxy-4,2'-dimethoxy-biphenyl-2-yl)-5,6a,7,11b-tetrahydro-6H-indeno[2,1-c]quinoline-2-carboxamidine.

Step a: 5'-Fluoro-5-hydroxy-4,2'-dimethoxy-biphenyl-2-carbaldehyde was made according to the protocol used for Example 144, step a using 5-fluoro-2-methoxyphenyl boronic acid. Mass Spectrum: 278 (M+1).

Step b: 6-(5'-Fluoro-5-hydroxy-4,2'-dimethoxy-biphenyl-2-yl)-5,6a,7,11b-tetrahydro-6H-indeno[2,1-c]quinoline-2-carboxamidine was prepared according to the protocol used for Example 144, step b using indene and 5'-Fluoro-5-hydroxy-4,2'-dimethoxy-biphenyl-2-carbaldehyde. Mass spectrum: 509 (M+1).

Example 178

6-(2',4'-Dichloro-5-hydroxy-4-methoxy-biphenyl-2-yl)-5,6a,7,11b-tetrahydro-6H-indeno[2,1-c]quinoline-2-carboxamidine.

Step a: 2',4'-Dichloro-5-hydroxy-4-methoxy-biphenyl-2-carbaldehyde was made according to the protocol used for Example 144, step a using 2,4-dichlorophenyl boronic acid. Mass Spectrum: 297 (M+1).

Step b: 6-(2',4'-Dichloro-5-hydroxy-4-methoxy-biphenyl-2-yl)-5,6a,7,11b-tetrahydro-6H-indeno[2,1-c]quinoline-2-carboxamidine was prepared according to the protocol used for Example 144, step b using indene and 2',4'-Dichloro-5-hydroxy-4-methoxy-biphenyl-2-carbaldehyde. Mass spectrum: 529 (M+1).

Example 179

6-(2',6'-Difluoro-5-hydroxy-4-methoxy-biphenyl-2-yl)-5,6a,7,11b-tetrahydro-6H-indeno[2,1-c]quinoline-2-carboxamidine.

Step a: 2',6'-Difluoro-5-hydroxy-4-methoxy-biphenyl-2-carbaldehyde was made according to the protocol used for Example 144, step a using 2,6-difluorophenyl boronic acid. Mass Spectrum: 265 (M+1).

Step b: 6-(2',6'-Difluoro-5-hydroxy-4-methoxy-biphenyl-2-yl)-5,6a,7,11b-tetrahydro-6H-indeno[2,1-c]quinoline-2-carboxamidine was prepared according to the protocol used for Example 144, step b using indene and 2',6'-Difluoro-5-hydroxy-4-methoxy-biphenyl-2-carbaldehyde. Mass spectrum: 497 (M+1).

Example 180

6-(5-Hydroxy-4-methoxy-3'-trifluoromethoxy-biphenyl-2-yl)-5,6a,7,11b-tetrahydro-6H-indeno[2,1-c]quinoline-2-carboxamidine.

Step a: 5-Hydroxy-4-methoxy-3'-trifluoromethoxy-biphenyl-2-carbaldehyde was made according to the protocol used for Example 144, step a using 3-trifluoromethoxyphenyl boronic acid. Mass Spectrum: 313 (M+1).

Step b: 6-(5-Hydroxy-4-methoxy-3'-trifluoromethoxy-biphenyl-2-yl)-5,6a,7,11b-tetrahydro-6H-indeno[2,1-c]quinoline-2-carboxamidine was prepared according to the protocol used for Example 144, step b using indene and 5-Hydroxy-4-methoxy-3'-trifluoromethoxy-biphenyl-2-carbaldehyde. Mass spectrum: 545 (M+1).

Example 181

6-(3'-Chloro-5-hydroxy-4-methoxy-biphenyl-2-yl)-5,6a,7,11b-tetrahydro-6H-indeno[2,1-c]quinoline-2-carboxamidine.

Step a: 3'-Chloro-5-hydroxy-4-methoxy-biphenyl-2-carbaldehyde was made according to the protocol used for Example 144, step a using 3-chlorophenyl boronic acid. Mass Spectrum: 263 (M+1).

Step b: 6-(3'-Chloro-5-hydroxy-4-methoxy-biphenyl-2-yl)-5,6a,7,11b-tetrahydro-6H-indeno[2,1-c]quinoline-2-carboxamidine was prepared according to the protocol used for Example 144, step b using indene and 3'-Chloro-5-hydroxy-4-methoxy-biphenyl-2-carbaldehyde. Mass spectrum: 495 (M+1).

Example 182

6-(5-Hydroxy-4-methoxy-4'-methylsulfanyl-biphenyl-2-yl)-5,6a,7,11b-tetrahydro-6H-indeno[2,1-c]quinoline-2-carboxamidine.

Step a: 5-Hydroxy-4-methoxy-4'-methylsulfanyl-biphenyl-2-carbaldehyde was made according to the protocol used for Example 144, step a using 4-methylsulfanylphenyl boronic acid. Mass Spectrum: 275 (M+1).

Step b: 6-(5-Hydroxy-4-methoxy-4'-methylsulfanyl-biphenyl-2-yl)-5,6a,7,11b-tetrahydro-6H-indeno[2,1-c]quinoline-2-carboxamidine was prepared according to the protocol used for Example 144, step b using indene and 5-Hydroxy-4-methoxy-4'-methylsulfanyl-biphenyl-2-carbaldehyde. Mass spectrum: 507 (M+1).

Example 183

6-(5-Hydroxy-4-methoxy-2'-methyl-biphenyl-2-yl)-5,6a,7,11b-tetrahydro-6H-indeno[2,1-c]quinoline-2-carboxamidine.

Step a: 5-Hydroxy-4-methoxy-2'-methyl-biphenyl-2-carbaldehyde was made according to the protocol used for Example 144, step a using 2-methylphenyl boronic acid. Mass Spectrum: 243 (M+1).

Step b: 6-(5-Hydroxy-4-methoxy-2'-methyl-biphenyl-2-yl)-5,6a,7,11b-tetrahydro-6H-indeno[2,1-c]quinoline-2-carboxamidine was prepared according to the protocol used for Example 144, step b using indene and 5-Hydroxy-4-methoxy-2'-methyl-biphenyl-2-carbaldehyde. Mass spectrum: 475 (M+1).

Example 184

6-[2-(5-Chloro-thiophen-2-yl)-4-hydroxy-5-methoxy-phenyl]-5,6a,7,11b-tetrahydro-6H-indeno[2,1-c]quinoline-2-carboxamidine.

Step a: 2-(5-Chloro-thiophen-2-yl)-4-hydroxy-5-methoxy-benzaldehyde was made according to the protocol used for Example 144, step a using 5-chlorothiophen-2-yl boronic acid. Mass Spectrum: 269 (M+1).

Step b: 6-[2-(5-Chloro-thiophen-2-yl)-4-hydroxy-5-methoxy-phenyl]-5,6a,7,11b-tetrahydro-6H-indeno[2,1-c]quinoline-2-carboxamidine was prepared according to the protocol used for Example 144, step b using indene and 2-(5-Chloro-thiophen-2-yl)-4-hydroxy-5-methoxy-benzaldehyde. Mass spectrum: 501 (M+1).

Example 185

6-(5-Hydroxy-5'-isopropyl-4,2'-dimethoxy-biphenyl-2-yl)-5,6a,7,11b-tetrahydro-6H-indeno[2,1-c]quinoline-2-carboxamidine.

Step a: 5-Hydroxy-5'-isopropyl-4,2'-dimethoxy-biphenyl-2-carbaldehyde was made according to the protocol used for Example 144, step a using 5-isopropyl-2-methoxyphenyl boronic acid. Mass Spectrum: 301 (M+1).

Step b: 6-(5-Hydroxy-5'-isopropyl-4,2'-dimethoxy-biphenyl-2-yl)-5,6a,7,11b-tetrahydro-6H-indeno[2,1-c]quinoline-2-carboxamidine was prepared according to the protocol used for Example 144, step b using indene and 5-Hydroxy-5'-isopropyl-4,2'-dimethoxy-biphenyl-2-carbaldehyde. Mass spectrum: 533 (M+1).

Example 186

6-(5-Hydroxy-4-methoxy-4'-trifluoromethyl-biphenyl-2-yl)-5,6a,7,11b-tetrahydro-6H-indeno[2,1-c]quinoline-2-carboxamidine.

Step a: 5-Hydroxy-4-methoxy-4'-trifluoromethyl-biphenyl-2-carbaldehyde was made according to the protocol used for Example 144, step a using 4-trifluoromethylphenyl boronic acid. Mass Spectrum: 297 (M+1).

Step b: 6-(5-Hydroxy-4-methoxy-4'-trifluoromethyl-biphenyl-2-yl)-5,6a,7,11b-tetrahydro-6H-indeno[2,1-c]quinoline-2-carboxamidine was prepared according to the protocol used for Example 144, step b using indene and 5-Hydroxy-4-methoxy-4'-trifluoromethyl-biphenyl-2-carbaldehyde. Mass spectrum: 529 (M+1).

Example 187

6-(5-Hydroxy-4-methoxy-3'-trifluoromethyl-biphenyl-2-yl)-5,6a,7,11b-tetrahydro-6H-indeno[2,1-c]quinoline-2-carboxamidine.

Step a: 5-Hydroxy-4-methoxy-3'-trifluoromethyl-biphenyl-2-carbaldehyde was made according to the protocol used for Example 144, step a using 3-trifluoromethylphenyl boronic acid. Mass Spectrum: 297 (M+1).

Step b: 6-(5-Hydroxy-4-methoxy-3'-trifluoromethyl-biphenyl-2-yl)-5,6a,7,11b-tetrahydro-6H-indeno[2,1-c]quinoline-2-carboxamidine was prepared according to the protocol used for Example 144, step b using indene and 5-Hydroxy-4-methoxy-3'-trifluoromethyl-biphenyl-2-carbaldehyde. Mass spectrum: 529 (M+1).

Example 188

6-(5-Hydroxy-4,4'-dimethoxy-biphenyl-2-yl)-5,6a,7,11b-tetrahydro-6H-indeno[2,1-c]quinoline-2-carboxamidine.

Step a: 5-Hydroxy-4,4'-dimethoxy-biphenyl-2-carbaldehyde was made according to the protocol used for Example 144, step a using 4-methoxyphenyl boronic acid. Mass Spectrum: 259 (M+1).

Step b: 6-(5-Hydroxy-4,4'-dimethoxy-biphenyl-2-yl)-5,6a,7,11b-tetrahydro-6H-indeno[2,1-c]quinoline-2-carboxamidine was prepared according to the protocol used for Example 144, step b using indene and 5-Hydroxy-4,4'-dimethoxy-biphenyl-2-carbaldehyde. Mass spectrum: 491 (M+1).

Example 189

6-(2'-Fluoro-5-hydroxy-4-methoxy-biphenyl-2-yl)-5,6a,7,11b-tetrahydro-6H-indeno[2,1-c]quinoline-2-carboxamidine.

Step a: 2'-Fluoro-5-hydroxy-4-methoxy-biphenyl-2-carbaldehyde was made according to the protocol used for Example 144, step a using 2-fluorophenyl boronic acid. Mass Spectrum: 247 (M+1).

Step b: 6-(2'-Fluoro-5-hydroxy-4-methoxy-biphenyl-2-yl)-5,6a,7,11b-tetrahydro-6H-indeno[2,1-c]quinoline-2-carboxamidine was prepared according to the protocol used for Example 144, step b using indene and 2'-Fluoro-5-hydroxy-4-methoxy-biphenyl-2-carbaldehyde. Mass spectrum: 479 (M+1).

Example 190

6-(5-Hydroxy-4,2',4'-trimethoxy-biphenyl-2-yl)-5,6a,7,11b-tetrahydro-6H-indeno[2,1-c]quinoline-2-carboxamidine.

Step a: 5-Hydroxy-4,2',4'-trimethoxy-biphenyl-2-carbaldehyde was made according to the protocol used for Example 144, step a using 2,4-dimethoxyphenyl boronic acid. Mass Spectrum: 289 (M+1).

Step b: 6-(5-Hydroxy-4,2',4'-trimethoxy-biphenyl-2-yl)-5,6a,7,11b-tetrahydro-6H-indeno[2,1-c]quinoline-2-carboxamidine was prepared according to the protocol used for Example 144, step b using indene and 5-Hydroxy-4,2',4'-trimethoxy-biphenyl-2-carbaldehyde. Mass spectrum: 521 (M+1).

Example 191

6-(5-Hydroxy-4-methoxy-[1,1';3',1'']terphenyl-2-yl)-5,6a,7,11b-tetrahydro-6H-indeno[2,1-c]quinoline-2-carboxamidine.

Step a: 5-Hydroxy-4-methoxy-[1,1';3',1'']terphenyl-2-carbaldehyde was made according to the protocol used for Example 144, step a using 3-biphenyl boronic acid. Mass Spectrum: 305 (M+1).

Step b: 6-(5-Hydroxy-4-methoxy-[1,1';3',1'']terphenyl-2-yl)-5,6a,7,11b-tetrahydro-6H-indeno[2,1-c]quinoline-2-carboxamidine was prepared according to the protocol used for Example 144, step b using indene and 5-Hydroxy-4-methoxy-[1,1';3',1'']terphenyl-2-carbaldehyde. Mass spectrum: 537 (M+1).

Example 192

6-(5'-Chloro-5-hydroxy-4,2'-dimethoxy-biphenyl-2-yl)-5,6a,7,11b-tetrahydro-6H-indeno[2,1-c]quinoline-2-carboxamidine.

Step a: 5'-Chloro-5-hydroxy-4,2'-dimethoxy-biphenyl-2-carbaldehyde was made according to the protocol used for Example 144, step a using 5-chloro-2-methoxyphenyl boronic acid. Mass Spectrum: 293 (M+1).

Step b: 6-(5'-Chloro-5-hydroxy-4,2'-dimethoxy-biphenyl-2-yl)-5,6a,7,11b-tetrahydro-6H-indeno[2,1-c]quinoline-2-carboxamidine was prepared according to the protocol used for Example 144, step b using indene and 5'-Chloro-5-hydroxy-4,2'-dimethoxy-biphenyl-2-carbaldehyde. Mass spectrum: 525 (M+1).

Example 193

6-(4'-Dimethylamino-5-hydroxy-4-methoxy-biphenyl-2-yl)-5,6a,7,11b-tetrahydro-6H-indeno[2,1-c]quinoline-2-carboxamidine.

Step a: 4'-Dimethylamino-5-hydroxy-4-methoxy-biphenyl-2-carbaldehyde was made according to the protocol used for Example 144, step a using 4-dimethylaminophenyl boronic acid. Mass Spectrum: 272 (M+1).

Step b: 6-(4'-Dimethylamino-5-hydroxy-4-methoxy-biphenyl-2-yl)-5,6a,7,11b-tetrahydro-6H-indeno[2,1-c]quinoline-2-carboxamidine was prepared according to the protocol used for Example 144, step b using indene and 4'-Dimethylamino-5-hydroxy-4-methoxy-biphenyl-2-carbaldehyde. Mass spectrum: 504 (M+1).

Example 194

6-[4-Hydroxy-5-methoxy-2-(6-methoxy-pyridin-3-yl)-phenyl]-5,6a,7,11b-tetrahydro-6H-indeno[2,1-c]quinoline-2-carboxamidine.

Step a: 4-Hydroxy-5-methoxy-2-(6-methoxy-pyridin-3-yl)-benzaldehyde was made according to the protocol used for Example 144, step a using 4-methoxy-pyridin-3-yl boronic acid. Mass Spectrum: 260 (M+1).

Step b: 6-[4-Hydroxy-5-methoxy-2-(6-methoxy-pyridin-3-yl)-phenyl]-5,6a,7,11b-tetrahydro-6H-indeno[2,1-c]quinoline-2-carboxamidine was prepared according to the protocol used for Example 144, step b using indene and 4-Hydroxy-5-methoxy-2-(6-methoxy-pyridin-3-yl)-benzaldehyde. Mass spectrum: 492 (M+1).

Example 195

6-(4'-Benzyloxy-5-hydroxy-4-methoxy-biphenyl-2-yl)-5,6a,7,11b-tetrahydro-6H-indeno[2,1-c]quinoline-2-carboxamidine.

Step a: 4'-Benzyloxy-5-hydroxy-4-methoxy-biphenyl-2-carbaldehyde was made according to the protocol used for Example 144, step a using 4-benzyloxyphenyl boronic acid. Mass Spectrum: 335 (M+1).

Step b: 6-(4'-Benzyloxy-5-hydroxy-4-methoxy-biphenyl-2-yl)-5,6a,7,11b-tetrahydro-6H-indeno[2,1-c]quinoline-2-carboxamidine was prepared according to the protocol used for Example 144, step b using indene and 4'-Benzyloxy-5-hydroxy-4-methoxy-biphenyl-2-carbaldehyde. Mass spectrum: 567 (M+1).

Example 196

6-(4'-tert-Butyl-5-hydroxy-4-methoxy-biphenyl-2-yl)-5,6a,7,11b-tetrahydro-6H-indeno[2,1-c]quinoline-2-carboxamidine.

Step a: 4'-tert-Butyl-5-hydroxy-4-methoxy-biphenyl-2-carbaldehyde was made according to the protocol used for Example 144, step a using 2-tert-butylphenyl boronic acid. Mass Spectrum: 285 (M+1).

Step b: 6-(4'-tert-Butyl-5-hydroxy-4-methoxy-biphenyl-2-yl)-5,6a,7,11b-tetrahydro-6H-indeno[2,1-c]quinoline-2-carboxamidine was prepared according to the protocol used for Example 144, step b using indene and 4'-tert-Butyl-5-hydroxy-4-methoxy-biphenyl-2-carbaldehyde. Mass spectrum: 517 (M+1).

Example 197

6-(5-Hydroxy-4,2'-dimethoxy-5'-methyl-biphenyl-2-yl)-5,6a,7,11b-tetrahydro-6H-indeno[2,1-c]quinoline-2-carboxamidine.

Step a: 5-Hydroxy-4,2'-dimethoxy-5'-methyl-biphenyl-2-carbaldehyde was made according to the protocol used for Example 144, step a using 2-methoxy-5-methylphenyl boronic acid. Mass Spectrum: 273 (M+1).

Step b: 6-(5-Hydroxy-4,2'-dimethoxy-5'-methyl-biphenyl-2-yl)-5,6a,7,11b-tetrahydro-6H-indeno[2,1-c]quinoline-2-carboxamidine was prepared according to the protocol used for Example 144, step b using indene and 5-Hydroxy-4,2'-dimethoxy-5'-methyl-biphenyl-2-carbaldehyde. Mass spectrum: 505 (M+1).

Example 198

6-(5-Hydroxy-4'-isobutyl-4-methoxy-biphenyl-2-yl)-5,6a,7,11b-tetrahydro-6H-indeno[2,1-c]quinoline-2-carboxamidine.

Step a: 5-Hydroxy-4'-isobutyl-4-methoxy-3'-methyl-biphenyl-2-carbaldehyde was made according to the protocol used for Example 144, step a using 4-isobutylphenyl boronic acid. Mass Spectrum: 285 (M+1).

Step b: 6-(5-Hydroxy-4'-isobutyl-4-methoxy-biphenyl-2-yl)-5,6a,7,11b-tetrahydro-6H-indeno[2,1-c]quinoline-2-carboxamidine was prepared according to the protocol used for Example 144, step b using indene and 5-Hydroxy-4'-isobutyl-4-methoxy-3'-methyl-biphenyl-2-carbaldehyde. Mass spectrum: 517 (M+1).

Example 199

6-(2'-Ethoxy-5-hydroxy-4-methoxy-biphenyl-2-yl)-5,6a,7,11b-tetrahydro-6H-indeno[2,1-c]quinoline-2-carboxamidine.

Step a: 2'-Ethoxy-5-hydroxy-4-methoxy-biphenyl-2-carbaldehyde was made according to the protocol used for Example 144, step a using 2-ethoxyphenyl boronic acid. Mass Spectrum: 273 (M+1).

Step b: 6-(2'-Ethoxy-5-hydroxy-4-methoxy-biphenyl-2-yl)-5,6a,7,11b-tetrahydro-6H-indeno[2,1-c]quinoline-2-carboxamidine was prepared according to the protocol used for Example 144, step b using indene and 2'-Ethoxy-5-hydroxy-4-methoxy-biphenyl-2-carbaldehyde. Mass spectrum: 505 (M+1).

Example 200

6-(5-Hydroxy-4-methoxy-2'-trifluoromethoxy-biphenyl-2-yl)-5,6a,7,11b-tetrahydro-6H-indeno[2,1-c]quinoline-2-carboxamidine.

Step a: 5-Hydroxy-4-methoxy-2'-trifluoromethoxy-biphenyl-2-carbaldehyde was made according to the protocol used for Example 144, step a using 2-trifluoromethoxyphenyl boronic acid. Mass Spectrum: 313 (M+1).

Step b: 6-(5-Hydroxy-4-methoxy-2'-trifluoromethoxy-biphenyl-2-yl)-5,6a,7,11b-tetrahydro-6H-indeno[2,1-c]quinoline-2-carboxamidine was prepared according to the protocol used for Example 144, step b using indene and 5-Hydroxy-4-methoxy-2'-trifluoromethoxy-biphenyl-2-carbaldehyde. Mass spectrum: 545 (M+1).

Example 201

6-(2'-Benzyloxy-5-hydroxy-4-methoxy-biphenyl-2-yl)-5,6a,7,11b-tetrahydro-6H-indeno[2,1-c]quinoline-2-carboxamidine.

Step a: 2'-Benzyloxy-5-hydroxy-4-methoxy-biphenyl-2-carbaldehyde was made according to the protocol used for Example 144, step a using 2-benzyloxyphenyl boronic acid. Mass Spectrum: 335 (M+1).

Step b: 6-(2'-Benzyloxy-5-hydroxy-4-methoxy-biphenyl-2-yl)-5,6a,7,11b-tetrahydro-6H-indeno[2,1-c]quinoline-2-carboxamidine was prepared according to the protocol used for Example 144, step b using indene and 2'-Benzyloxy-5-hydroxy-4-methoxy-biphenyl-2-carbaldehyde. Mass spectrum: 567 (M+1).

Example 202

6-(2'-Ethyl-5-hydroxy-4-methoxy-biphenyl-2-yl)-5,6a,7,11b-tetrahydro-6H-indeno[2,1-c]quinoline-2-carboxamidine.

Step a: 2'-Ethyl-5-hydroxy-4-methoxy-biphenyl-2-carbaldehyde was made according to the protocol used for Example 144, step a using 2-ethylphenyl boronic acid. Mass Spectrum: 257 (M+1).

Step b: 6-(2'-Ethyl-5-hydroxy-4-methoxy-biphenyl-2-yl)-5,6a,7,11b-tetrahydro-6H-indeno[2,1-c]quinoline-2-carboxamidine was prepared according to the protocol used for Example 144, step b using indene and 2'-Ethyl-5-hydroxy-4-methoxy-biphenyl-2-carbaldehyde. Mass spectrum: 489 (M+1).

Example 203

6-(5-Hydroxy-4-methoxy-4'-phenoxy-biphenyl-2-yl)-5,6a,7,11b-tetrahydro-6H-indeno[2,1-c]quinoline-2-carboxamidine.

Step a: 5-Hydroxy-4-methoxy-4'-phenoxy-biphenyl-2-carbaldehyde was made according to the protocol used for Example 144, step a using 4-phenoxyphenyl boronic acid. Mass Spectrum: 321 (M+1).

Step b: 6-(5-Hydroxy-4-methoxy-4'-phenoxy-biphenyl-2-yl)-5,6a,7,11b-tetrahydro-6H-indeno[2,1-c]quinoline-2-carboxamidine was prepared according to the protocol used for Example 144, step b using indene and 5-Hydroxy-4-methoxy-4'-phenoxy-biphenyl-2-carbaldehyde. Mass spectrum: 553 (M+1).

Example 204

6-(5-Hydroxy-4-methoxy-2',4'-bis-trifluoromethyl-biphenyl-2-yl)-5,6a,7,11b-tetrahydro-6H-indeno[2,1-c]quinoline-2-carboxamidine.

Step a: 5-Hydroxy-4-methoxy-2',4'-bis-trifluoromethyl-biphenyl-2-carbaldehyde was made according to the protocol used for Example 144, step a using 2,4-bis-trifluoromethylphenyl boronic acid. Mass Spectrum: 365 (M+1).

Step b: 6-(5-Hydroxy-4-methoxy-2',4'-bis-trifluoromethyl-biphenyl-2-yl)-5,6a,7,11b-tetrahydro-6H-indeno[2,1-c]quinoline-2-carboxamidine was prepared according to the protocol used for Example 144, step b using indene and 5-Hydroxy-4-methoxy-2',4'-bis-trifluoromethyl-biphenyl-2-carbaldehyde. Mass spectrum: 597 (M+1).

Example 205

[2'-(2-Carbamimidoyl-5,6a,7,11b-tetrahydro-6H-indeno[2,1-c]quinolin-6-yl)-5'-hydroxy-4'-methoxy-biphenyl-4-yl]-carbamic acid benzyl ester.

Step a: (2'-Formyl-5'-hydroxy-4'-methoxy-biphenyl-4-yl)-carbamic acid benzyl ester was made according to the protocol used for Example 144, step a using 4-benzyloxycarbamoylphenyl boronic acid. Mass Spectrum: 378 (M+1).

Step b: [2'-(2-Carbamimidoyl-5,6a,7,11b-tetrahydro-6H-indeno[2,1-c]quinolin-6-yl)-5'-hydroxy-4'-methoxy-biphenyl-4-yl]-carbamic acid benzyl ester was prepared according to the protocol used for Example 144, step b using indene and (2'-Formyl-5'-hydroxy-4'-methoxy-biphenyl-4-yl)-carbamic acid benzyl ester. Mass spectrum: 610 (M+1).

Example 206

6-(5-Hydroxy-4-methoxy-4'-trifluoromethoxy-biphenyl-2-yl)-5,6a,7,11b-tetrahydro-6H-indeno[2,1-c]quinoline-2-carboxamidine.

Step a: 5-Hydroxy-4-methoxy-4'-trifluoromethoxy-biphenyl-2-carbaldehyde was made according to the protocol used for Example 144, step a using 4-trifluoromethoxyphenyl boronic acid. Mass Spectrum: 312 (M+1).

Step b: 6-(5-Hydroxy-4-methoxy-4'-trifluoromethoxy-biphenyl-2-yl)-5,6a,7,11b-tetrahydro-6H-indeno[2,1-c]quinoline-2-carboxamidine was prepared according to the protocol used for Example 144, step b using indene and 5-Hydroxy-4-methoxy-4'-trifluoromethoxy-biphenyl-2-carbaldehyde. Mass spectrum: 545 (M+1).

Example 207

6-(3',5'-Difluoro-5-hydroxy-4-methoxy-biphenyl-2-yl)-5,6a,7,11b-tetrahydro-6H-indeno[2,1-c]quinoline-2-carboxamidine.

Step a: 3',5'-Difluoro-5-hydroxy-4-methoxy-biphenyl-2-carbaldehyde was made according to the protocol used for Example 144, step a using 3,5-difluorophenyl boronic acid. Mass Spectrum: 265 (M+1).

Step b: 6-(3',5'-Difluoro-5-hydroxy-4-methoxy-biphenyl-2-yl)-5,6a,7,11b-tetrahydro-6H-indeno[2,1-c]quinoline-2-carboxamidine was prepared according to the protocol used for Example 144, step b using indene and 3',5'-Difluoro-5-hydroxy-4-methoxy-biphenyl-2-carbaldehyde. Mass spectrum: 497 (M+1).

Example 208

4-[2-(2-Carbamimidoyl-5,6a,7,11b-tetrahydro-6H-indeno[2,1-c]quinolin-6-yl)-5-hydroxy-4-methoxy-phenoxy]-benzoic acid.

Step a: To a mixture of 4-benzyloxy-3-methoxybenzaldehyde (10.0 g, 41 mmol; compound 10, scheme 7) and NaOAc.3H$_2$O (11.2 g, 82 mmol) of in 25 mL of acetic acid and 2.5 mL of water was added dropwise bromine (2.6 mL, 49 mmol). The mixture was stirred at room temperature overnight and quenched with water. After stirring at room temperature for ca. 15 min, the precipitate was collected via filtration and chromatographed (20% ethyl acetate-hexane) to give 5.7 g of 4-benzyloxy-2-bromo-3-methoxybenzaldehyde (43%; compound 11, scheme 7).

Step b: To a mixture of 4-benzyloxy-2-bromo-3-methoxybenzaldehyde (385 mg, 1.2 mmol), methyl 4-hydroxybenzoate (56 mg, 1 mmol) and caesium carbonate (650 mg, 2 mmol) in 8 mL of pyridine was added under argon copper oxide (160 mg, 2 mmol). The mixture was purged with argon for 10 min, heated at 130° C. overnight and then quenched with 5% HCl solution. The mixture was extracted with ethyl acetate, washed with 1N NaOH solution and water before drying over sodium sulfate. After the removal of the solvent, the residue was chromatographed to give 147 mg of 4-(5-Benzyloxy-2-formyl-4-methoxy-phenoxy)-benzoic acid methyl ester (30%; compound 12 as para ester, scheme 7).

Step c: 4-amino-benzamidine mono HCl salt (120 mg, 0.7 mmole) was suspended in acetonitrile (4 mL). The suspension was treated with 4-(5-Benzyloxy-2-formyl-4-methoxy-phenoxy)-benzoic acid methyl ester (274 mg, 0.7 mmole) and indene (162 mg, 1.4 mmole). Indium triflate (79 mg, 0.14 mmole) was added and the reaction was heated at 75° C. for 18 hours to give 4-[5-Benzyloxy-2-(2-carbamimidoyl-5,6a,7,11b-tetrahydro-6H-indeno[2,1-c]quinolin-6-yl)-4-methoxy-phenoxy]-benzoic acid methyl ester which was purified by column chromatography (10%methanol in ethyl acetate).

Step d: A solution of 4-[5-Benzyloxy-2-(2-carbamimidoyl-5,6a,7,11b-tetrahydro-6H-indeno[2,1-c]quinolin-6-yl)-4-methoxy-phenoxy]-benzoic acid methyl ester (63 mg, 0.1 mmol) in 2 mL of MeOH was hydrogenated overnight using 10%Pd—C (20 mg) to give 4-[2-(2-Carbamimidoyl-5,6a,7,11b-tetrahydro-6H-indeno[2,1-c]quinolin-6-yl)-5-hydroxy-4-methoxy-phenoxy]-benzoic acid methyl ester that was used without further purification.

Step e: The mixture of 4-[2-(2-Carbamimidoyl-5,6a,7,11b-tetrahydro-6H-indeno[2,1-c]quinolin-6-yl)-5-hydroxy-4-methoxy-phenoxy]-benzoic acid methyl ester (54 mg, 0.1 mmol) and lithium hydroxide monohydrate (21 mg, 0.5 mmol) in 2.5 mL of MeOH and 1.5 mL of H$_2$O was stirred at room temperature overnight. The desired product 4-[2-(2-Carbamimidoyl-5,6a,7,11b-tetrahydro-6H-indeno[2,1-c]quinolin-6-yl)-5-hydroxy-4-methoxy-phenoxy]-benzoic acid was purified using reverse phase HPLC. Mass spectrum 521 (M+1).

Example 209

3-[2-(2-Carbamimidoyl-5,6a,7,11b-tetrahydro-6H-indeno[2,1-c]quinolin-6-yl)-5-hydroxy-4-methoxy-phenoxy]-benzoic acid.

Step a: To a mixture of 4-benzyloxy-2-bromo-3-methoxybenzaldehyde (642 mg, 2 mmol; prepared in Example 208, step a), methyl 3-hydroxybenzoate (312 mg, 2 mmol) and caesium carbonate (1.3 g, 4 mmol) in 16 mL of pyridine was added copper oxide(320 mg, 4 mmol)under argon. The mixture was purged with argon for 10 min, heated at 130° C. overnight and then quenched with 5% HCl solution. The mixture was extracted with ethyl acetate, washed with 1N NaOH solution and water before drying over sodium sulfate. After the removal of the solvent, the residue was chromatographed to give 218 mg of 3-(5-Benzyloxy-2-formyl-4-methoxy-phenoxy)-benzoic acid methyl ester (28%; compound 12 as meta ester, scheme 7).

Step b: 3-[5-Benzyloxy-2-(2-carbamimidoyl-5,6a,7,11b-tetrahydro-6H-indeno[2,1-c]quinolin-6-yl)-4-methoxy-phenoxy]-benzoic acid methyl ester was prepared using a similar protocol to that used in Example 208, step c from 3-(5-Benzyloxy-2-formyl-4-methoxy-phenoxy)-benzoic acid methyl ester.

Step c: 3-[2-(2-Carbamimidoyl-5,6a,7,11b-tetrahydro-6H-indeno[2,1-c]quinolin-6-yl)-5-hydroxy-4-methoxy-phenoxy]-benzoic acid methyl ester was prepared using a similar protocol to that used in Example 208, step d from 3-[5-Benzyloxy-2-(2-carbamimidoyl-5,6a,7,11b-tetrahydro-6H-indeno[2,1-c]quinolin-6-yl)-4-methoxy-phenoxy]-benzoic acid methyl ester.

Step d: 3-[2-(2-Carbamimidoyl-5,6a,7,11b-tetrahydro-6H-indeno[2,1-c]quinolin-6-yl)-5-hydroxy-4-methoxy-phenoxy]-benzoic acid was prepared using a similar protocol to that used in Example 208, step e from 3-[5-Benzyloxy-2-(2-carbamimidoyl-5,6a,7,11b-tetrahydro-6H-indeno[2,1-c]quinolin-6-yl)-4-methoxy-phenoxy]-benzoic acid methyl ester. Mass spectrum 521 (M+1).

Example 210

4-[5-Benzyloxy-2-(2-carbamimidoyl-5,6a,7,11b-tetrahydro-6H-indeno[2,1-c]quinolin-6-yl)-4-methoxy-phenoxy]-benzoic acid.

Step a: 4-[5-Benzyloxy-2-(2-carbamimidoyl-5,6a,7,11b-tetrahydro-6H-indeno[2,1-c]quinolin-6-yl)-4-methoxy-phenoxy]-benzoic acid methyl ester was prepared according to the protocol described for Example 208, steps a–c.

Step b: 4-[5-Benzyloxy-2-(2-carbamimidoyl-5,6a,7,11b-tetrahydro-6H-indeno[2,1-c]quinolin-6-yl)-4-methoxy-phenoxy]-benzoic acid was prepared according to the protocol described for Example 208, step e from 4-[5-Benzyloxy-2-(2-carbamimidoyl-5,6a,7,11b-tetrahydro-6H-indeno[2,1-c]quinolin-6-yl)-4-methoxy-phenoxy]-benzoic acid methyl ester. Mass spectrum 611 (M+1).

Example 211

3-[5-Benzyloxy-2-(2-carbamimidoyl-5,6a,7,11b-tetrahydro-6H-indeno[2,1-c]quinolin-6-yl)-4-methoxy-phenoxy]-benzoic acid.

Step a: 3-[5-Benzyloxy-2-(2-carbamimidoyl-5,6a,7,11b-tetrahydro-6H-indeno[2,1-c]quinolin-6-yl)-4-methoxy-phenoxy]-benzoic acid methyl ester was prepared according to the protocol described for Example 209, steps a–c.

Step b: 3-[5-Benzyloxy-2-(2-carbamimidoyl-5,6a,7,11b-tetrahydro-6H-indeno[2,1-c]quinolin-6-yl)-4-methoxy-phenoxy]-benzoic acid was prepared according to the protocol described for Example 208, step e from 3-[5-Benzyloxy-2-(2-carbamimidoyl-5,6a,7,11b-tetrahydro-6H-indeno[2,1-c]quinolin-6-yl)-4-methoxy-phenoxy]-benzoic acid methyl ester. Mass spectrum 611 (M+1).

Example 212

4-(2-Aminomethyl-5,6,6a,7,8,12b-hexahydro-benzo[k]phenanthridin-6-yl)-2-methoxy-phenol.

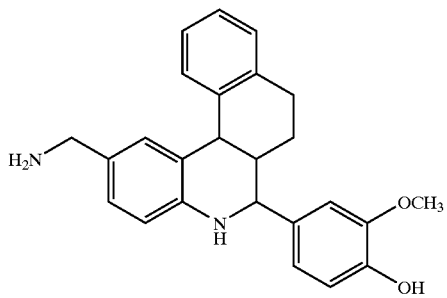

Step a: 6-(4-Hydroxy-3-methoxy-phenyl)-5,6,6a,7,8,12b-hexahydro-benzo[k]phenanthridine-2-carbonitrile was prepared according to the protocol described in Example 2 using 4-cyanophenyl amine instead of 4-amino-benzamidine mono HCl salt, 1,2-dihydronapthalene and 4-acetoxy-3-methoxybenzaldehyde. Mass spectrum 400 (M+1).

Step b: 6-(4-Hydroxy-3-methoxy-phenyl)-5,6,6a,7,8,12b-hexahydro-benzo[k]phenanthridine-2-carbonitrile (0.1 mmol; 38.2 mg) was added at 10° C. to a mixture obtained by pre-treating sodium borohydride (600 mg) in 4 mL of THF with a mixture of THF (2 mL) and TFA (1.2 mL). The reaction mixture was reacted overnight before quenching with 1 mL of 10% HCl solution. The mixture was further heated for 1 hour before it was extracted using ammonium hydroxide and water. The organic phase was dried over magnesium sulfate and evaporated to dryness. The residue was purified using HPLC to yield compound 4-(2-Aminomethyl-5,6,6a,7,8,12b-hexahydro-benzo[k]phenanthridin-6-yl)-2-methoxy-phenol. Mass spectrum 369 (M-17);in the presence of 0.1M ammonium acetate 385 (M-1) observed for negative ion mode.

Alternatively step b can be completed according to the following protocol:

A solution of 0.1 mmol of 6-(4-Hydroxy-3-methoxy-phenyl)-5,6,6a,7,8,12b-hexahydro-benzo[k]phenanthridine-2-carbonitrile (38.2 mg) in 17 mL of anhydrous THF was added drop-wise to a well stirred 1M solution of borane-THF complex (2 mL) at 0° C. The reaction mixture was refluxed under nitrogen for 2 hours before quenching with 1 mL of 10% HCl solution. The mixture was further heated for 1 hour before it was extracted using ammonium hydroxide and water. The organic phase was dried over magnesium sulfate and evaporated to dryness. The residue was purified using HPLC

Example 213

2'-(2-Aminomethyl-5,6a,7,11b-tetrahydro-6H-indeno[2,1-c]quinolin-6-yl)-5'-hydroxy-4'-methoxy-biphenyl-2-carboxylic acid.

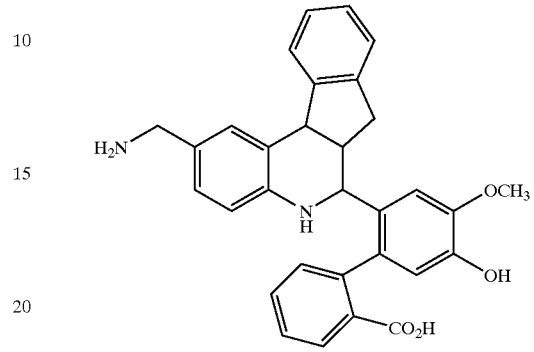

Step a: 2'-Formyl-5'-hydroxy-4'-methoxy-biphenyl-2-carboxylic acid was prepared according to the protocol described in Example 147, steps a and b. Mass spectrum 273 (M+1).

Step b: 4—N-Boc-aminomethylphenyl amine (22.2 mg, 0.1 mmole) was suspended in acetonitrile (1 mL). The suspension was treated with 2'-Formyl-5'-hydroxy-4'-methoxy-biphenyl-2-carboxylic acid (27.2 mg, 0.1 mmole) and indene(23.2 mg, 0.2 mmole). Indium triflate (11.2 mg, 0.02 mmole) was added and the reaction was heated at 70° C. for 48 hours. The mixture was filtered and treated with an excess of TFA for 5 hours after which the crude reaction mixture was evaporated and taken up in 2 mL of DMSO-MeOH (50—50). The desired product was purified using reverse phase HPLC. Mass spectrum 475 (M-17); in the presence of 0.1M ammonium acetate 491 (M-1) observed for negative ion mode.

Example 214

2'-(2-Carbamimidoyl-5,6a,7,11b-tetrahydro-6H-indeno[2,1-c]quinolin-6-yl)-5'-hydroxy-4'-methoxy-biphenyl-4-carboxylic acid amide.

Step a: 2'-Formyl-5'-hydroxy-4'-methoxy-biphenyl-3-carboxylic acid amide was prepared according to the protocol described for Example 165 using 4-bromobenzamide.

Step b: 2'-(2-Carbamimidoyl-5,6a,7,11b-tetrahydro-6H-indeno[2,1-c]quinolin-6-yl)-5'-hydroxy-4'-methoxy-biphenyl-4-carboxylic acid amide was prepared according to the protocol used for Example 144, step b using indene and 2'-Formyl-5'-hydroxy-4'-methoxy-biphenyl-4-carboxylic acid amide. Mass spectrum: 504 (M+1).

Example 215
9-Hydroxy-6-(4-hydroxy-3-methoxy-phenyl)-5,6,6a,7,8,12b-hexahydro-benzo[k]phenanthridine-2-carboxamidine.

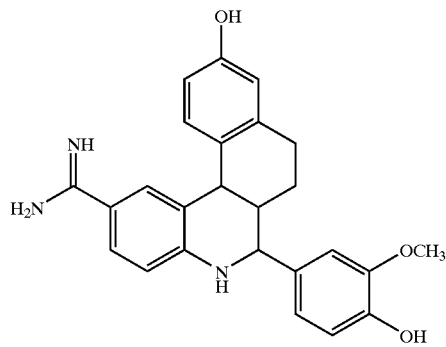

Step a: To a solution of 1,2,3,4-Tetrahydro-naphthalene-1,5-diol (1.64 g, 10 mmol; compound 24, scheme 7) in 75 ml of benzene was added 19 mg (0.1 mmol) of para-toluenesulfonic acid. The mixture was refluxed overnight using Dean-Stark equipment. After removal of the solvent, the residue was repartitioned between ethyl acetate and water. The organic layers were washed with saturated sodium bicarbonate solution, water and brine and dried over sodium sulfate. After removal of the solvent, the residue was chromatographed (10–20% EtOAc-Hex) to give 320 mg (22%) of 7,8-Dihydro-naphthalen-2-ol (Compound 25, scheme 7).

Step b: 9-Hydroxy-6-(4-hydroxy-3-methoxy-phenyl)-5,6,6a,7,8,12b-hexahydro-benzo[k]phenanthridine-2-carboxamidine was obtained by reacting olefin 7,8-Dihydro-naphthalen-2-ol according to the protocol described for Example (2) with 4-amino-benzamidine mono HCl salt and 4-Hydroxy-2-methoxy-benzaldehyde. Mass spectrum: 416 (M+1).

Example 216
6-(2-Aminomethyl-5,6a,7,11b-tetrahydro-6H-indeno[2,1-c]quinolin-6-yl)-4,2'-dimethoxy-biphenyl-3-ol.

Step a: 5-Hydroxy-4,2'-dimethoxy-biphenyl-2-carbaldehyde was made according to the protocol used for example 144, step a using 2-methoxyphenyl boronic acid. Mass Spectrum: 259 (M+1)

Step b: 6-(2-Aminomethyl-5,6a,7,11b-tetrahydro-6H-indeno[2,1-c]quinolin-6-yl)-4,2'-dimethoxy-biphenyl-3-ol was made according to the protocol used for example 213, step b using 5-Hydroxy-4,2'-dimethoxy-biphenyl-2-carbaldehyde.

Mass spectrum 461 (M−17); in the presence of 0.1M ammonium acetate 477 (M−1) observed for negative ion mode.

Example 217
6-(2-Aminomethyl-5,6a,7,11b-tetrahydro-6H-indeno[2,1-c]quinolin-6-yl)-4,2'-dimethoxy-5'-methyl-biphenyl-3-ol.

Step a: 5-Hydroxy-4,2'-dimethoxy-5'-methyl-biphenyl-2-carbaldehyde was made according to the protocol used for example 144, step a using 2-methoxy-5-methylphenyl boronic acid. Mass Spectrum: 273 (M+1).

Step b: 6-(2-Aminomethyl-5,6a,7,11b-tetrahydro-6H-indeno[2,1-c]quinolin-6-yl)-4,2'-dimethoxy-5'-methyl-biphenyl-3-ol was made according to the protocol used for example 213, step b using 5-Hydroxy-4,2'-dimethoxy-5'-methyl-biphenyl-2-carbaldehyde.

Mass spectrum 475 (M−17);in the presence of 0.1M ammonium acetate 491 (M−1) observed for negative ion mode.

Example 218
6-(2-Aminomethyl-5,6a,7,11b-tetrahydro-6H-indeno[2,1-c]quinolin-6-yl)-4-methoxy-2'-methylsulfanyl-biphenyl-3-ol.

Step a: 5-Hydroxy-4-methoxy-2'-methylsulfanyl-biphenyl-2-carbaldehyde was made according to the protocol used for example 144, step a using 2-methylsulfanylphenyl boronic acid. Mass Spectrum: 275 (M+1).

Step b: 6-(2-Aminomethyl-5,6a,7,11b-tetrahydro-6H-indeno[2,1-c]quinolin-6-yl)-4-methoxy-2'-methylsulfanyl-biphenyl-3-ol was made according to the protocol used for example 213, step b using 5-Hydroxy-4-methoxy-2'-methylsulfanyl-biphenyl-2-carbaldehyde.

Mass spectrum 477 (M−17); in the presence of 0.1M ammonium acetate 493 (M−1) observed for negative ion mode.

Example 219
6-(2-Aminomethyl-5,6a,7,11b-tetrahydro-6H-indeno[2,1-c]quinolin-6-yl)-2'-fluoro-4-methoxy-biphenyl-3-ol.

Step a: 2'-Fluoro-5-hydroxy-4-methoxy-biphenyl-2-carbaldehyde was made according to the protocol used for example 144, step a using 2-fluorophenyl boronic acid. Mass Spectrum: 247 (M+1).

Step b: 6-(2-Aminomethyl-5,6a,7,11b-tetrahydro-6H-indeno[2,1-c]quinolin-6-yl)-2'-fluoro-4-methoxy-biphenyl-3-ol was made according to the protocol used for example 213, step b using 2'-Fluoro-5-hydroxy-4-methoxy-biphenyl-2-carbaldehyde.

Mass spectrum 449 (M−17); in the presence of 0.1M ammonium acetate 465 (M−1) observed for negative ion mode.

Example 220
6-(2-Aminomethyl-5,6a,7,11b-tetrahydro-6H-indeno[2,1-c]quinolin-6-yl)-5'-fluoro-4,2'-dimethoxy-biphenyl-3-ol.

Step a: 5'-Fluoro-5-hydroxy-4,2'-dimethoxy-biphenyl-2-carbaldehyde was made according to the protocol used for example 144, step a using 5-fluoro-2-methoxyphenyl boronic acid. Mass Spectrum: 278 (M+1).

Step b: 6-(2-Aminomethyl-5,6a,7,11b-tetrahydro-6H-indeno[2,1-c]quinolin-6-yl)-5'-fluoro-4,2'-dimethoxy-biphenyl-3-ol was made according to the protocol used for example 213, step b using 5'-Fluoro-5-hydroxy-4,2'-dimethoxy-biphenyl-2-carbaldehyde.

Mass spectrum 479 (M−17); in the presence of 0.1M ammonium acetate 495 (M−1) observed for negative ion mode.

Example 221
6-(2-Aminomethyl-5,6a,7,11b-tetrahydro-6H-indeno[2,1-c]quinolin-6-yl)-5'-chloro-4,2'-dimethoxy-biphenyl-3-ol.

Step a: 5'-Chloro-5-hydroxy-4,2'-dimethoxy-biphenyl-2-carbaldehyde was made according to the protocol used for example 144, step a using 5-chloro-2-methoxyphenyl boronic acid. Mass Spectrum: 293 (M+1).

Step b: 6-(2-Aminomethyl-5,6a,7,11b-tetrahydro-6H-indeno[2,1-c]quinolin-6-yl)-5'-chloro-4,2'-dimethoxy-biphenyl-3-ol was made according to the protocol used for example 213, step b using 5'-Chloro-5-hydroxy-4,2'-dimethoxy-biphenyl-2-carbaldehyde.

Mass spectrum 495 (M−17); in the presence of 0.1M ammonium acetate 511 (M−1) observed for negative ion mode.

Example 222
6-(2-Aminomethyl-5,6a,7,11b-tetrahydro-6H-indeno[2,1-c]quinolin-6-yl)-2'-ethoxy-4-methoxy-biphenyl-3-ol.

Step a: 2'-Ethoxy-5-hydroxy-4-methoxy-biphenyl-2-carbaldehyde was made according to the protocol used for example 144, step a using 2-ethoxyphenyl boronic acid. Mass Spectrum: 273 (M+1).

Step b: 6-(2-Aminomethyl-5,6a,7,11b-tetrahydro-6H-indeno[2,1-c]quinolin-6-yl)-2'-ethoxy-4-methoxy-biphenyl-3-ol was made according to the protocol used for example 213, step b using 2'-Ethoxy-5-hydroxy-4-methoxy-biphenyl-2-carbaldehyde.

Mass spectrum 475 (M−17); in the presence of 0.1M ammonium acetate 491 (M−1) observed for negative ion mode.

Example 223
6-(2-Aminomethyl-5,6a,7,11b-tetrahydro-6H-indeno[2,1-c]quinolin-6-yl)-2'-ethyl-4-methoxy-biphenyl-3-ol.

Step a: 2'-Ethyl-5-hydroxy-4-methoxy-biphenyl-2-carbaldehyde was made according to the protocol used for example 144, step a using 2-ethylphenyl boronic acid. Mass Spectrum: 257 (M+1).

Step b: 6-(2-Aminomethyl-5,6a,7,11b-tetrahydro-6H-indeno[2,1-c]quinolin-6-yl)-2'-ethyl-4-methoxy-biphenyl-3-ol was made according to the protocol used for example 213, step b using 2'-Ethyl-5-hydroxy-4-methoxy-biphenyl-2-carbaldehyde.

Mass spectrum 459 (M−17); in the presence of 0.1M ammonium acetate 475 (M−1) observed for negative ion mode.

Example 224
6-(2-Aminomethyl-5,6a,7,11b-tetrahydro-6H-indeno[2,1-c]quinolin-6-yl)-4-methoxy-2'-trifluoromethoxy-biphenyl-3-ol.

Step a: 5-Hydroxy-4-methoxy-2'-trifluoromethoxy-biphenyl-2-carbaldehyde was made according to the protocol used for example 144, step a using 2-trifluoromethoxyphenyl boronic acid. Mass Spectrum: 313 (M+1).

Step b: 6-(2-Aminomethyl-5,6a,7,11b-tetrahydro-6H-indeno[2,1-c]quinolin-6-yl)-4-methoxy-2'-trifluoromethoxy-biphenyl-3-ol was made according to the protocol used for example 213, step b using 5-hydroxy-4-methoxy-2'-trifluoromethoxy-biphenyl-2-carbaldehyde.

Mass spectrum 515 (M−17); in the presence of 0.1M ammonium acetate 531 (M−1) observed for negative ion mode.

Example 225
6-(2-Aminomethyl-5,6a,7,11b-tetrahydro-6H-indeno[2,1-c]quinolin-6-yl)-2'-benzyloxy-4-methoxy-biphenyl-3-ol.

Step a: 2'-Benzyloxy-5-hydroxy-4-methoxy-biphenyl-2-carbaldehyde was made according to the protocol used for example 144, step a using 2-benzyloxyphenyl boronic acid. Mass Spectrum: 335 (M+1).

Step b: 6-(2-Aminomethyl-5,6a,7,11b-tetrahydro-6H-indeno[2,1-c]quinolin-6-yl)-2'-benzyloxy-4-methoxy-biphenyl-3-ol was made according to the protocol used for example 213, step b using 2'-Benzyloxy-5-hydroxy-4-methoxy-biphenyl-2-carbaldehyde.

Mass spectrum 537 (M−17); in the presence of 0.1M ammonium acetate 553 (M−1) observed for negative ion mode.

Example 226
N-[2'-(2-Aminomethyl-5,6a,7,11b-tetrahydro-6H-indeno[2,1-c]quinolin-6-yl)-5'-hydroxy-4'-methoxy-biphenyl-4-yl]-methanesulfonamide.

Step a: N-(2'-Formyl-5'-hydroxy-4'-methoxy-biphenyl-4-yl)-methanesulfonamide was made according to the protocol used for example 144, step a using 4-N-methanesulfonamido-phenyl boronic acid. Mass Spectrum: 322 (M+1).

Step b: N-[2'-(2-Aminomethyl-5,6a,7,11b-tetrahydro-6H-indeno[2,1-c]quinolin-6-yl)-5'-hydroxy-4'-methoxy-biphenyl-4-yl]-methanesulfonamide was made according to the protocol used for example 213, step b using N-(2'-Formyl-5'-hydroxy-4'-methoxy-biphenyl-4-yl)-methanesulfonamide.

Mass spectrum 524 (M−17); in the presence of 0.1M ammonium acetate 540 (M−1) observed for negative ion mode.

Example 227
6-(2-Aminomethyl-5,6a,7,11b-tetrahydro-6H-indeno[2,1-c]quinolin-6-yl)-4,2',4'-trimethoxy-biphenyl-3-ol.

Step a: 5-Hydroxy-4,2',4'-trimethoxy-biphenyl-2-carbaldehyde was made according to the protocol used for example 144, step a using 2,4-dimethoxyphenyl boronic acid. Mass Spectrum: 289 (M+1).

Step b: 6-(2-Aminomethyl-5,6a,7,11b-tetrahydro-6H-indeno[2,1-c]quinolin-6-yl)-4,2',4'-trimethoxy-biphenyl-3-ol was made according to the protocol used for example 213, step b using 5-Hydroxy-4,2',4'-trimethoxy-biphenyl-2-carbaldehyde.

Mass spectrum 491 (M−17); in the presence of 0.1M ammonium acetate 507 (M−1) observed for negative ion mode.

Example 228
6-(2-Aminomethyl-5,6a,7,11b-tetrahydro-6H-indeno[2,1-c]quinolin-6-yl)-2',6'-difluoro-4-methoxy-biphenyl-3-ol.

Step a: 2',6'-Difluoro-5-hydroxy-4-methoxy-biphenyl-2-carbaldehyde was made according to the protocol used for example 144, step a using 2,6-difluorophenyl boronic acid. Mass Spectrum: 265 (M+1).

Step b: 6-(2-Aminomethyl-5,6a,7,11b-tetrahydro-6H-indeno[2,1-c]quinolin-6-yl)-2',6'-difluoro-4-methoxy-biphenyl-3-ol was made according to the protocol used for example 213, step b using 2',6'-Difluoro-5-hydroxy-4-methoxy-biphenyl-2-carbaldehyde.

Mass spectrum 467 (M−17); in the presence of 0.1M ammonium acetate 483 (M−1) observed for negative ion mode.

Example 229
2'-(2-Aminomethyl-5,6a,7,11b-tetrahydro-6H-indeno[2,1-c]quinolin-6-yl)-5'-hydroxy-4'-methoxy-biphenyl-3-carboxylic acid.

Step a: 2'-Formyl-5'-hydroxy-4'-methoxy-biphenyl-3-carboxylic acid was made according to the protocol used for example 144, step a using 3-carboxyphenyl boronic acid. Mass Spectrum: 273 (M+1).

Step b: 2'-(2-Aminomethyl-5,6a,7,11b-tetrahydro-6H-indeno[2,1-c]quinolin-6-yl)-5'-hydroxy-4'-methoxy-biphenyl-3-carboxylic acid was made according to the protocol used for example 213, step b using 2'-Formyl-5'-hydroxy-4'-methoxy-biphenyl-3-carboxylic acid.

Mass spectrum 475 (M−17); in the presence of 0.1M ammonium acetate 491 (M−1) observed for negative ion mode.

Example 230

2'-(2-Aminomethyl-5,6a,7,11b-tetrahydro-6H-indeno[2,1-c] quinolin-6-yl)-5'-hydroxy-2,4'-dimethoxy-biphenyl-4-carboxylic acid.

Step a: To a solution of 4-hydroxy-3-methoxy-benzoic acid methyl ester (75 g, 410 mmol) and 2,4,6-collidine (75 g, 620 mmol) in dichloromethane (750 mL) was added trifluoromethanesulfonic anhydride (94 mL, 560 mmol)at −78° C. under nitrogen. After the addition, the reaction was warmed to room temperature, stirred for 4 h and quenched with saturated aqueous copper sulfate (500 mL). The phases were separated and the aqueous phase was extracted with dichloromethane (2×250 mL). The organic phases were combined, dried and concentrated under reduced pressure. The residue was purified by column chromatography (4:1 hexane/EtOAc) to yield 3-methoxy-4-trifluoromethane-sulfonyloxy-benzoic acid methyl ester (129 g, quantitative as an oil that crystallized upon standing.

Step b: To a stirred mixture of 3-methoxy-4-trifluoromethanesulfonyloxy-benzoic acid methyl ester (41 g, 130 mmol), Lithium chloride (1.1 g, 30 mmol) and $PdCl_2(PPh_3)_2$ (11.3 g, 16 mmol) in dioxane (400 mL) was added bis(tributyl)tin (80 g, 160 mmol) and the resulting mixture was heated at 70 ° C. for 16 h. Additional $PdCl_2(PPh_3)_2$(2 g, 3 mmol) was added and heating was continued for 24 h. The reaction mixture was concentrated under reduced pressure. The residue was filtered trough a plug of silica, and then purified by chromatography (19:1 hexane/EtOAc) to give 3-methoxy-4-tributylstannanyl-benzoic acid methyl ester (31 g, 51%) as an oil.

Step c: To a stirred solution of 3-methoxy-4-tributylstannanyl-benzoic acid methyl ester (16g, 35 mmol) and 4-benzyloxy-2-bromo-5-methoxy-benzaldehyde (9.4 g, 29 mmol) in acetonitrile (150 mL) were added CuI (5.5 g, 29 mmol) and Pd(dppf)Cl$_2$ (4.2 g, 6 mmol). The resulting mixture was refluxed for 14 h under argon and concentrated. The residue was purified by column chromatography (4:1 hexane/EtOAc) to provide 5'-benzyloxy-2'-formyl-2,4'-dimethoxy-biphenyl-4-carboxylic acid methyl ester (6.4 g, 54%).

Step d: A solution of 5'-benzyloxy-2'-formyl-2,4'-dimethoxy-biphenyl-4-carboxylic acid methyl ester (5.7 g, 14 mmol) and Lithium hydroxide (0.6 g, 26 mmol) in THF/water(1:1, 30 mL) was stirred overnight at room temperature. Additional Lithium hydroxide (0.2 g, 8.8 mmol) was added and stirring was continued for another 3 h. The reaction mixture was acidified with 2 M hydrochloric acid (500 mL) to pH=4, extracted with ethyl acetate (2×100 mL) and then dichloromethane (50 mL). The organic phases were combined, washed with saturated aqueous ammonium chloride followed by drying and concentration under reduced pressure. Crystallization of the residue from dichloromethane/hexane provided 5'-benzyloxy-2'-formyl-2,4'-dimethoxy-biphenyl-4-carboxylic acid (3.1 g, 57%).

Step e: To a suspension of 5'-Benzyloxy-2'-formyl-2,4'-dimethoxy-biphenyl-4-carboxylic acid (50 mg, 0.127 mmol) and (4-Amino-benzyl)-carbamic acid tert-butyl ester (28 mg, 0.127 mmole) in 2 ml dry acetonitrile was added 30µl of indene and a catalytic amount of In(OTf)$_3$. The reaction was sealed and heated at 75° C. for 16 h. The reaction was then allowed to cool to room temperature and then purified by HPLC. Mass spectrum 505 (M−17); in the presence of 0.1M ammonium acetate 521 (M−1) observed for negative ion mode.

Example 231

4-(2-Aminomethyl-5,6a,7,11b-tetrahydro-6H-indeno[2,1-c] quinolin-6-yl)-2-methoxy-5-(2-methoxy-phenoxy)-phenol.

Step a: To a mixture of 4-acetoxy-2-bromo-3-methoxybenzaldehyde (546 mg, 2 mmol; prepared in example 105, step a), 2-methoxy-phenol (280 mg, 2 mmol) and cesium carbonate (1.3 g, 4 mmol) in 16 mL of pyridine was added copper oxide(320 mg, 4 mmol)under argon. The mixture was purged with argon for 10 min, heated at 130° C. overnight and then quenched with 5% HCl solution. The mixture was extracted with ethyl acetate, washed with 1N NaOH solution and water before drying over sodium sulfate. After the removal of the solvent, the residue was chromatographed to give the product, 4-hydroxy-5-methoxy-2-(2-methoxy-phenoxy)-benzaldehyde.

Step b: (4-Amino-benzyl)-carbamic acid tert-butyl ester (200 mg, 0.9 mmole) was dissolved in acetonitrile (5 mL). The solution was treated with 4-Hydroxy-5-methoxy-2-(2-methoxy-phenoxy)-benzaldehyde (250 mg, 0.9 mmole) and indene (130 mg, 1.1 mmole). Indium triflate (600 mg, 1.1 mmole) was added and the reaction was heated at 70° C. for 18 hours to give 4-(2-Aminomethyl-5,6a,7,11b-tetrahydro-6H-indeno[2,1-c]quinolin-6-yl)-2-methoxy-5-(2-methoxy-phenoxy)-phenol which was then purified using reverse phase HPLC.

Mass spectrum 477 (M−17); in the presence of 0.1M ammonium acetate 493 (M−1) observed for negative ion mode.

Example 232

6-(2-Aminomethyl-5,6a,7,11b-tetrahydro-6H-indeno[2,1-c] quinolin-6-yl)-4,2',6'-trimethoxy-biphenyl-3-ol.

Step a: 5-Hydroxy-4,2',6'-trimethoxy-biphenyl-2-carbaldehyde was made according to the protocol used for Example 144, step a using 2,6-dimethoxyphenyl boronic acid. Mass Spectrum: 289 (M+1).

Step b: (4-Amino-benzyl)-carbamic acid tert-butyl ester (307 mg, 1.4 mmole) was dissolved in acetonitrile (approx. 5 mL). The solution was treated with 5-hydroxy-4,2',6'-trimethoxy-biphenyl-2-carbaldehyde (390 mg, 1.4 mmole) and indene (157 mg, 1.4 mmole). Indium triflate (1.2 g, 2.2 mmole) was added and the reaction was heated at 70° C. for 18 hours to give 6-(2-Aminomethyl-5,6a,7,11b-tetrahydro-6H-indeno[2,1-c]quinolin-6-yl)-4,2',6'-trimethoxy-biphenyl-3-ol which was then purified using reverse phase HPLC. Mass spectrum 491 (M−17); in the presence of 0.1M ammonium acetate 507 (M−1) observed for negative ion mode.

Example 233

6-[5-Hydroxy-4-methoxy-4'-(1H-tetrazol-5-yl)-biphenyl-2-yl]-5,6a,7,11b-tetrahydro-6H-indeno[2,1-c]quinoline-2-carboxamidine.

Step a: To a tube charged with 2-Bromo-4-(tert-butyl-dimethyl-silanoxy)-5-methoxy-benzaldehyde (50 mg, 0.161 mmol), 5-(4-Bromo-phenyl)-1H-tetrazole (30.2 mg, 0.134 mmol) and 0.09 eq of Pd(dppf)Cl$_2$ was added 2 ml of DMF and 500·1 of an aqueous solution of K$_2$CO$_3$ (37 mg, 0.268 mmol). The tube was sealed with a cap and heated for two hours at 85° C. The reaction was allowed to cool to room temperature, filtered and the product, 5-Hydroxy-4-methoxy-4'-(1H-tetrazol-5-yl)-biphenyl-2-carbaldehyde, purified by reverse phase chromatography.

Step b: To a suspension of 5-Hydroxy-4-methoxy-4'-(1H-tetrazol-5-yl)-biphenyl-2-carbaldehyde (56 mg, 0.189 mmol) and 4-Amino-benzamadine HCl (65 mg, 0.378) in 2 ml dry acetonitrole was added 44 µl of indene and a catalytic amount of Indium triflate (>0.2 equivalents). The reaction was sealed and heated at 75° C. for 16 h. At this time the reaction was then allowed to cool to room temperature and the product, 6-[5-Hydroxy-4-methoxy-4'-(1H-tetrazol-5-yl)-biphenyl-2-yl]-5,6a,7,11b-tetrahydro-6H-indeno[2,1-c]quinoline-2-carboxamidine, purified by HPLC. Mass Spectrum: 530 (M+1).

Example 234

2'-(2-Carbamimidoyl-5,6a,7,11b-tetrahydro-6H-indeno[2,1-c]quinolin-6-yl)-5'-hydroxy-2,4'-dimethoxy-biphenyl-4-carboxylic acid.

A suspension of 5'-benzyloxy-2'-formyl-2,4'-dimethoxy-biphenyl-4-carboxylic acid (example 230, steps a-d; 50 mg, 0.125 mmol) and 4-amino-benzamidine HCl (17 mg, 0.1 mmole) in 2 ml dry acetonitrile was heated at 75° C. for 5 hours. To this mixture was added indene (11 mg, 0.1 mmole) and indium triflate (55 mg, 0.1 mmole)and the reaction heated at 75° C. for a further 24 hours. The reaction was allowed to cool to room temperature before the addition of trifluoroacetic acid. This mixture was heated at 40° C. for 5 hours before evaporation of the solvent and purification of the product by HPLC. Mass Spectrum: 536 (M+1).

Example 235

2'-(2-Carbamimidoyl-5,6a,7,11b-tetrahydro-6H-indeno[2,1-c]quinolin-6-yl)-5'-hydroxy-2,4'-dimethoxy-biphenyl-4-carboxylic acid isobutyl-amide.

Step a: 5'-Benzyloxy-2'-formyl-2,4'-dimethoxy-biphenyl-4-carboxylic acid was treated with trifluoroacetic acid at 40° C. for 3 hours. After this time the mixture was concentrated and the product, 2'-formyl-5'-hydroxy-2,4'-dimethoxy-biphenyl-4-carboxylic acid was purified by HPLC.

Step b: A suspension of 2'-formyl-5'-hydroxy-2,4'-dimethoxy-biphenyl-4-carboxylic acid (107 mg, 0.337 mmol) and 4-amino-benzamidine HCl (115 mg, 0.675 mmole) in dry acetonitrile was heated at 75° C. for 5 hours. To this mixture was added indene (37 mg, 0.337 mmole) and indium triflate (185 mg, 0.337 mmole)and the reaction heated at 75° C. for a further 24 hours. The reaction was allowed to cool to room temperature before purification of the product, 2'-(2-Carbamimidoyl-5,6a,7,11b-tetrahydro-6H-indeno[2,1-c]quinolin-6-yl)-5'-hydroxy-2,4,-dimethoxy-biphenyl-4-carboxylic acid, by HPLC.

Step c: A mixture of 2'-(2-Carbamimidoyl-5,6a,7,11b-tetrahydro-6H-indeno[2,1-c]quinolin-6-yl)-5'-hydroxy-2,4'-dimethoxy-biphenyl-4-carboxylic acid (10.7 mg, 0.02 mmol), BOP, (0.04 mmol), diidopropylethylamine (10.3 mg, 0.08 mmol) and isobutylamine (4.4 mg, 0.06 mmol) in DMF was allowed to react at room temperature. Example 235 was purified by HPLC. Mass Spectrum: 591 (M+1).

Example 236

2'-(2-Carbamimidoyl-5,6a,7,11b-tetrahydro-6H-indeno[2,1-c]quinolin-6-yl)-5'-hydroxy-2,4'-dimethoxy-biphenyl-4-carboxylic acid benzylamide.

Example 236 was prepared according to the protocol described for example 235 from 2'-(2-Carbamimidoyl-5,6a,7,11b-tetrahydro-6H-indeno[2,1-c]quinolin-6-yl)-5'-hydroxy-2,4'-dimethoxy-biphenyl-4-carboxylic acid (example 235 step a) and benzylamine. Mass Spectrum: 625 (M+1).

Example 237

2'-(2-Carbamimidoyl-5,6a,7,11b-tetrahydro-6H-indeno[2,1-c]quinolin-6-yl)-5'-hydroxy-2,4'-dimethoxy-biphenyl-4-carboxylic acid (2-morpholin-4-yl-ethyl)-amide.

Example 237 was prepared according to the protocol described for example 235 from 2'-(2-Carbamimidoyl-5,6a,7,11b-tetrahydro-6H-indeno[2,1-c]quinolin-6-yl)-5'-hydroxy-2,4'-dimethoxy-biphenyl-4-carboxylic acid (example 235 step a) and 2-morpholin-4-yl-ethylamine. Mass Spectrum: 648 (M+1).

Example 238

2'-(2-Carbamimidoyl-5,6a,7,11b-tetrahydro-6H-indeno[2,1-c]quinolin-6-yl)-5'-hydroxy-2,4'-dimethoxy-biphenyl-4-carboxylic acid cyclohexylamide.

Example 238 was prepared according to the protocol described for example 235 from 2'-(2-Carbamimidoyl-5,6a,7,11b-tetrahydro-6H-indeno[2,1-c]quinolin-6-yl)-5'-hydroxy-2,4'-dimethoxy-biphenyl-4-carboxylic acid (example 235 step a) and cyclohexylamine. Mass Spectrum: 617 (M+1).

Example 239

2'-(2-Carbamimidoyl-5,6a,7,11b-tetrahydro-6H-indeno[2,1-c]quinolin-6-yl)-5'-hydroxy-2,4'-dimethoxy-biphenyl-4-carboxylic acid cyclopropylamide.

Example 239 was prepared according to the protocol described for example 235 from 2'-(2-Carbamimidoyl-5,6a,7,11b-tetrahydro-6H-indeno[2,1-c]quinolin-6-yl)-5'-hydroxy-2,4'-dimethoxy-biphenyl-4-carboxylic acid (example 235 step a) and cyclopropylamine. Mass Spectrum: 575 (M+1).

Example 240

2'-(2-Carbamimidoyl-5,6a,7,11b-tetrahydro-6H-indeno[2,1-c]quinolin-6-yl)-5'-hydroxy-2,4'-dimethoxy-biphenyl-4-carboxylic acid (2-pyrrolidin-1-yl-ethyl)-amide Example 240 was prepared according to the protocol described for example 235 from 2'-(2-Carbamimidoyl-5,6a,7,11b-tetrahydro-6H-indeno[2,1-c]quinolin-6-yl)-5'-hydroxy-2,4'-dimethoxy-biphenyl-4-carboxylic acid (example 235 step a) and 2-pyrrolidin-1-yl-ethylamine. Mass Spectrum: 632 (M+1).

The following Tables 1–5 demonstrate Examples of compounds of Formula (I) that have been prepared by the methods disclosed herein and/or known to one skilled in the art.

TABLE 1

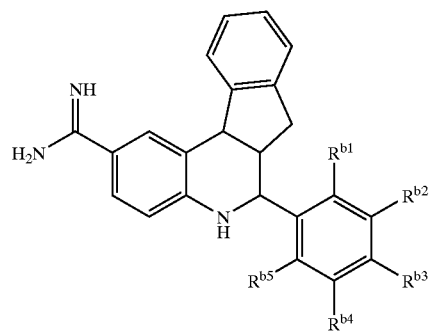

| Ex. | Rb1 | Rb2 | Rb3 | Rb4 | Rb5 |
|---|---|---|---|---|---|
| 1 | H | chloro | H | H | H |
| 2 | H | methoxy | hydroxy | H | H |
| 2A | H | ethoxy | hydroxy | H | H |
| 3 | methoxy | methoxy | H | H | H |
| 4 | methoxy | H | H | methoxy | H |
| 5 | hydroxy | methoxy | H | H | H |
| 6 | hydroxy | H | H | methoxy | H |
| 7 | methoxy | methoxy | methoxy | H | H |
| 8 | methyl | methyl | methoxy | H | H |
| 9 | methyl | H | methoxy | methyl | H |
| 10 | H | hydroxy | methoxy | H | H |
| 11 | H | H | methoxy | H | H |
| 12 | H | methoxy | OH | methoxy | H |
| 13 | H | H | $CH_3OC(=O)-$ | H | H |
| 14 | H | methoxy | OH | nitro | H |
| 15 | H | OH | methoxy | methoxy | H |
| 16 | OH | methoxy | H | nitro | H |
| 17 | H | methoxy | (5-Cl-2-MeO-phenyl)-NHC(=O)O- | H | H |
| 18 | OH | methoxy | H | H | bromo |
| 19 | fluoro | H | H | methoxy | H |
| 20 | benzyloxy | methoxy | H | H | H |
| 21 | fluoro | H | methoxy | H | H |
| 22 | H | iodo | methoxy | methoxy | H |
| 23 | 2,6-diCl-benzyloxy | H | H | H | H |
| 24 | (4-Cl-phenyl)-S- | H | H | H | H |
| 25 | methylenedioxy (Rb1/b2) | | H | H | H |
| 26 | benzyloxy | H | H | H | H |
| 27 | allyloxy | H | H | H | H |
| 28 | methoxy | H | H | bromo | H |
| 29 | H | 4-MeO-phenoxy | H | H | H |
| 30 | H | methoxy | H | H | H |
| 31 | H | H | $MeSO_2-$ | H | H |
| 32 | H | H | $HOCH_2CH_2-O-$ | H | H |
| 33 | chloro | methoxy | methoxy | H | H |
| 34 | hydroxy | H | H | H | methoxy |
| 35 | H | $CH_3OC(=O)-$ | H | H | H |
| 36 | H | $(HO)_2B-$ | methoxy | H | H |
| 37 | H | bromo | OH | methoxy | H |
| 38 | fluoro | fluoro | fluoro | fluoro | fluoro |
| 39 | chloro | H | chloro | H | H |
| 40 | chloro | H | H | H | fluoro |
| 41 | H | chloro | chloro | H | H |
| 42 | H | chloro | H | chloro | H |
| 43 | H | 3,5-diCl-phenoxy | H | H | H |
| 44 | H | benzyloxy | H | H | H |
| 45 | H | $-CF_3$ | H | H | H |
| 46 | H | H | bromo | H | H |
| 47 | H | H | fluoro | H | H |
| 48 | H | H | chloro | H | H |
| 49 | H | H | ethoxy | H | H |
| 51 | H | H | $-CF_3$ | H | H |
| 52 | fluoro | fluoro | H | H | H |
| 53 | fluoro | H | fluoro | H | H |
| 54 | fluoro | H | H | fluoro | H |
| 55 | H | fluoro | fluoro | H | H |
| 56 | H | chloro | fluoro | H | H |
| 57 | H | H | pyrrolidin- | H | H |

TABLE 1-continued

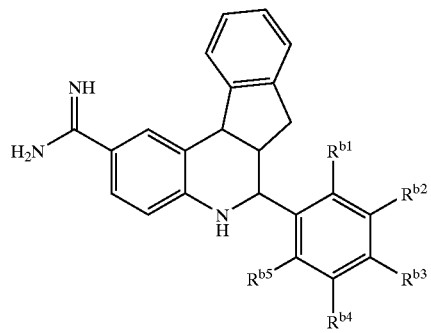

| Ex. | Rb1 | Rb2 | Rb3 | Rb4 | Rb5 |
|---|---|---|---|---|---|
| 58 | ethoxy | H | 1-yl H | bromo | H |
| 59 | H | H | —OCF$_3$ | H | H |
| 60 | H | H | propyl | H | H |
| 61 | H | bromo | fluoro | H | H |
| 63 | fluoro | fluoro | H | H | fluoro |
| 64 | fluoro | H | fluoro | fluoro | H |
| 65 | fluoro | H | fluoro | H | fluoro |
| 66 | fluoro | fluoro | fluoro | H | H |
| 67 | fluoro | —CF$_3$ | H | H | H |
| 68 | fluoro | H | H | H | —CF$_3$ |
| 69 | H | fluoro | H | —CF$_3$ | H |
| 70 | —CF$_3$ | H | fluoro | H | H |
| 71 | fluoro | fluoro | H | fluoro | H |
| 72 | 4-tBu-phenoxy | H | H | nitro | H |
| 73 | chloro | H | H | —CF$_3$ | H |
| 74 | fluoro | H | chloro | H | H |
| 75 | H | fluoro | chloro | H | H |
| 76 | benzyl-S- | H | H | nitro | H |
| 77 | morpholin-4-yl | H | H | nitro | H |
| 144 | H | methoxy | hydroxy | H | 4-i-Pr-phenyl- |
| 145 | H | methoxy | hydroxy | H | 4-HO$_2$C-phenyl- |
| 146 | H | methoxy | hydroxy | H | 4-(iBu-NHCO)-phenyl- |
| 147 | H | methoxy | hydroxy | H | 2-HO$_2$C-phenyl- |
| 148 | H | methoxy | hydroxy | H | 3-HO$_2$C-phenyl- |
| 149 | H | methoxy | hydroxy | H | phenyl- |
| 150 | H | methoxy | hydroxy | H | 2-MeO-phenyl- |
| 151 | H | methoxy | hydroxy | H | 4-EtO-phenyl- |
| 152 | H | methoxy | hydroxy | H | 3-cyano-phenyl- |
| 153 | H | methoxy | hydroxy | H | 4-cyano-phenyl- |
| 154 | H | methoxy | hydroxy | H | 3-HOCH$_2$-phenyl- |
| 155 | H | methoxy | hydroxy | H | 4-MeSO$_2$NH-phenyl- |
| 156 | H | methoxy | hydroxy | H | 4-MeSO$_2$-phenyl- |
| 157 | H | methoxy | hydroxy | H | 4-HOCH$_2$-phenyl- |
| 158 | H | methoxy | hydroxy | H | pyridin-3-yl- |
| 159 | H | methoxy | hydroxy | H | 2,4-diMeO-pyrimidin-5-yl- |
| 160 | H | methoxy | hydroxy | H | 4-(iBu-NHCO)-2-(benzyl-OC(=O))-phenyl |
| 161 | H | methoxy | hydroxy | H | 4-(iBu-NHCO)-2-HO$_2$C-phenyl- |
| 162 | H | methoxy | hydroxy | methoxy | 2-HO$_2$C-phenyl- |
| 165 | H | methoxy | hydroxy | H | 3-H$_2$NCO-phenyl- |
| 166 | H | methoxy | hydroxy | H | 4-H$_2$NSO$_2$-phenyl- |
| 167 | H | methoxy | hydroxy | H | 3-H$_2$NSO$_2$-phenyl- |
| 169 | H | methoxy | hydroxy | methoxy | 3-HO$_2$C-phenyl- |
| 170 | H | methoxy | hydroxy | methoxy | 4-HO$_2$C-phenyl- |
| 171 | H | methoxy | hydroxy | H | thiophen-3-yl- |
| 172 | H | methoxy | hydroxy | H | 2,5-diMeO-phenyl- |
| 173 | H | methoxy | hydroxy | H | 2-chloro-phenyl- |
| 174 | H | methoxy | hydroxy | H | 2,6-diMeO-phenyl- |
| 175 | H | methoxy | hydroxy | H | 2-H$_3$CS-phenyl- |
| 176 | H | methoxy | hydroxy | H | 2-(phenyl)-phenyl- |
| 177 | H | methoxy | hydroxy | H | 2-MeO-5-F-phenyl- |
| 178 | H | methoxy | hydroxy | H | 2,4-diCl-phenyl- |
| 179 | H | methoxy | hydroxy | H | 2,6-diF-phenyl- |
| 180 | H | methoxy | hydroxy | H | 3-F$_3$CO-phenyl- |
| 181 | H | methoxy | hydroxy | H | 3-Cl-phenyl- |
| 182 | H | methoxy | hydroxy | H | 4-H$_3$CS-phenyl- |
| 183 | H | methoxy | hydroxy | H | 2-methyl-phenyl- |
| 184 | H | methoxy | hydroxy | H | 5-Cl-thiophen-2-yl- |
| 185 | H | methoxy | hydroxy | H | 2-MeO-5-i-propyl-phenyl- |

TABLE 1-continued

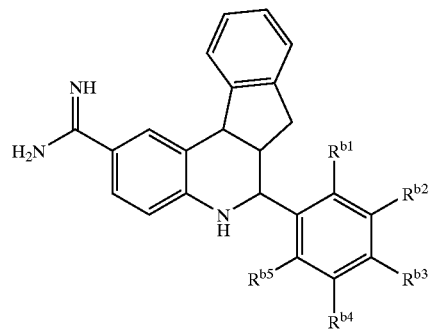

| Ex. | Rb1 | Rb2 | Rb3 | Rb4 | Rb5 |
|---|---|---|---|---|---|
| 186 | H | methoxy | hydroxy | H | 4-F₃C-phenyl- |
| 187 | H | methoxy | hydroxy | H | 3-F₃C-phenyl- |
| 188 | H | methoxy | hydroxy | H | 4-MeO-phenyl- |
| 189 | H | methoxy | hydroxy | H | 2-F-phenyl- |
| 190 | H | methoxy | hydroxy | H | 2,4-diMeO-phenyl- |
| 191 | H | methoxy | hydroxy | H | 3-(phenyl)-phenyl- |
| 192 | H | methoxy | hydroxy | H | 2-MeO-5-Cl-phenyl- |
| 193 | H | methoxy | hydroxy | H | 4-Me₂N-phenyl- |
| 194 | H | methoxy | hydroxy | H | 6-MeO-pyridin-3-yl- |
| 195 | H | methoxy | hydroxy | H | 4-(benzyloxy)-phenyl- |
| 196 | H | methoxy | hydroxy | H | 4-t-butyl-phenyl- |
| 197 | H | methoxy | hydroxy | H | 2-MeO-5-Me-phenyl- |
| 198 | H | methoxy | hydroxy | H | 4-i-butyl-phenyl- |
| 199 | H | methoxy | hydroxy | H | 2-EtO-phenyl- |
| 200 | H | methoxy | hydroxy | H | 2-F₃CO-phenyl- |
| 201 | H | methoxy | hydroxy | H | 2-(benzyloxy)-phenyl- |
| 202 | H | methoxy | hydroxy | H | 2-ethyl-phenyl- |
| 203 | H | methoxy | hydroxy | H | 4-(phenoxy)-phenyl- |
| 204 | H | methoxy | hydroxy | H | 2,4-bis-F₃C-phenyl- |
| 205 | H | methoxy | hydroxy | H | 4-(benzyloxy-CONH)-phenyl- |
| 206 | H | methoxy | hydroxy | H | 4-F₃CO-phenyl- |
| 207 | H | methoxy | hydroxy | H | 3,5-diF-phenyl- |
| 208 | H | methoxy | hydroxy | H | 4-HO₂C-phenoxy- |
| 209 | H | methoxy | hydroxy | H | 3-HO₂C-phenoxy- |
| 210 | H | methoxy | benzyloxy | H | 4-HO₂C-phenoxy- |
| 211 | H | methoxy | benzyloxy | H | 3-HO₂C-phenoxy- |
| 214 | H | methoxy | hydroxy | H | 4-H₂NCO-phenyl- |
| 233 | H | methoxy | hydroxy | H | 4-tetrazol-5-yl-phenyl- |
| 234 | H | methoxy | hydroxy | H | 2-MeO-4-HO₂C-phenyl |
| 235 | H | methoxy | hydroxy | H | 2-MeO-4-iBuNHCO-phenyl- |
| 236 | H | methoxy | hydroxy | H | 2-MeO-4-benzylNHCO-phenyl- |
| 237 | H | methoxy | hydroxy | H | 2-MeO-4-(morpholin-4-yl-ethyl)NHCO-phenyl- |
| 238 | H | methoxy | hydroxy | H | 2-MeO-4-cyclohexylNHCO-phenyl- |
| 239 | H | methoxy | hydroxy | H | 2-MeO-4-cyclopropylNHCO-phenyl- |
| 240 | H | methoxy | hydroxy | H | 2-MeO-4-(pyrrolidin-1-yl-ethyl)NHCO-phenyl- |

TABLE 2

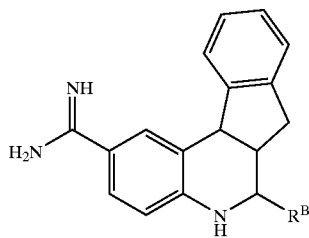

| Ex. | R^B |
|---|---|
| 50 | 4-Methoxy-naphthalen-1-yl |
| 62 | 2,2-Dimethyl-chroman-6-yl |

TABLE 2-continued

| Ex. | R^B |
|---|---|
| 78 | 3-Phenyl-1H-pyrazol-4-yl |
| 79 | 2,4-Dioxo-1,2,3,4-tetrahydro-pyrimidin-5-yl |
| 80 | 2-Phenyl-1H-imidazol-4-yl |
| 81 | 1H-imidazol-4-yl |
| 82 | 5-Methyl-1H-pyrazol-4-yl |
| 83 | Thiophen-2-yl |
| 84 | 5-(3-Trifluoromethyl-phenyl)-furan-2-yl |
| 85 | 5-(2-Chloro-phenyl)-furan-2-yl |
| 86 | 5-(2,5-diChloro-phenyl)-furan-2-yl |
| 87 | 5-(2-Trifluoromethoxy-phenyl)-furan-2-yl |
| 88 | 4,5-Dibromo-thiophen-2-yl |
| 89 | 5-(1-Methyl-5-trifluoromethyl-1H-pyrazol-3-yl)-thiophen-2-yl |

TABLE 3

| Ex. | Rb1 | Rb2 | Rb3 | Rb4 | Rb5 |
|---|---|---|---|---|---|
| 90 | H | phenoxy | H | H | H |
| 91 | chloro | H | fluoro | H | H |
| 92 | H | methoxy | hydroxy | H | H |
| 93 | H | bromo | hydroxy | bromo | H |
| 94 | H | methoxy | H | methoxy | H |
| 95 | —OH | methoxy | H | nitro | H |
| 96 | H | methoxy | $CH_3C(=O)O$— | H | H |
| 97 | methoxy | H | H | bromo | H |
| 98 | fluoro | H | H | methoxy | H |
| 99 | H | H | $CH_3CO(=O)$— | H | H |
| 100 | benzyloxy | methoxy | H | H | H |
| 101 | fluoro | H | methoxy | H | H |
| 102 | H | H | MeSO2- | H | H |
| 103 | benzyloxy | H | H | H | H |
| 104 | methylenedioxy (Rb1/b2) | | H | H | H |
| 105 | H | —$CF_3$ | H | H | H |
| 106 | morpholin-4-yl | H | H | nitro | H |
| 108 | H | H | $CH_3C(=O)NH$— | H | H |
| 109 | H | iodo | hydroxy | methoxy | H |
| 110 | H | bromo | hydroxy | methoxy | H |
| 111 | H | ethoxy | hydroxy | H | H |
| 112 | H | methyl | hydroxy | methyl | H |
| 113 | H | methoxy | hydroxy | methoxy | H |
| 114 | H | fluoro | hydroxy | H | H |
| 115 | H | methyl | hydroxy | H | H |
| 116 | chloro | | hydroxy | H | H |

TABLE 3-continued

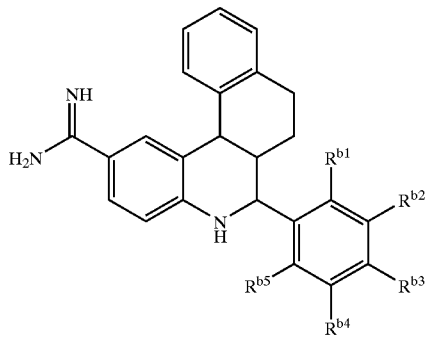

| Ex. | Rb1 | Rb2 | Rb3 | Rb4 | Rb5 |
|---|---|---|---|---|---|
| 117 | H | H | —CO$_2$H | H | H |
| 138 | H | H | (2-cyano-thiophen-3-yl)-methoxy- | H | H |
| 140 | bromo | bromo | hydroxy | methoxy | H |
| 141 | H | methoxy | HO$_2$C—CH$_2$O— | H | H |
| 163 | H | methoxy | hydroxy | H | 3-HO$_2$C-phenyl- |
| 164 | H | methoxy | hydroxy | H | 4-HO$_2$C-phenyl- |
| 168 | H | methoxy | hydroxy | H | 2-HO$_2$C-phenyl- |

TABLE 4

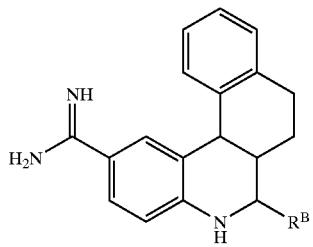

| Ex. | R$^B$ |
|---|---|
| 107 | 4-Methoxy-naphthalen-1-yl |
| 121 | 3,4-dimethyl-thieno[2,3-b]thiophen-2-yl |
| 122 | 4-phenylethynyl-thiophen-2-yl |
| 123 | 3-phenoxy-thiophen-2-yl |
| 124 | 6-CH$_3$OC(=O)-1H-indol-3-yl |
| 125 | 5-(2-Trifluoromethoxy-phenyl)-furan-2-yl |
| 126 | 4-bromo-thiophen-2-yl |
| 127 | 5-methyl-thiophen-2-yl |
| 128 | 3,4-dibromo-5-methyl-1H-pyrrol-2-yl |
| 129 | 5-(1-Methyl-5-trifluoromethyl-1H-pyrazol-3-yl)-thiophen-2-yl |
| 130 | 5-phenylethynyl-thiophen-2-yl |
| 131 | 1-methyl-1H-benzoimidazol-2-yl |
| 132 | 5-(4-H$_2$NSO$_2$-phenyl)-furan-2-yl |
| 133 | 5-(2-chloro-phenyl)-furan-2-yl |
| 134 | (1-methyl-3-phenyl-5-(p-tolyl-S-))-1H-pyrazol-4-yl |
| 135 | 5-(2-trifluoromethyl-phenyl)-furan-2-yl |
| 136 | 4-bromo-furan-2-yl |
| 137 | 5-(thiophen-2-yl)-thiophen-2-yl |
| 139 | 1-(4-chlorophenyl)-1H-pyrrol-2-yl |
| 142 | (1,3-dioxo-1,3-dihydro-isoindol-2-yl)methyl- |

TABLE 5

| Ex. | Rb1 | Rb2 | Rb3 | Rb4 | Rb5 |
|---|---|---|---|---|---|
| 143 | H | methoxy | hydroxy | H | H |

TABLE 6

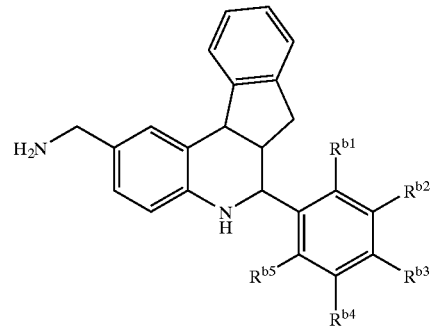

| Ex. | Rb1 | Rb2 | Rb3 | Rb4 | Rb5 |
|---|---|---|---|---|---|
| 213 | H | methoxy | hydroxy | H | 2-HO$_2$C-phenyl- |
| 216 | H | methoxy | hydroxy | H | 2-MeO-phenyl- |
| 217 | H | methoxy | hydroxy | H | 2-MeO-5-Me-phenyl- |
| 218 | H | methoxy | hydroxy | H | 2-MeS-phenyl- |
| 219 | H | methoxy | hydroxy | H | 2-F-phenyl- |
| 220 | H | methoxy | hydroxy | H | 2-MeO-5-F-phenyl- |
| 221 | H | methoxy | hydroxy | H | 2-MeO-5-Cl-phenyl- |
| 222 | H | methoxy | hydroxy | H | 2-EtO-phenyl- |
| 223 | H | methoxy | hydroxy | H | 2-Et-phenyl- |
| 224 | H | methoxy | hydroxy | H | 2-F$_3$CO-phenyl- |
| 225 | H | methoxy | hydroxy | H | 2-benzyloxy-phenyl- |
| 226 | H | methoxy | hydroxy | H | 4-MeSO$_2$NH-phenyl- |
| 227 | H | methoxy | hydroxy | H | 2,4-diMeO-phenyl- |
| 228 | H | methoxy | hydroxy | H | 2,6-diF-phenyl- |
| 229 | H | methoxy | hydroxy | H | 3-HO$_2$C-phenyl- |
| 230 | H | methoxy | hydroxy | H | 2-MeO-4-HO$_2$C-phenyl- |
| 231 | H | methoxy | hydroxy | H | 2-MeO-phenoxy- |
| 232 | H | methoxy | hydroxy | H | 2,6-diMeO-phenyl- |

The following Tables 1A–5A demonstrate envisioned Examples of compounds of Formula (I) that can be prepared by the methods disclosed herein and/or known to one skilled in the art.

TABLE 1A

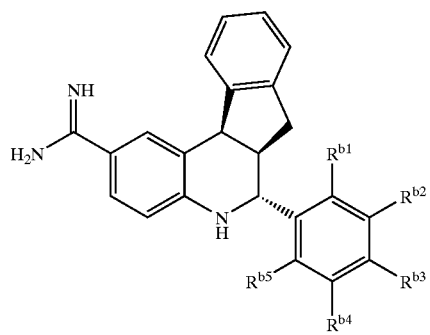

| Ex. | Rb1 | Rb2 | Rb3 | Rb4 | Rb5 |
|---|---|---|---|---|---|
| 1a | H | chloro | H | H | H |
| 2a | H | methoxy | hydroxy | H | H |
| 2Aa | H | ethoxy | hydroxy | H | H |
| 3a | methoxy | methoxy | H | H | H |
| 4a | methoxy | H | H | methoxy | H |
| 5a | hydroxy | methoxy | H | H | H |
| 6a | hydroxy | H | H | methoxy | H |
| 7a | methoxy | methoxy | methoxy | H | H |
| 8a | methyl | methyl | methoxy | H | H |
| 9a | methyl | H | methoxy | methyl | H |
| 10a | H | hydroxy | methoxy | H | H |
| 11a | H | H | methoxy | H | H |
| 12a | H | methoxy | OH | methoxy | H |
| 13a | H | H | CH$_3$OC(=O)— | H | H |
| 14a | H | methoxy | OH | nitro | H |
| 15a | H | OH | methoxy | methoxy | H |
| 16a | OH | methoxy | H | nitro | H |
| 17a | H | methoxy | (5-Cl-2-MeO-phenyl)-NHC(=O)O— | H | H |
| 18a | OH | methoxy | H | H | bromo |
| 19a | fluoro | H | H | methoxy | H |
| 20a | benzyloxy | methoxy | H | H | H |
| 21a | fluoro | H | methoxy | H | H |
| 22a | H | iodo | methoxy | methoxy | H |
| 23a | 2,6-diCl-benzyloxy | H | H | H | H |
| 24a | (4-Cl-phenyl)-S- | H | H | H | H |
| 25a | methylenedioxy (Rb1/b2) | | H | H | H |
| 26a | benzyloxy | H | H | H | H |
| 27a | allyloxy | H | H | H | H |
| 28a | methoxy | H | H | bromo | H |
| 29a | H | 4-MeO-phenoxy | H | H | H |
| 30a | H | methoxy | H | H | H |
| 31a | H | H | MeSO$_2$— | H | H |
| 32a | H | H | HOCH$_2$CH$_2$—O— | H | H |
| 33a | chloro | methoxy | methoxy | H | H |
| 34a | hydroxy | H | H | H | methoxy |
| 35a | H | CH$_3$OC(=O)— | H | H | H |
| 36a | H | (HO)$_2$B— | methoxy | H | H |
| 37a | H | bromo | OH | methoxy | H |
| 38a | fluoro | fluoro | fluoro | fluoro | fluoro |
| 39a | chloro | H | chloro | H | H |
| 40a | chloro | H | H | H | fluoro |
| 41a | H | chloro | chloro | H | H |
| 42a | H | chloro | H | chloro | H |
| 43a | H | 3,5-diCl-phenoxy | H | H | H |
| 44a | H | benzyloxy | H | H | H |
| 45a | H | —CF$_3$ | H | H | H |
| 46a | H | H | bromo | H | H |
| 47a | H | H | fluoro | H | H |
| 48a | H | H | chloro | H | H |
| 49a | H | H | ethoxy | H | H |
| 51a | H | H | —CF$_3$ | H | H |
| 52a | fluoro | fluoro | H | H | H |
| 53a | fluoro | H | fluoro | H | H |
| 54a | fluoro | H | H | fluoro | H |
| 55a | H | fluoro | fluoro | H | H |
| 56a | H | chloro | fluoro | H | H |
| 57a | H | H | pyrrolidin- | H | H |

TABLE 1A-continued

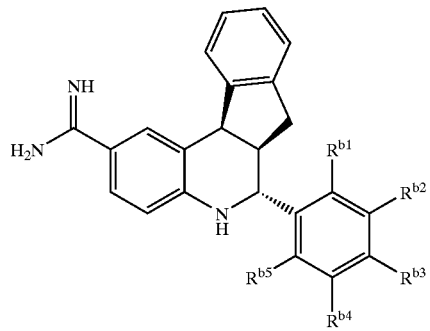

| Ex. | Rb1 | Rb2 | Rb3 | Rb4 | Rb5 |
|---|---|---|---|---|---|
| 58a | ethoxy | H | H | bromo | 1-yl H |
| 59a | H | H | —OCF$_3$ | H | H |
| 60a | H | H | propyl | H | H |
| 61a | H | bromo | fluoro | H | H |
| 63a | fluoro | fluoro | H | H | fluoro |
| 64a | fluoro | H | fluoro | fluoro | H |
| 65a | fluoro | H | fluoro | H | fluoro |
| 66a | fluoro | fluoro | fluoro | H | H |
| 67a | fluoro | —CF$_3$ | H | H | H |
| 68a | fluoro | H | H | H | —CF$_3$ |
| 69a | H | fluoro | H | —CF$_3$ | H |
| 70a | —CF$_3$ | H | fluoro | H | H |
| 71a | fluoro | fluoro | H | fluoro | H |
| 72a | 4-tBu-phenoxy | H | H | nitro | H |
| 73a | chloro | H | H | —CF$_3$ | H |
| 74a | fluoro | H | chloro | H | H |
| 75a | H | fluoro | chloro | H | H |
| 76a | benzyl-S— | H | H | nitro | H |
| 77a | morpholin-4-yl | H | H | nitro | H |
| 144a | H | methoxy | hydroxy | H | 4-i-Pr-phenyl- |
| 145a | H | methoxy | hydroxy | H | 4-HO$_2$C-phenyl- |
| 146a | H | methoxy | hydroxy | H | 4-(iBu-NHCO)-phenyl- |
| 147a | H | methoxy | hydroxy | H | 2-HO$_2$C-phenyl- |
| 148a | H | methoxy | hydroxy | H | 3-HO$_2$C-phenyl- |
| 149a | H | methoxy | hydroxy | H | phenyl- |
| 150a | H | methoxy | hydroxy | H | 2-MeO-phenyl- |
| 151a | H | methoxy | hydroxy | H | 4-EtO-phenyl- |
| 152a | H | methoxy | hydroxy | H | 3-cyano-phenyl- |
| 153a | H | methoxy | hydroxy | H | 4-cyano-phenyl- |
| 154a | H | methoxy | hydroxy | H | 3-HOCH$_2$-phenyl- |
| 155a | H | methoxy | hydroxy | H | 4-MeSO$_2$NH-phenyl- |
| 156a | H | methoxy | hydroxy | H | 4-MeSO$_2$-phenyl- |
| 157a | H | methoxy | hydroxy | H | 4-HOCH$_2$-phenyl- |
| 158a | H | methoxy | hydroxy | H | pyridin-3-yl- |
| 159a | H | methoxy | hydroxy | H | 2,4-diMeo-pyrimidin-5-yl- |
| 160a | H | methoxy | hydroxy | H | 4-(iBu-NHCO)-2-(benzyl-OC(=O))-phenyl- |
| 161a | H | methoxy | hydroxy | H | 4-(iBu-NHCO)-2-HO$_2$C-phenyl- |
| 162a | H | methoxy | hydroxy | methoxy | 2-HO$_2$C-Phenyl- |
| 165a | H | methoxy | hydroxy | H | 3-H$_2$NCO-phenyl- |
| 166a | H | methoxy | hydroxy | H | 4-H$_2$NSO$_2$-phenyl- |
| 167a | H | methoxy | hydroxy | H | 3-H$_2$NSO$_2$-phenyl- |
| 169a | H | methoxy | hydroxy | methoxy | 3-HO$_2$C-phenyl- |
| 170a | H | methoxy | hydroxy | methoxy | 4-HO$_2$C-phenyl- |
| 171a | H | methoxy | hydroxy | H | thiophen-3-yl- |
| 172a | H | methoxy | hydroxy | H | 2,5-diMeO-phenyl- |
| 173a | H | methoxy | hydroxy | H | 2-chloro-phenyl- |
| 174a | H | methoxy | hydroxy | H | 2,6-diMeO-phenyl- |
| 175a | H | methoxy | hydroxy | H | 2-H$_3$CS-phenyl- |
| 176a | H | methoxy | hydroxy | H | 2-(phenyl)-phenyl- |
| 177a | H | methoxy | hydroxy | H | 2-MeO-5-F-phenyl- |
| 178a | H | methoxy | hydroxy | H | 2,4-diCl-phenyl- |
| 179a | H | methoxy | hydroxy | H | 2,6-diF-phenyl- |
| 180a | H | methoxy | hydroxy | H | 3-F$_3$CO-phenyl- |
| 181a | H | methoxy | hydroxy | H | 3-Cl-phenyl- |
| 182a | H | methoxy | hydroxy | H | 4-H$_3$CS-phenyl- |
| 183a | H | methoxy | hydroxy | H | 2-methyl-phenyl- |
| 184a | H | methoxy | hydroxy | H | 5-Cl-thiophen-2-yl- |
| 185a | H | methoxy | hydroxy | H | 2-MeO-5-i-propyl-phenyl- |

TABLE 1A-continued

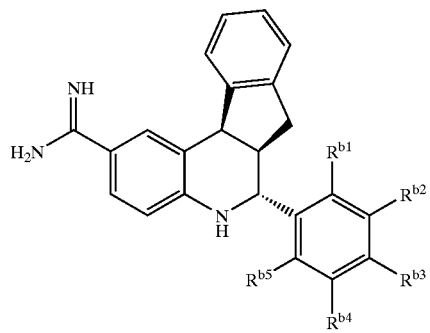

| Ex. | Rb1 | Rb2 | Rb3 | Rb4 | Rb5 |
|---|---|---|---|---|---|
| 186a | H | methoxy | hydroxy | H | 4-F$_3$C-phenyl- |
| 187a | H | methoxy | hydroxy | H | 3-F$_3$C-phenyl- |
| 188a | H | methoxy | hydroxy | H | 4-MeO-phenyl- |
| 189a | H | methoxy | hydroxy | H | 2-F-phenyl- |
| 190a | H | methoxy | hydroxy | H | 2,4-diMeO-phenyl- |
| 191a | H | methoxy | hydroxy | H | 3-(phenyl)-phenyl- |
| 192a | H | methoxy | hydroxy | H | 2-MeO-5-Cl-phenyl- |
| 193a | H | methoxy | hydroxy | H | 4-Me$_2$N-phenyl- |
| 194a | H | methoxy | hydroxy | H | 6-MeO-pyridin-3-yl- |
| 195a | H | methoxy | hydroxy | H | 4-(benzyloxy)-phenyl- |
| 196a | H | methoxy | hydroxy | H | 4-t-butyl-phenyl- |
| 197a | H | methoxy | hydroxy | H | 2-MeO-5-Me-phenyl- |
| 198a | H | methoxy | hydroxy | H | 4-i-butyl-phenyl- |
| 199a | H | methoxy | hydroxy | H | 2-EtO-phenyl- |
| 200a | H | methoxy | hydroxy | H | 2-F$_3$COphenyl- |
| 201a | H | methoxy | hydroxy | H | 2-(benzyloxy)-phenyl- |
| 202a | H | methoxy | hydroxy | H | 2-ethyl-phenyl- |
| 203a | H | methoxy | hydroxy | H | 4-(phenoxy)-phenyl- |
| 204a | H | methoxy | hydroxy | H | 2,4-bis-F$_3$C-phenyl- |
| 205a | H | methoxy | hydroxy | H | 4-(benzyloxy-CONH)-phenyl- |
| 206a | H | methoxy | hydroxy | H | 4-F$_3$COphenyl- |
| 207a | H | methoxy | hydroxy | H | 3,5-diF-phenyl- |
| 208a | H | methoxy | hydroxy | H | 4-HO$_2$C-phenoxy- |
| 209a | H | methoxy | hydroxy | H | 3-HO$_2$C-phenoxy- |
| 210a | H | methoxy | benzyloxy | H | 4-HO$_2$C-phenoxy- |
| 211a | H | methoxy | benzyloxy | H | 3-HO$_2$C-phenoxy- |
| 214a | H | methoxy | hydroxy | H | 4-H$_2$NCO-phenyl- |
| 233a | H | methoxy | hydroxy | H | 4-tetrazol-5-yl-phenyl- |
| 234a | H | methoxy | hydroxy | H | 2-MeO-4-HO$_2$C-phenyl- |
| 235a | H | methoxy | hydroxy | H | 2-MeO-4-iBuNHCO-phenyl- |
| 236a | H | methoxy | hydroxy | H | 2-MeO-4-benzylNHCO-phenyl- |
| 237a | H | methoxy | hydroxy | H | 2-MeO-4-(morpholin-4-yl-ethyl)NHCO-phenyl- |
| 238a | H | methoxy | hydroxy | H | 2-MeO-4-cyclohexylNHCO-phenyl- |
| 239a | H | methoxy | hydroxy | H | 2-MeO-4-cyclopropylNHCO-phenyl- |
| 240a | H | methoxy | hydroxy | H | 2-MeO-4-(pyrrolidin-1-yl-ethyl)NHCO-phenyl- |

TABLE 2A

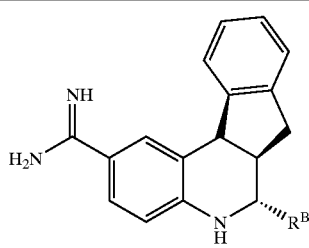

| Ex. | R$^B$ |
|---|---|
| 50a | 4-Methoxy-naphthalen-1-yl |
| 62a | 2,2-Dimethyl-chroman-6-yl |

TABLE 2A-continued

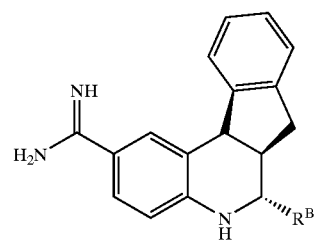

| Ex. | R$^B$ |
|---|---|
| 78a | 3-Phenyl-1H-pyrazol-4-yl |
| 79a | 2,4-Dioxo-1,2,3,4-tetrahydro-pyrimidin-5-yl |

TABLE 2A-continued

| Ex. | R$^B$ |
|---|---|
| 80a | 2-Phenyl-1H-imidazol-4-yl |
| 81a | 1H-imidazol-4-yl |
| 82a | 5-Methyl-1H-pyrazol-4-yl |
| 83a | Thiophen-2-yl |
| 84a | 5-(3-Trifluoromethyl-phenyl)-furan-2-yl |
| 85a | 5-(2-Chloro-phenyl)-furan-2-yl |
| 86a | 5-(2,5-diChloro-phenyl)-furan-2-yl |
| 87a | 5-(2-Trifluoromethoxy-phenyl)-furan-2-yl |
| 88a | 4,5-Dibromo-thiophen-2-yl |
| 89a | 5-(1-Methyl-5-trifluoromethyl-1H-pyrazol-3-yl)-thiophen-2-yl |

TABLE 3A

| Ex. | Rb1 | Rb2 | Rb3 | Rb4 | Rb5 |
|---|---|---|---|---|---|
| 90a | H | phenoxy | H | H | H |
| 91a | chloro | H | fluoro | H | H |
| 92a | H | methoxy | hydroxy | H | H |
| 93a | H | bromo | hydroxy | bromo | H |
| 94a | H | methoxy | H | methoxy | H |
| 95a | —OH | methoxy | H | nitro | H |
| 96a | H | methoxy | CH$_3$C(=O)O— | H | H |
| 97a | methoxy | H | H | bromo | H |
| 98a | fluoro | H | H | methoxy | H |
| 99a | H | H | CH$_3$CO(=O)— | H | H |
| 100a | benzyloxy | methoxy | H | H | H |
| 101a | fluoro | H | methoxy | H | H |
| 102a | H | H | MeSO$_2$— | H | H |
| 103a | benzyloxy | H | H | H | H |
| 104a | methylenedioxy (Rb1/b2) | | H | H | H |
| 105a | H | —CF$_3$ | H | H | H |
| 106a | morpholin-4-yl | H | H | nitro | H |
| 108a | H | H | CH$_3$C(=O)NH— | H | H |
| 109a | H | iodo | hydroxy | methoxy | H |
| 110a | H | bromo | hydroxy | methoxy | H |
| 111a | H | ethoxy | hydroxy | H | H |
| 112a | H | methyl | hydroxy | methyl | H |
| 113a | H | methoxy | hydroxy | methoxy | H |
| 114a | H | fluoro | hydroxy | H | H |
| 115a | H | methyl | hydroxy | H | H |
| 116a | chloro | | hydroxy | H | H |
| 117a | H | H | —CO$_2$H | H | H |

TABLE 3A-continued

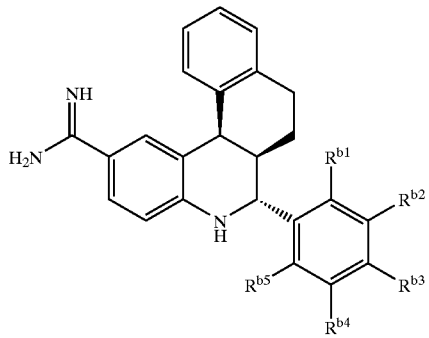

| Ex. | Rb1 | Rb2 | Rb3 | Rb4 | Rb5 |
|---|---|---|---|---|---|
| 138a | H | H | (2-cyano-thiophen-3-yl)-methoxy | H | H |
| 140a | bromo | bromo | hydroxy | methoxy | H |
| 141a | H | methoxy | $HO_2C-CH_2O$ | H | H |
| 163a | H | methoxy | hydroxy | H | 3-$HO_2C$-phenyl- |
| 164a | H | methoxy | hydroxy | H | 4-$HO_2C$-phenyl- |
| 168a | H | methoxy | hydroxy | H | 2-$HO_2C$-phenyl- |

TABLE 4A

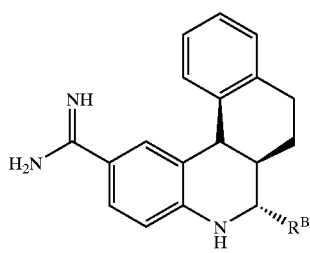

| Ex. | $R^B$ |
|---|---|
| 107a | 4-Methoxy-naphthalen-1-yl |
| 121a | 3,4-dimethyl-thieno[2,3-b]thiophen-2-yl |
| 122a | 4-phenylethynyl-thiophen-2-yl |
| 123a | 3-phenoxy-thiophen-2-yl |
| 124a | 6-$CH_3OC(=O)$-1H-indol-3-yl |
| 125a | 5-(2-Trifluoromethoxy-phenyl)-furan-2-yl |
| 126a | 4-bromo-thiophen-2-yl |
| 127a | 5-methyl-thiophen-2-yl |
| 128a | 3,4-dibromo-5-methyl-1H-pyrrol-2-yl |
| 129a | 5-(1-Methyl-5-trifluoromethyl-1H-pyrazol-3-yl)-thiophen-2-yl |
| 130a | 5-phenylethynyl-thiophen-2-yl |
| 131a | 1-methyl-1H-benzoimidazol-2-yl |
| 132a | 5-(4-$H_2NSO_2$-phenyl)-furan-2-yl |
| 133a | 5-(2-chloro-phenyl)-furan-2-yl |
| 134a | (1-methyl-3-phenyl-5-(p-tolyl-S-))-1H-pyrazol-4-yl |
| 135a | 5-(2-trifluoromethyl-phenyl)-furan-2-yl |
| 136a | 4-bromo-furan-2-yl |
| 137a | 5-(thiophen-2-yl)-thiophen-2-yl |
| 139a | 1-(4-chlorophenyl)-1H-pyrrol-2-yl |
| 142a | (1,3-dioxo-1,3-dihydro-isoindol-2-yl)methyl- |

TABLE 5A

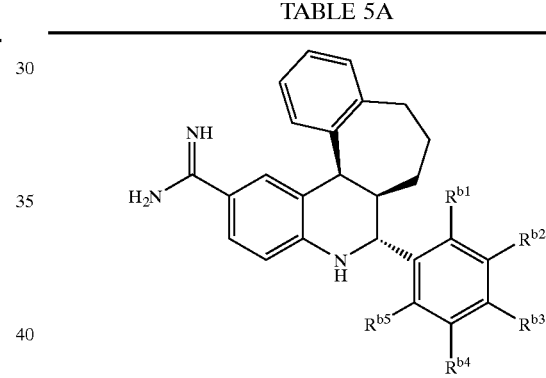

| Ex. | Rb1 | Rb2 | Rb3 | Rb4 | Rb5 |
|---|---|---|---|---|---|
| 143a | H | methoxy | hydroxy | H | H |

TABLE 6A

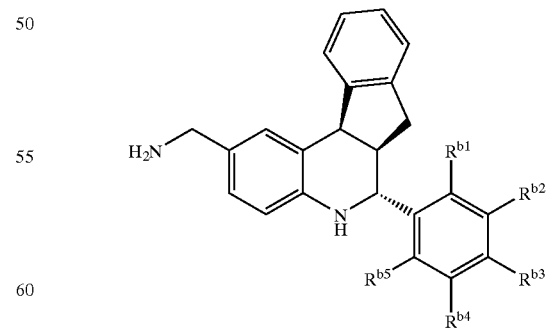

| Ex. | Rb1 | Rb2 | Rb3 | Rb4 | Rb5 |
|---|---|---|---|---|---|
| 213a | H | methoxy | hydroxy | H | 2-$HO_2C$-phenyl- |
| 216a | H | methoxy | hydroxy | H | 2-MeO-phenyl- |
| 217a | H | methoxy | hydroxy | H | 2-MeO-5-Me-phenyl- |

TABLE 6A-continued

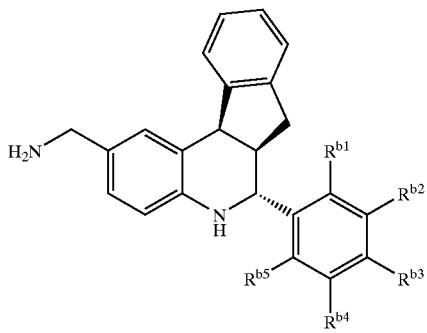

| Ex. | Rb1 | Rb2 | Rb3 | Rb4 | Rb5 |
|---|---|---|---|---|---|
| 218a | H | methoxy | hydroxy | H | 2-MeS-phenyl- |
| 219a | H | methoxy | hydroxy | H | 2-F-phenyl- |
| 220a | H | methoxy | hydroxy | H | 2-MeO-5-F-phenyl- |
| 221a | H | methoxy | hydroxy | H | 2-MeO-5-Cl-phenyl- |
| 222a | H | methoxy | hydroxy | H | 2-EtO-phenyl- |
| 223a | H | methoxy | hydroxy | H | 2-Et-phenyl- |
| 224a | H | methoxy | hydroxy | H | 2-F$_3$CO-phenyl- |
| 225a | H | methoxy | hydroxy | H | 2-benzyloxy-phenyl- |
| 226a | H | methoxy | hydroxy | H | 4-MeSO$_2$NH-phenyl- |
| 227a | H | methoxy | hydroxy | H | 2,4-diMeO-phenyl- |
| 228a | H | methoxy | hydroxy | H | 2,6-diF-phenyl- |
| 229a | H | methoxy | hydroxy | H | 3-HO$_2$C-phenyl- |
| 230a | H | methoxy | hydroxy | H | 2-MeO-4-HO$_2$C-phenyl- |
| 231a | H | methoxy | hydroxy | H | 2-MeO-phenoxy- |
| 232a | H | methoxy | hydroxy | H | 2,6-diMeO-phenyl- |

UTILITY

The compounds of this invention are useful as anticoagulants for the prevention or treatment of thromboembolic disorders in mammals. The term "thromboembolic disorders" as used herein includes arterial or venous cardiovascular or cerebrovascular thromboembolic disorders, including, for example, unstable angina, first or recurrent myocardial infarction, ischemic sudden death, transient ischemic attack, stroke, atherosclerosis, venous thrombosis, deep vein thrombosis, thrombophlebitis, arterial embolism, coronary and cerebral arterial thrombosis, cerebral embolism, kidney embolisms, and pulmonary embolisms. The anticoagulant effect of compounds of the present invention is believed to be due to inhibition serine proteases involved in the coagulation cascade, more specifically, inhibition of the coagulation factors: factor VIIa, factor IXa, factor Xa, factor XIa, or thrombin.

The effectiveness of compounds of the present invention as inhibitors of the coagulation factors VIIa, IXa, Xa, XIa, or thrombin, was determined using a relevant purified serine protease, respectively, and an appropriate synthetic substrate. The rate of hydrolysis of the chromogenic substrate by the relevant serine protease was measured both in the absence and presence of compounds of the present invention. Hydrolysis of the substrate resulted in the release of pNA, which was monitored spectrophotometrically by measuring the increase in absorbance at 405 nM. A decrease in the rate of absorbance change at 405 nM in the presence of inhibitor is indicative of enzyme inhibition. Such methods are known to one skilled in the art. The results of this assay are expressed as inhibitory constant, $K_i$.

Factor VIIa determinations were made in 0.07 M calcium chloride, 0.1M sodium chloride, 0.05 M trizma base containing 0.1% bovine serum albumin at a pH of 7.6. Determinations were made using purified human factor VIIa (Enzyme Research Laboratories, South Bend, Ind.) at a final assay concentration of 5 nM, soluble tissue factor at a concentration of 0.5 μg/mL and the synthetic substrate S-2288 (Chromogenix) at a concentration of 0.001 M. Compounds of the present invention have demonstrated Ki values of equal to or less than 50 μM in this assay.

Factor IXa determinations were made in 0.05 M calcium chloride, 0.1M sodium chloride, 0.05 M trizma base and 0.5% Carbowax PEG 8000 at a pH of 7.4. Determinations were made using purified human factor IXa (Haematologic Technologies) at a final assay concentration of 150 nM and the synthetic substrate PCIXA2100-B (CenterChem) at a concentration of 0.0004 M.

Factor Xa determinations were made in 0.1 M sodium phosphate buffer at a pH of 7.5 containing 0.2M sodium chloride and 0.5% Carbowax PEG 8000. Determinations of the Michaelis constant, Km, for substrate hydrolysis were made using purified human factor Xa (Enzyme Research Laboratories, South Bend, Ind.) at a final assay concentration of 2 nM and the synthetic substrate S-2222 (Chromogenix) at a concentration of 0.0002 M. Compounds of the present invention have demonstrated Ki values of equal to or less than 50 μM in this assay.

Factor XIa determinations were made in 50 mM HEPES buffer at pH 7.4 containing 145 mM NaCl, 5 mM KCl, and 0.1% PEG 8000. Determinations were made using factor XIa at a final concentration of 75 pM and the synthetic substrate S-2366 (Chromogenix) at a concentration of 0.0002 M. Compounds tested in the factor XIa assay are considered to be active if they exhibit a Ki of equal to or less than 25 μM.

Thrombin determinations were made in 0.1 M sodium phosphate buffer at a pH of 7.5 containing 0.2M sodium chloride and 0.5% Carbowax PEG 8000. Determinations were made using purified human alpha Thrombin (Enzyme Research Laboratories, South Bend, Ind.) at a final assay concentration of 0.375 nM and the synthetic substrate S-2366 (Chromogenix) at a concentration of 0.0002 M. Compounds of the present invention have demonstrated Ki values of equal to or less than 50 μM in this assay.

The Michaelis constant, Km, for substrate hydrolysis by each protease was determined at 25° C. using the method of Lineweaver and Burk. Values of $K_i$ were determined by allowing the protease to react with the substrate in the presence of the inhibitor. Reactions were allowed to go for periods of 60–180 minutes (depending on the protease) and the velocities (rate of absorbance change vs time) were measured. The following relationship was used to calculate $K_i$ values:

$$(v_o-v_s)/v_s=I/(K_i(1+S/K_m))$$

where:

$v_o$ is the velocity of the control in the absence of inhibitor;

$v_s$ is the velocity in the presence of inhibitor;

I is the concentration of inhibitor;

$K_i$ is the dissociation constant of the enzyme:inhibitor complex;

S is the concentration of substrate; and $K_m$ is the Michaelis constant.

Compounds tested in the above assay are considered to be active if they exhibit a Ki of equal to or less than 50 μM. Preferred compounds of the present invention have Ki's of equal to or less than 1 μM. More preferred compounds of the present invention have Ki's of equal to or less than 0.1 μM.

Even more preferred compounds of the present invention have Ki's of equal to or less than 0.01 μM. Compounds of the present invention have demonstrated Ki values of equal to or less than 50 μM in the above assays, thereby confirming the utility of the compounds of the present invention as effective inhibitors of the coagulation factors.

In Vivo Electrically-induced Carotid Artery Thrombosis Model:

The antithrombotic effect of compounds of the present invention can be demonstrated in the electrically-induced carotid artery thrombosis (ECAT) model in rats. In this model, rats are anesthetized with a mixture of ketamine (110 mg/kg i.m.) and xylazine (10 mg/kg i.m.). A femoral vein and a femoral artery are isolated and catheterized. The carotid artery is also isolated such that its blood flow can be measured with a calibrated flow probe that is linked to a flowmeter. A stainless steel bipolar hook electrode is placed on the carotid artery and positioned caudally in relationship to the flow probe as a means of applying electrical stimulus. In order to protect the surrounding tissue, a piece of Parafilm is placed under the electrode.

Test compounds are considered to be effective as anticoagulants based on their ability to maintain blood flow in the carotid artery following the induction of thrombosis by an electrical stimulus. A test compound or vehicle is given as continuous intravenous infusion via the femoral vein, starting 1 hour before electrical stimulation and continuing to the end of the test. Thrombosis is induced by applying a direct electrical current of 4 mA for 3 min to the external arterial surface, using a constant current unit and a d.c. stimulator. The carotid blood flow is monitored and the time to occlusion (decrease of blood flow to zero following induction of thrombosis) in minutes is noted. The change in observed blood flow is calculated as a percentage of the blood flow prior to induction of thrombosis and provides a measure of the effect of a test compound when compared to the case where no compound is administered. This information is used to estimate the $ED_{50}$ value, the dose that increases blood flow to 50% of the control (blood flow prior to induction of thrombosis) and is accomplished by nonlinear least square regression.

In Vivo Rabbit Arterio-venous Shunt Thrombosis Model:

The antithrombotic effect of compounds of the present invention can be demonstrated in a rabbit arterio-venous (AV) shunt thrombosis model. In this model, rabbits weighing 2–3 kg anesthetized with a mixture of xylazine (10 mg/kg i.m.) and ketamine (50 mg/kg i.m.) are used. A saline-filled AV shunt device is connected between the femoral arterial and the femoral venous cannulae. The AV shunt device consists of a piece of 6-cm tygon tubing that contains a piece of silk thread. Blood will flow from the femoral artery via the AV-shunt into the femoral vein. The exposure of flowing blood to a silk thread will induce the formation of a significant thrombus. After forty minutes, the shunt is disconnected and the silk thread covered with thrombus is weighed. Test agents or vehicle will be given (i.v., i.p., s.c., or orally) prior to the opening of the AV shunt. The percentage inhibition of thrombus formation is determined for each treatment group. The ID50 values (dose which produces 50% inhibition of thrombus formation) are estimated by linear regression.

In Vivo Rabbit Electrically Induced Carotid Artery Thrombosis Model:

The antithrombotic effect of compounds of the present invention can be demonstrated in a rabbit electrically induced carotid artery thrombosis (ECAT) model. The rabbit ECAT model of thrombosis is described by Wong et al. (Wong P C, Crain E J, Knabb R M, Meade R P, Quan M L, Watson C A, Wexler R R, Wright M R and Slee A M. Nonpeptide factor Xa inhibitors: II. Antithrombotic evaluation in a rabbit model of electrically induced carotid artery thrombosis. *J Pharmacol Exp Ther* 295:212–218, 2000). In this model, male New Zealand White rabbits were anesthetized with ketamine (50 mg/kg+50 mg/kg/h IM) and xylazine (10 mg/kg+10 mg/kg/h IM). These anesthetics were supplemented as needed. An electromagnetic flow probe was placed on a segment of an isolated carotid artery to monitor blood flow. Thrombus formation was induced by electrical stimulation of the carotid artery for 3 min at 4 mA using an external stainless-steel bipolar electrode. Carotid blood flow was measured continuously over a 90-min period to monitor thrombus-induced occlusion. Compounds or vehicle was infused intravenously 1 h prior to the electrical stimulation of the carotid artery and continuously during the 90-min period.

In addition, total carotid blood flow over 90 min was calculated by trapezoidal rule. Average carotid flow over 90 min was then determined by converting total carotid blood flow over 90 min to percent of total control carotid blood flow, which would result if control blood flow had been maintained continuously for 90 min. The $ED_{50}$ (dose that increased carotid blood flow to 50% of the control) of compounds were estimated by a nonlinear least square regression program using the Hill sigmoid $E_{max}$ equation.

The compounds of Formula (I) may also be useful as inhibitors of serine proteases, notably human thrombin, plasma kallikrein and plasmin. Because of their inhibitory action, these compounds are indicated for use in the prevention or treatment of physiological reactions, blood coagulation and inflammation, catalyzed by the aforesaid class of enzymes. Specifically, the compounds have utility as drugs for the treatment of diseases arising from elevated thrombin activity such as myocardial infarction, and as reagents used as anticoagulants in the processing of blood to plasma for diagnostic and other commercial purposes.

Some compounds of the present invention may be shown to be direct acting inhibitors of the serine protease thrombin by their ability to inhibit the cleavage of small molecule substrates by thrombin in a purified system. In vitro inhibition constants may be determined by the method described by Kettner et al. in *J. Biol. Chem.* 1990, 265, 18289–18297, herein incorporated by reference. In these assays, thrombin-mediated hydrolysis of the chromogenic substrate S2238 (Helena Laboratories, Beaumont, Tex.) are monitored spectrophotometrically. Addition of an inhibitor to the assay mixture results in decreased absorbance and is indicative of thrombin inhibition. Human thrombin (Enzyme Research Laboratories, Inc., South Bend, Ind.) at a concentration of 0.2 nM in 0.10 M sodium phosphate buffer, pH 7.5, 0.20 M NaCl, and 0.5% PEG 6000, is incubated with various substrate concentrations ranging from 0.20 to 0.02 mM. After 25 to 30 minutes of incubation, thrombin activity is assayed by monitoring the rate of increase in absorbance at 405 nm that arises owing to substrate hydrolysis. Inhibition constants are derived from reciprocal plots of the reaction velocity as a function of substrate concentration using the standard method of Lineweaver and Burk.

The compounds of the present invention can be administered alone or in combination with one or more additional therapeutic agents. These include other anti-coagulant or coagulation inhibitory agents, anti-platelet or platelet inhibitory agents, thrombin inhibitors, or thrombolytic or fibrinolytic agents.

The compounds are administered to a mammal in a therapeutically effective amount. By "therapeutically effective amount" it is meant an amount of a compound of Formula (I) that, when administered alone or in combination with an additional therapeutic agent to a mammal, is effective to prevent or ameliorate the thromboembolic disease condition or the progression of the disease.

The compounds of the present invention can be administered alone or in combination with one or more additional therapeutic agents. By "administered in combination" or "combination therapy" it is meant that a compound of the present invention and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect.

Additional therapeutic agents include other anti-coagulant or coagulation inhibitory agents, anti-platelet or platelet inhibitory agents, thrombin inhibitors, thrombolytic or fibrinolytic agents, anti-arrythmic agents, anti-hypertensive agents, calcium channel blockers (L-type and T-type), cardiac glycosides, diruetics, mineralocorticoid receptor antagonists, phospodiesterase inhibitors, cholesterol/lipid lowering agents and lipid profile therapies, anti-diabetic agents, anti-depressants, anti-inflammatory agents (steroidal and non-steroidal), anti-osteoporosis agents, hormone replacement therapies, oral contraceptives, anti-obesity agents, anti-anxiety agents, anti-proliferative agents, anti-tumor agents, anti-ulcer and gastroesophageal reflux disease agents, growth hormone and/or growth hormone secretagogues, thyroid mimetics (including thyroid receptor antagonist), anti-infective agents, anti-viral agents, anti-bacterial agents, and anti-fungal agents.

Other anticoagulant agents (or coagulation inhibitory agents) that may be used in combination with the compounds of this invention include warfarin and heparin (either unfractionated heparin or any commercially available low molecular weight heparin), synthetic pentasaccharide, direct acting thrombin inhibitors including hirudin and argatroban as well as other factor VIIa inhibitors such as those described in the publications identified above under Background of the Invention.

The term anti-platelet agents (or platelet inhibitory agents), as used herein, denotes agents that inhibit platelet function, for example by inhibiting the aggregation, adhesion or granular secretion of platelets. Agents include, but are not limited to, the various known non-steroidal anti-inflammatory drugs (NSAIDS) such as aspirin, ibuprofen, naproxen, sulindac, indomethacin, mefenamate, droxicam, diclofenac, sulfinpyrazone, piroxicam, and pharmaceutically acceptable salts or prodrugs thereof. Of the NSAIDS, aspirin (acetylsalicyclic acid or ASA) and piroxicam are preferred. Other suitable platelet inhibitory agents include IIb/IIIa antagonists (e.g., tirofiban, eptifibatide, and abciximab), thromboxane-A2-receptor antagonists (e.g., ifetroban), thromboxane-A2-synthetase inhibitors, PDE-III inhibitors (e.g., dipyridamole), and pharmaceutically acceptable salts or prodrugs thereof.

The term anti-platelet agents (or platelet inhibitory agents), as used herein, is also intended to include ADP (adenosine diphosphate) receptor antagonists, preferably antagonists of the purinergic receptors $P_2Y_1$ and $P_2Y_{12}$, with $P_2Y_{12}$ being even more preferred. Preferred $P_2Y_{12}$ receptor antagonists include ticlopidine and clopidogrel, including pharmaceutically acceptable salts or prodrugs thereof. Clopidogrel is an even more preferred agent. Ticlopidine and clopidogrel are also preferred compounds since they are known to be gentle on the gastro-intestinal tract in use.

The term thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the granular secretion of plasminogen activator inhibitor-1 and/or serotonin) and/or fibrin formation are disrupted. A number of thrombin inhibitors are known to one of skill in the art and these inhibitors are contemplated to be used in combination with the present compounds. Such inhibitors include, but are not limited to, boroarginine derivatives, boropeptides, heparins, hirudin, argatroban, and melagatran, including pharmaceutically acceptable salts and prodrugs thereof. Boroarginine derivatives and boropeptides include N-acetyl and peptide derivatives of boronic acid, such as C-terminal α-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin.

The term thrombolytics or fibrinolytic agents (or thrombolytics or fibrinolytics), as used herein, denote agents that lyse blood clots (thrombi). Such agents include tissue plasminogen activator (natural or recombinant) and modified forms thereof, anistreplase, urokinase, streptokinase, tenecteplase (TNK), lanoteplase (nPA), factor VIIa inhibitors, PAI-1 inhibitors (i.e., inactivators of tissue plasminogen activator inhibitors), alpha2-antiplasmin inhibitors, and anisoylated plasminogen streptokinase activator complex, including pharmaceutically acceptable salts or prodrugs thereof. The term anistreplase, as used herein, refers to anisoylated plasminogen streptokinase activator complex, as described, for example, in EP 028,489, the disclosure of which is hereby incorporated herein by reference herein. The term urokinase, as used herein, is intended to denote both dual and single chain urokinase, the latter also being referred to herein as prourokinase.

Examples of suitable anti-arrythmic agents for use in combination with the present compounds include: Class I agents (such as propafenone); Class II agents (such as carvadiol and propranolol); Class III agents (such as sotalol, dofetilide, amiodarone, azimilide and ibutilide); Class IV agents (such as ditiazem and verapamil); K⁺channel openers such as $I_{Ach}$ inhibitors, and $I_{Kur}$ inhibitors (e.g., compounds such as those disclosed in WO01/40231).

Examples of suitable anti-hypertensive agents for use in combination with the compounds of the present invention include: alpha adrenergic blockers; beta adrenergic blockers; calcium channel blockers (e.g., diltiazem, verapamil, nifedipine, amlodipine and mybefradil); diruetics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone); renin inhibitors; ACE inhibitors (e.g., captopril, zofenopril, fosinopril, enalapril, ceranopril, cilazopril, delapril, pentopril, quinapril, ramipril, lisinopril); AT-1 receptor antagonists (e.g., losartan, irbesartan, valsartan); ET receptor antagonists (e.g., sitaxsentan, atrsentan and compounds disclosed in U.S. Pat. Nos. 5,612,359 and 6,043,265); Dual ET/AII antagonist (e.g., compounds disclosed in WO 00/01389); neutral endopeptidase (NEP) inhibitors; vasopepsidase inhibitors (dual NEP-ACE inhibitors) (e.g., omapatrilat, gemopatrilat and nitrates).

Examples of suitable calcium channel blockers (L-type or T-type) for use in combination with the compounds of the present invention include diltiazem, verapamil, nifedipine, amlodipine and mybefradil.

Examples of suitable cardiac glycosides for use in combination with the compounds of the present invention include digitalis and ouabain.

Examples of suitable diruetics for use in combination with the compounds of the present invention include: chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, and spironolactone.

Examples of suitable mineralocorticoid receptor antagonists for use in combination with the compounds of the present invention include sprionolactone and eplirinone.

Examples of suitable phospodiesterase inhibitors for use in combination with the compounds of the present invention include: PDE III inhibitors (such as cilostazol); and PDE V inhibitors (such as sildenafil).

Examples of suitable cholesterol/lipid lowering agents and lipid profile therapies for use in combination with the compounds of the present invention include: HMG-CoA reductase inhibitors (e.g., pravastatin, lovastatin, atorvastatin, simvastatin, fluvastatin, NK-104 (a.k.a. itavastatin, or nisvastatin or nisbastatin) and ZD-4522 (a.k.a. rosuvastatin, or atavastatin or visastatin)); squalene synthetase inhibitors; fibrates; bile acid sequestrants (such as questran); ACAT inhibitors; MTP inhibitors; lipooxygenase inhibitors; choesterol absorption inhibitors; and cholesterol ester transfer protein inhibitors (e.g., CP-529414).

Examples of suitable anti-diabetic agents for use in combination with the compounds of the present invention include: biguanides (e.g., metformin); glucosidase inhibitors (e.g., acarbose); insulins (including insulin secretagogues or insulin sensitizers); meglitinides (e.g., repaglinide); sulfonylureas (e.g., glimepiride, glyburide and glipizide); biguanide/glyburide combinations (e.g., glucovance), thiozolidinediones (e.g., troglitazone, rosiglitazone and pioglitazone), PPAR-alpha agonists, PPAR-gamma agonists, PPAR alpha/gamma dual agonists, SGLT2 inhibitors, inhibitors of fatty acid binding protein (aP2) such as those disclosed in WO00/59506, glucagon-like peptide-1 (GLP-1), and dipeptidyl peptidase IV (DP4) inhibitors.

Examples of suitable anti-depressant agents for use in combination with the compounds of the present invention include nefazodone and sertraline.

Examples of suitable anti-inflammatory agents for use in combination with the compounds of the present invention include: prednisone; dexamethasone; enbrel; protien tyrosine kinase (PTK) inhibitors; cyclooxygenase inhibitors (including NSAIDs, and COX-1 and/or COX-2 inhibitors); aspirin; indomethacin; ibuprofen; prioxicam; naproxen; celecoxib; and/or rofecoxib.

Examples of suitable anti-osteoporosis agents for use in combination with the compounds of the present invention include alendronate and raloxifene.

Examples of suitable hormone replacement therapies for use in combination with the compounds of the present invention include estrogen (e.g., congugated estrogens) and estradiol.

Examples of suitable anti-coagulants for use in combination with the compounds of the present invention include heparins (e.g., unfractioned and low molecular weight heparins such as enoxaparin and dalteparin).

Examples of suitable anti-obesity agents for use in combination with the compounds of the present invention include orlistat and aP2 inhibitors (such as those disclosed in WO00/59506).

Examples of suitable anti-anxiety agents for use in combination with the compounds of the present invention include diazepam, lorazepam, buspirone, and hydroxyzine pamoate.

Examples of suitable anti-proliferative agents for use in combination with the compounds of the present invention include cyclosporin A, paclitaxel, adriamycin; epithilones, cisplatin, and carboplatin.

Examples of suitable anti-ulcer and gastroesophageal reflux disease agents for use in combination with the compounds of the present invention include famotidine, ranitidine, and omeprazole.

Administration of the compounds of the present invention (i.e., a first therapeutic agent) in combination with at least one additional therapeutic agent (i.e., a second therapeutic agent), preferably affords an efficacy advantage over the compounds and agents alone, preferably while permitting the use of lower doses of each (i.e., a synergistic combination). A lower dosage minimizes the potential of side effects, thereby providing an increased margin of safety. It is preferred that at least one of the therapeutic agents is administered in a sub-therapeutic dose. It is even more preferred that all of the therapeutic agents be administered in sub-therapeutic doses. Sub-therapeutic is intended to mean an amount of a therapeutic agent that by itself does not give the desired therapeutic effect for the condition or disease being treated. Synergistic combination is intended to mean that the observed effect of the combination is greater than the sum of the individual agents administered alone.

The compounds of the present invention are also useful as standard or reference compounds, for example as a quality standard or control, in tests or assays involving the inhibition of factor VIIa, IXa, Xa and/or XIa. Such compounds may be provided in a commercial kit, for example, for use in pharmaceutical research involving factor VIIa, IXa, Xa and/or XIa. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness.

The compounds of the present invention may also be used in diagnostic assays involving factor VIIa, IXa, Xa and/or XIa. For example, the presence of factor VIIa, IXa, Xa and/or XIa in an unknown sample could be determined by addition of the relevant chromogenic substrate, example S2222 for factor Xa, to a series of solutions containing test sample and optionally one of the compounds of the present invention. If production of pNA is observed in the solutions containing test sample, but not in the presence of a compound of the present invention, then one would conclude factor Xa was present.

Dosage and Formulation

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice. They can also be administered with other therapeutic agents known to those of skill in the art. The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder. Description of appropriate means of administration as well as dosages and formulations can be found in WO97/23212, WO97/30971, WO97/38984, WO98/06694, WO98/01428, WO98/28269, WO98/28282, WO99/12903, WO98/57934, WO98/57937, WO98/57951, WO99/32454, WO99/50255, and WO00/39131, the contents of which are incorporated herein by reference.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. Intravenously, the most preferred doses will range from about 1 to about 10 mg/kg/minute during a constant rate infusion. Compounds of this invention may be administered in a single daily dose, or the total daily dosage may be administered in divided doses of two, three, or four times daily.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5–95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field.

Representative useful pharmaceutical dosage-forms for administration of the compounds of this invention can be illustrated as follows:

Capsules

A large number of unit capsules can be prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestable oil such as soybean oil, cottonseed oil or olive oil may be prepared and injected by means of a positive displacement pump into gelatin to form soft gelatin capsules containing 100 milligrams of the active ingredient. The capsules should be washed and dried.

Tablets

Tablets may be prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection may be prepared by stirring 1.5% by weight of active ingredient in 10% by volume propylene glycol and water. The solution should be made isotonic with sodium chloride and sterilized.

Suspension

An aqueous suspension can be prepared for oral administration so that each 5 mL contain 100 mg of finely divided active ingredient, 200 mg of sodium carboxymethyl cellulose, 5 mg of sodium benzoate, 1.0 g of sorbitol solution, U.S.P., and 0.025 mL of vanillin.

Where the compounds of this invention are combined with other anticoagulant agents, for example, a daily dosage may be about 0.1 to 100 milligrams of the compound of Formula (I) and about 1 to 7.5 milligrams of the second anticoagulant, per kilogram of patient body weight. For a tablet dosage form, the compounds of this invention generally may be present in an amount of about 5 to 10 milligrams per dosage unit, and the second anti-coagulant in an amount of about 1 to 5 milligrams per dosage unit.

Where the compounds of Formula (I) are administered in combination with an anti-platelet agent, by way of general guidance, typically a daily dosage may be about 0.01 to 25 milligrams of the compound of Formula (I) and about 50 to 150 milligrams of the anti-platelet agent, preferably about 0.1 to 1 milligrams of the compound of Formula (I) and about 1 to 3 milligrams of antiplatelet agents, per kilogram of patient body weight.

Where the compounds of Formula (I) are adminstered in combination with thrombolytic agent, typically a daily dosage may be about 0.1 to 1 milligrams of the compound of Formula I, per kilogram of patient body weight and, in the case of the thrombolytic agents, the usual dosage of the thrombolyic agent when administered alone may be reduced by about 70–80% when administered with a compound of Formula I.

Where two or more of the foregoing second therapeutic agents are administered with the compound of Formula I, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when the compound of Formula (I) and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low-viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

Obviously, numerous modifications and variations of the present invention are possible in light of the above teachings. It is therefore to be understood that within the scope of the appended claims, the invention may be practiced otherwise that as specifically described herein.

What is claimed is:

1. A compound of Formula (I):

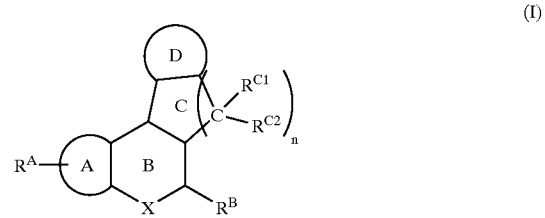

or a stereoisomer or pharmaceutically acceptable salt form thereof, wherein;

X is —NH—;

ring A, including the two atoms of Ring B to which it is attached, is a phenyl ring; wherein, in addition to $R^A$, ring A is substituted with 0–3 $R^{AA}$;

$R^A$ is selected from: F, Cl, Br, OH, $OCH_3$, $OCH_2CH_3$, $OCH(CH_3)_2$, $-OCH_2CH_2CH_3$, $-OCF_3$, $-CN$, $-NH_2$, $-NH_2NH_3$, $C(=NR^1)NR^2R^3$, $-NHC(=NR^1)NR^2R^3$, $-NR^2CH(=NR^1)$, $-C(O)NR^2R^3$, $-S(O)_2NR^{2a}R^3$, $-NR^2R^3$, $-CH_2NR^2R^3$, $-CH_2CH_2NR^2R^3$, $-CH(CH_3)NR^2R^3$, $-CH_2CH_2CH_2NR^2R^3$, $-CH_2CH(CH_3)NR^2R^3$, $-CH(CH_2CH_3)NR^2R^3$, $-CH(CH_3)CH_2NR^2R^3$, $-C(CH_3)_2NR^2R^3$, $-(C_{1-3}$ alkyl$)CO_2H$, $-O-(C_{1-3}$ alkyl$)$ $CO_2H$, —S—($C_{1-3}$ alkyl)$CO_2H$, —($C_{1-3}$ alkyl)CH($NH_2$)$CO_2H$, —C(O)NHCH$_2$CH$_2$NH($C_{1-3}$ alkyl), —C(O)NHCH$_2$CH$_2$N($C_{1-3}$ alkyl)$_2$, —CH$_2$NCOO($C_{1-4}$ alkyl),

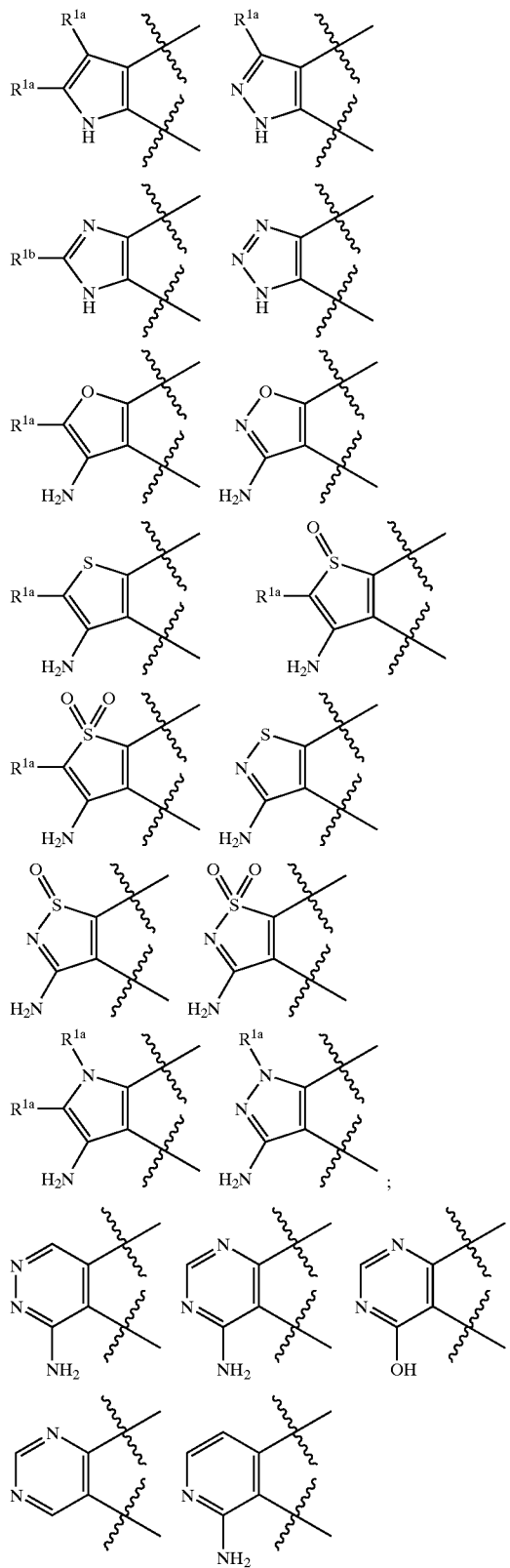

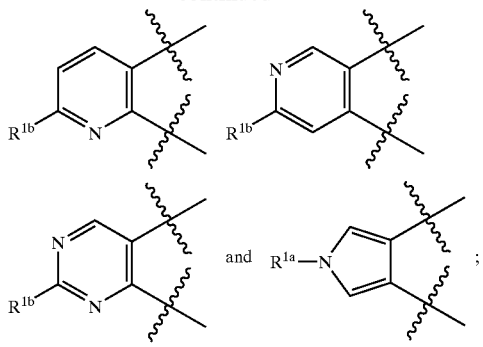

$R^1$ is selected from: H, OH, —NH$_2$, $C_{1-6}$ alkyl, $C_{1-6}$ alkoxy, phenylCH$_2$—, and phenylCH$_2$CH$_2$—;

$R^{1a}$, at each occurrence, is selected from: H and $C_{1-4}$ alkyl;

$R^{1b}$ is selected from: H, Cl, $C_{1-4}$ alkyl, NH$_2$, and NHNH$_2$;

$R^{1c}$ is selected from: H and $C_{1-4}$ alkyl;

$R^2$, at each occurrence, is selected from: H, OH, $C_{1-6}$ alkyl, $C_{1-6}$ alkylcarbonyl, $C_{1-4}$ alkoxycarbonyl, phenyl, phenyl($C_{1-3}$ alkyl)—, $C_{6-10}$ aryloxy, $C_{6-10}$ aryloxycarbonyl, $C_{6-10}$ arylmethylcarbonyl, ($C_{1-4}$ alkylcarbonyloxy)$C_{1-4}$ alkoxycarbonyl, ($C_{6-10}$ arylcarbonyloxy)$C_{1-4}$ alkoxycarbonyl, $C_{1-6}$ alkylaminocarbonyl, phenylaminocarbonyl, and (phenyl)$C_{1-4}$ alkoxycarbonyl;

$R^{2a}$, at each occurrence, is selected from: H, $C_{1-6}$ alkyl, —C(=NH)NH$_2$, pyridinyl, pyrimidinyl, (CH$_3$O)pyrimidinyl, (CH$_3$O)$_2$pyrimidinyl, oxazolyl, (CH$_3$)oxazolyl, and (CH$_3$)$_2$oxazolyl;

$R^3$, at each occurrence, is selected from: H, $C_{1-6}$ alkyl, phenylCH$_2$—, and phenylCH$_2$CH$_2$—;

$R^{AA}$ is, at each occurrence, selected from: H, halo, $C_{1-4}$ alkyl, $C_{3-6}$ cycloalkyl—, —OH, $C_{1-4}$ alkoxy, ($C_{1-4}$ alkyl)S—, ($C_{1-4}$ alkyl)S(O)—, ($C_{1-4}$ alkyl)SO$_2$—, —NH$_2$, ($C_{1-4}$ alkyl)$_2$N—, ($C_{1-4}$ alkyl)NH—, —CN, —NO$_2$, ($C_{1-4}$ alkyl)C(=O)—, HO$_2$C—, ($C_{1-4}$ alkyl)OC(=O)—, H$_2$NC(=O)—, ($C_{1-4}$ alkyl)NHC(=O)—, ($C_{1-4}$ alkyl)C(=O)NH—, $C_{1-4}$ haloalkyl, and $C_{1-4}$ haloalkyloxy;

$R^B$ is a 5–10 membered ring system consisting of carbon atoms and 0, 1 or 2 heteroatoms selected from the group consisting of N, O, and S; wherein said ring system may be unsaturated, partially unsaturated or saturated; and $R^B$ is substituted with 0, 1, 2, 3, 4, or 5 substituents selected from $R^{b1}$, $R^{b2}$, $R^{b3}$, $R^{b4}$, and $R^{b5}$;

alternatively $R^B$ is $C_{1-4}$ alkyl substituted with 5–10 membered ring system consisting of carbon atoms and 0, 1 or 2 heteroatoms selected from the group consisting of N, O, and S; wherein said ring system may be unsaturated, partially unsaturated or saturated; and $R^B$ is substituted with 0, 1, 2, 3, 4, or 5 substituents selected from $R^{b1}$, $R^{b2}$, $R^{b3}$, $R^{b4}$, and $R^{b5}$;

$R^{b1}$, $R^{b2}$, $R^{b3}$, $R^{b4}$, and $R^{b5}$, at each occurrence, are independently selected from: H, F, Cl, Br, I, =O, —CN, —NO$_2$, OR$^{12}$, SR$^{12}$, NR$^{12}$R$^{13}$, C(O)H, C(O)R$^{12}$, C(O)OR$^{12}$, C(O)NR$^{12}$R$^{13}$, OC(O)NR$^{12}$R$^{13}$, NR$^{14}$C(O)R$^{12}$, OC(O)R$^{12}$, CH(=NR$^{14}$)NR$^{12}$R$^{13}$, NHC(=NR$^{14}$)NR$^{12}$R$^{13}$, S(O)R$^{12}$, S(O)$_2$R$^{12}$, S(O)H, S(O)$_2$H, S(O)NR$^{12}$R$^{13}$, S(O)$_2$NR$^{12}$R$^{13}$, NR$^{14}$S(O)R$^{12}$, NR$^{14}$S(O)$_2$R$^{12}$, NR$^{12}$C(O)R$^{15}$, NR$^{12}$C(O)OR$^{15}$, NR$^{12}$S(O)$_2$R$^{15}$, NR$^{12}$C(O)NHR$^{15}$, (HO)$_2$B—, $C_{1-4}$ haloalkyl, $C_{1-4}$ alkoxy, $C_{2-4}$ alkenyloxy, $C_{2-4}$ alkynyloxy, ($C_{1-4}$ haloalkyl)oxy, $C_{1-4}$ alkyl substituted with 0–3 $R^{11}$, $C_{2-4}$ alkenyl substituted with 0–3 $R^{11}$, $C_{2-4}$ alkynyl substituted with 0–3 $R^{11}$, $C_{1-4}$ alkoxy substituted with 0–3 $R^{11}$, $C_{3-10}$ carbocyclic residue substituted with 0–3 $R^{31}$, aryl substituted with 0–5 $R^{31}$, and 5–10 membered heterocyclic ring system containing from 1–4 heteroatoms selected from the group consisting of N, O, and S substituted with 0–3 $R^{31}$;

alternatively, $R^{b1}$ and $R^{b2}$, when substituents on adjacent carbons, or $R^{b2}$ and $R^{b3}$, when substituents on adjacent carbons, may be combined to form a methylenedioxy group;

n is 1, 2, or 3;

$R^{C1}$, at each occurrence, is independently selected from: H, halo, —CN, —NO$_2$, OR$^{12}$, SR$^{12}$, NR$^{12}$R$^{13}$, C(O)H, C(O)R$^{12}$, C(O)NR$^{12}$R$^{13}$, OC(O)NR$^{12}$R$^{13}$, NR$^{14}$C(O)R$^{12}$, NR$^{14}$C(S)R$^{12}$, C(O)OR$^{12}$, OC(O)R$^{12}$, OC(O)OR$^{12}$, CH(=NR$^{14}$)NR$^{12}$R$^{13}$, NHC(=NR$^{14}$)NR$^{12}$R$^{13}$, S(O)R$^{12}$, S(O)$_2$R$^{12}$, S(O)NR$^{12}$R$^{13}$, S(O)$_2$NR$^{12}$R$^{13}$, NR$^{14}$S(O)R$^{12}$, NR$^{14}$S(O)$_2$R$^{12}$, NR$^{12}$C(O)R$^{15}$, NR$^{12}$C(S)R$^{15}$, NR$^{12}$C(O)OR$^{15}$, NR$^{12}$S(O)$_2$R$^{15}$, NR$^{12}$C(O)NHR$^{15}$, $C_{1-4}$ haloalkyl, ($C_{1-4}$ haloalkyl)oxy, $C_{1-10}$ alkyl substituted with 0–3 $R^{CC}$, $C_{2-10}$ alkenyl substituted with 0–3 $R^{CC}$, $C_{2-10}$ alkynyl substituted with 0–3 $R^{CC}$, $C_{1-10}$ alkoxy substituted with 0–3 $R^{CC}$, $C_{3-6}$ carbocyclic residue substituted with 0–3 $R^{CC}$, aryl substituted with 0–5 $R^{CC}$, and 5–6 membered heterocyclic ring system containing from 1–4 heteroatoms selected from the group consisting of N, O, and S substituted with 0–3 $R^{CC}$;

$R^{C2}$ is selected from: H, $C_{1-4}$ alkyl, OH, CN, and $C_{1-4}$ alkoxy;

$R^{CC}$, at each occurrence, is independently selected from: H, halo, —CN, —NO$_2$, OR$^{12}$, SR$^{12}$, NR$^{12}$R$^{13}$, C(O)H, C(O)R$^{12}$, C(O)NR$^{12}$R$^{13}$, OC(O)NR$^{12}$R$^{13}$, NR$^{14}$C(O)R$^{12}$, NR$^{14}$C(S)R$^{12}$, C(S)NR$^{12}$R$^{13}$, C(O)OR$^{12}$, OC(O)R$^{12}$, OC(O)OR$^{12}$, CH(=NR$^{14}$)NR$^{12}$R$^{13}$, NHC(=NR$^{14}$)NR$^{12}$R$^{13}$, S(O)R$^{12}$, S(O)$_2$R$^{12}$, S(O)NR$^{12}$R$^{13}$, S(O)$_2$NR$^{12}$R$^{13}$, NR$^{14}$S(O)R$^{12}$, NR$^{14}$S(O)$_2$R$^{12}$, NR$^{12}$C(O)R$^{15}$, NR$^{12}$C(S)R$^{15}$, NR$^{12}$C(O)OR$^{15}$, NR$^{12}$S(O)$_2$R$^{15}$, NR$^{12}$C(O)NHR$^{15}$, $C_{1-4}$ haloalkyl, ($C_{1-4}$ haloalkyl)oxy, $C_{1-4}$ alkyl substituted with 0–3 $R^{11}$, $C_{2-4}$ alkenyl substituted with 0–3 $R^{11}$, $C_{2-4}$ alkynyl substituted with 0–3 $R^{11}$, $C_{1-4}$ alkoxy substituted with 0–3 $R^{11}$, $C_{3-6}$ carbocyclic residue substituted with 0–3 $R^{31}$, aryl substituted with 0–5 $R^{31}$, and 5–6 membered heterocyclic ring system containing from 1–4 heteroatoms selected from the group consisting of N, O, and S substituted with 0–3 $R^{31}$;

ring D, including the two atoms of Ring C to which it is attached, is a phenyl ring; and ring D is substituted with 0–4 $R^D$;

$R^D$, at each occurrence, is independently selected from: H, halo, —CN, —NO$_2$, OR$^{16}$, SR$^{16}$, NR$^{16}$R$^{16}$, C(O)H, C(O)R$^{16}$, C(O)NR$^{16}$R$^{16}$, OC(O)NR$^{16}$R$^{16}$, NR$^{14}$C(O)R$^{16}$, C(O)OR$^{16}$, OC(O)R$^{16}$, OC(O)OR$^{16}$, CH(=NR$^{14}$)NR$^{16}$R$^{16}$, NHC(=NR$^{14}$)NR$^{16}$R$^{16}$, S(O)R$^{16}$, S(O)$_2$R$^{16}$, S(O)NR$^{16}$R$^{16}$, S(O)$_2$NR$^{16}$R$^{16}$, NR$^{14}$S(O)R$^{16}$, NR$^{14}$S(O)$_2$R$^{16}$, NR16C(O)R$^{17}$, NR$^{16}$C(O)OR$^{17}$, NR$^{16}$S(O)$_2$R$^{17}$, NR$^{16}$C(O)NHR$^{17}$, $C_{1-4}$ haloalkyl, $C_{1-4}$ alkoxy, ($C_{1-4}$ haloalkyl)oxy, $C_{1-4}$ alkyl substituted with 0–3 $R^{31}$, $C_{2-4}$ alkenyl substituted with 0–3 $R^{31}$, and $C_{2-4}$ alkynyl substituted with 0–3 $R^{31}$;

$R^{11}$, at each occurrence, is independently selected from: H, halo, —CN, —NO$_2$, OR$^{12}$, SR$^{12}$, NR$^{12}$R$^{13}$, C(O)H, C(O)R$^{12}$, C(O)NR$^{12}$R$^{13}$, OC(O)NR$^{12}$R$^{13}$, NR$^{14}$C(O)R$^{12}$, C(O)OR$^{12}$, OC(O)R$^{12}$, OC(O)OR$^{12}$, CH(=NR$^{14}$)NR$^{12}$R$^{13}$, NHC(=NR$^{14}$)NR$^{12}$R$^{13}$, S(O)R$^{12}$, S(O)$_2$R$^{12}$, S(O)NR$^{12}$R$^{13}$, S(O)$_2$NR$^{12}$R$^{13}$, NR$^{14}$S(O)R$^{12}$, NR$^{14}$S(O)$_2$R$^{12}$, NR$^{12}$C(O)R$^{15}$, NR$^{12}$C(O)OR$^{15}$, NR$^{12}$S(O)$_2$R$^{15}$, NR$^{12}$C(O)NHR$^{15}$, $C_{1-4}$ haloalkyl, $C_{1-4}$ alkoxy, $C_{2-4}$ alkenyloxy, $C_{2-4}$ alkynyloxy, ($C_{1-4}$ haloalkyl)oxy, $C_{1-4}$ alkyl substituted with 0–3 $R^{12a}$, $C_{2-4}$ alkenyl substituted with 0–3 $R^{12a}$, $C_{3-6}$ carbocyclic residue substituted with 0–3 $R^{31}$, aryl substituted with 0–5 $R^{31}$, and 5–6 membered heterocyclic ring system containing from 1–4 heteroatoms selected from the group consisting of N, O, and S substituted with 0–3 $R^{31}$;

$R^{12}$, at each occurrence, is independently selected from: H, $C_{1-4}$ alkyl substituted with 0–1 $R^{12a}$, $C_{2-4}$ alkenyl substituted with 0–1 $R^{12a}$, $C_{2-4}$ alkynyl substituted with 0–1 $R^{12a}$, $C_{3-6}$ cycloalkyl substituted with 0–3 $R^{31}$, aryl substituted with 0–5 $R^{31}$; $C_{3-10}$ carbocyclic residue substituted with 0–3 $R^{31}$, and 5–10 membered heterocyclic ring system containing from 1–4 heteroatoms selected from the group consisting of N, O, and S substituted with 0–3 $R^{31}$;

$R^{12a}$, at each occurrence, is independently selected from: phenyl substituted with 0–5 $R^{31}$, $C_{3-6}$ carbocyclic residue substituted with 0–3 $R^{31}$, and 5–6 membered heterocyclic ring system containing from 1–4 heteroatoms selected from the group consisting of N, O, and S substituted with 0–3 $R^{31}$;

$R^{13}$, at each occurrence, is independently selected from: H, $C_{1-4}$ alkyl, $C_{2-4}$ alkenyl, and $C_{2-4}$ alkynyl;

alternatively, $R^{12}$ and $R^{13}$ may be combined, along with the nitrogen to which they are attached, to form a 5- or 6-membered ring optionally substituted with —O— or —N(R$^{14}$)—;

$R^{14}$, at each occurrence, is independently selected from: H and $C_{1-4}$ alkyl;

$R^{15}$, at each occurrence, is independently selected from: H, $C_{1-4}$ alkyl, $C_{2-4}$ alkenyl, and $C_{2-4}$ alkynyl;

$R^{16}$, at each occurrence, is independently selected from: H, $C_{1-4}$ alkyl, $C_{2-4}$ alkenyl, $C_{2-4}$ alkynyl, and phenyl;

$R^{17}$, at each occurrence, is independently selected from: H, $C_{1-4}$ alkyl, $C_{2-4}$ alkenyl, and $C_{2-4}$ alkynyl;

$R^{31}$, at each occurrence, is independently selected from: H, F, Cl, Br, I, =O, —CN, —NO$_2$, OR$^{32}$, SR$^{32}$, NR$^{32}$R$^{33}$, C(O)H, C(O)R$^{32}$, C(O)OH, C(O)OR$^{32}$, C(O)NR$^{32}$R$^{33}$, OC(O)NR$^{32}$R$^{33}$, NR$^{34}$C(O)R$^{32}$, OC(O)R$^{32}$, CH(=NR$^{34}$)NR$^{32}$R$^{33}$, NHC(=NR$^{34}$)NR$^{32}$R$^{33}$, S(O)R$^{32}$, S(O)$_2$R$^{32}$, S(O)H, S(O)$_2$H, S(O)$_3$H, S(O)NR$^{32}$R$^{33}$, S(O)$_2$NR$^{32}$R$^{33}$, NR$^{34}$S(O)R$^{32}$, NR$^{34}$S(O)$_2$R$^{32}$, NR$^{32}$C(O)R$^{35}$, NR$^{32}$C(O)OR$^{35}$, NR$^{32}$S(O)$_2$R$^{35}$, NR$^{32}$C(O)NHR$^{35}$, tetrazole, $C_{1-4}$ haloalkyl, $C_{1-4}$ alkoxy, $C_{2-4}$ alkenyloxy, $C_{2-4}$ alkynyloxy, ($C_{1-4}$ haloalkyl)oxy, $C_{1-4}$ alkyl, $C_{2-4}$ alkenyl, and $C_{2-4}$ alkynyl; and $R^{32}$, $R^{33}$, $R^{34}$, $R^{35}$, at each occurrence, are independently selected from: H, $C_{1-4}$ alkyl, $C_{2-4}$ alkenyl, $C_{2-4}$ alkynyl, and benzyl;

provided $R^B$ is phenyl, or chloro-substituted phenyl, then $R^A$ is not chloro, bromo or methoxy.

2. A compound of claim 1, wherein:

$R^{C1}$ is H, methyl, ethyl, propyl, or butyl; and $R^{C2}$ is H or methyl.

3. A compound of claim 1, wherein;
$R^B$ is

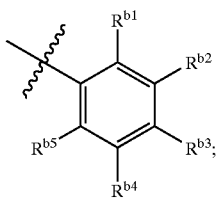

or a stereoisomer or pharmaceutically acceptable salt form thereof.

4. A compound of claim 1 of Formula (Ib):

(Ib)

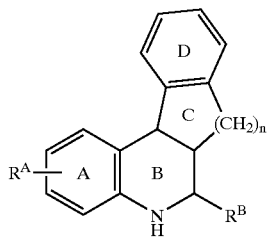

or a stereoisomer or pharmaceutically acceptable salt form thereof, wherein;

ring A, including the two atoms of Ring B to which it is attached, is a phenyl ring; wherein, in addition to $R^A$, ring A is substituted with 0–1 $R^{AA}$;

$R^A$ is selected from: Cl, $OCH_3$, $C(=NH)NH_2$, $C(O)NH_2$, $S(O)_2NH_2$, $—NH_2$, $—NH_2NH_3$, $—CH_2NH_2$, $—NR^2R^3$, $—CH_2NR^2R^3$, and $—CH(CH_3)NR^2R^3$;

$R^2$ is selected from: H and $C_{1-4}$ alkyl;

$R^3$ is selected from: H and $C_{1-4}$ alkyl;

$R^{AA}$ is H, F, Cl, methoxy, $—NH_2$, or $—CH_2NH_2$;

ring D, including the two atoms of Ring C to which it is attached, is a phenyl ring; and ring D is substituted with 0–2 $R^D$;

$R^D$, at each occurrence, is independently selected from: H, halo, $—CN$, $—NO_2$, $OR^{16}$, $SR^{16}$, $NR^{16}R^{16}$, $C(O)H$, $C(O)R^{16}$, $C(O)NR^{16}R^{16}$, $OC(O)NR^{16}R^{16}$, $NR^{14}C(O)R^{16}$, $C(O)OR^{16}$, $OC(O)R^{16}$, $OC(O)OR^{16}$, $CH(=NR^{14})NR^{16}R^{16}$, $NHC(=NR^{14})NR^{16}R^{16}$, $S(O)R^{16}$, $S(O)_2R^{16}$, $S(O)NR^{16}R^{16}$, $S(O)_2NR^{16}R^{16}$, $NR^{14}S(O)R^{16}$, $NR^{14}S(O)_2R^{16}$, $NR^{16}C(O)R^{17}$, $NR^{16}C(O)OR^{17}$, $NR^{16}S(O)_2R^{17}$, $NR^{16}C(O)NHR^{17}$, $C_{1-3}$ haloalkyl, $(C_{1-2}$ haloalkyl)oxy, $C_{1-4}$ alkoxy, and $C_{1-4}$ alkyl;

$R^{16}$, at each occurrence, is independently selected from: H, methyl, and ethyl; and $R^{17}$, at each occurrence, is independently selected from: H, methyl, and ethyl.

5. A compound of claim 4 of Formula (Ib) or a stereoisomer or pharmaceutically acceptable salt form thereof, wherein;

$R^A$ is selected from: $—C(=NH)NH_2$, $—C(O)NH_2$, $—S(O)_2NH_2$, $—NH_2$, and $—CH_2NH_2$.

6. A compound of claim 4 of Formula (Ic)

(Ic)

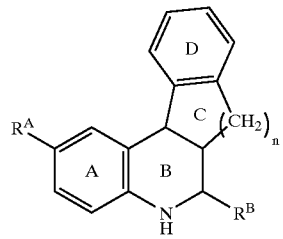

or a stereoisomer or pharmaceutically acceptable salt form thereof, wherein;

$R^A$ is $C(=NH)NH_2$ or $—CH_2NH_2$; and $R^B$ is a 5–10 membered ring system consisting of carbon atoms and 0, 1 or 2 heteroatoms selected from the group consisting of N, O, and S; wherein said ring system is selected from phenyl, naphthyl, furanyl, thienyl, pyrrolyl, imidazolyl, triazinyl, thiazolyl, oxazolyl, isoxazolyl, tetrazolyl, pyrazolyl, pyridinyl, pyrimidinyl, pyridazinyl, quinolinyl, isoquinolinyl, benzofuranyl, 1H-indazolyl, benzothienyl, benzotriazolyl, benzoxazolyl, benzisoxazolyl, indolyl, chromanyl, benzimidazolyl; and $R^B$ is substituted with 0, 1, 2, 3, 4, or 5 substituents selected from $R^{b1}$, $R^{b2}$, $R^{b3}$, $R^{b4}$, and $R^{b5}$.

7. A compound of claim 4, wherein;

$R^A$ is selected from: $—C(=NH)NH_2$, $—C(O)NH_2$, $—S(O)_2NH_2$, $—NH_2$, and $—CH_2NH_2$;

$R^B$ is a 5–10 membered ring system consisting of carbon atoms and 0, 1 or 2 heteroatoms selected from the group consisting of N, O, and S; wherein said ring system is selected from phenyl, naphthyl, furanyl, thienyl, pyrrolyl, imidazolyl, triazinyl, thiazolyl, oxazolyl, isoxazolyl, tetrazolyl, pyrazolyl, pyridinyl, pyrimidinyl, pyridazinyl, quinolinyl, isoquinolinyl, benzofuranyl, benzothienyl, 1H-indazolyl, oxazolidinyl, isoxazolidinyl, benzotriazolyl, benzoxazolyl, benzisoxazolyl, oxindolyl, benzoxazolinyl, indolyl, chromanyl, benzimidazolyl; and $R^B$ is substituted with 0, 1, 2, 3, 4, or 5 substituents selected from $R^{b1}$, $R^{b2}$, $R^{b3}$, $R^{b4}$, $R^{b5}$; and $R^D$, at each occurrence, is independently selected from: H, halo, $—CN$, OH, $—COOH$, $—CONH_2$, $—CF_3$, $—SO_2CH_3$, $C_{1-4}$ alkoxy, and $C_{1-4}$ alkyl.

8. A compound of claim 7, wherein;

$R^A$ is $C(=NH)NH_2$ or $—CH_2NH_2$;

$R^B$ is a 5–10 membered ring system selected from: phenyl, naphthyl, furanyl, thienyl, pyrrolyl, imidazolyl, pyrazolyl, pyridinyl, indolyl, and benzimidazolyl; and $R^B$ is substituted with 0, 1, 2, 3, 4, or 5 substituents selected from $R^{b1}$, $R^{b2}$, $R^{b3}$, $R^{b4}$, and $R^{b5}$;

$R^{b1}$, $R^{b2}$, $R^{b3}$, $R^{b4}$, and $R^{b5}$, at each occurrence, are independently selected from: H, F, Cl, Br, I, $=O$, $—CN$, $—NO_2$, $—OH$, $OR^{12}$, $SR^{12}$, $NR^{12}R^{13}$, $C(O)H$, $C(O)R^{12}$, $C(O)OR^{12}$, $C(O)NR^{12}R^{13}$, $OC(O)NR^{12}R^{13}$, $NR^{14}C(O)R^{12}$, $OC(O)R^{12}$, $CH(=NR^{14})NR^{12}R^{13}$, $NHC(=NR^{14})NR^{12}R^{13}$, $S(O)R^{12}$, $S(O)_2R^{12}$, $S(O)H$, $S(O)_2H$, $S(O)NR^{12}R^{13}$, $S(O)_2NR^{12}R_{13}$, $NR^{14}S(O)R^{12}$, $NR^{14}S(O)_2R^{12}$, $NR^{12}C(O)R^{15}$, $NR^{12}C(O)OR^{15}$, $NR^{12}S(O)_2R^{15}$, $NR^{12}C(O)NHR^{15}$, $(HO)_2B—$, $—CF_3$, $—OCF_3$, methoxy, ethoxy, propoxy, butoxy, methyl, ethyl, propyl, butyl, $C_{1-4}$ alkyl substituted with 0–3 $R^{11}$, $C_{2-4}$ alkenyl substituted with 0–3 $R^{11}$, $C_{2-4}$ alkynyl substituted with 0–3 $R^{11}$, $C_{1-4}$ alkoxy substituted with 0–3 $R^{11}$, $C_{3-6}$ carbocyclic residue substituted with 0–3 $R^{31}$, phenyl substituted with 0–5 $R^{31}$, and 5–10 membered heterocyclic ring system selected from furanyl, thienyl, pyrrolyl, pyrrolidinyl, imidazolyl, pyrazolyl, pyridinyl, pyrimidinyl, indolyl, and N-morpholinyl, said heterocyclic ring system substituted with 0–3 $R^{31}$;

alternatively, $R^{b1}$ and $R^{b2}$, when substituents on adjacent carbons, or $R^{b2}$ and $R^{b3}$, when substituents on adjacent carbons, may be combined to form a methylenedioxy group;

$R^D$, at each occurrence, is independently selected from: H, F, Cl, Br, —CN, OH, —COOH, —$CONH_2$, —$CF_3$, —$SO_2CH_3$, methoxy, ethoxy, methyl and ethyl;

$R^{11}$, at each occurrence, is independently selected from: H, halo, —CN, —NO2, OH, $OR^{12}$, $SR^{12}$, $NR^{12}R^{13}$, C(O)H, $C(O)R^{12}$, $C(O)NR^{12}R^{13}$, $OC(O)NR^{12}R^{13}$, $NR^{14}C(O)R^{12}$, $C(O)OR^{12}$, $OC(O)R^{12}$, $OC(O)OR^{12}$, $CH(=NR^{14})NR^{12}R^{13}$, $NHC(=NR^{14})NR^{12}R^{13}$, $S(O)R^{12}$, $S(O)_2R^{12}$, $S(O)NR^{12}R^{13}$, $S(O)_2NR^{12}R^{13}$, $NR^{14}S(O)R^{12}$, $NR^{14}S(O)_2R^{12}$, $NR^{12}C(O)R^{15}$, $NR^{12}C(O)OR^{15}$, $NR^{12}S(O)_2R^{15}$, $NR^{12}C(O)NHR^{15}$, —$CF_3$, —$OCF_3$, methoxy, ethoxy, propoxy, butoxy, $C_{1-4}$ alkyl substituted with 0–3 $R^{12a}$, $C_{2-4}$ alkenyl substituted with 0–3 $R^{12a}$, $C_{3-6}$ carbocyclic residue substituted with 0–3 $R^{31}$, phenyl substituted with 0–5 $R^{31}$, and 5–6 membered heterocyclic ring system selected from furanyl, thienyl, pyrrolyl, pyrrolidinyl, imidazolyl, pyrazolyl, pyridinyl, pyrimidinyl, and N-morpholinyl, said heterocyclic ring system substituted with 0–3 $R^{31}$;

$R^{12}$, at each occurrence, is independently selected from: H, $C_{1-4}$ alkyl substituted with 0–1 $R^{12a}$, $C_{2-4}$ alkenyl substituted with 0–1 $R^{12a}$, C2-4 alkynyl substituted with 0–1 $R^{12a}$, $C_{3-6}$ cycloalkyl substituted with 0–3 $R^{31}$, phenyl substituted with 0–5 $R^{31}$; and 5–6 membered heterocyclic ring system selected from furanyl, thienyl, pyrrolyl, pyrrolidinyl, imidazolyl, pyrazolyl, pyridinyl, and pyrimidinyl, said heterocyclic ring system substituted with 0–3 $R^{31}$;

$R^{12a}$, at each occurrence, is independently selected from: phenyl substituted with 0–5 $R^{31}$; $C_{3-6}$ carbocyclic residue substituted with 0–3 $R^{31}$, and 5–6 membered heterocyclic ring system selected from furanyl, thienyl, pyrrolyl, pyrrolidinyl, imidazolyl, pyrazolyl, pyridinyl, and pyrimidinyl, said heterocyclic ring system substituted with 0–3 $R^{31}$;

$R^{13}$, at each occurrence, is independently selected from: H, methyl, ethyl, propyl, butyl, ethenyl, propenyl, butenyl, ethynyl, propynyl, and butynyl;

alternatively, $R^{12}$ and $R^{13}$ may be combined, along with the nitrogen to which they are attached, to form a 5- or 6-membered ring optionally substituted with —O— or —$N(R^{14})$—;

$R^{14}$, at each occurrence, is independently selected from: H, methyl, ethyl, propyl, and butyl;

$R^{15}$, at each occurrence, is independently selected from: H, methyl, ethyl, propyl, butyl, ethenyl, propenyl, butenyl, ethynyl, propynyl, and butynyl;

$R^{31}$, at each occurrence, is independently selected from: H, F, Cl, Br, I, =O, —CN, —$NO_2$, —OH, —$OR^{32}$, —$SR^{32}$, —$NR^{32}R^{33}$, —C(O)H, —$C(O)R^{32}$, —C(O) OH, —$C(O)OR^{32}$, —$C(O)NR^{32}R^{33}$, —OC(O) $NR^{32}R^{33}$, —$NR^{34}C(O)R^{32}$, —$OC(O)R^{32}$, —CH (=$NR^{34}$)$NR^{32}R^{33}$, —NHC(=$NR^{34}$)$NR^{32}R^{33}$, —S(O) $R^{32}$, —$S(O)_2R^{32}$, —S(O)H, —$S(O)_2H$, —$S(O)_3H$, —$S(O)NR^{32}R^{33}$, —$S(O)_2NR^{32}R^{33}$, —$S(O)_2NH_2$, —$NR^{34}S(O)R^{32}$, —$NR^{34}S(O)_2R^{32}$, —$NR^{32}C(O)R^{35}$, —$NR^{32}C(O)OR^{35}$, —$NR^{32}S(O)_2R^{35}$, —$NR^{32}C(O)$ $NHR^{35}$, tetrazolyl, —$CF_3$, —$OCF_3$, methoxy, ethoxy, n-propoxy, i-propoxy, methyl, ethyl, n-propyl, i-propyl, n-butyl, i-butyl, s-butyl, t-butyl, hydroxymethyl-, hydroxyethyl-, vinyl, and allyl; and $R^{32}$, $R^{33}$, $R^{34}$, $R^{35}$, at each occurrence, are independently selected from: H, methyl, ethyl, n-propyl, i-propyl, n-butyl, i-butyl, s-butyl, t-butyl, and benzyl.

9. A compound of claim 8 wherein:

$R^{b1}$, $R^{b2}$, $R^{b3}$, $R^{b4}$, and $R^{b5}$, at each occurrence, are independently selected from: H, F, Cl, Br, cyano, nitro, methyl, ethyl, n-propyl, i-propyl, vinyl, allyl, hydroxy, hydroxymethyl, hydroxyethyl, hydroxy-n-propyl, hydroxy-i-propyl, methoxy, ethoxy, n-propoxy, i-propoxy, allyloxy-, methyl-S—, ethyl-S—, n-propyl-S—, i-propyl-S—, allyl-S—, —$CF_3$, —$CHF_2$, —$OCF_3$, —$SCF_3$, —$CO_2H$, —$C(=O)OCH_3$, —$C(=O)CH_3$, —$SO_2CH_3$, and —$SO_2CH_2CH_3$.

10. A compound of claim 6 of Formula (Id):

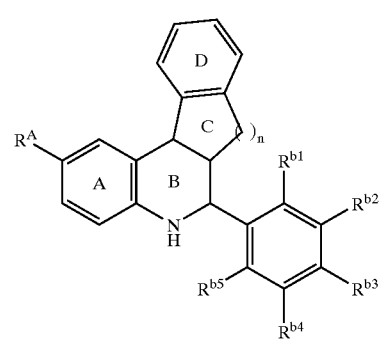

(Id)

or a stereoisomer or pharmaceutically acceptable salt form thereof, wherein;

$R^A$ is selected from: Cl, $OCH_3$, C(=NH)$NH_2$, $C(O)NH_2$, $S(O)_2NH_2$, —$NH_2$, and —$CH_2NH_2$;

$R^{b1}$, $R^{b2}$, $R^{b3}$, and $R^{b4}$, at each occurrence, are independently selected from: H, F, Cl, Br, I, —CN, —$NO_2$, —OH, $OR^{12}$, $SR^{12}$, $NR^{12}R^{13}$, C(O)H, $C(O)R^{12}$, C(O) $OR^{12}$, $C(O)NR^{12}R^{13}$, $OC(O)NR^{12}R^{13}$, $NR^{14}C(O)R^{12}$, $OC(O)R^{12}$, $CH(=NR^{14})NR^{12}R^{13}$, $NHC(=NR^{14})NR^{12}R^{13}$, $S(O)R^{12}$, $S(O)_2R^{12}$, S(O)H, $S(O)_2H$, $S(O)NR^{12}R^{13}$, $S(O)_2NR^{12}R^{13}$, $NR^{14}S(O)R^{12}$, $NR^{14}S(O)_2R^{12}$, $NR^{12}C(O)R^{15}$, $NR^{12}C(O)OR^{15}$, $NR^{12}S(O)_2R^{15}$, $NR^{12}C(O)NHR^{15}$, $(HO)_2B$—, $C_{1-4}$ haloalkyl, $C_{1-4}$ alkoxy, $C_{2-4}$ alkenyloxy, $C_{2-4}$ alkynyloxy, ($C_{1-4}$ haloalkyl)oxy, $C_{1-4}$ alkyl substituted with 0–3 $R^{11}$, $C_{2-4}$ alkenyl substituted with 0–3 $R^{11}$, $C_{2-4}$ alkynyl substituted with 0–3 $R^{11}$, $C_{1-4}$ alkoxy substituted with 0–3 $R^{11}$, $C_{3-10}$ carbocyclic residue substituted with 0–3 $R^{31}$, aryl substituted with 0–5 $R^{31}$, and 5–10 membered heterocyclic ring system containing from 1–4 heteroatoms selected from the group consisting of N, O, and S substituted with 0–3 $R^{31}$; and $R^{b5}$ is phenyl substituted with 0–5 $R^{31}$.

11. A compound of claim 10, wherein;

$R^{b1}$, $R^{b2}$, $R^{b3}$, and $R^{b4}$, at each occurrence, are independently selected from: H, F, Cl, Br, I, —CN, —$NO_2$, —OH, $OR^{12}$, $SR^{12}$, $NR^{12}R^{13}$, C(O)H, $C(O)R^{12}$, C(O) $OR^{12}$, $C(O)NR^{12}R^{13}$, $OC(O)NR^{12}R^{13}$, $NR^{14}C(O)R^{12}$, OC(O)R$^{12}$, CH(=NR$^{14}$)NR$^{12}$R$^{13}$, NHC(=NR$^{14}$)NR$^{12}$R$^{13}$, S(O)R$^{12}$, S(O)$_2$R$^{12}$, S(O)H, S(O)$_2$H, S(O)NR$^{12}$R$^{13}$, S(O)$_2$NR$^{12}$R$^{13}$, NR$^{14}$S(O)R$^{12}$, NR$^{14}$S(O)$_2$R$^{12}$, NR$^{12}$C(O)R$^{15}$, NR$^{12}$C(O)OR$^{15}$, NR$^{12}$S(O)$_2$R$^{15}$, NR$^{12}$C(O)NHR$^{15}$, (HO)$_2$B—, C$_{1-4}$ haloalkyl, C$_{1-4}$ alkoxy, C$_{2-4}$ alkenyloxy, C$_{2-4}$ alkynyloxy, (C$_{1-4}$ haloalkyl)oxy, C$_{1-4}$ alkyl substituted with 0–3 R$^{11}$, C$_{2-4}$ alkenyl substituted with 0–3 R$^{11}$, C$_{2-4}$ alkynyl substituted with 0–3 R$^{11}$, and C$_{1-4}$ alkoxy substituted with 0–3 R$^{11}$; and R$^D$, at each occurrence, is independently selected from: H, halo, —CN, OH, —COOH, —CONH$_2$, —CF$_3$, —SO$_2$CH$_3$, C$_{1-4}$ alkoxy, and C$_{1-4}$ alkyl.

12. A compound of claim 11, wherein;
R$^A$ is C(=NH)NH$_2$ or —CH$_2$NH$_2$;
R$^{b1}$, R$^{b2}$, R$^{b3}$, and R$^{b4}$, at each occurrence, are independently selected from: H, F, Cl, Br, I, —CN, —NO$_2$, —OH, OR$^{12}$, SR$^{12}$, NR$^{12}$R$^{13}$, C(O)H, C(O)R$^{12}$, C(O)OR$^{12}$, C(O)NR$^{12}$R$^{13}$, OC(O)NR$^{12}$R$^{13}$, NR$^{14}$C(O)R$^{12}$, OC(O)R$^{12}$, CH(=NR$^{14}$)NR$^{12}$R$^{13}$, NHC(=NR$^{14}$)NR$^{12}$R$^{13}$, S(O)R$^{12}$, S(O)$_2$R$^{12}$, S(O)H, S(O)$_2$H, S(O)NR$^{12}$R$^{13}$, S(O)$_2$NR$^{12}$R$^{13}$, NR$^{14}$S(O)R$^{12}$, NR$^{14}$S(O)$_2$R$^{12}$, NR$^{12}$C(O)R$^{15}$, NR$^{12}$C(O)OR$^{15}$, NR$^{12}$S(O)$_2$R$^{15}$, NR$^{12}$C(O)NHR$^{15}$, (HO)$_2$B—, —CF$_3$, —OCF$_3$, methoxy, ethoxy, propoxy, butoxy, methyl, ethyl, propyl, butyl, C$_{1-4}$ alkyl substituted with 0–3 R$^{11}$, C$_{2-4}$ alkenyl substituted with 0–3 R$^{11}$, C$_{2-4}$ alkynyl substituted with 0–3 R$^{11}$, and C$_{1-4}$ alkoxy substituted with 0–3 R$^{11}$;

R$^D$, at each occurrence, is independently selected from: H, F, Cl, Br, —CN, OH, —COCH, —CONH$_2$, —CF$_3$, —SO2CH$_3$, methoxy, ethoxy, methyl and ethyl;

R$^{11}$, at each occurrence, is independently selected from: H, halo, —CN, —NO$_2$, OH, OR$^{12}$, SR$^{12}$, NR$^{12}$R$^{13}$, C(O)H, C(O)R$^{12}$, C(O)NR$^{12}$R$^{13}$, OC(O)NR$^{12}$R$^{13}$, NR$^{14}$C(O)R$^{12}$, C(O)OR$^{12}$, OC(O)R$^{12}$, OC(O)OR$^{12}$, CH(=NR$^{14}$)NR$^{12}$R$^{13}$, NHC(=NR$^{14}$)NR$^{12}$R$^{13}$, S(O)R$^{12}$, S(O)$_2$R$^{12}$, S(O)NR$^{12}$R$^{13}$, S(O)$_2$NR$^{12}$R$^{13}$, NR$^{14}$S(O)R$^{12}$, NR$^{14}$S(O)$_2$R$^{12}$, NR$^{12}$C(O)R$^{15}$, NR$^{12}$C(O)OR$^{15}$, NR$^{12}$S(O)$_2$R$^{15}$, NR$^{12}$C(O)NHR$^{15}$, —CF$_3$, —OCF$_3$, methoxy, ethoxy, propoxy, butoxy, C$_{1-4}$ alkyl substituted with 0–3 R$^{12a}$, C$_{2-4}$ alkenyl substituted with 0–3 R$^{12a}$, C$_{3-6}$ carbocyclic residue substituted with 0–3 R$^{31}$, phenyl substituted with 0–5 R$^{31}$, and 5–6 membered heterocyclic ring system selected from furanyl, thienyl, pyrrolyl, pyrrolidinyl, imidazolyl, pyrazolyl, pyridinyl, pyrimidinyl, and N-morpholinyl, said heterocyclic ring system substituted with 0–3 R$^{31}$;

R$^{12}$, at each occurrence, is independently selected from: H, C$_{1-4}$ alkyl substituted with 0–1 R$^{12a}$, C$_{2-4}$ alkenyl substituted with 0–1 R$^{12a}$, C$_{2-4}$ alkynyl substituted with 0–1 R$^{12a}$, C$_{3-6}$ cycloalkyl substituted with 0–3 R$^{31}$, phenyl substituted with 0–5 R$^{31}$; and 5–6 membered heterocyclic ring system selected from furanyl, thienyl, pyrrolyl, pyrrolidinyl, imidazolyl, pyrazolyl, pyridinyl, and pyrimidinyl, said heterocyclic ring system substituted with 0–3 R$^{31}$;

R$^{12a}$, at each occurrence, is independently selected from: phenyl substituted with 0–5 R$^{31}$; C$_{3-6}$ carbocyclic residue substituted with 0–3 R$^{31}$, and 5–6 membered heterocyclic ring system selected from furanyl, thienyl, pyrrolyl, pyrrolidinyl, imidazolyl, pyrazolyl, pyridinyl, and pyrimidinyl, said heterocyclic ring system substituted with 0–3 R$^{31}$;

R$^{13}$, at each occurrence, is independently selected from: H, methyl, ethyl, propyl, butyl, ethenyl, propenyl, butenyl, ethynyl, propynyl, and butynyl;

alternatively, R$^{12}$ and R$^{13}$ may be combined, along with the nitrogen to which they are attached, to form a 5- or 6-membered ring optionally substituted with —O— or —N(R$^{14}$)—;

R$^{14}$, at each occurrence, is independently selected from: H, methyl, ethyl, propyl, and butyl;

R$^{15}$, at each occurrence, is independently selected from: H, methyl, ethyl, propyl, butyl, ethenyl, propenyl, butenyl, ethynyl, propynyl, and butynyl;

R$^{31}$, at each occurrence, is independently selected from: H, F, Cl, Br, I, —CN, —NO$_2$, —OH, —OR$^{32}$, —SR$^{32}$, —NR$^{32}$R$^{33}$, —C(O)H, —C(O)R$^{32}$, —C(O)OH, —C(O)OR$^{32}$, —C(O)NR$^{32}$R$^{33}$, —OC(O)NR$^{32}$R$^{33}$, —NR$^{34}$C(O)R$^{32}$, —OC(O)R$^{32}$, —CH(=NR$^{34}$)NR$^{32}$R$^{33}$, —NHC(=NR$^{34}$)NR$^{32}$R$^{33}$, —S(O)R$^{32}$, —S(O)$_2$R$^{32}$, —S(O)H, —S(O)$_2$H, —S(O)$_3$H, —S(O)NR$^{32}$R$^{33}$, —S(O)$_2$NR$^{32}$R$^{33}$, —S(O)$_2$NH$_2$, —NR$^{34}$S(O)R$^{32}$, —NR$^{34}$S(O)$_2$R$^{32}$, —NR$^{32}$C(O)R$^{35}$, —NR$^{32}$C(O)OR$^{35}$, —NR$^{32}$S(O)$_2$R$^{35}$, —NR$^{32}$C(O)NHR$^{35}$, tetrazolyl, —CF$_3$, —OCF$_3$, methoxy, ethoxy, n-propoxy, i-propoxy, methyl, ethyl, n-propyl, i-propyl, n-butyl, i-butyl, s-butyl, t-butyl, hydroxymethyl-, hydroxyethyl-, vinyl, and allyl; and R$^{32}$, R$^{33}$, R$^{34}$, R$^{35}$, at each occurrence, are independently selected from: H, methyl, ethyl, n-propyl, i-propyl, n-butyl, i-butyl, s-butyl, t-butyl, and benzyl.

13. A compound of claim 12, wherein;
n is 1 or 2; and
R$^{b1}$, R$^{b2}$, R$^{b3}$, and R$^{b4}$, at each occurrence, are independently selected from: H, F, Cl, Br, cyano, nitro, methyl, ethyl, n-propyl, i-propyl, vinyl, allyl, hydroxy, hydroxymethyl, hydroxyethyl, methoxy, ethoxy, n-propoxy, i-propoxy, allyloxy-, methyl-S—, ethyl-S—, n-propyl-S—, i-propyl-S—, allyl-S—, —CF$_3$, —CHF$_2$, —OCF$_3$, —SCF$_3$, —CO$_2$H, —C(=O)OCH$_3$, —C(=O)CH$_3$, —SO$_2$CH$_3$, and —SO$_2$CH$_2$CH$_3$.

14. A compound of claim 12, wherein;
n is 1 or 2;
R$^{b1}$ is selected from: H, F, Cl, Br, cyano, nitro, methyl, ethyl, hydroxy, methoxy, ethoxy, n-propoxy, i-propoxy, allyloxy-, methyl-S—, ethyl-S—, n-propyl-S—, i-propyl-S—, allyl-S—, —CF$_3$, —CHF$_2$, —OCF$_3$, —SCF$_3$, —SO$_2$CH$_3$, and —SO$_2$CH$_2$CH$_3$;

R$^{b2}$ is H, methoxy or ethoxy;

R$^{b3}$ is hydroxy;

R$^{b4}$ is selected from: H, F, Cl, Br, cyano, nitro, methyl, ethyl, hydroxy, methoxy, ethoxy, n-propoxy, i-propoxy, allyloxy-, methyl-S—, ethyl-S—, n-propyl-S—, i-propyl-S—, allyl-S—, —CF$_3$, —CHF$_2$, —OCF$_3$, —SCF$_3$, —SO$_2$CH$_3$, and —SO$_2$CH$_2$CH$_3$; and R$^{b5}$ is phenyl substituted with 0–2 R$^{31}$.

15. A compound of claim 12, wherein;
n is 1 or 2;
R$^{b1}$ is selected from: H, F, Cl, Br, cyano, nitro, methyl, ethyl, hydroxy, methoxy, ethoxy, n-propoxy, i-propoxy, allyloxy-, methyl-S—, ethyl-S—, n-propyl-S—, i-propyl-S—, allyl-S—, —CF$_3$, —CHF$_2$, —OCF$_3$, —SCF$_3$, —SO$_2$CH$_3$, and —SO$_2$CH$_2$CH$_3$;

R$^{b2}$ is H, methoxy or ethoxy;

R$^{b3}$ is hydroxy;

R$^{b4}$ is selected from: H, F, Cl, Br, cyano, nitro, methyl, ethyl, hydroxy, methoxy, ethoxy, n-propoxy, i-propoxy, allyloxy-, methyl-S—, ethyl-S—, n-propyl-S—, i-propyl-S—, allyl-S—, —CF$_3$, —CHF$_2$, —OCF$_3$, —SCF$_3$, —SO$_2$CH$_3$, and —SO$_2$CH$_2$CH$_3$; and $R^{b5}$ is phenyl-; 2-chloro-phenyl-; 2-fluoro-phenyl-; 2-cyano-phenyl-; 2-$HO_2C$-phenyl-; 2-methyl-phenyl-; 2-ethyl-phenyl-; 2-methoxy-phenyl-; 2-ethoxy-phenyl-; 2-$H_3CS$-phenyl-; 2-trifluoromethoxy-phenyl-; 3-fluoro-phenyl-; 3-chloro-phenyl-; 3-$HO_2C$-phenyl-; 3-$H_2NCO$-phenyl-; 3-cyano-phenyl-; 3-$HOCH_2$-phenyl-; 3-$H_2NSO_2$-phenyl-; 3-$F_3C$-phenyl-; 3-$F_3CO$-phenyl-; 4-methyl-phenyl-; 4-ethyl-phenyl-; 4-i-Pr-phenyl-; 4-i-butyl-phenyl-; 4-t-butyl-phenyl-; 4-$MeSO_2NH$-phenyl-; 4-$HO_2C$-phenyl-; 4-$H_2NCO$-phenyl-; 4-(methyl-NHCO)-phenyl-; 4-(ethyl-NHCO)-phenyl-; 4-(n-propyl-NHCO)-phenyl-; 4-(i-propyl-NHCO)-phenyl-; 4-(i-butyl-NHCO)-phenyl-; 4-methoxy-phenyl-; 4-ethoxy-phenyl-; 4-$H_3CS$-phenyl-; 4-trifluoromethoxy-phenyl-; 4-cyano-phenyl-; 4-$HOCH_2$-phenyl-; 4-$MeSO_2$-phenyl-; 4-$H_2NSO_2$-phenyl-; 4-trifluoromethyl-phenyl-; 4-$Me_2N$-phenyl-; 4-tetrazol-5-yl-phenyl-; 2,4-bis-trifluoromethyl-phenyl-; 3,5-difluoro-phenyl-; 2,6-difluoro-phenyl-; 2,4-dichloro-phenyl-; 2,5-dimethoxy-phenyl-; 2,4-dimethoxy-phenyl-; 2,6-dimethoxy-phenyl-; 2-methoxy-4-cyclohexylNHCO-phenyl-; 2-methoxy-4-cyclopentylNHCO-phenyl-; 2-methoxy-4-cyclobutylNHCO-phenyl-; 2-methoxy-4-cyclopropylNHCO-phenyl-; 2-methoxy-4-$HO_2C$-phenyl-; 2-methoxy-4-iBuNHCO-phenyl-; 2-methoxy-5-fluoro-phenyl-; 2-methoxy-5-chloro-phenyl-; 2-methoxy-5-methyl-phenyl-; 2-methoxy-5-ethyl-phenyl-; 2-methoxy-5-i-propyl-phenyl-; or 4-(iBu-NHCO)-2-$HO_2C$-phenyl-.

16. A compound according to claim 1 wherein;

$R^B$ is:

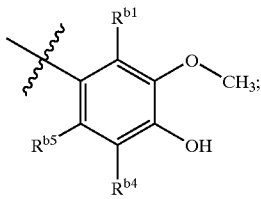

or a stereoisomer or pharmaceutically acceptable salt form thereof.

17. A compound according to claim 1 of stereoisomeric Formula (Ie):

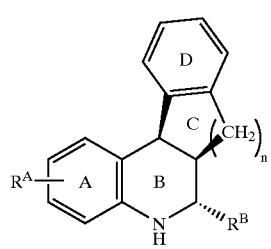

or pharmaceutically acceptable salt form thereof.

18. A compound according to claim 1 of stereoisomeric Formula (If):

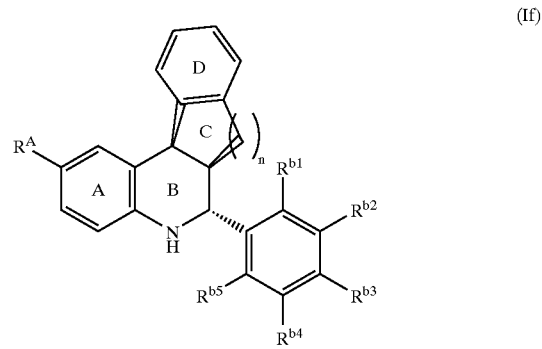

or pharmaceutically acceptable salt form thereof.

19. A compound of claim 1 of Formula (I) selected from:
6-(3-chloro-phenyl)-5,6a,7,11b-tetrahydro-6H-indeno[2,1-c]quinoline-3-carboxamidine;
6-(4-hydroxy-3-methoxy-phenyl)-5,6a,7,11b-tetrahydro-6H-indeno[2,1-c]quinoline-2-carboxamidine;
6-(4-hydroxy-3-ethoxy-phenyl)-5,6a,7,11b-tetrahydro-6H-indeno[2,1-c]quinoline-2-carboxamidine;
6-(2,3-dimethoxy-phenyl)-5,6a,7,11b-tetrahydro-6H-indeno[2,1-c]quinoline-2-carboxamidine;
6-(2,5-dimethoxy-phenyl)-5,6a,7,11b-tetrahydro-6H-indeno[2,1-c]quinoline-2-carboxamidine;
6-(2-hydroxy-3-methoxy-phenyl)-5,6a,7,11b-tetrahydro-6H-indeno[2,1-c]quinoline-2-carboxamidine;
6-(2-hydroxy-5-methoxy-phenyl)-5,6a,7,11b-tetrahydro-6H-indeno[2,1-c]quinoline-2-carboxamidine;
6-(2,3,4-trimethoxy-phenyl)-5,6a,7,11b-tetrahydro-6H-indeno[2,1-c]quinoline-2-carboxamidine;
6-(4-methoxy-2,3-dimethyl-phenyl)-5,6a,7,11b-tetrahydro-6H1-indeno[2,1-c]quinoline-2-carboxamidine;
6-(4-methoxy-2,5-dimethyl-phenyl)-5,6a,7,11b-tetrahydro-6H-indeno[2,1-c]quinoline-2-carboxamidine;
6-(3-hydroxy-4-methoxy-phenyl)-5,6a,7,11b-tetrahydro-6H-indeno[2,1-c]quinoline-2-carboxamidine;
6-(4-methoxy-phenyl)-5,6a,7,11b-tetrahydro-6H-indeno[2,1-c]quinoline-2-carboxamidine;
6-(4-hydroxy-3,5-dimethoxy-phenyl)-5,6a,7,11b-tetrahydro-6H-indeno[2,1-c]quinoline-2-carboxamidine;
4-(2-carbamimidoyl-5,6a,7,11b-tetrahydro-6H-indeno[2,1-c]quinolin-6-yl)-benzoic acid methyl ester;
6-(4-hydroxy-3-methoxy-5-nitro-phenyl)-5,6a,7,11b-tetrahydro-6H-indeno[2,1-c]quinoline-2-carboxamidine;
6-(3-hydroxy-4,5-dimethoxy-phenyl)-5,6a,7,11b-tetrahydro-6H-indeno[2,1-c]quinoline-2-carboxamidine;
6-(2-hydroxy-3-methoxy-5-nitro-phenyl)-5,6a,7,11b-tetrahydro-6H-indeno[2,1-c]quinoline-2-carboxamidine;
(5-chloro-2-methoxy-phenyl)-carbamic acid 4-(2-carbamimidoyl-5,6a,7,11 b-tetrahydro-6H-indeno[2,1-c]quinolin-6-yl)-2-methoxy-phenyl ester;
6-(6-bromo-2-hydroxy-3-methoxy-phenyl)-5,6a,7,11b-tetrahydro-6H-indeno[2,1- c]quinoline-2-carboxamidine;

6-(2-fluoro-5-methoxy-phenyl)-5,6a,7,11b-tetrahydro-6H-indeno[2,1-c]quinoline-2-carboxamidine;
6-(2-benzyloxy-3-methoxy-phenyl)-5,6a,7,11b-tetrahydro-6H-indeno[2,1-c]quinoline-2-carboxamidine;
6-(2-fluoro-4-methoxy-phenyl)5,6a7,11b-tetrahydro-6H-indeno[2,1-c]quinoline-2-carboxamidine;
6-(3iodo-4,5-dimethoxy-phenyl)-5,6a,7,11b-tetrahydro-6H-indeno[2,1-c]quinoline-2-carboxamidine;
6-[2-(2,6dichloro-benzyloxy)-phenyl]-5,6a,7,11b-tetrahydro-6H-indeno[2,1-c]quinoline-2-carboxamidine;
6-[2-(4-chloro-phenylthio)-phenyl-]5,6a,7,11b-tetrahydro-6H-indeno[2,1-c]quinoline-2-carboxamidine;
6-benzo[1,3]dioxol-4-yl-5,6a,7,11b-tetrahydro-6H-indeno[2,1-c]quinoline-2-carboxamidine;
6-(2-benzyloxy-phenyl)-5,6a,7,11b-tetrahydro-6H-indeno[2,1-c]quinoline-2-carboxamidine;
6-(2-allyloxy-phenyl)-5,6a,7,11b-tetrahydro-6H-indeno[2,1-c]quinoline-2-carboxamidine;
6-(5-bromo-2-methoxy-phenyl)-5,6a,7,11b-tetrahydro-6H-indeno[2,1-c]quinoline-2-carboxamidine;
6-[3-(4-methoxy-phenoxy)-phenyl]-5,6a,7,11b-tetrahydro-6H-indeno[2,1-c]quinoline-2-carboxamidine;
6-(3,4-dimethoxy-phenyl)-5,6a,7,11b-tetrahydro-6H-indeno[2,1-c]quinoline-2-carboxamidine;
6-(4-methanesulfonyl-phenyl)-5,6a,7,11b-tetrahydro-6H-indeno[2,1-c]quinoline-2-carboxamidine;
6-[4-(2-hydroxy-ethoxy)-phenyl]-5,6a,7,11b-tetrahydro-6H-indeno[2,1-c]quinoline-2-carboxamidine;
6-(2-chloro-3,4-dimethoxy-phenyl)-5,6a,7,11b-tetrahydro-6H-indeno[2,1-c]quinoline-2-carboxamidine;
6-(2-hydroxy-6-methoxy-phenyl)-5,6a,7,11b-tetrahydro-6H-indeno[2,1-c]quinoline-2-carboxamidine;
3-(2-carbamimidoyl-5,6a,7,11b-tetrahydro-6H-indeno[2,1-c]quinolin-6-yl)-benzoic acid methyl ester;
5-(2-carbamimidoyl-5,6a,7,11b-tetrahydro-6H-indeno[2,1-c]quinolin-6-yl)-2-methoxybenzeneboronic acid;
6-(3-bromo-4-hydroxy-5-methoxy-phenyl)-5,6a,7,11b-tetrahydro-6H-indeno[2,1-c]quinoline-2-carboxamidine;
6-pentafluorophenyl-5,6a,7,11b-tetrahydro-6H-indeno[2,1-c]quinoline-2-carboxamidine;
6-(2,4-dichloro-phenyl)-5,6a,7,11b-tetrahydro-6H-indeno[2,1-c]quinoline-2-carboxamidine;
6-(2-chloro-6-fluoro-phenyl)-5,6a,7,11b-tetrahydro-6H-indeno[2,1-c]quinoline-2-carboxamidine;
6-(3,4-dichloro-phenyl)-5,6a,7,11b-tetrahydro-6H-indeno[2,1-c]quinoline-2-carboxamidine;
6-(3,5-dichloro-phenyl)-5,6a,7,11b-tetrahydro-6H-indeno[2,1-c]quinoline-2-carboxamidine;
6-[3-(3,5-dichloro-phenoxy)-phenyl]-5,6a,7,11b-tetrahydro-6H-indeno[2,1-c]quinoline-2-carboxamidine;
6-(3-benzyloxy-phenyl)-5,6a,7,11b-tetrahydro-6H-indeno[2,1-c]quinoline-2-carboxamidine;
6-(3-trifluoromethyl-phenyl)-5,6a,7,11b-tetrahydro-6H-indeno[2,1-c]quinoline-2-carboxamidine;
6-(4-bromo-phenyl)-5,6a,7,11b-tetrahydro-6H-indeno[2,1-c]quinoline-2-carboxamidine;
6-(4-fluoro-phenyl)-5,6a,7,11b-tetrahydro-6H-indeno[2,1-c]quinoline-2-carboxamidine;
6-(4-chloro-phenyl)-5,6a,7,11b-tetrahydro-6H-indeno[2,1-c]quinoline-2-carboxamidine;
6-(4-ethoxy-phenyl)-5,6a,7,11b-tetrahydro-6H-indeno[2,1-c]quinoline-2-carboxamidine;
6-(4-methoxy-naphthalen-1-yl)-5,6a,7,11b-tetrahydro-6H-indeno[2,1-c]quinoline-2-carboxamidine;
6-(4-trifluoromethyl-phenyl)-5,6a,7,11b-tetrahydro-6H-indeno[2,1-c]quinoline-2-carboxamidine;
6-(2,3-difluoro-phenyl)-5,6a,7,11b-tetrahydro-6H-indeno[2,1-c]quinoline-2-carboxamidine;
6-(2,4-difluoro-phenyl)-5,6a,7,11b-tetrahydro-6H-indeno[2,1-c]quinoline-2-carboxamidine;
6-(2,5-difluoro-phenyl)-5,6a,7,11b-tetrahydro-6H-indeno[2,1-c]quinoline-2-carboxamidine;
6-(3,4-difluoro-phenyl)-5,6a,7,11b-tetrahydro-6H-indeno[2,1-c]quinoline-2-carboxamidine;
6-(3-chloro-4-fluoro-phenyl)-5,6a,7,11b-tetrahydro-6H-indeno[2,1-c]quinoline-2-carboxamidine;
6-(4-pyrrolidin-1-yl-phenyl)-5,6a,7,11b-tetrahydro-6H-indeno[2,1-c]quinoline-2-carboxamidine;
6-(5-bromo-2-ethoxy-phenyl)-5,6a,7,11b-tetrahydro-6H-indeno[2,1-c]quinoline-2-carboxamidine;
6-(4-trifluoromethoxy-phenyl)-5,6a,7,11b-tetrahydro-6H-indeno[2,1-c]quinoline-2-carboxamidine;
6-(4-propyl-phenyl)-5,6a,7,11b-tetrahydro-6H-indeno[2,1-c]quinoline-2-carboxamidine;
6-(3-bromo-4-fluoro-phenyl)-5,6a,7,11b-tetrahydro-6H-indeno[2,1-c]quinoline-2-carboxamidine;
6-(2,2-dimethyl-chroman-6-yl)-5,6a,7,11b-tetrahydro-6H-indeno[2,1-c]quinoline-2-carboxamidine;
6-(2,3,6-trifluoro-phenyl)-5,6a,7,11b-tetrahydro-6H-indeno[2,1-c]quinoline-2-carboxamidine;
6-(2,4,5-trifluoro-phenyl)-5,6a,7,11b-tetrahydro-6H-indeno[2,1-c]quinoline-2-carboxamidine;
6-(2,4,6-trifluoro-phenyl)-5,6a,7,11b-tetrahydro-6H-indeno[2,1-c]quinoline-2-carboxamidine;
6-(2,3,4-trifluoro-phenyl)-5,6a,7,11b-tetrahydro-6H-indeno[2,1-c]quinoline-2-carboxamidine;
6-(2-fluoro-3-trifluoromethyl-phenyl)-5,6a,7,11b-tetrahydro-6H-indeno[2,1-c]quinoline-2-carboxamidine;
6-(2-fluoro-6-trifluoromethyl-phenyl)-5,6a,7,11b-tetrahydro-6H-indeno[2,1-c]quinoline-2-carboxamidine;
6-(3-fluoro-5-trifluoromethyl-phenyl)-5,6a,7,11b-tetrahydro-6H-indeno[2,1-c]quinoline-2-carboxamidine;
6-(4-fluoro-2-trifluoromethyl-phenyl)-5,6a,7,11b-tetrahydro-6H-indeno[2,1-c]quinoline-2-carboxamidine;
6-(2,3,5-trifluoro-phenyl)-5,6a,7,11b-tetrahydro-6H-indeno[2,1-c]quinoline-2-carboxamidine;
6-[2-(4-tert-butyl-phenoxy)-5-nitro-phenyl]-5,6a,7,11b-tetrahydro-6H-indeno[2,1-c]quinoline-2-carboxamidine;
6-(2-chloro-5-trifluoromethyl-phenyl)-5,6a,7,11b-tetrahydro-6H-indeno[2,1-c]quinoline-2-carboxamidine;
6-(4-chloro-2-fluoro-phenyl)-5,6a,7,11b-tetrahydro-6H-indeno[2,1-c]quinoline-2-carboxamidine;

6-(4-chloro-3-fluoro-phenyl)-5,6a,7,11b-tetrahydro-6H-indeno[2,1-c]quinoline-2-carboxamidine;
6-(2-benzylmercapto-5-nitro-phenyl)-5,6a,7,11b-tetrahydro-6H-indeno[2,1-c]quinoline-2-carboxamidine;
6-(2-morpholin-4-yl-5-nitro-phenyl)-5,6a,7,11b-tetrahydro-6H-indeno[2,1-c]quinoline-2-carboxamidine;
6-(3-phenyl-1H-pyrazol-4-yl)-5,6a,7,11b-tetrahydro-6H-indeno[2,1-c]quinoline-2-carboxamidine;
6-(2,4-dioxo-1,2,3,4-tetrahydro-pyrimidin-5-yl)-5,6a,7,11b-tetrahydro-6H-indeno[2,1-c]quinoline-2-carboxamidine;
6-(2-phenyl-1H-imidazol-4-yl)-5,6a,7,11b-tetrahydro-6H-indeno[2,1-c]quinoline-2-carboxamidine;
6-(1H-imidazol-4-yl)-5,6a,7,11b-tetrahydro-6H-indeno[2,1-c]quinoline-2-carboxamidine;
6-(5-methyl-1H-pyrazol-4-yl)-5,6a,7,11b-tetrahydro-6H-indeno[2,1-c]quinoline-2-carboxamidine;
6-thiophen-2-yl-5,6a,7,11b-tetrahydro-6H-indeno[2,1-c]quinoline-2-carboxamidine;
6-[5-(3-trifluoromethyl-phenyl)-furan-2-yl]-5,6a,7,11b-tetrahydro-6H-indeno[2,1-c]quinoline-2-carboxamidine;
6-[5-(2-chloro-phenyl)-furan-2-yl]-5,6a,7,11b-tetrahydro-6H-indeno[2,1-c]quinoline-2-carboxamidine;
6-[5-(2,5-dichloro-phenyl)-furan-2-yl]-5,6a,7,11b-tetrahydro-6H-indeno[2,1-c]quinoline-2-carboxamidine;
6-[5-(2-trifluoromethoxy-phenyl)-furan-2-yl]-5,6a,7,11b-tetrahydro-6H-indeno[2,1-c]quinoline-2-carboxamidine;
6-(4,5-dibromo-thiophen-2-yl)-5,6a,7,11b-tetrahydro-6H-indeno[2,1-c]quinoline-2-carboxamidine;
6-[5-(1-methyl-5-trifluoromethyl-1H-pyrazol-3-yl)-thiophen-2-yl]-5,6a,7,11b-tetrahydro-6H-indeno[2,1-c]quinoline-2-carboxamidine;
6-(3-phenoxy-phenyl)-5,6,6a,7,8,12b-hexahydro-benzo[k]phenanthridine-3-carboxamidine;
6-(2-chloro-4-fluoro-phenyl)-5,6,6a,7,8,12b-hexahydro-benzo[k]phenanthridine-2-carboxamidine;
6-(4-hydroxy-3-methoxy-phenyl)-5,6,6a,7,8,12b-hexahydro-benzo[k]phenanthridine-2-carboxamidine;
6-(3,5-dibromo-4-hydroxy-phenyl)-5,6,6a,7,8,12b-hexahydro-benzo[k]phenanthridine-2-carboxamidine;
6-(3,5-dimethoxy-phenyl)-5,6,6a,7,8,12b-hexahydro-benzo[k]phenanthridine-2-carboxamidine;
6-(2-hydroxy-3-methoxy-5-nitro-phenyl)-5,6,6a,7,8,12b-hexahydro-benzo[k]phenanthridine-2-carboxamidine;
acetic acid 4-(2-carbamimidoyl-5,6,6a,7,8,12b-hexahydro-benzo[k]phenanthridin-6-yl)-2-methoxyphenyl ester
6-(5-bromo-2-methoxy-phenyl)-5,6,6a,7,8,12b-hexahydro-benzo[k]phenanthridine-2-carboxamidine;
6-(2-fluoro-5-methoxy-phenyl)-5,6,6a,7,8,12b-hexahydro-benzo[k]phenanthridine-2-carboxamidine;
3-(2-carbamimidoyl-5,6,6a,7,8,12b-hexahydro-benzo[k]phenanthridin-6-yl)-benzoic acid methyl ester;
6-(2-benzyloxy-3-methoxy-phenyl)-5,6,6a,7,8,12b-hexahydro-benzo[k]phenanthridine-2-carboxamidine;
6-(2-fluoro-4-methoxy-phenyl)-5,6,6a,7,8,12b-hexahydro-benzo[k]phenanthridine-2-carboxamidine;
6-(4-methanesulfonyl-phenyl)-5,6,6a,7,8,12b-hexahydro-benzo[k]phenanthridine-2-carboxamidine;
6-(2-benzyloxy-phenyl)-5,6,6a,7,8,12b-hexahydro-benzo[k]phenanthridine-2-carboxamidine;
6-benzo[1,3]dioxol-4-yl-5,6,6a,7,8,12b-hexahydro-benzo[k]phenanthridine-2-carboxamidine;
6-(3-trifluoromethyl-phenyl)-5,6,6a,7,8,12b-hexahydro-benzo[k]phenanthridine-2-carboxamidine;
6-(2-morpholin-4-yl-5-nitro-phenyl)-5,6,6a,7,8,12b-hexahydro-benzo[k]phenanthridine-2-carboxamidine;
6-(4-hydroxy-naphthalen-1-yl)-5,6,6a,7,8,12b-hexahydro-benzo[k]phenanthridine-2-carboxamidine;
N-[4-(2-carbamimidoyl-5,6,6a,7,8,12b-hexahydro-benzo[k]phenanthridin-6-yl)-phenyl]-acetamide;
6-(4-hydroxy-3-iodo-5-methoxy-phenyl)-5,6,6a,7,8,12b-hexahydro-benzo[k]phenanthridine-2-carboxamidine;
6-(3-bromo-4-hydroxy-5-methoxy-phenyl)-5,6,6a,7,8,12b-hexahydro-benzo[k]phenanthridine-2-carboxamidine;
6-(3-ethoxy-4-hydroxy-phenyl)-5,6,6a,7,8,12b-hexahydro-benzo[k]phenanthridine-2-carboxamidine;
6-(4-hydroxy-3,5-dimethyl-phenyl)-5,6,6a,7,8,12b-hexahydro-benzo[k]phenanthridine-2-carboxamidine;
6-(4-hydroxy-3,5-dimethoxy-phenyl)-5,6,6a,7,8,12b-hexahydro-benzo[k]phenanthridine-2-carboxamidine;
6-(3-fluoro-4-hydroxy-phenyl)-5,6,6a,7,8,12b-hexahydro-benzo[k]phenanthridine-2-carboxamidine;
6-(4-hydroxy-3-methyl-phenyl)-5,6,6a,7,8,12b-hexahydro-benzo[k]phenanthridine-2-carboxamidine;
6-(2-chloro-4-hydroxy-phenyl)-5,6,6a,7,8,12b-hexahydro-benzo[k]phenanthridine-2-carboxamidine;
4-(2-carbamimidoyl-5,6,6a,7,8,12b-hexahydro-benzo[k]phenanthridin-6-yl)-benzoic acid;
6-phenethyl-5,6,6a,7,8,12b-hexahydro-benzo[k]-phenanthridine-2-carboxamidine;
6-(3,4-dimethyl-thieno[2,3-b]thiophen-2-yl)-5,6,6a,7,8,12b-hexahydro-benzo[k]phenanthridine-2-carboxamidine;
6-(4-phenylethynyl-thiophen-2-yl)-5,6,6a,7,8,12b-hexahydro-benzo[k]phenanthridine-2-carboxamidine;
6-(3-phenoxy-thiophen-2-yl)-5,6,6a,7,8,12b-hexahydro-benzo[k]phenanthridine-2-carboxamidine;
6–3-(2-carbamimidoyl-5,6,6a,7,8,12b-hexahydro-benzo[k]phenanthridin-6-yl)-1H-indole-6-carboxylic acid methyl ester;
6-[5-(2-trifluoromethoxy-phenyl)-furan-2-yl]-5,6,6a,7,8,12b-hexahydro-benzo[k]phenanthridine-2-carboxamidine;
6-(4-bromo-thiophen-2-yl)-5,6,6a,7,8,12b-hexahydro-benzo[k]phenanthridine-2-carboxamidine;
6-(5-methyl-thiophen-2-yl)-5,6,6a,7,8,12b-hexahydro-benzo[k]phenanthridine-2-carboxamidine;
6-(3,4-dibromo-5-methyl-1H-pyrrol-2-yl)-5,6,6a,7,8,12b-hexahydro-benzo[k]phenanthridine-2-carboxamidine;
6-[5-(1-methyl-5-trifluoromethyl-1H-pyrazol-3-yl)-thiophen-2-yl]-5,6,6a,7,8,12b-hexahydro-benzo[k]phenanthridine-2-carboxamidine;
6-(5-phenylethynyl-thiophen-2-yl)-5,6,6a,7,8,12b-hexahydro-benzo[k]phenanthridine-2-carboxamidine;
6-(1-methyl-1H-benzoimidazol-2-yl)-5,6,6a,7,8,12b-hexahydro-benzo[k]phenanthridine-2-carboxamidine;

6-[5-(4-sulfamoyl-phenyl)-furan-2-yl]-5,6,6a,7,8,12b-hexahydro-benzo[k]phenanthridine-2-carboxamidine;

6-[5-(2-chloro-phenyl)-furan-2-yl]-5,6,6a,7,8,12b-hexahydro-benzo[k]phenanthridine-2-carboxamidine;

6-(1-methyl-3-phenyl-5-p-tolylsulfanyl-1H-pyrazol-4-yl)-5,6,6a,7,8,12b-hexahydro-benzo[k]phenanthridine-2-carboxamidine;

6-[5-(2-trifluoromethyl-phenyl)-furan-2-yl]-5,6,6a,7,8,12b-hexahydro-benzo[k]phenanthridine-2-carboxamidine;

6-(4-bromo-furan-2-yl)-5,6,6a,7,8,12b-hexahydro-benzo[k]phenanthridine-2-carboxamidine;

6-[2,2']bithiophenyl-5-yl-5,6,6a,7,8,12b-hexahydro-benzo[k]phenanthridine-2-carboxamidine;

6-[4-(2-cyano-thiophen-3-ylmethoxy)-phenyl]-5,6,6a,7,8,12b-hexahydro-benzo[k]phenanthridine-2-carboxamidine;

6-[1-(4-chloro-phenyl)-1H-pyrrol-2-yl]-5,6,6a,7,8,12b-hexahydro-benzo[k]phenanthridine-2-carboxamidine;

6-(2,3-dibromo-4-hydroxy-5-methoxy-phenyl)-5,6,6a,7,8,12b-hexahydro-benzo[k]phenanthridine-2-carboxamidine;

[4-(2-carbamimidoyl-5,6,6a,7,8,12b-hexahydro-benzo[k]phenanthridin-6-yl)-2-methoxy-phenoxy]-acetic acid;

6-(1,3-dioxo-1,3-dihydro-isoindol-2-ylmethyl)-5,6,6a,7,8,12b-hexahydro-benzo[k]phenanthridine-2-carboxamidine;

6-(4-hydroxy-3-methoxy-phenyl)-5,6a,7,8,9,13b-hexahydro-6H-5-aza-benzo[6,7]cyclohepta[1,2-a]naphthalene-2-carboxamidine;

6-(5-hydroxy-4'-isopropyl-4-methoxy-biphenyl-2-yl)-5,6a,7,11b-tetrahydro-6H-indeno[2,1-c]quinoline-2-carboxamidine;

2'-(2-carbamimidoyl-5,6a,7,11b-tetrahydro-6H-indeno[2,1-c]quinolin-6-yl)-5'-hydroxy-4'-methoxy-biphenyl-4-carboxylic acid;

2'-(2-carbamimidoyl-5,6a,7,11b-tetrahydro-6H-indeno[2,1-c]quinolin-6-yl)-5'-hydroxy-4'-methoxy-biphenyl-4-carboxylic acid isobutyl-amide;

2'-(2-carbamimidoyl-5,6a,7,11b-tetrahydro-6H-indeno[2,1-c]quinolin-6-yl)-5'-hydroxy-4'-methoxy-biphenyl-2-carboxylic acid;

2'-(2-carbamimidoyl-5,6a,7,11b-tetrahydro-6H-indeno[2,1-c]quinolin-6-yl)-5'-hydroxy-4'-methoxy-biphenyl-3-carboxylic acid;

6-(5-hydroxy-4-methoxy-biphenyl-2-yl)-5,6a,7,11b-tetrahydro-6H-indeno[2,1-c]quinoline-2-carboxamidine;

6-(5-hydroxy-4,2'-dimethoxy-biphenyl-2-yl)-5,6a,7,11b-tetrahydro-6H-indeno[2,1-c]quinoline-2-carboxamidine;

6-(4'-ethoxy-5-hydroxy-4-methoxy-biphenyl-2-yl)-5,6a,7,11b-tetrahydro-6H-indeno[2,1-c]quinoline-2-carboxamidine;

6-(3'-cyano-5-hydroxy-4-methoxy-biphenyl-2-yl)-5,6a,7,11b-tetrahydro-6H-indeno[2,1-c]quinoline-2-carboxamidine;

6-(4'-cyano-5-hydroxy-4-methoxy-biphenyl-2-yl)-5,6a,7,11b-tetrahydro-6H-indeno[2,1-c]quinoline-2-carboxamidine;

6-(5-hydroxy-3'-hydroxymethyl-4-methoxy-biphenyl-2-yl)-5,6a,7,11b-tetrahydro-6H-indeno[2,1-c]quinoline-2-carboxamidine;

6-(5-hydroxy-4'-methanesulfonylamino-4-methoxy-biphenyl-2-yl)-5,6a,7,11b-tetrahydro-6H-indeno[2,1-c]quinoline-2-carboxamidine;

6-(5-hydroxy-4'-methanesulfonyl-4-methoxy-biphenyl-2-yl)-5,6a,7,11b-tetrahydro-6H-indeno[2,1-c]quinoline-2-carboxamidine;

6-(5-hydroxy-4'-hydroxymethyl-4-methoxy-biphenyl-2-yl)-5,6a,7,11b-tetrahydro-6H-indeno[2,1-c]quinoline-2-carboxamidine;

6-(4-hydroxy-5-methoxy-2-pyridin-3-yl-phenyl)-5,6a,7,11b-tetrahydro-6H-indeno[2,1-c]quinoline-2-carboxamidine;

6-[2-(2,4-dimethoxy-pyrimidin-5-yl)-4-hydroxy-5-methoxy-phenyl]-5,6a,7,11b-tetrahydro-6H-indeno[2,1-c]quinoline-2-carboxamidine;

2'-(2-carbamimidoyl-5,6a,7,11b-tetrahydro-6H-indeno[2,1-c]quinolin-6-yl)-5'-hydroxy-4-isobutylcarbamoyl-4'-methoxy-biphenyl-2-carboxylic acid benzyl ester;

2'-(2-carbamimidoyl-5,6a,7,11b-tetrahydro-6H-indeno[2,1-c]quinolin-6-yl)-5'-hydroxy-4-isobutylcarbamoyl-4'-methoxy-biphenyl-2-carboxylic acid;

6'-(2-carbamimidoyl-5,6a,7,11b-tetrahydro-6H-indeno[2,1-c]quinolin-6-yl)-3'-hydroxy-2',4'-dimethoxy-biphenyl-2-carboxylic acid;

2'-(2-carbamimidoyl-5,6,6a,7,8,12b-hexahydro-benzo[k]phenanthridin-6-yl)-5'-hydroxy-4'-methoxy-biphenyl-3-carboxylic acid;

2'-(2-carbamimidoyl-5,6,6a,7,8,12b-hexahydro-benzo[k]phenanthridin-6-yl)-5'-hydroxy-4'-methoxy-biphenyl-4-carboxylic acid;

2'-(2-carbamimidoyl-5,6a,7,11b-tetrahydro-6H-indeno[2,1-c]quinolin-6-yl)-5'-hydroxy-4'-methoxy-biphenyl-3-carboxylic acid amide;

6-(5-hydroxy-4-methoxy-4'-sulfamoyl-biphenyl-2-yl)-5,6a,7,11b-tetrahydro-6H-indeno[2,1-c]quinoline-2-carboxamidine;

6-(5-hydroxy-4-methoxy-3'-sulfamoyl-biphenyl-2-yl)-5,6a,7,11b-tetrahydro-6H-indeno[2,1-c]quinoline-2-carboxamidine;

2'-(2-carbamimidoyl-5,6,6a,7,8,12b-hexahydro-benzo[k]phenanthridin-6-yl)-5'-hydroxy-4'-methoxy-biphenyl-2-carboxylic acid;

6'-(2-carbamimidoyl-5,6a,7,11b-tetrahydro-6H-indeno[2,1-c]quinolin-6-yl)-3'-hydroxy-2',4'-dimethoxy-biphenyl-3-carboxylic acid;

6'-(2-carbamimidoyl-5,6a,7,11b-tetrahydro-6H-indeno[2,1-c]quinolin-6-yl)-3'-hydroxy-2',4'-dimethoxy-biphenyl-4-carboxylic acid;

6-(4-hydroxy-5-methoxy-2-thiophen-3-yl-phenyl)-5,6a,7,11b-tetrahydro-6H-indeno[2,1-c]quinoline-2-carboxamidine;

6-(5-hydroxy-4,2',5'-trimethoxy-biphenyl-2-yl)-5,6a,7,11b-tetrahydro-6H-indeno[2,1-c]quinoline-2-carboxamidine;

6-(2'-chloro-5-hydroxy-4-methoxy-biphenyl-2-yl)-5,6a,7,11b-tetrahydro-6H-indeno[2,1-c]quinoline-2-carboxamidine;

6-(5-hydroxy-4,2',6'-trimethoxy-biphenyl-2-yl)-5,6a,7,11b-tetrahydro-6H-indeno[2,1-c]quinoline-2-carboxamidine;

6-(5-hydroxy-4-methoxy-2'-methylsulfanyl-biphenyl-2-yl)-5,6a,7,11b-tetrahydro-6H-indeno[2,1-c]quinoline-2-carboxamidine;

6-(5-hydroxy-4-methoxy-[1,1';2',1"]terphenyl-2-yl)-5,6a,7,11b-tetrahydro-6H-indeno[2,1-c]quinoline-2-carboxamidine;

6-(5'-fluoro-5-hydroxy-4,2'-dimethoxy-biphenyl-2-yl)-5,6a,7,11b-tetrahydro-6H-indeno[2,1-c]quinoline-2-carboxamidine;

6-(2',4'-dichloro-5-hydroxy-4-methoxy-biphenyl-2-yl)-5,6a,7,11b-tetrahydro-6H-indeno[2,1-c]quinoline-2-carboxamidine;

6-(2',6'-difluoro-5-hydroxy-4-methoxy-biphenyl-2-yl)-5,6a,7,11b-tetrahydro-6H-indeno[2,1-c]quinoline-2-carboxamidine;

6-(5-hydroxy-4-methoxy-3'-trifluoromethoxy-biphenyl-2-yl)-5,6a,7,11b-tetrahydro-6H-indeno[2,1-c]quinoline-2-carboxamidine;

6-(3'-chloro-5-hydroxy-4,2'-dimethoxy-biphenyl-2-yl)-5,6a,7,11b-tetrahydro-6H-indeno[2,1-c]quinoline-2-carboxamidine;

6-(5-hydroxy-4-methoxy-4'-methylsulfanyl-biphenyl-2-yl)-5,6a,7,11b-tetrahydro-6H-indeno[2,1-c]quinoline-2-carboxamidine;

6-(5-hydroxy-4-methoxy-2'-methyl-biphenyl-2-yl)-5,6a,7,11b-tetrahydro-6H-indeno[2,1-c]quinoline-2-carboxamidine;

6-[2-(5-chloro-thiophen-2-yl)-4-hydroxy-5-methoxy-phenyl]-5,6a,7,11b-tetrahydro-6H-indeno[2,1-c]quinoline-2-carboxamidine;

6-(5-hydroxy-5'-isopropyl-4,2'-dimethoxy-biphenyl-2-yl)-5,6a,7,11b-tetrahydro-6H-indeno[2,1-c]quinoline-2-carboxamidine;

6-(5-hydroxy-4-methoxy-4'-trifluoromethyl-biphenyl-2-yl)-5,6a,7,11b-tetrahydro-6H-indeno[2,1-c]quinoline-2-carboxamidine;

6-(5-hydroxy-4-methoxy-3'-trifluoromethyl-biphenyl-2-yl)-5,6a,7,11b-tetrahydro-6H-indeno[2,1-c]quinoline-2-carboxamidine;

6-(5-hydroxy-4,4'-dimethoxy-biphenyl-2-yl)-5,6a,7,11b-tetrahydro-6H-indeno[2,1-c]quinoline-2-carboxamidine;

6-(2'-fluoro-5-hydroxy-4-methoxy-biphenyl-2-yl)-5,6a,7,11b-tetrahydro-6H-indeno[2,1-c]quinoline-2-carboxamidine;

6-(5-hydroxy-4,2',4'-trimethoxy-biphenyl-2-yl)-5,6a,7,11b-tetrahydro-6H-indeno[2,1-c]quinoline-2-carboxamidine;

6-(5-hydroxy-4-methoxy-[1,1';3',1"]terphenyl-2-yl)-5,6a,7,11b-tetrahydro-6H-indeno[2,1-c]quinoline-2-carboxamidine;

6-(5'-chloro-5-hydroxy-4,2'-dimethoxy-biphenyl-2-yl)-5,6a,7,11b-tetrahydro-6H-indeno[2,1-c]quinoline-2-carboxamidine;

6-(4'-dimethylamino-5-hydroxy-4-methoxy-biphenyl-2-yl)-5,6a,7,11b-tetrahydro-6H-indeno[2,1-c]quinoline-2-carboxamidine;

6-[4-hydroxy-5-methoxy-2-(6-methoxy-pyridin-3-yl)-phenyl]-5,6a,7,11b-tetrahydro-6H-indeno[2,1-c]quinoline-2-carboxamidine;

6-(4'-benzyloxy-5-hydroxy-4-methoxy-biphenyl-2-yl)-5,6a,7,11b-tetrahydro-6H-indeno[2,1-c]quinoline-2-carboxamidine;

6-(4'-tert-butyl-5-hydroxy-4-methoxy-biphenyl-2-yl)-5,6a,7,11b-tetrahydro-6H-indeno[2,1-c]quinoline-2-carboxamidine;

6-(5-hydroxy-4,2'-dimethoxy-5'-methyl-biphenyl-2-yl)-5,6a,7,11b-tetrahydro-6H-indeno[2,1-c]quinoline-2-carboxamidine;

6-(5-hydroxy-4'-isobutyl-4-methoxy-biphenyl-2-yl)-5,6a,7,11b-tetrahydro-6H-indeno[2,1-c]quinoline-2-carboxamidine;

6-(2'-ethoxy-5-hydroxy-4-methoxy-biphenyl-2-yl)-5,6a,7,11b-tetrahydro-6H-indeno[2,1-c]quinoline-2-carboxamidine;

6-(5-hydroxy-4-methoxy-2'-trifluoromethoxy-biphenyl-2-yl)-5,6a,7,11b-tetrahydro-6H-indeno[2,1-c]quinoline-2-carboxamidine;

6-(2'-benzyloxy-5-hydroxy-4-methoxy-biphenyl-2-yl)-5,6a,7,11b-tetrahydro-6H-indeno[2,1-c]quinoline-2-carboxamidine;

6-(2'-ethyl-5-hydroxy-4-methoxy-biphenyl-2-yl)-5,6a,7,11b-tetrahydro-6H-indeno[2,1-c]quinoline-2-carboxamidine;

6-(5-hydroxy-4-methoxy-4'-phenoxy-biphenyl-2-yl)-5,6a,7,11b-tetrahydro-6H-indeno[2,1-c]quinoline-2-carboxamidine;

6-(5-hydroxy-4-methoxy-2',4'-bis-trifluoromethyl-biphenyl-2-yl)-5,6a,7,11b-tetrahydro-6H-indeno[2,1-c]quinoline-2-carboxamidine;

[2'-(2-carbamimidoyl-5,6a,7,11b-tetrahydro-6H-indeno[2,1-c]quinolin-6-yl)-5'-hydroxy-4'-methoxy-biphenyl-4-yl]-carbamic acid benzyl ester;

6-(5-hydroxy-4-methoxy-4'-trifluoromethoxy-biphenyl-2-yl)-5,6a,7,11b-tetrahydro-6H-indeno[2,1-c]quinoline-2-carboxamidine;

6-(3',5'-difluoro-5-hydroxy-4-methoxy-biphenyl-2-yl)-5,6a,7,11b-tetrahydro-6H-indeno[2,1-c]quinoline-2-carboxamidine;

4-[2-(2-carbamimidoyl-5,6a,7,11b-tetrahydro-6H-indeno[2,1-c]quinolin-6-yl)-5-hydroxy-4-methoxy-phenoxy]-benzoic acid;

3-[2-(2-carbamimidoyl-5,6a,7,11b-tetrahydro-6H-indeno[2,1-c]quinolin-6-yl)-5-hydroxy-4-methoxy-phenoxy]-benzoic acid;

4-[5-benzyloxy-2-(2-carbamimidoyl-5,6a,7,11b-tetrahydro-6H-indeno[2,1-c]quinolin-6-yl)-4-methoxy-phenoxy]-benzoic acid;

3-[5-benzyloxy-2-(2-carbamimidoyl-5,6a,7,11b-tetrahydro-6H-indeno[2,1-c]quinolin-6-yl)-4-methoxy-phenoxy]-benzoic acid;

4-(2-aminomethyl-5,6,6a,7,8,12b-hexahydro-benzo[k]phenanthridin-6-yl)-2-methoxy-phenol;

2'-(2-aminomethyl-5,6a,7,11b-tetrahydro-6H-indeno[2,1-c]quinolin-6-yl)-5'-hydroxy-4'-methoxy-biphenyl-2-carboxylic acid;

2'-(2-carbamimidoyl-5,6a,7,11b-tetrahydro-6H-indeno[2,1-c]quinolin-6-yl)-5'-hydroxy-4'-methoxy-biphenyl-4-carboxylic acid amide;

9-hydroxy-6-(4-hydroxy-3-methoxy-phenyl)-5,6,6a,7,8,12b-hexahydro-benzo[k]phenanthridine-2-carboxamidine;

6-(2-aminomethyl-5,6a,7,11b-tetrahydro-6H-indeno[2,1-c]quinolin-6-yl)-4,2'-dimethoxy-biphenyl-3-ol;

6-(2-aminomethyl-5,6a,7,11b-tetrahydro-6H-indeno[2,1-c]quinolin-6-yl)-4,2'-dimethoxy-5'-methyl-biphenyl-3-ol;

6-(2-aminomethyl-5,6a,7,11b-tetrahydro-6H-indeno[2,1-c]quinolin-6-yl)-4-methoxy-2'-methylsulfanyl-biphenyl-3-ol;

6-(2-aminomethyl-5,6a,7,11b-tetrahydro-6H-indeno[2,1-c]quinolin-6-yl)-2'-fluoro-4-methoxy-biphenyl-3-ol;

6-(2-aminomethyl-5,6a,7,11b-tetrahydro-6H-indeno[2,1-c]quinolin-6-yl)-5'-fluoro-4,2'-dimethoxy-biphenyl-3-ol;

6-(2-aminomethyl-5,6a,7,11b-tetrahydro-6H-indeno[2,1-c]quinolin-6-yl)-5'-chloro-4,2'-dimethoxy-biphenyl-3-ol;

6-(2-aminomethyl-5,6a,7,11b-tetrahydro-6H-indeno[2,1-c]quinolin-6-yl)-2'-ethoxy-4-methoxy-biphenyl-3-ol;

6-(2-aminomethyl-5,6a,7,11b-tetrahydro-6H-indeno[2,1-c]quinolin-6-yl)-2'-ethyl-4-methoxy-biphenyl-3-ol;

6-(2-aminomethyl-5,6a,7,11b-tetrahydro-6H-indeno[2,1-c]quinolin-6-yl)-4-methoxy-2'-trifluoromethoxy-biphenyl-3-ol;

6-(2-aminomethyl-5,6a,7,11b-tetrahydro-6H-indeno[2,1-c]quinolin-6-yl)-2'-benzyloxy-4-methoxy-biphenyl-3-ol;

N-[2'-(2-aminomethyl-5,6a,7,11b-tetrahydro-6H-indeno[2,1-c]quinolin-6-yl)-5'-hydroxy-4'-methoxy-biphenyl-4-yl]-methanesulfonamide;

6-(2-aminomethyl-5,6a,7,11b-tetrahydro-6H-indeno[2,1-c]quinolin-6-yl)-4,2',4'-trimethoxy-biphenyl-3-ol;

6-(2-aminomethyl-5,6a,7,11b-tetrahydro-6H-indeno[2,1-c]quinolin-6-yl)-2',6'-difluoro-4-methoxy-biphenyl-3-ol;

2'-(2-aminomethyl-5,6a,7,11b-tetrahydro-6H-indeno[2,1-c]quinolin-6-yl)-5'-hydroxy-4'-methoxy-biphenyl-3-carboxylic acid;

2'-(2-aminomethyl-5,6a,7,11b-tetrahydro-6H-indeno[2,1-c]quinolin-6-yl)-5'-hydroxy-2,4'-dimethoxy-biphenyl-4-carboxylic acid;

4-(2-aminomethyl-5,6a,7,11b-tetrahydro-6H-indeno[2,1-c]quinolin-6-yl)-2-methoxy-5-(2-methoxy-phenoxy)-phenol;

6-(2-aminomethyl-5,6a,7,11b-tetrahydro-6H-indeno[2,1-c]quinolin-6-yl)-4,2',6'-trimethoxy-biphenyl-3-ol;

6-[5-hydroxy-4-methoxy-4'-(1H-tetrazol-5-yl)-biphenyl-2-yl]-5,6a,7,11b-tetrahydro-6H-indeno[2,1-c]quinoline-2-carboxamidine;

2'-(2-carbamimidoyl-5,6a,7,11b-tetrahydro-6H-indeno[2,1-c]quinolin-6-yl)-5'-hydroxy-2,4'-dimethoxy-biphenyl-4-carboxylic acid;

2'-(2-carbamimidoyl-5,6a,7,11b-tetrahydro-6H-indeno[2,1-c]quinolin-6-yl)-5'-hydroxy-2,4'-dimethoxy-biphenyl-4-carboxylic acid isobutyl-amide;

2'-(2-carbamimidoyl-5,6a,7,11b-tetrahydro-6H-indeno[2,1-c]quinolin-6-yl)-5'-hydroxy-2,4'-dimethoxy-biphenyl-4-carboxylic acid benzylamide;

2'-(2-carbamimidoyl-5,6a,7,11b-tetrahydro-6H-indeno[2,1-c]quinolin-6-yl)-5'-hydroxy-2,4'-dimethoxy-biphenyl-4-carboxylic acid (2-morpholin-4-yl-ethyl)-amide;

2'-(2-carbamimidoyl-5,6a,7,11b-tetrahydro-6H-indeno[2,1-c]quinolin-6-yl)-5'-hydroxy-2,4'-dimethoxy-biphenyl-4-carboxylic acid cyclohexylamide;

2'-(2-carbamimidoyl-5,6a,7,11b-tetrahydro-6H-indeno[2,1-c]quinolin-6-yl)-5'-hydroxy-2,4'-dimethoxy-biphenyl-4-carboxylic acid cyclopropylamide; and 2'-(2-carbamimidoyl-5,6a,7,11b-tetrahydro-6H-indeno[2,1-c]quinolin-6-yl)-5'-hydroxy-2,4'-dimethoxy-biphenyl-4-carboxylic acid (2-pyrrolidin-1-yl-ethyl)-amide;

or a stereoisomer or pharmaceutically acceptable salt form thereof.

20. A pharmaceutical composition, comprising: a pharmaceutically acceptable carrier and a therapeutically effective amount of a compound of claim 1 or a pharmaceutically acceptable salt form thereof.

21. A method for treating a thromboembolic disorder, comprising: administering to a patient in need thereof a therapeutically effective amount of a compound of claim 1 or a pharmaceutically acceptable salt form thereof.

22. A method according to claim 21, wherein the thromboembolic disorder is selected from the group consisting of arterial cardiovascular thromboembolic disorders, venous cardiovascular thromboembolic disorders, and thromboembolic disorders in the chambers of the heart.

23. A method according to claim 21, wherein the thromboembolic disorder is selected from unstable angina, an acute coronary syndrome, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis.

24. A method for treating a thromboembolic disorder, comprising: administering to a patient in need thereof a therapeutically effective amount of a first and second therapeutic agent, wherein the first therapeutic agent is compound of claim 1 or a pharmaceutically acceptable salt thereof and the second therapeutic agent is at least one agent selected from a second factor VIIa inhibitor, an anti-coagulant agent, an anti-platelet agent, a thrombin inhibiting agent, a thrombolytic agent, and a fibrinolytic agent.

25. A method according to claim 24, wherein the second therapeutic agent is at least one agent selected from warfarin, unfractionated heparin, low molecular weight heparin, synthetic pentasaccharide, hirudin, argatrobanas, aspirin, ibuprofen, naproxen, sulindac, indomethacin, mefenamate, droxicam, diclofenac, sulfinpyrazone, piroxicam, ticlopidine, clopidogrel, tirofiban, eptifibatide, abciximab, melagatran, disulfatohirudin, tissue plasminogen activator, modified tissue plasminogen activator, anistreplase, urokinase, and streptokinase.

26. The method according to claim 24, wherein the second therapeutic agent is at least one anti-platelet agent.

27. The method according to claim 26, wherein the anti-platelet agent is aspirin and clopidogrel.

28. The method according to claim 26, wherein the anti-platelet agent is clopidogrel.

29. A pharmaceutical composition, comprising: a pharmaceutically acceptable carrier and a therapeutically effective amount of a compound of claim 19 or a pharmaceutically acceptable salt form thereof.

30. A method for treating a thromboembolic disorder, comprising: administering to a patient in need thereof a therapeutically effective amount of a compound of claim 19 or a pharmaceutically acceptable salt form thereof.

31. A method according to claim 30, wherein the thromboembolic disorder is selected from the group consisting of arterial cardiovascular thromboembolic disorders, venous cardiovascular thromboembolic disorders, and thromboembolic disorders in the chambers of the heart.

32. A method according to claim 30, wherein the thromboembolic disorder is selected from unstable angina, an acute coronary syndrome, first myocardial infarction, recurrent myocardial infarction, ischemic sudden death, transient ischemic attack, stroke, atherosclerosis, peripheral occlusive arterial disease, venous thrombosis, deep vein thrombosis, thrombophiebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis.

33. A method for treating a thromboembolic disorder, comprising: administering to a patient in need thereof a therapeutically effective amount of a first and second therapeutic agent, wherein the first therapeutic agent is compound of claim 19 or a pharmaceutically acceptable salt thereof and the second therapeutic agent is at least one agent selected from a second factor VIIa inhibitor, an anti-coagulant agent, an anti-platelet agent, a thrombin inhibiting agent, a thrombolytic agent, and a fibrinolytic agent.

34. A method according to claim 33, wherein the second therapeutic agent is at least one agent selected from warfarin, unfractionated heparin, low molecular weight heparin, synthetic pentasaccharide, hirudin, argatrobanas, aspirin, ibuprofen, naproxen, sulindac, indomethacin, mefenamate, droxicam, diclofenac, sulfinpyrazone, piroxicam, ticlopidine, clopidogrel, tirofiban, eptifibatide, abciximab, melagatran, disulfatohirudin, tissue plasminogen activator, modified tissue plasminogen activator, anistreplase, urokinase, and streptokinase.

35. The method according to claim 33, wherein the second therapeutic agent is at least one anti-platelet agent.

36. The method according to claim 35, wherein the anti-platelet agent is aspirin and clopidogrel.

37. The method according to claim 35, wherein the anti-platelet agent is clopidogrel.

* * * * *